US008206947B2

(12) United States Patent
Tang et al.

(10) Patent No.: US 8,206,947 B2
(45) Date of Patent: Jun. 26, 2012

(54) HUMAN TRANSMEMBRANE PROTEINS

(75) Inventors: Y. Tom Tang, San Jose, CA (US); Preeti G. Lal, Santa Clara, CA (US); Jennifer L. Jackson, Santa Cruz, CA (US); Henry Yue, Sunnyvale, CA (US); Karl J. Guegler, Menlo Park, CA (US); Neil C. Corley, Castro Valley, CA (US); Olga Bandman, Mountain View, CA (US); Chandra S. Arvizu, San Diego, CA (US); Gina A. Gorgone Simone, Earleville, MD (US); Matthew R. Kaser, Castro Valley, CA (US); Mariah R. Baughn, Los Angeles, CA (US); Janice K. Au-Young, Brisbane, CA (US)

(73) Assignee: Incyte Corporation, Palo Alto, CA (US)

( * ) Notice: Subject to any disclaimer, the term of this patent is extended or adjusted under 35 U.S.C. 154(b) by 1378 days.

(21) Appl. No.: 11/594,148

(22) Filed: Nov. 8, 2006

(65) Prior Publication Data

US 2007/0054312 A1     Mar. 8, 2007

Related U.S. Application Data

(62) Division of application No. 09/700,590, filed as application No. PCT/US99/11904 on May 28, 1999, now abandoned.

(60) Provisional application No. 60/087,260, filed on May 29, 1998, provisional application No. 60/091,674, filed on Jul. 2, 1998, provisional application No. 60/102,954, filed on Oct. 2, 1998, provisional application No. 60/109,869, filed on Nov. 24, 1998.

(51) Int. Cl.
*C12P 21/06* (2006.01)
*C12P 21/04* (2006.01)
*C07H 21/04* (2006.01)

(52) U.S. Cl. ............ 435/69.1; 435/70.1; 536/23.5; 536/24.1

(58) Field of Classification Search .................. None
See application file for complete search history.

(56) References Cited

U.S. PATENT DOCUMENTS 6,395,882 B1 * 5/2002 Rosen et al. ............... 530/395

OTHER PUBLICATIONS

Wells, Additivity of Mutational Effects in Proteins, 1990, Biochemistry 29:8509-8517.*
Ngo et al., Computational Complexity, Protein Structure Prediction, and Levinthal Paradox, 1994, The Protein Folding Problem and Tertiary Structure Prediction, pp. 492-495.*
Bork, Powers and Pitfalls in Sequence Analysis: The 70% Hurdle, 2000, Genome Research 10:398-400.*
Bork et al., Go hunting in sequence databases but watch out for the traps, 1996, Trends in Genetics 12:425-427.*
Scott et al. The Pendred syndrome gene encodes a chloride-iodide transport protein, (1999), Nature Genetics, vol. 21, pp. 440-443.*
Fletcher, C.A., et al., BRD4 Bromodomain Gene Rearrangement in Aggressive Cardinoma with Translocation t (15:19), (2001), Am. J. Pathol. 159, pp. 1987-1992.
Database Genbank Accession No. Y12059, Weber, B.H. *sapiens* HUNKI mRNA (May 2, 1998).
Database Genbank Accession No. AC004798, Lamerdin, J.E. et. al., *Homo sapiens* Chromosome 19, cosmid R31546, complete sequence (Jun. 9, 1998).
Database Genbank Accession No. X97593, Weber B., M. musculus mRNA for fsh-like protein, (Sep. 16, 1997).
Thorpe et a., "DNA sequence and structure of the mouse RING3 gene: identification of variant RING3 transcripts," *Immunogenetics*, vol. 48, pp. 82-86 (1998).

* cited by examiner

*Primary Examiner* — Gary Nickol
*Assistant Examiner* — Jegatheesan Seharaseyon
(74) *Attorney, Agent, or Firm* — Foley & Lardner LLP

(57) ABSTRACT

The invention provides human transmembrane proteins (HTMPN) and polynucleotides which identify and encode HTMPN. The invention also provides expression vectors, host cells, antibodies, agonists, and antagonists. The invention also provides methods for diagnosing, treating, or preventing disorders associated with expression of HTMPN.

8 Claims, No Drawings

```
                       SEQUENCE LISTING

<160> NUMBER OF SEQ ID NOS: 158

<210> SEQ ID NO 1
<211> LENGTH: 240
<212> TYPE: PRT
<213> ORGANISM: Homo sapiens
<220> FEATURE:
<221> NAME/KEY: misc_feature
<223> OTHER INFORMATION: Incyte ID No: 153831

<400> SEQUENCE: 1

Met Gly Asn Cys Gln Ala Gly His Asn Leu His Leu Cys Leu Ala
 1               5                  10                  15

His His Pro Pro Leu Val Cys Ala Thr Leu Ile Leu Leu Leu Leu
```

```
                    20                  25                  30

Gly Leu Ser Gly Leu Gly Leu Gly Ser Phe Leu Leu Thr His Arg
                35                  40                  45

Thr Gly Leu Arg Ser Pro Asp Ile Pro Gln Asp Trp Val Ser Phe
            50                  55                  60

Leu Arg Ser Phe Gly Gln Leu Thr Leu Cys Pro Arg Asn Gly Thr
        65                  70                  75

Val Thr Gly Lys Trp Arg Gly Ser His Val Val Gly Leu Leu Thr
    80                  85                  90

Thr Leu Asn Phe Gly Asp Gly Pro Asp Arg Asn Lys Thr Arg Thr
            95                 100                 105

Phe Gln Ala Thr Val Leu Gly Ser Gln Met Gly Leu Lys Gly Ser
               110                 115                 120

Ser Ala Gly Gln Leu Val Leu Ile Thr Ala Arg Val Thr Thr Glu
               125                 130                 135

Arg Thr Ala Gly Thr Cys Leu Tyr Phe Ser Ala Val Pro Gly Ile
               140                 145                 150

Leu Pro Ser Ser Gln Pro Pro Ile Ser Cys Ser Glu Glu Gly Ala
               155                 160                 165

Gly Asn Ala Thr Leu Ser Pro Arg Met Gly Glu Glu Cys Val Ser
               170                 175                 180

Val Trp Ser His Glu Gly Leu Val Leu Thr Lys Leu Leu Thr Ser
               185                 190                 195

Glu Glu Leu Ala Leu Cys Gly Ser Arg Leu Leu Val Leu Gly Ser
               200                 205                 210

Phe Leu Leu Leu Phe Cys Gly Leu Leu Cys Cys Val Thr Ala Met
               215                 220                 225

Cys Phe His Pro Arg Arg Glu Ser His Trp Ser Arg Thr Arg Leu
               230                 235                 240

<210> SEQ ID NO 2
<211> LENGTH: 100
<212> TYPE: PRT
<213> ORGANISM: Homo sapiens
<220> FEATURE:
<221> NAME/KEY: misc_feature
<223> OTHER INFORMATION: Incyte ID No: 350629

<400> SEQUENCE: 2

Met Glu Gly Leu Arg Ser Ser Val Glu Leu Asp Pro Glu Leu Thr
  1               5                  10                  15

Pro Gly Lys Leu Asp Glu Glu Met Val Gly Leu Pro Pro His Asp
             20                  25                  30

Ala Ser Pro Gln Val Thr Phe His Ser Leu Asp Gly Lys Thr Val
         35                  40                  45

Val Cys Pro His Phe Met Gly Leu Leu Gly Leu Leu Leu Leu
     50                  55                  60

Leu Thr Leu Ser Val Arg Asn Gln Leu Cys Val Arg Gly Glu Arg
 65                  70                  75

Gln Leu Ala Glu Thr Leu His Ser Gln Val Lys Glu Lys Ser Gln
             80                  85                  90

Leu Ile Gly Lys Lys Thr Asp Cys Arg Asp
             95                 100

<210> SEQ ID NO 3
<211> LENGTH: 416
<212> TYPE: PRT
```

-continued

<213> ORGANISM: Homo sapiens
<220> FEATURE:
<221> NAME/KEY: misc_feature
<223> OTHER INFORMATION: Incyte ID No: 729171

<400> SEQUENCE: 3

Met Ser Gly His Arg Ser Thr Arg Lys Arg Cys Gly Asp Ser His
 1               5                  10                  15

Pro Glu Ser Pro Val Gly Phe Gly His Met Ser Thr Thr Gly Cys
                20                  25                  30

Val Leu Asn Lys Leu Phe Gln Leu Pro Thr Pro Pro Leu Ser Arg
                35                  40                  45

His Gln Leu Lys Arg Leu Glu Glu His Arg Tyr Gln Ser Ala Gly
                50                  55                  60

Arg Ser Leu Leu Glu Pro Leu Val Gln Gly Tyr Trp Glu Trp Leu
                65                  70                  75

Val Arg Arg Val Pro Ser Trp Ile Ala Pro Asn Leu Ile Thr Ile
                80                  85                  90

Ile Gly Leu Ser Ile Asn Ile Cys Thr Thr Ile Leu Leu Val Phe
                95                 100                 105

Tyr Cys Pro Thr Ala Thr Glu Gln Ala Pro Leu Trp Ala Tyr Ile
               110                 115                 120

Ala Cys Ala Cys Gly Leu Phe Ile Tyr Gln Ser Leu Asp Ala Ile
               125                 130                 135

Gly Gly Lys Gln Ala Arg Arg Thr Asn Ser Ser Ser Pro Leu Gly
               140                 145                 150

Glu Leu Phe Asp His Gly Cys Asp Ser Leu Ser Thr Val Phe Val
               155                 160                 165

Val Leu Gly Thr Cys Ile Ala Val Gln Leu Gly Thr Asn Pro Asp
               170                 175                 180

Trp Met Phe Phe Cys Cys Phe Ala Gly Thr Phe Met Phe Tyr Cys
               185                 190                 195

Ala His Trp Gln Thr Tyr Val Ser Gly Thr Leu Arg Phe Gly Ile
               200                 205                 210

Ile Asp Val Thr Glu Val Gln Ile Phe Ile Ile Met His Leu
               215                 220                 225

Leu Ala Val Met Gly Gly Pro Pro Phe Trp Gln Ser Met Ile Pro
               230                 235                 240

Val Leu Asn Ile Gln Met Lys Ile Phe Pro Ala Leu Cys Thr Val
               245                 250                 255

Ala Gly Thr Ile Phe Pro Val Thr Asn Tyr Phe Arg Val Ile Phe
               260                 265                 270

Thr Gly Gly Val Gly Lys Asn Gly Ser Thr Ile Ala Gly Thr Ser
               275                 280                 285

Val Leu Ser Pro Phe Leu His Ile Gly Ser Val Ile Thr Leu Ala
               290                 295                 300

Ala Met Ile Tyr Lys Lys Ser Ala Val Gln Leu Phe Glu Lys His
               305                 310                 315

Pro Cys Leu Tyr Ile Leu Thr Phe Gly Phe Val Ser Ala Lys Ile
               320                 325                 330

Thr Asn Lys Leu Val Val Ala His Met Thr Lys Ser Glu Met His
               335                 340                 345

Leu His Asp Thr Ala Phe Ile Gly Pro Ala Leu Leu Phe Leu Asp
               350                 355                 360

Gln Tyr Phe Asn Ser Phe Ile Asp Glu Tyr Ile Val Leu Trp Ile

```
                    365                 370                 375

Ala Leu Val Phe Ser Phe Phe Asp Leu Ile Arg Tyr Cys Val Ser
                380                 385                 390

Val Cys Asn Gln Ile Ala Ser His Leu His Ile His Val Phe Arg
            395                 400                 405

Ile Lys Val Ser Thr Ala His Ser Asn His His
        410                 415
```

<210> SEQ ID NO 4
<211> LENGTH: 224
<212> TYPE: PRT
<213> ORGANISM: Homo sapiens
<220> FEATURE:
<221> NAME/KEY: misc_feature
<223> OTHER INFORMATION: Incyte ID No: 1273641

<400> SEQUENCE: 4

```
Met Thr Ile Thr Ser Phe Tyr Ala Val Cys Phe Tyr Leu Leu Met
  1               5                  10                  15

Leu Val Met Val Glu Gly Phe Gly Gly Lys Glu Ala Val Leu Arg
                 20                  25                  30

Thr Leu Arg Asp Thr Pro Met Met Val His Thr Gly Pro Cys Cys
             35                  40                  45

Cys Cys Cys Pro Cys Cys Gln Arg Leu Leu Leu Thr Arg Lys Lys
         50                  55                  60

Leu Gln Leu Leu Met Leu Gly Pro Phe Gln Tyr Ala Phe Leu Lys
 65                  70                  75

Ile Thr Leu Thr Trp Trp Ala Leu Phe Ser Ser Pro Thr Glu Ser
                 80                  85                  90

Tyr Asp Pro Ala Asp Ile Ser Glu Gly Ser Thr Ala Leu Trp Ile
             95                 100                 105

Asn Thr Phe Leu Gly Val Ser Thr Leu Leu Ala Leu Trp Thr Leu
        110                 115                 120

Gly Ile Ile Ser Arg Gln Ala Arg Leu His Leu Gly Glu Gln Asn
    125                 130                 135

Met Gly Ala Lys Phe Ala Leu Phe Gln Val Leu Leu Ile Leu Thr
140                 145                 150

Ala Leu Gln Pro Ser Ile Phe Ser Val Leu Ala Asn Gly Gly Gln
                155                 160                 165

Ile Ala Cys Ser Pro Pro Tyr Ser Ser Lys Thr Arg Ser Gln Val
            170                 175                 180

Met Asn Cys His Leu Leu Ile Leu Glu Thr Phe Leu Met Thr Val
        185                 190                 195

Leu Thr Arg Met Tyr Tyr Arg Arg Lys Asp His Lys Val Gly Tyr
    200                 205                 210

Glu Thr Phe Ser Ser Pro Asp Leu Asp Leu Asn Leu Lys Ala
215                 220
```

<210> SEQ ID NO 5
<211> LENGTH: 247
<212> TYPE: PRT
<213> ORGANISM: Homo sapiens
<220> FEATURE:
<221> NAME/KEY: misc_feature
<223> OTHER INFORMATION: Incyte ID No: 1427389

<400> SEQUENCE: 5

```
Met Gly Ala Ala Val Phe Phe Gly Cys Thr Phe Val Ala Phe Gly
  1               5                  10                  15
```

```
Pro Ala Phe Ala Leu Phe Leu Ile Thr Val Ala Gly Asp Pro Leu
            20                  25                  30

Arg Val Ile Ile Leu Val Ala Gly Ala Phe Phe Trp Leu Val Ser
            35                  40                  45

Leu Leu Leu Ala Ser Val Val Trp Phe Ile Leu Val His Val Thr
            50                  55                  60

Asp Arg Ser Asp Ala Arg Leu Gln Tyr Gly Leu Leu Ile Phe Gly
            65                  70                  75

Ala Ala Val Ser Val Leu Leu Gln Glu Val Phe Arg Phe Ala Tyr
            80                  85                  90

Tyr Lys Leu Leu Lys Lys Ala Asp Glu Gly Leu Ala Ser Leu Ser
            95                 100                 105

Glu Asp Gly Arg Ser Pro Ile Ser Ile Arg Gln Met Ala Tyr Val
           110                 115                 120

Ser Gly Leu Ser Phe Gly Ile Ile Ser Gly Val Phe Ser Val Ile
           125                 130                 135

Asn Ile Leu Ala Asp Ala Leu Gly Pro Gly Val Val Gly Ile His
           140                 145                 150

Gly Asp Ser Pro Tyr Tyr Phe Leu Thr Ser Ala Phe Leu Thr Ala
           155                 160                 165

Ala Ile Ile Leu Leu His Thr Phe Trp Gly Val Val Phe Phe Asp
           170                 175                 180

Ala Cys Glu Arg Arg Arg Tyr Trp Ala Leu Gly Leu Val Val Gly
           185                 190                 195

Ser His Leu Leu Thr Ser Gly Leu Thr Phe Leu Asn Pro Trp Tyr
           200                 205                 210

Glu Ala Ser Leu Leu Pro Ile Tyr Ala Val Thr Val Ser Met Gly
           215                 220                 225

Leu Trp Ala Phe Ile Thr Ala Gly Gly Ser Leu Arg Ser Ile Gln
           230                 235                 240

Arg Ser Leu Leu Cys Lys Asp
           245

<210> SEQ ID NO 6
<211> LENGTH: 72
<212> TYPE: PRT
<213> ORGANISM: Homo sapiens
<220> FEATURE:
<221> NAME/KEY: misc_feature
<223> OTHER INFORMATION: Incyte ID No: 1458357

<400> SEQUENCE: 6

Met Tyr Trp Leu His Gln Asp Met Phe Trp Leu Leu Val Leu Ile
  1               5                  10                  15

Leu Ile Cys Leu Val Thr His Leu Ile Thr Arg Glu Thr Ile Tyr
            20                  25                  30

Val Lys Ser Leu Phe Tyr Phe Lys Ile Leu Phe Val Tyr Leu Glu
            35                  40                  45

Ser Lys Pro Ala His Cys Asn Leu Cys Leu Tyr Ala Lys Glu Leu
            50                  55                  60

Asp Phe Phe Val Phe Val Leu Phe Phe Lys Leu Leu
            65                  70

<210> SEQ ID NO 7
<211> LENGTH: 106
<212> TYPE: PRT
<213> ORGANISM: Homo sapiens
```

```
<220> FEATURE:
<221> NAME/KEY: misc_feature
<223> OTHER INFORMATION: Incyte ID No: 1482837

<400> SEQUENCE: 7

Met His Tyr Gly Phe Leu Leu Trp Ser Gly Lys Lys Arg Gly Leu
  1               5                  10                  15

Ala Gly Pro Gln Gly Ile Cys Lys Ser Gln Lys Thr Val Phe Leu
                 20                  25                  30

Thr Ala Arg Cys His Ser Thr Leu Val Gly Lys Glu Glu Lys Lys
                 35                  40                  45

Ile Lys Leu Phe His Arg Thr Ser Trp Pro Pro His Ser His Ala
                 50                  55                  60

Leu Pro Thr Gln Pro Gly Pro Leu Pro Ala Pro Phe Ile Lys Ala
                 65                  70                  75

Glu Arg Val Glu Leu Ile Phe Thr Asn Cys Asn Ile Phe Val Val
                 80                  85                  90

Ser Val Ser Ser Phe Val Ser Ser Ala Glu Pro Cys Pro Phe Leu
                 95                 100                 105

Leu

<210> SEQ ID NO 8
<211> LENGTH: 239
<212> TYPE: PRT
<213> ORGANISM: Homo sapiens
<220> FEATURE:
<221> NAME/KEY: misc_feature
<223> OTHER INFORMATION: Incyte ID No: 1517434

<400> SEQUENCE: 8

Met Cys Val Thr Gln Leu Arg Leu Ile Phe Tyr Met Gly Ala Met
  1               5                  10                  15

Asn Asn Ile Leu Lys Phe Leu Val Ser Gly Asp Gln Lys Thr Val
                 20                  25                  30

Gly Leu Tyr Thr Ser Ile Phe Gly Val Leu Gln Leu Leu Cys Leu
                 35                  40                  45

Leu Thr Ala Pro Val Ile Gly Tyr Ile Met Asp Trp Arg Leu Lys
                 50                  55                  60

Glu Cys Glu Asp Ala Ser Glu Glu Pro Glu Leu Lys Asp Ala Asn
                 65                  70                  75

Gln Gly Glu Lys Lys Lys Lys Arg Asp Arg Gln Ile Gln Lys
                 80                  85                  90

Ile Thr Asn Ala Met Arg Ala Phe Ala Phe Thr Asn Leu Leu Leu
                 95                 100                 105

Val Gly Phe Gly Val Thr Cys Leu Ile Pro Asn Leu Pro Leu Gln
                110                 115                 120

Ile Leu Ser Phe Ile Leu His Thr Ile Val Arg Gly Phe Ile His
                125                 130                 135

Ser Ala Val Gly Gly Leu Tyr Ala Ala Val Tyr Pro Ser Thr Gln
                140                 145                 150

Phe Gly Ser Leu Thr Gly Leu Gln Ser Leu Ile Ser Ala Leu Phe
                155                 160                 165

Ala Leu Leu Gln Gln Pro Leu Phe Leu Ala Met Met Gly Pro Leu
                170                 175                 180

Gln Gly Asp Pro Leu Trp Val Asn Val Gly Leu Leu Leu Leu Ser
                185                 190                 195

Leu Leu Gly Phe Cys Leu Pro Leu Tyr Leu Ile Cys Tyr Arg Arg
```

```
                    200                 205                 210
Gln Leu Glu Arg Gln Leu Gln Gln Arg Gln Glu Asp Asp Lys Leu
                215                 220                 225
Phe Leu Lys Ile Asn Gly Ser Ser Asn Gln Glu Ala Phe Val
                230                 235

<210> SEQ ID NO 9
<211> LENGTH: 150
<212> TYPE: PRT
<213> ORGANISM: Homo sapiens
<220> FEATURE:
<221> NAME/KEY: misc_feature
<223> OTHER INFORMATION: Incyte ID No: 1536052

<400> SEQUENCE: 9

Met Trp Leu Pro Trp Ala Leu Leu Leu Trp Val Pro Ala Ser
  1               5                  10                  15

Thr Ser Met Thr Pro Ala Ser Ile Thr Ala Ala Lys Thr Ser Thr
                 20                  25                  30

Ile Thr Thr Ala Phe Pro Pro Val Ser Ser Thr Thr Leu Phe Ala
                 35                  40                  45

Val Gly Ala Thr His Ser Ala Ser Ile Gln Glu Glu Thr Glu Glu
                 50                  55                  60

Val Val Asn Ser Gln Leu Pro Leu Leu Ser Leu Leu Ala Leu
 65                  70                                  75

Leu Leu Leu Leu Leu Val Gly Ala Ser Leu Leu Ala Trp Arg Met
                 80                  85                  90

Phe Gln Lys Trp Ile Lys Ala Gly Asp His Ser Glu Leu Ser Gln
                 95                 100                 105

Asn Pro Lys Gln Ala Ser Pro Arg Glu Glu Leu His Tyr Ala Ser
                110                 115                 120

Val Val Phe Asp Ser Asn Thr Asn Arg Ile Ala Ala Gln Arg Pro
                125                 130                 135

Arg Glu Glu Glu Pro Asp Ser Asp Tyr Ser Val Ile Arg Lys Thr
                140                 145                 150

<210> SEQ ID NO 10
<211> LENGTH: 110
<212> TYPE: PRT
<213> ORGANISM: Homo sapiens
<220> FEATURE:
<221> NAME/KEY: misc_feature
<223> OTHER INFORMATION: Incyte ID No: 1666118

<400> SEQUENCE: 10

Met Pro Ala Cys Ile Leu Glu Asp Val Glu Ile Ser Phe Arg Gln
  1               5                  10                  15

Lys Trp Ser Ile Asn Ser Asp Thr Leu Leu Gly Cys Leu Thr Leu
                 20                  25                  30

Phe Ile Ser Ala Phe Phe Ala Ser Glu Thr Trp Gln Lys Leu Val
                 35                  40                  45

Ser Gln Ser Thr Ala Phe Leu Thr Met Cys Gly Val Thr Tyr Ala
                 50                  55                  60

Trp Tyr Met Pro Leu Leu Leu Lys Phe Tyr Ser Leu Leu Leu
 65                                  70                  75

Ala Gln Val Leu Leu Asn Pro Phe Leu Met Cys Thr Gly Trp Arg
                 80                  85                  90

Lys Asn Tyr Ser Gln His Phe Glu Arg Lys Val Phe Arg Asn Asn
                 95                 100                 105
```

Ile Asn Trp His Tyr
            110

<210> SEQ ID NO 11
<211> LENGTH: 58
<212> TYPE: PRT
<213> ORGANISM: Homo sapiens
<220> FEATURE:
<221> NAME/KEY: misc_feature
<223> OTHER INFORMATION: Incyte ID No: 1675560

<400> SEQUENCE: 11

Met Leu Val Thr Asn Ile Thr Val Asn Arg Ser Leu Leu His Ala
  1               5                  10                  15

Lys Asp Gln Cys Asp Leu Trp Met Glu Met Ile Val Met Lys Phe
                 20                  25                  30

Leu Phe His Gly Ala Val Phe Leu Phe Ile Ser Leu Gly Ser Arg
                 35                  40                  45

Phe Ser Glu Ala Val Arg Cys Cys Cys Cys Gly Phe Leu
                 50                  55

<210> SEQ ID NO 12
<211> LENGTH: 221
<212> TYPE: PRT
<213> ORGANISM: Homo sapiens
<220> FEATURE:
<221> NAME/KEY: misc_feature
<223> OTHER INFORMATION: Incyte ID No: 1687323

<400> SEQUENCE: 12

Met Ala Ala Ser Ser Ile Ser Ser Pro Trp Gly Lys His Val Phe
  1               5                  10                  15

Lys Ala Ile Leu Met Val Leu Val Ala Leu Ile Leu Leu His Ser
                 20                  25                  30

Ala Leu Ala Gln Ser Arg Arg Asp Phe Ala Pro Pro Gly Gln Gln
                 35                  40                  45

Lys Arg Glu Ala Pro Val Asp Val Leu Thr Gln Ile Gly Arg Ser
                 50                  55                  60

Val Arg Gly Thr Leu Asp Ala Trp Ile Gly Pro Glu Thr Met His
                 65                  70                  75

Leu Val Ser Glu Ser Ser Ser Gln Val Leu Trp Ala Ile Ser Ser
                 80                  85                  90

Ala Ile Ser Val Ala Phe Phe Ala Leu Ser Gly Ile Ala Ala Gln
                 95                 100                 105

Leu Leu Asn Ala Leu Gly Leu Ala Gly Asp Tyr Leu Ala Gln Gly
                110                 115                 120

Leu Lys Leu Ser Pro Gly Gln Val Gln Thr Phe Leu Leu Trp Gly
                125                 130                 135

Ala Gly Ala Leu Val Val Tyr Trp Leu Leu Ser Leu Leu Leu Gly
                140                 145                 150

Leu Val Leu Ala Leu Leu Gly Arg Ile Leu Trp Gly Leu Lys Leu
                155                 160                 165

Val Ile Phe Leu Ala Gly Phe Val Ala Leu Met Arg Ser Val Pro
                170                 175                 180

Asp Pro Ser Thr Arg Ala Leu Leu Leu Ala Leu Leu Ile Leu
                185                 190                 195

Tyr Ala Leu Leu Ser Arg Leu Thr Gly Ser Arg Ala Ser Gly Ala
                200                 205                 210

Gln Leu Glu Ala Lys Val Arg Gly Leu Glu Arg
            215                 220

<210> SEQ ID NO 13
<211> LENGTH: 262
<212> TYPE: PRT
<213> ORGANISM: Homo sapiens
<220> FEATURE:
<221> NAME/KEY: misc_feature
<223> OTHER INFORMATION: Incyte ID No: 1692236

<400> SEQUENCE: 13

Met Ala Leu Gly Leu Lys Cys Phe Arg Met Val His Pro Thr Phe
  1               5                  10                  15

Arg Asn Tyr Leu Ala Ala Ser Ile Arg Pro Val Ser Glu Val Thr
                 20                  25                  30

Leu Lys Thr Val His Glu Arg Gln His Gly His Arg Gln Tyr Met
                 35                  40                  45

Ala Tyr Ser Ala Val Pro Val Arg His Phe Ala Thr Lys Lys Ala
                 50                  55                  60

Lys Ala Lys Gly Lys Gly Gln Ser Gln Thr Arg Val Asn Ile Asn
             65                  70                  75

Ala Ala Leu Val Glu Asp Ile Ile Asn Leu Glu Val Asn Glu
             80                  85                  90

Glu Met Lys Ser Val Ile Glu Ala Leu Lys Asp Asn Phe Asn Leu
                 95                 100                 105

Thr Leu Asn Ile Arg Ala Ser Pro Gly Ser Leu Asp Lys Ile Ala
                110                 115                 120

Val Val Thr Ala Asp Gly Lys Leu Ala Leu Asn Gln Ile Ser Gln
                125                 130                 135

Ile Ser Met Lys Ser Pro Gln Leu Ile Leu Val Asn Met Ala Ser
                140                 145                 150

Phe Pro Glu Cys Thr Ala Ala Ile Lys Ala Ile Arg Glu Ser
                155                 160                 165

Gly Met Asn Leu Asn Pro Glu Val Glu Gly Thr Leu Ile Arg Val
                170                 175                 180

Pro Ile Pro Gln Val Thr Arg Glu His Arg Glu Met Leu Val Lys
                185                 190                 195

Leu Ala Lys Gln Asn Thr Asn Lys Ala Lys Asp Ser Leu Arg Lys
                200                 205                 210

Val Arg Thr Asn Ser Met Asn Lys Leu Lys Lys Ser Lys Asp Thr
                215                 220                 225

Val Ser Glu Asp Thr Ile Arg Leu Ile Glu Lys Gln Ile Ser Gln
                230                 235                 240

Met Ala Asp Asp Thr Val Ala Glu Leu Asp Arg His Leu Ala Val
                245                 250                 255

Lys Thr Lys Glu Leu Leu Gly
                260

<210> SEQ ID NO 14
<211> LENGTH: 90
<212> TYPE: PRT
<213> ORGANISM: Homo sapiens
<220> FEATURE:
<221> NAME/KEY: misc_feature
<223> OTHER INFORMATION: Incyte ID No: 1720847

<400> SEQUENCE: 14

Met Glu Ala Ala Met Glu Trp Glu Gly Gly Ala Ile Arg His Pro

```
                1               5              10              15
Ser Thr Glu Leu Gly Ile Met Gly Ser Trp Phe Tyr Leu Phe Leu
               20              25              30

Ala Pro Leu Phe Lys Gly Leu Ala Gly Ser Leu Pro Phe Gly Cys
               35              40              45

Leu Ser Leu Leu Gln Pro Thr Glu Lys Thr Ala Leu Gln Arg Trp
               50              55              60

Arg Val Phe Met Lys His Ser Cys Gln Glu Pro Arg His Arg Ala
               65              70              75

Gly Gly Leu Glu Lys Gly Gly His Thr Gly Gly Arg Ser Trp
               80              85              90
```

<210> SEQ ID NO 15
<211> LENGTH: 208
<212> TYPE: PRT
<213> ORGANISM: Homo sapiens
<220> FEATURE:
<221> NAME/KEY: misc_feature
<223> OTHER INFORMATION: Incyte ID No: 1752821

<400> SEQUENCE: 15

```
                1               5              10              15
Met Ala Ser Ser Leu Leu Ala Gly Glu Arg Leu Val Arg Ala Leu
               20              25              30

Gly Pro Gly Gly Glu Leu Glu Pro Glu Arg Leu Pro Arg Lys Leu
               35              40              45

Arg Ala Glu Leu Glu Ala Ala Leu Gly Lys Lys His Lys Gly Gly
               50              55              60

Asp Ser Ser Ser Gly Pro Gln Arg Leu Val Ser Phe Arg Leu Ile
               65              70              75

Arg Asp Leu His Gln His Leu Arg Glu Arg Asp Ser Lys Leu Tyr
               80              85              90

Leu His Glu Leu Leu Glu Gly Ser Glu Ile Tyr Leu Pro Glu Val
               95             100             105

Val Lys Pro Pro Arg Asn Pro Glu Leu Val Ala Arg Leu Glu Lys
              110             115             120

Ile Lys Ile Gln Leu Ala Asn Glu Glu Tyr Lys Arg Ile Thr Arg
              125             130             135

Asn Val Thr Cys Gln Asp Thr Arg His Gly Gly Thr Leu Ser Asp
              140             145             150

Leu Gly Lys Gln Val Arg Ser Leu Lys Ala Leu Val Ile Thr Ile
              155             160             165

Phe Asn Phe Ile Val Thr Val Val Ala Ala Phe Val Cys Thr Tyr
              170             175             180

Leu Gly Ser Gln Tyr Ile Phe Thr Glu Met Ala Ser Arg Val Leu
              185             190             195

Ala Ala Leu Ile Val Ala Ser Val Val Gly Leu Ala Glu Leu Tyr
              200             205

Val Met Val Arg Ala Met Glu Gly Glu Leu Gly Glu Leu
```

<210> SEQ ID NO 16
<211> LENGTH: 97
<212> TYPE: PRT
<213> ORGANISM: Homo sapiens
<220> FEATURE:
<221> NAME/KEY: misc_feature
<223> OTHER INFORMATION: Incyte ID No: 1810923

<400> SEQUENCE: 16

```
Met Thr Lys Lys Lys Arg Glu Asn Leu Gly Val Ala Leu Glu Ile
  1               5                  10                  15

Asp Gly Leu Glu Glu Lys Leu Ser Gln Cys Arg Arg Asp Leu Glu
                 20                  25                  30

Ala Val Asn Ser Arg Leu His Ser Arg Glu Leu Ser Pro Glu Ala
                 35                  40                  45

Arg Arg Ser Leu Glu Lys Glu Lys Asn Ser Leu Met Asn Lys Ala
                 50                  55                  60

Ser Asn Tyr Glu Lys Glu Leu Lys Phe Leu Arg Gln Glu Asn Arg
                 65                  70                  75

Lys Asn Met Leu Leu Ser Val Ala Ile Phe Ile Leu Leu Thr Leu
                 80                  85                  90

Val Tyr Ala Tyr Trp Thr Met
                 95
```

<210> SEQ ID NO 17
<211> LENGTH: 243
<212> TYPE: PRT
<213> ORGANISM: Homo sapiens
<220> FEATURE:
<221> NAME/KEY: misc_feature
<223> OTHER INFORMATION: Incyte ID No: 1822315

<400> SEQUENCE: 17

```
Met Phe Phe Leu Ser Ser Ser Lys Leu Thr Lys Trp Lys Gly Glu
  1               5                  10                  15

Val Lys Lys Arg Leu Asp Ser Glu Tyr Lys Glu Gly Gly Gln Arg
                 20                  25                  30

Asn Trp Val Gln Val Phe Cys Asn Gly Ala Val Pro Thr Glu Leu
                 35                  40                  45

Ala Leu Leu Tyr Met Ile Glu Asn Gly Pro Gly Glu Ile Pro Val
                 50                  55                  60

Asp Phe Ser Lys Gln Tyr Ser Ala Ser Trp Met Cys Leu Ser Leu
                 65                  70                  75

Leu Ala Ala Leu Ala Cys Ser Ala Gly Asp Thr Trp Ala Ser Glu
                 80                  85                  90

Val Gly Pro Val Leu Ser Lys Ser Ser Pro Arg Leu Ile Thr Thr
                 95                 100                 105

Trp Glu Lys Val Pro Val Gly Thr Asn Gly Gly Val Thr Val Val
                110                 115                 120

Gly Leu Val Ser Ser Leu Leu Gly Gly Thr Phe Val Gly Ile Ala
                125                 130                 135

Tyr Phe Leu Thr Gln Leu Ile Phe Val Asn Asp Leu Asp Ile Ser
                140                 145                 150

Ala Pro Gln Trp Pro Ile Ile Ala Phe Gly Gly Leu Ala Gly Leu
                155                 160                 165

Leu Gly Ser Ile Val Asp Ser Tyr Leu Gly Ala Thr Met Gln Tyr
                170                 175                 180

Thr Gly Leu Asp Glu Ser Thr Gly Met Val Val Asn Ser Pro Thr
                185                 190                 195

Asn Lys Ala Arg His Ile Ala Gly Lys Pro Ile Leu Asp Asn Asn
                200                 205                 210

Ala Trp Ile Cys Phe Leu Leu Phe Leu Pro Ser Cys Ser Gln
                215                 220                 225

Leu Leu Leu Gly Val Phe Gly Pro Gly Gly Glu Leu Tyr Phe Ile
                230                 235                 240
```

```
<210> SEQ ID NO 18
<211> LENGTH: 162
<212> TYPE: PRT
<213> ORGANISM: Homo sapiens
<220> FEATURE:
<221> NAME/KEY: misc_feature
<223> OTHER INFORMATION: Incyte ID No: 1877777

<400> SEQUENCE: 18
```

Ser Thr Gly

Met Leu Gln Thr Ser Asn Tyr Ser Leu Val Leu Ser Leu Gln Phe
 1               5                  10                  15

Leu Leu Leu Ser Tyr Asp Leu Phe Val Asn Ser Phe Ser Glu Leu
                20                  25                  30

Leu Gln Lys Thr Pro Val Ile Gln Leu Val Leu Phe Ile Ile Gln
                35                  40                  45

Asp Ile Ala Val Leu Phe Asn Ile Ile Ile Phe Leu Met Phe
            50                  55                  60

Phe Asn Thr Phe Val Phe Gln Ala Gly Leu Val Asn Leu Leu Phe
        65                  70                  75

His Lys Phe Lys Gly Thr Ile Ile Leu Thr Ala Val Tyr Phe Ala
            80                  85                  90

Leu Ser Ile Ser Leu His Val Trp Val Met Asn Leu Arg Trp Lys
                95                 100                 105

Asn Ser Asn Ser Phe Ile Trp Thr Asp Gly Leu Gln Met Leu Phe
               110                 115                 120

Val Phe Gln Arg Leu Ala Ala Val Leu Tyr Cys Tyr Phe Tyr Lys
               125                 130                 135

Arg Thr Ala Val Arg Leu Gly Asp Pro His Phe Tyr Gln Asp Ser
               140                 145                 150

Leu Trp Leu Arg Lys Glu Phe Met Gln Val Arg Arg
               155                 160

```
<210> SEQ ID NO 19
<211> LENGTH: 470
<212> TYPE: PRT
<213> ORGANISM: Homo sapiens
<220> FEATURE:
<221> NAME/KEY: misc_feature
<223> OTHER INFORMATION: Incyte ID No: 1879819

<400> SEQUENCE: 19
```

Met Leu Ser Pro Ser Pro Gly Lys Gly Pro Pro Ala Val Ala
 1               5                  10                  15

Pro Arg Pro Lys Ala Pro Leu Gln Leu Gly Pro Ser Ser Ile
                20                  25                  30

Lys Glu Lys Gln Gly Pro Leu Leu Asp Leu Phe Gly Gln Lys Leu
                35                  40                  45

Pro Ile Ala His Thr Pro Pro Pro Ala Pro Pro Leu Pro
            50                  55                  60

Leu Pro Glu Asp Pro Gly Thr Leu Ser Ala Glu Arg Arg Cys Leu
        65                  70                  75

Thr Gln Pro Val Glu Asp Gln Gly Val Ser Thr Gln Leu Leu Ala
            80                  85                  90

Pro Ser Gly Ser Val Cys Phe Ser Tyr Thr Gly Thr Pro Trp Lys
                95                 100                 105

Leu Phe Leu Arg Lys Glu Val Phe Tyr Pro Arg Glu Asn Phe Ser

```
                    110                 115                 120
His Pro Tyr Tyr Leu Arg Leu Leu Cys Glu Gln Ile Leu Arg Asp
                125                 130                 135
Thr Phe Ser Glu Ser Cys Ile Arg Ile Ser Gln Asn Glu Arg Arg
                140                 145                 150
Lys Met Lys Asp Leu Leu Gly Gly Leu Glu Val Asp Leu Asp Ser
                155                 160                 165
Leu Thr Thr Thr Glu Asp Ser Val Lys Lys Arg Ile Val Val Ala
                170                 175                 180
Ala Arg Asp Asn Trp Ala Asn Tyr Phe Ser Arg Phe Phe Pro Val
                185                 190                 195
Ser Gly Glu Ser Gly Ser Asp Val Gln Leu Leu Ala Val Ser His
                200                 205                 210
Arg Gly Leu Arg Leu Leu Lys Val Thr Gln Gly Pro Gly Leu Arg
                215                 220                 225
Pro Asp Gln Leu Lys Ile Leu Cys Ser Tyr Ser Phe Ala Glu Val
                230                 235                 240
Leu Gly Val Glu Cys Arg Gly Gly Ser Thr Leu Glu Leu Ser Leu
                245                 250                 255
Lys Ser Glu Gln Leu Val Leu His Thr Ala Arg Ala Arg Ala Ile
                260                 265                 270
Glu Ala Leu Val Glu Leu Phe Leu Asn Glu Leu Lys Lys Asp Ser
                275                 280                 285
Gly Tyr Val Ile Ala Leu Arg Ser Tyr Ile Thr Asp Asn Cys Ser
                290                 295                 300
Leu Leu Ser Phe His Arg Gly Asp Leu Ile Lys Leu Leu Pro Val
                305                 310                 315
Cys His Pro Gly Ala Arg Leu Ala Val Trp Leu Cys Arg Gly Pro
                320                 325                 330
Phe Arg Thr Leu Ser Cys Arg His Ser Ala Ala Gly Cys Arg Ser
                335                 340                 345
Arg Leu Phe Leu Leu Gln Gly Ala Glu Glu Trp Leu Ala Gln Gly
                350                 355                 360
Ser Ala Val Gln Arg Gly Thr Arg Ala Gly Ser Val Gly Gln Gly
                365                 370                 375
Leu Arg Gly Glu Glu Asp Gly Arg Gly Thr Ser Arg Gly Lys Ala
                380                 385                 390
Cys Leu Arg Leu Arg Lys Glu Arg Gly Leu Thr Thr Pro Glu Ala
                395                 400                 405
Ala Met Arg Trp Asp His Pro Ala Val Arg Leu Leu Trp Leu Pro
                410                 415                 420
Leu Cys Pro Leu Leu Met Ala Arg Leu Val Ser Pro Ala Arg Leu
                425                 430                 435
Cys Thr Pro Cys Arg Gln Gly Leu Gly Trp Met Leu Leu Leu Cys
                440                 445                 450
Pro Thr Trp Tyr Leu Val Gln Gly Cys Pro Ser Arg Cys Leu Ile
                455                 460                 465
Asn Ser Ser Ser Leu
                470

<210> SEQ ID NO 20
<211> LENGTH: 144
<212> TYPE: PRT
<213> ORGANISM: Homo sapiens
<220> FEATURE:
```

```
<221> NAME/KEY: misc_feature
<223> OTHER INFORMATION: Incyte ID No: 1932945

<400> SEQUENCE: 20

Met Glu Arg Glu Gly Ser Gly Ser Gly Gly Ser Ala Gly Leu
  1               5                  10                  15

Leu Gln Gln Ile Leu Ser Leu Lys Val Val Pro Arg Val Asn
             20                  25                  30

Gly Thr Leu Cys Pro Asn Ser Thr Ser Leu Cys Ser Phe Pro Glu
             35                  40                  45

Met Trp Tyr Gly Val Phe Leu Trp Ala Leu Val Ser Ser Leu Phe
             50                  55                  60

Phe His Val Pro Ala Gly Leu Leu Ala Leu Phe Thr Leu Arg His
             65                  70                  75

His Lys Tyr Gly Arg Phe Met Ser Val Ser Ile Leu Leu Met Gly
             80                  85                  90

Ile Val Gly Pro Ile Thr Ala Gly Ile Leu Thr Ser Ala Ala Ile
             95                 100                 105

Ala Gly Val Tyr Arg Ala Ala Gly Lys Glu Met Ile Pro Phe Glu
            110                 115                 120

Ala Leu Thr Leu Gly Thr Gly Gln Thr Phe Cys Val Leu Val Val
            125                 130                 135

Ser Phe Leu Arg Ile Leu Ala Thr Leu
            140

<210> SEQ ID NO 21
<211> LENGTH: 221
<212> TYPE: PRT
<213> ORGANISM: Homo sapiens
<220> FEATURE:
<221> NAME/KEY: misc_feature
<223> OTHER INFORMATION: Incyte ID No: 2061026

<400> SEQUENCE: 21

Met Ala Leu Ala Leu Ala Ala Leu Ala Ala Val Glu Pro Ala Cys
  1               5                  10                  15

Gly Ser Arg Tyr Gln Gln Leu Gln Asn Glu Glu Ser Gly Glu
             20                  25                  30

Pro Glu Gln Ala Ala Gly Asp Ala Pro Pro Tyr Ser Ser Ile
             35                  40                  45

Ser Ala Glu Ser Ala Ala Tyr Phe Asp Tyr Lys Asp Glu Ser Gly
             50                  55                  60

Phe Pro Lys Pro Pro Ser Tyr Asn Val Ala Thr Thr Leu Pro Ser
             65                  70                  75

Tyr Asp Glu Ala Glu Arg Thr Lys Ala Glu Ala Thr Ile Pro Leu
             80                  85                  90

Val Pro Gly Arg Asp Glu Asp Phe Val Gly Arg Asp Asp Phe Asp
             95                 100                 105

Asp Ala Asp Gln Leu Arg Ile Gly Asn Asp Gly Ile Phe Met Leu
            110                 115                 120

Thr Phe Phe Met Ala Phe Leu Phe Asn Trp Ile Gly Phe Leu
            125                 130                 135

Ser Phe Cys Leu Thr Thr Ser Ala Ala Gly Arg Tyr Gly Ala Ile
            140                 145                 150

Ser Gly Phe Gly Leu Ser Leu Ile Lys Trp Ile Leu Ile Val Arg
            155                 160                 165

Phe Ser Thr Tyr Phe Pro Gly Tyr Phe Asp Gly Gln Tyr Trp Leu
```

```
                           170                 175                 180

Trp Trp Val Phe Leu Val Leu Gly Phe Leu Phe Leu Arg Gly
                185                 190                 195

Phe Ile Asn Tyr Ala Lys Val Arg Lys Met Pro Glu Thr Phe Ser
                200                 205                 210

Asn Leu Pro Arg Thr Arg Val Leu Phe Ile Tyr
                215                 220

<210> SEQ ID NO 22
<211> LENGTH: 688
<212> TYPE: PRT
<213> ORGANISM: Homo sapiens
<220> FEATURE:
<221> NAME/KEY: misc_feature
<223> OTHER INFORMATION: Incyte ID No: 2096687

<400> SEQUENCE: 22

Met Ser Ala Glu Ser Gly Pro Gly Thr Arg Leu Arg Asn Leu Pro
  1               5                  10                  15

Val Met Gly Asp Gly Leu Glu Thr Ser Gln Met Ser Thr Thr Gln
                 20                  25                  30

Ala Gln Ala Gln Pro Gln Pro Ala Asn Ala Ala Ser Thr Asn Pro
                 35                  40                  45

Pro Pro Pro Glu Thr Ser Asn Pro Asn Lys Pro Lys Arg Gln Thr
                 50                  55                  60

Asn Gln Leu Gln Tyr Leu Leu Arg Val Val Leu Lys Thr Leu Trp
                 65                  70                  75

Lys His Gln Phe Ala Trp Pro Phe Gln Gln Pro Val Asp Ala Val
                 80                  85                  90

Lys Leu Asn Leu Pro Asp Tyr Tyr Lys Ile Ile Lys Thr Pro Met
                 95                 100                 105

Asp Met Gly Thr Ile Lys Lys Arg Leu Glu Asn Asn Tyr Tyr Trp
                110                 115                 120

Asn Ala Gln Glu Cys Ile Gln Asp Phe Asn Thr Met Phe Thr Asn
                125                 130                 135

Cys Tyr Ile Tyr Asn Lys Pro Gly Asp Asp Ile Val Leu Met Ala
                140                 145                 150

Glu Ala Leu Glu Lys Leu Phe Leu Gln Lys Ile Asn Glu Leu Pro
                155                 160                 165

Thr Glu Glu Thr Glu Ile Met Ile Val Gln Ala Lys Gly Arg Gly
                170                 175                 180

Arg Gly Arg Lys Glu Thr Gly Thr Ala Lys Pro Gly Val Ser Thr
                185                 190                 195

Val Pro Asn Thr Thr Gln Ala Ser Thr Pro Gln Thr Gln Thr
                200                 205                 210

Pro Gln Pro Asn Pro Pro Pro Val Gln Ala Thr Pro His Pro Phe
                215                 220                 225

Pro Ala Val Thr Pro Asp Leu Ile Val Gln Thr Pro Val Met Thr
                230                 235                 240

Val Val Pro Pro Gln Pro Leu Gln Thr Pro Pro Val Pro Pro
                245                 250                 255

Gln Pro Gln Pro Pro Ala Pro Ala Pro Gln Pro Val Gln Ser
                260                 265                 270

His Pro Pro Ile Ile Ala Ala Thr Pro Gln Pro Val Lys Thr Lys
                275                 280                 285

Lys Gly Val Lys Arg Lys Ala Asp Thr Thr Thr Pro Thr Thr Ile
```

```
                     290                 295                 300
Asp Pro Ile His Glu Pro Pro Ser Leu Pro Glu Pro Lys Thr
                305                 310                 315
Thr Lys Leu Gly Gln Arg Arg Glu Ser Ser Arg Pro Val Lys Pro
                320                 325                 330
Pro Lys Lys Asp Val Pro Asp Ser Gln Gln His Pro Ala Pro Glu
                335                 340                 345
Lys Ser Ser Lys Val Ser Glu Gln Leu Lys Cys Cys Ser Gly Ile
                350                 355                 360
Leu Lys Glu Met Phe Ala Lys Lys His Ala Ala Tyr Ala Trp Pro
                365                 370                 375
Phe Tyr Lys Pro Val Asp Val Glu Ala Leu Gly Leu His Asp Tyr
                380                 385                 390
Cys Asp Ile Ile Lys His Pro Met Asp Met Ser Thr Ile Lys Ser
                395                 400                 405
Lys Leu Glu Ala Arg Glu Tyr Arg Asp Ala Gln Glu Phe Gly Ala
                410                 415                 420
Asp Val Arg Leu Met Phe Ser Asn Cys Tyr Lys Tyr Asn Pro Pro
                425                 430                 435
Asp His Glu Val Val Ala Met Ala Arg Lys Leu Gln Asp Val Phe
                440                 445                 450
Glu Met Arg Phe Ala Lys Met Pro Asp Glu Pro Glu Glu Pro Val
                455                 460                 465
Val Ala Val Ser Ser Pro Ala Val Pro Pro Thr Lys Val Val
                470                 475                 480
Ala Pro Pro Ser Ser Ser Asp Ser Ser Ser Asp Ser Ser Ser Asp
                485                 490                 495
Ser Asp Ser Ser Thr Asp Asp Ser Glu Glu Glu Arg Ala Gln Arg
                500                 505                 510
Leu Ala Glu Leu Gln Glu Gln Leu Lys Ala Val His Glu Gln Leu
                515                 520                 525
Ala Ala Leu Ser Gln Pro Gln Gln Asn Lys Pro Lys Lys Lys Glu
                530                 535                 540
Lys Asp Lys Lys Glu Lys Lys Lys Glu Lys His Lys Arg Lys Glu
                545                 550                 555
Glu Val Glu Glu Asn Lys Lys Ser Lys Ala Lys Glu Pro Pro Pro
                560                 565                 570
Lys Lys Thr Lys Lys Asn Asn Ser Ser Asn Ser Asn Val Ser Lys
                575                 580                 585
Lys Glu Pro Ala Pro Met Lys Ser Lys Pro Pro Pro Thr Tyr Glu
                590                 595                 600
Ser Glu Glu Glu Asp Lys Cys Lys Pro Met Ser Tyr Glu Glu Lys
                605                 610                 615
Arg Gln Leu Ser Leu Asp Ile Asn Lys Leu Pro Gly Glu Lys Leu
                620                 625                 630
Gly Arg Val Val His Ile Ile Gln Ser Arg Glu Pro Ser Leu Lys
                635                 640                 645
Asn Ser Asn Pro Asp Glu Ile Glu Ile Asp Phe Glu Thr Leu Lys
                650                 655                 660
Pro Ser Thr Leu Arg Glu Leu Gly Ala Leu Cys His Leu Leu Phe
                665                 670                 675
Ala Glu Glu Lys Glu Thr Phe Lys Leu Arg Lys Leu Met
                680                 685
```

```
<210> SEQ ID NO 23
<211> LENGTH: 439
<212> TYPE: PRT
<213> ORGANISM: Homo sapiens
<220> FEATURE:
<221> NAME/KEY: misc_feature
<223> OTHER INFORMATION: Incyte ID No: 2100530
<220> FEATURE:
<221> NAME/KEY: unsure
<222> LOCATION: 434
<223> OTHER INFORMATION: unknown or other

<400> SEQUENCE: 23

Met Gly Ser Gln Glu Val Leu Gly His Ala Ala Arg Leu Ala Ser
 1               5                   10                  15

Ser Gly Leu Leu Leu Gln Val Leu Phe Arg Leu Ile Thr Phe Val
                20                  25                  30

Leu Asn Ala Phe Ile Leu Arg Phe Leu Ser Lys Glu Ile Val Gly
                35                  40                  45

Val Val Asn Val Arg Leu Thr Leu Leu Tyr Ser Thr Thr Leu Phe
                50                  55                  60

Leu Ala Arg Glu Ala Phe Arg Arg Ala Cys Leu Ser Gly Gly Thr
                65                  70                  75

Gln Arg Asp Trp Ser Gln Thr Leu Asn Leu Leu Trp Leu Thr Val
                80                  85                  90

Pro Leu Gly Val Phe Trp Ser Leu Phe Leu Gly Trp Ile Trp Leu
                95                  100                 105

Gln Leu Leu Glu Val Pro Asp Pro Asn Val Val Pro His Tyr Ala
                110                 115                 120

Thr Gly Val Val Leu Phe Gly Leu Ser Ala Val Val Glu Leu Leu
                125                 130                 135

Gly Glu Pro Phe Trp Val Leu Ala Gln Ala His Met Phe Val Lys
                140                 145                 150

Leu Lys Val Ile Ala Glu Ser Leu Ser Val Ile Leu Lys Ser Val
                155                 160                 165

Leu Thr Ala Phe Leu Val Leu Trp Leu Pro His Trp Gly Leu Tyr
                170                 175                 180

Ile Phe Ser Leu Ala Gln Leu Phe Tyr Thr Thr Val Leu Val Leu
                185                 190                 195

Cys Tyr Val Ile Tyr Phe Thr Lys Leu Leu Gly Ser Pro Glu Ser
                200                 205                 210

Thr Lys Leu Gln Thr Leu Pro Val Ser Arg Ile Thr Asp Leu Leu
                215                 220                 225

Pro Asn Ile Thr Arg Asn Gly Ala Phe Ile Asn Trp Lys Glu Ala
                230                 235                 240

Lys Leu Thr Trp Ser Phe Phe Lys Gln Ser Phe Leu Lys Gln Ile
                245                 250                 255

Leu Thr Glu Gly Glu Arg Tyr Val Met Thr Phe Leu Asn Val Leu
                260                 265                 270

Asn Phe Gly Asp Gln Gly Val Tyr Asp Ile Val Asn Asn Leu Gly
                275                 280                 285

Ser Leu Val Ala Arg Leu Ile Phe Gln Pro Ile Glu Glu Ser Phe
                290                 295                 300

Tyr Ile Phe Phe Ala Lys Val Leu Glu Arg Gly Lys Asp Ala Thr
                305                 310                 315

Leu Gln Lys Gln Glu Asp Val Ala Val Ala Ala Val Leu Glu
                320                 325                 330
```

```
Ser Leu Leu Lys Leu Ala Leu Leu Ala Gly Leu Thr Ile Thr Val
            335                 340                 345

Phe Gly Phe Ala Tyr Ser Gln Leu Ala Leu Asp Ile Tyr Gly Gly
            350                 355                 360

Thr Met Leu Ser Ser Gly Ser Gly Pro Val Leu Leu Arg Ser Tyr
            365                 370                 375

Cys Leu Tyr Val Leu Leu Leu Ala Ile Asn Gly Val Thr Glu Cys
            380                 385                 390

Phe Thr Phe Ala Ala Met Ser Lys Glu Glu Val Asp Arg Tyr Ser
            395                 400                 405

Ser Ala Val Ser Arg Ala Gly Gln Pro Asp Trp His Thr Leu Leu
            410                 415                 420

Trp Gly Pro Ser Val Trp Glu Gln Leu Ser Gly Gln His Xaa Ser
            425                 430                 435

Gln Arg Pro Ser

<210> SEQ ID NO 24
<211> LENGTH: 192
<212> TYPE: PRT
<213> ORGANISM: Homo sapiens
<220> FEATURE:
<221> NAME/KEY: misc_feature
<223> OTHER INFORMATION: Incyte ID No: 2357636

<400> SEQUENCE: 24

Met Thr Ala Val Gly Val Gln Ala Gln Arg Pro Leu Gly Gln Arg
  1               5                  10                  15

Gln Pro Arg Arg Ser Phe Phe Glu Ser Phe Ile Arg Thr Leu Ile
             20                  25                  30

Ile Thr Cys Val Ala Leu Ala Val Val Leu Ser Ser Val Ser Ile
             35                  40                  45

Cys Asp Gly His Trp Leu Leu Ala Glu Asp Arg Leu Phe Gly Leu
             50                  55                  60

Trp His Phe Cys Thr Thr Thr Asn Gln Ser Val Pro Ile Cys Phe
             65                  70                  75

Arg Asp Leu Gly Gln Ala His Val Pro Gly Leu Ala Val Gly Met
             80                  85                  90

Gly Leu Val Arg Ser Val Gly Ala Leu Ala Val Val Ala Ala Ile
             95                 100                 105

Phe Gly Leu Glu Phe Leu Met Val Ser Gln Leu Cys Glu Asp Lys
            110                 115                 120

His Ser Gln Cys Lys Trp Val Met Gly Ser Ile Leu Leu Val
            125                 130                 135

Ser Phe Val Leu Ser Ser Gly Leu Leu Gly Phe Val Ile Leu
            140                 145                 150

Leu Arg Asn Gln Val Thr Leu Ile Gly Phe Thr Leu Met Phe Trp
            155                 160                 165

Cys Glu Phe Thr Ala Ser Phe Leu Leu Phe Leu Asn Ala Ile Ser
            170                 175                 180

Gly Leu His Ile Asn Ser Ile Thr His Pro Trp Glu
            185                 190

<210> SEQ ID NO 25
<211> LENGTH: 175
<212> TYPE: PRT
<213> ORGANISM: Homo sapiens
<220> FEATURE:
```

```
<221> NAME/KEY: misc_feature
<223> OTHER INFORMATION: Incyte ID No: 2365230

<400> SEQUENCE: 25

Met Lys Glu Val Thr Arg Thr Trp Lys Ile Val Gly Gly Val Thr
 1               5                  10                  15

His Ala Asn Ser Tyr Tyr Lys Asn Gly Trp Ile Val Met Ile Ala
            20                  25                  30

Ile Gly Trp Ala Arg Gly Ala Gly Gly Thr Ile Ile Thr Asn Phe
        35                  40                  45

Glu Arg Leu Val Lys Gly Asp Trp Lys Pro Glu Gly Asp Glu Trp
    50                  55                  60

Leu Lys Met Ser Tyr Pro Ala Lys Val Thr Leu Leu Gly Ser Val
65                  70                  75

Ile Phe Thr Phe Gln His Thr Gln His Leu Ala Ile Ser Lys His
            80                  85                  90

Asn Leu Met Phe Leu Tyr Thr Ile Phe Ile Val Ala Thr Lys Ile
        95                 100                 105

Thr Met Met Thr Thr Gln Thr Ser Thr Met Thr Phe Ala Pro Phe
    110                 115                 120

Glu Asp Thr Leu Ser Trp Met Leu Phe Gly Trp Gln Gln Pro Phe
125                 130                 135

Ser Ser Cys Glu Lys Lys Ser Glu Ala Lys Ser Pro Ser Asn Gly
            140                 145                 150

Val Gly Ser Leu Ala Ser Lys Pro Val Asp Val Ala Ser Asp Asn
        155                 160                 165

Val Lys Lys Lys His Thr Lys Lys Asn Glu
    170                 175

<210> SEQ ID NO 26
<211> LENGTH: 91
<212> TYPE: PRT
<213> ORGANISM: Homo sapiens
<220> FEATURE:
<221> NAME/KEY: misc_feature
<223> OTHER INFORMATION: Incyte ID No: 2455121

<400> SEQUENCE: 26

Met Tyr Pro Pro Pro Pro Pro Pro His Arg Asp Phe Ile Ser
 1               5                  10                  15

Val Thr Leu Ser Phe Gly Glu Ser Tyr Asp Asn Ser Lys Ser Trp
            20                  25                  30

Arg Arg Arg Ser Cys Trp Arg Lys Trp Lys Gln Leu Ser Arg Leu
        35                  40                  45

Gln Arg Asn Met Ile Leu Phe Leu Leu Ala Phe Leu Leu Phe Cys
    50                  55                  60

Gly Leu Leu Phe Tyr Ile Asn Leu Ala Asp His Trp Lys Ala Leu
65                  70                  75

Ala Phe Arg Leu Gly Glu Glu Gln Lys Met Arg Pro Glu Ile Ala
            80                  85                  90

Gly

<210> SEQ ID NO 27
<211> LENGTH: 214
<212> TYPE: PRT
<213> ORGANISM: Homo sapiens
<220> FEATURE:
<221> NAME/KEY: misc_feature
<223> OTHER INFORMATION: Incyte ID No: 2472514
```

<400> SEQUENCE: 27

```
Met Gln Pro Thr Ser Trp Ala Val Ser Cys Gly Leu Arg Pro Leu
 1               5                  10                  15

Pro Ser Trp Lys Pro Gln Gly Gly Glu Gly Arg Gly Gly Glu
             20                  25                  30

Arg Arg Gly Thr Val Met Gly Pro Trp Ser Arg Val Arg Val Ala
             35                  40                  45

Lys Cys Gln Met Leu Val Thr Cys Phe Phe Ile Leu Leu Leu Gly
             50                  55                  60

Leu Ser Val Ala Thr Met Val Thr Leu Thr Tyr Phe Gly Ala His
             65                  70                  75

Phe Ala Val Ile Arg Arg Ala Ser Leu Glu Lys Asn Pro Tyr Gln
             80                  85                  90

Ala Val His Gln Trp Ala Phe Ser Ala Gly Leu Ser Leu Val Gly
             95                 100                 105

Leu Leu Thr Leu Gly Ala Val Leu Ser Ala Ala Thr Val Arg
            110                 115                 120

Glu Ala Gln Gly Leu Met Ala Gly Gly Phe Leu Cys Phe Ser Leu
            125                 130                 135

Ala Phe Cys Ala Gln Val Gln Val Val Phe Trp Arg Leu His Ser
            140                 145                 150

Pro Thr Gln Val Glu Asp Ala Met Leu Asp Thr Tyr Asp Leu Val
            155                 160                 165

Tyr Glu Gln Ala Met Lys Gly Thr Ser His Val Arg Arg Gln Glu
            170                 175                 180

Leu Ala Ala Ile Gln Asp Val Val Ser Val Gly Thr Ala Gly Trp
            185                 190                 195

Gln Gly Gly Gln Leu Leu Gly Leu Gln Phe Arg Glu Gln Ala
            200                 205                 210

Gln Gly Gly Gln
```

<210> SEQ ID NO 28
<211> LENGTH: 250
<212> TYPE: PRT
<213> ORGANISM: Homo sapiens
<220> FEATURE:
<221> NAME/KEY: misc_feature
<223> OTHER INFORMATION: Incyte ID No: 2543486

<400> SEQUENCE: 28

```
Met Ser Val Ile Phe Phe Ala Cys Val Val Arg Val Arg Asp Gly
 1               5                  10                  15

Leu Pro Leu Ser Ala Ser Thr Asp Phe Tyr His Thr Gln Asp Phe
             20                  25                  30

Leu Glu Trp Arg Arg Arg Leu Lys Ser Leu Ala Leu Arg Leu Ala
             35                  40                  45

Gln Tyr Pro Gly Arg Gly Ser Ala Glu Gly Cys Asp Phe Ser Ile
             50                  55                  60

His Phe Ser Ser Phe Gly Asp Val Ala Cys Met Ala Ile Cys Ser
             65                  70                  75

Cys Gln Cys Pro Ala Ala Met Ala Phe Cys Phe Leu Glu Thr Leu
             80                  85                  90

Trp Trp Glu Phe Thr Ala Ser Tyr Asp Thr Thr Cys Ile Gly Leu
             95                 100                 105

Ala Ser Arg Pro Tyr Ala Phe Leu Glu Phe Asp Ser Ile Ile Gln
```

-continued

```
                110                 115                 120
Lys Val Lys Trp His Phe Asn Tyr Val Ser Ser Gln Met Glu
            125                 130                 135

Cys Ser Leu Glu Lys Ile Gln Glu Leu Lys Leu Gln Pro Pro
            140                 145                 150

Ala Val Leu Thr Leu Glu Asp Thr Asp Val Ala Asn Gly Val Met
            155                 160                 165

Asn Gly His Thr Pro Met His Leu Glu Pro Ala Pro Asn Phe Arg
            170                 175                 180

Met Glu Pro Val Thr Ala Leu Gly Ile Leu Ser Leu Ile Leu Asn
            185                 190                 195

Ile Met Cys Ala Ala Leu Asn Leu Ile Arg Gly Val His Leu Ala
            200                 205                 210

Glu His Ser Leu Gln Val Ala His Glu Ile Gly Asn Ile Leu
            215                 220                 225

Ala Phe Leu Val Pro Phe Val Ala Cys Ile Phe Gln Asp Pro Arg
            230                 235                 240

Ser Trp Phe Cys Trp Leu Asp Gln Thr Ser
            245                 250

<210> SEQ ID NO 29
<211> LENGTH: 84
<212> TYPE: PRT
<213> ORGANISM: Homo sapiens
<220> FEATURE:
<221> NAME/KEY: misc_feature
<223> OTHER INFORMATION: Incyte ID No: 2778171

<400> SEQUENCE: 29

Met Ala Thr Gly Thr Asp Gln Val Val Gly Leu Gly Leu Val Ala
 1               5                  10                  15

Val Ser Leu Ile Ile Phe Thr Tyr Tyr Thr Ala Trp Val Ile Leu
                20                  25                  30

Leu Pro Phe Ile Asp Ser Gln His Val Ile His Lys Tyr Phe Leu
                35                  40                  45

Pro Arg Ala Tyr Ala Val Ala Ile Pro Leu Ala Ala Gly Leu Leu
                50                  55                  60

Leu Leu Leu Phe Val Gly Leu Phe Ile Ser Tyr Val Met Leu Lys
65                  70                  75

Ser Lys Arg Val Thr Lys Lys Ala Gln
                80

<210> SEQ ID NO 30
<211> LENGTH: 277
<212> TYPE: PRT
<213> ORGANISM: Homo sapiens
<220> FEATURE:
<221> NAME/KEY: misc_feature
<223> OTHER INFORMATION: Incyte ID No: 2799575

<400> SEQUENCE: 30

Met Ala Ser Ala Glu Leu Asp Tyr Thr Ile Glu Ile Pro Asp Gln
 1               5                  10                  15

Pro Cys Trp Ser Gln Lys Asn Ser Pro Ser Pro Gly Gly Lys Glu
                20                  25                  30

Ala Glu Thr Arg Gln Pro Val Val Ile Leu Leu Gly Trp Gly Gly
                35                  40                  45

Cys Lys Asp Lys Asn Leu Ala Lys Tyr Ser Ala Ile Tyr His Lys
                50                  55                  60
```

```
Arg Gly Cys Ile Val Ile Arg Tyr Thr Ala Pro Trp His Met Val
                65                  70                  75

Phe Phe Ser Glu Ser Leu Gly Ile Pro Ser Leu Arg Val Leu Ala
                80                  85                  90

Gln Lys Leu Leu Glu Leu Leu Phe Asp Tyr Glu Ile Glu Lys Glu
                95                 100                 105

Pro Leu Leu Phe His Val Phe Ser Asn Gly Gly Val Met Leu Tyr
               110                 115                 120

Arg Tyr Val Leu Glu Leu Leu Gln Thr Arg Arg Phe Cys Arg Leu
               125                 130                 135

Arg Val Val Gly Thr Ile Phe Asp Ser Ala Pro Gly Asp Ser Asn
               140                 145                 150

Leu Val Gly Ala Leu Arg Ala Leu Ala Ala Ile Leu Glu Arg Arg
               155                 160                 165

Ala Ala Met Leu Arg Leu Leu Leu Val Ala Phe Ala Leu Val
               170                 175                 180

Val Val Leu Phe His Val Leu Ala Pro Ile Thr Ala Leu Phe
               185                 190                 195

His Thr His Phe Tyr Asp Arg Leu Gln Asp Ala Gly Ser Arg Trp
               200                 205                 210

Pro Glu Leu Tyr Leu Tyr Ser Arg Ala Asp Glu Val Val Leu Ala
               215                 220                 225

Arg Asp Ile Glu Arg Met Val Glu Ala Arg Leu Ala Arg Arg Val
               230                 235                 240

Leu Ala Arg Ser Val Asp Phe Val Ser Ser Ala His Val Ser His
               245                 250                 255

Leu Arg Asp Tyr Pro Thr Tyr Tyr Thr Ser Leu Cys Val Asp Phe
               260                 265                 270

Met Arg Asn Cys Val Arg Cys
               275

<210> SEQ ID NO 31
<211> LENGTH: 273
<212> TYPE: PRT
<213> ORGANISM: Homo sapiens
<220> FEATURE:
<221> NAME/KEY: misc_feature
<223> OTHER INFORMATION: Incyte ID No: 2804955

<400> SEQUENCE: 31

Met Ser Gly Ser Gln Ser Glu Val Ala Pro Ser Pro Gln Ser Pro
  1               5                  10                  15

Arg Ser Pro Glu Met Gly Arg Asp Leu Arg Pro Gly Ser Arg Val
                 20                  25                  30

Leu Leu Leu Leu Leu Leu Leu Leu Val Tyr Leu Thr Gln Pro
                 35                  40                  45

Gly Asn Gly Asn Glu Gly Ser Val Thr Gly Ser Cys Tyr Cys Gly
                 50                  55                  60

Lys Arg Ile Ser Ser Asp Ser Pro Pro Ser Val Gln Phe Met Asn
                 65                  70                  75

Arg Leu Arg Lys His Leu Arg Ala Tyr His Arg Cys Leu Tyr Tyr
                 80                  85                  90

Thr Arg Phe Gln Leu Leu Ser Trp Ser Val Cys Gly Gly Asn Lys
                 95                 100                 105

Asp Pro Trp Val Gln Glu Leu Met Ser Cys Leu Asp Leu Lys Glu
                110                 115                 120
```

```
Cys Gly His Ala Tyr Ser Gly Ile Val Ala His Gln Lys His Leu
            125                 130                 135

Leu Pro Thr Ser Pro Pro Ile Ser Gln Ala Ser Glu Gly Ala Ser
            140                 145                 150

Ser Asp Ile His Thr Pro Ala Gln Met Leu Leu Ser Thr Leu Gln
            155                 160                 165

Ser Thr Gln Arg Pro Thr Leu Pro Val Gly Ser Leu Ser Ser Asp
            170                 175                 180

Lys Glu Leu Thr Arg Pro Asn Glu Thr Thr Ile His Thr Ala Gly
            185                 190                 195

His Ser Leu Ala Ala Gly Pro Glu Ala Gly Glu Asn Gln Lys Gln
            200                 205                 210

Pro Glu Lys Asn Ala Gly Pro Thr Ala Arg Thr Ser Ala Thr Val
            215                 220                 225

Pro Val Leu Cys Leu Leu Ala Ile Ile Phe Ile Leu Thr Ala Ala
            230                 235                 240

Leu Ser Tyr Val Leu Cys Lys Arg Arg Gly Gln Ser Pro Gln
            245                 250                 255

Ser Ser Pro Asp Leu Pro Val His Tyr Ile Pro Val Ala Pro Asp
            260                 265                 270

Ser Asn Thr

<210> SEQ ID NO 32
<211> LENGTH: 524
<212> TYPE: PRT
<213> ORGANISM: Homo sapiens
<220> FEATURE:
<221> NAME/KEY: misc_feature
<223> OTHER INFORMATION: Incyte ID No: 2806395

<400> SEQUENCE: 32

Met Ser Gln Gly Ser Pro Gly Asp Trp Ala Pro Leu Asp Pro Thr
  1               5                  10                  15

Pro Gly Pro Pro Ala Ser Pro Asn Pro Phe Val His Glu Leu His
             20                  25                  30

Leu Ser Arg Leu Gln Arg Val Lys Phe Cys Leu Leu Gly Ala Leu
             35                  40                  45

Leu Ala Pro Ile Arg Val Leu Leu Ala Phe Ile Val Leu Phe Leu
             50                  55                  60

Leu Trp Pro Phe Ala Trp Leu Gln Val Ala Gly Leu Ser Glu Glu
             65                  70                  75

Gln Leu Gln Glu Pro Ile Thr Gly Trp Arg Lys Thr Val Cys His
             80                  85                  90

Asn Gly Val Leu Gly Leu Ser Arg Leu Leu Phe Phe Leu Leu Gly
             95                 100                 105

Phe Leu Arg Ile Arg Val Arg Gly Gln Arg Ala Ser Arg Leu Gln
            110                 115                 120

Ala Pro Val Leu Val Ala Ala Pro His Ser Thr Phe Phe Asp Pro
            125                 130                 135

Ile Val Leu Leu Pro Cys Asp Leu Pro Lys Val Val Ser Arg Ala
            140                 145                 150

Glu Asn Leu Ser Val Pro Val Ile Gly Ala Leu Leu Arg Phe Asn
            155                 160                 165

Gln Ala Ile Leu Val Ser Arg His Asp Pro Ala Ser Arg Arg Arg
            170                 175                 180
```

```
Val Val Glu Glu Val Arg Arg Arg Ala Thr Ser Gly Gly Lys Trp
            185                 190                 195

Pro Gln Val Leu Phe Phe Pro Glu Gly Thr Cys Ser Asn Lys Lys
            200                 205                 210

Ala Leu Leu Lys Phe Lys Pro Gly Ala Phe Ile Ala Gly Val Pro
            215                 220                 225

Val Gln Pro Val Leu Ile Arg Tyr Pro Asn Ser Leu Asp Thr Thr
            230                 235                 240

Ser Trp Ala Trp Arg Gly Pro Gly Val Leu Lys Val Leu Trp Leu
            245                 250                 255

Thr Ala Ser Gln Pro Cys Ser Ile Val Asp Val Glu Phe Leu Pro
            260                 265                 270

Val Tyr His Pro Ser Pro Glu Glu Ser Arg Asp Pro Thr Leu Tyr
            275                 280                 285

Ala Asn Asn Val Gln Arg Val Met Ala Gln Ala Leu Gly Ile Pro
            290                 295                 300

Ala Thr Glu Cys Glu Phe Val Gly Ser Leu Pro Val Ile Val Val
            305                 310                 315

Gly Arg Leu Lys Val Ala Leu Glu Pro Gln Leu Trp Glu Leu Gly
            320                 325                 330

Lys Val Leu Arg Lys Ala Gly Leu Ser Ala Gly Tyr Val Asp Ala
            335                 340                 345

Gly Ala Glu Pro Gly Arg Ser Arg Met Ile Ser Gln Glu Glu Phe
            350                 355                 360

Ala Arg Gln Leu Gln Leu Ser Asp Pro Gln Thr Val Ala Gly Ala
            365                 370                 375

Phe Gly Tyr Phe Gln Gln Asp Thr Lys Gly Leu Val Asp Phe Arg
            380                 385                 390

Asp Val Ala Leu Ala Leu Ala Ala Leu Asp Gly Gly Arg Ser Leu
            395                 400                 405

Glu Glu Leu Thr Arg Leu Ala Phe Glu Leu Phe Ala Glu Glu Gln
            410                 415                 420

Ala Glu Gly Pro Asn Arg Leu Leu Tyr Lys Asp Gly Phe Ser Thr
            425                 430                 435

Ile Leu His Leu Leu Gly Ser Pro His Pro Ala Ala Thr Ala
            440                 445                 450

Leu His Ala Glu Leu Cys Gln Ala Gly Ser Ser Gln Gly Leu Ser
            455                 460                 465

Leu Cys Gln Phe Gln Asn Phe Ser Leu His Asp Pro Leu Tyr Gly
            470                 475                 480

Lys Leu Phe Ser Thr Tyr Leu Arg Pro His Thr Ser Arg Gly
            485                 490                 495

Thr Ser Gln Thr Pro Asn Ala Ser Ser Pro Gly Asn Pro Thr Ala
            500                 505                 510

Leu Ala Asn Gly Thr Val Gln Ala Pro Lys Gln Lys Gly Asp
            515                 520

<210> SEQ ID NO 33
<211> LENGTH: 257
<212> TYPE: PRT
<213> ORGANISM: Homo sapiens
<220> FEATURE:
<221> NAME/KEY: misc_feature
<223> OTHER INFORMATION: Incyte ID No: 2836858

<400> SEQUENCE: 33
```

```
Met Asp Phe Ser Arg Leu His Met Tyr Ser Pro Pro Gln Cys Val
 1               5                  10                  15

Pro Glu Asn Thr Gly Tyr Thr Tyr Ala Leu Ser Ser Ser Tyr Ser
                 20                  25                  30

Ser Asp Ala Leu Asp Phe Glu Thr Glu His Lys Leu Asp Pro Val
                 35                  40                  45

Phe Asp Ser Pro Arg Met Ser Arg Arg Ser Leu Arg Leu Ala Thr
                 50                  55                  60

Thr Ala Cys Thr Leu Gly Asp Gly Glu Ala Val Gly Ala Asp Ser
                 65                  70                  75

Gly Thr Ser Ser Ala Val Ser Leu Lys Asn Arg Ala Ala Arg Thr
                 80                  85                  90

Thr Lys Gln Arg Arg Ser Thr Asn Lys Ser Ala Phe Ser Ile Asn
                 95                 100                 105

His Val Ser Arg Gln Val Thr Ser Ser Gly Val Ser His Gly Gly
                110                 115                 120

Thr Val Ser Leu Gln Asp Ala Val Thr Arg Arg Pro Pro Val Leu
                125                 130                 135

Asp Glu Ser Trp Ile Arg Glu Gln Thr Thr Val Asp His Phe Trp
                140                 145                 150

Gly Leu Asp Asp Asp Gly Asp Leu Lys Gly Gly Asn Lys Ala Ala
                155                 160                 165

Ile Gln Gly Asn Gly Asp Val Gly Ala Ala Ala Thr Ala His
                170                 175                 180

Asn Gly Phe Ser Cys Ser Asn Cys Ser Met Leu Ser Glu Arg Lys
                185                 190                 195

Asp Val Leu Thr Ala His Pro Ala Ala Pro Gly Pro Val Ser Arg
                200                 205                 210

Val Tyr Ser Arg Asp Arg Asn Gln Lys Cys Lys Ser Gln Ser Phe
                215                 220                 225

Lys Thr Gln Lys Lys Val Cys Phe Pro Asn Leu Ile Phe Pro Phe
                230                 235                 240

Cys Lys Ser Gln Cys Leu His Tyr Leu Ser Trp Arg Leu Lys Ile
                245                 250                 255

Ile Pro

<210> SEQ ID NO 34
<211> LENGTH: 274
<212> TYPE: PRT
<213> ORGANISM: Homo sapiens
<220> FEATURE:
<221> NAME/KEY: misc_feature
<223> OTHER INFORMATION: Incyte ID No: 2844513

<400> SEQUENCE: 34

Met Arg Ala Ala Gly Val Gly Leu Val Asp Cys His Cys His Leu
 1               5                  10                  15

Ser Ala Pro Asp Phe Asp Arg Asp Leu Asp Asp Val Leu Glu Lys
                 20                  25                  30

Ala Lys Lys Ala Asn Val Val Ala Leu Val Ala Val Ala Glu His
                 35                  40                  45

Ser Gly Glu Phe Glu Lys Ile Met Gln Leu Ser Glu Arg Tyr Asn
                 50                  55                  60

Gly Phe Val Leu Pro Cys Leu Gly Val His Pro Val Gln Gly Leu
                 65                  70                  75

Pro Pro Glu Asp Gln Arg Ser Val Thr Leu Lys Asp Leu Asp Val
```

-continued

```
                    80                  85                  90
Ala Leu Pro Ile Ile Glu Asn Tyr Lys Asp Arg Leu Leu Ala Ile
                95                 100                 105
Gly Glu Val Gly Leu Asp Phe Ser Pro Arg Phe Ala Gly Thr Gly
               110                 115                 120
Glu Gln Lys Glu Gln Arg Gln Val Leu Ile Arg Gln Ile Gln
               125                 130                 135
Leu Ala Lys Arg Leu Asn Leu Pro Val Asn Val His Ser Arg Ser
               140                 145                 150
Ala Gly Arg Pro Thr Ile Asn Leu Leu Gln Glu Gln Gly Ala Glu
               155                 160                 165
Lys Val Leu Leu His Ala Phe Asp Gly Arg Pro Ser Val Ala Met
               170                 175                 180
Glu Gly Val Arg Ala Gly Tyr Phe Phe Ser Ile Pro Pro Ser Ile
               185                 190                 195
Ile Arg Ser Gly Gln Lys Gln Lys Leu Val Lys Gln Leu Pro Leu
               200                 205                 210
Thr Ser Ile Cys Leu Glu Thr Asp Ser Pro Ala Leu Gly Pro Glu
               215                 220                 225
Lys Gln Val Arg Asn Glu Pro Trp Asn Ile Ser Ile Ser Ala Glu
               230                 235                 240
Tyr Ile Ala Gln Val Lys Gly Ile Ser Val Glu Glu Val Ile Glu
               245                 250                 255
Val Thr Thr Gln Asn Ala Leu Lys Leu Phe Pro Lys Leu Arg His
               260                 265                 270
Leu Leu Gln Lys

<210> SEQ ID NO 35
<211> LENGTH: 281
<212> TYPE: PRT
<213> ORGANISM: Homo sapiens
<220> FEATURE:
<221> NAME/KEY: misc_feature
<223> OTHER INFORMATION: Incyte ID No: 3000380

<400> SEQUENCE: 35

Met Ser Glu Pro Gln Pro Asp Leu Glu Pro Gln His Gly Leu
  1               5                  10                  15
Tyr Met Leu Phe Leu Leu Val Leu Val Phe Phe Leu Met Gly Leu
                 20                  25                  30
Val Gly Phe Met Ile Cys His Val Leu Lys Lys Gly Tyr Arg
                 35                  40                  45
Cys Arg Thr Ser Arg Gly Ser Glu Pro Asp Asp Ala Gln Leu Gln
                 50                  55                  60
Pro Pro Glu Asp Asp Met Asn Glu Asp Thr Val Glu Arg Ile
                 65                  70                  75
Val Arg Cys Ile Ile Gln Asn Glu Val Trp Met Pro Pro Ala
                 80                  85                  90
Cys Arg Thr Glu Pro Pro Ile Ile Thr Gln Cys Thr Trp Ala
                 95                 100                 105
Leu Gln Pro Leu Ala Val His Cys Ser Arg Ser Lys Arg Pro
                110                 115                 120
Leu Val Arg Gln Gly Arg Ser Lys Glu Gly Lys Ser Arg Pro Arg
                125                 130                 135
Thr Gly Glu Thr Thr Val Phe Ser Val Gly Arg Phe Arg Val Thr
                140                 145                 150
```

His Ile Glu Lys Arg Tyr Gly Leu His Glu His Arg Asp Gly Ser
            155                 160                 165

Pro Thr Asp Arg Ser Trp Gly Ser Arg Gly Gly Gln Asp Pro Gly
            170                 175                 180

Gly Gly Gln Gly Ser Gly Gly Gly His Pro Lys Ala Gly Met Leu
            185                 190                 195

Pro Trp Arg Gly Cys Pro Pro Glu Arg Pro Gln Pro Gln Val Leu
            200                 205                 210

Ala Ser Pro Pro Val Gln Asn Gly Gly Leu Arg Asp Ser Ser Leu
            215                 220                 225

Thr Pro Arg Ala Leu Glu Gly Asn Pro Arg Ala Ser Ala Glu Pro
            230                 235                 240

Thr Leu Arg Ala Gly Gly Arg Gly Pro Ser Pro Gly Leu Pro Thr
            245                 250                 255

Gln Glu Ala Asn Gly Gln Pro Ser Lys Pro Asp Thr Ser Asp His
            260                 265                 270

Gln Val Ser Leu Pro Gln Gly Ala Gly Ser Met
            275                 280

<210> SEQ ID NO 36
<211> LENGTH: 335
<212> TYPE: PRT
<213> ORGANISM: Homo sapiens
<220> FEATURE:
<221> NAME/KEY: misc_feature
<223> OTHER INFORMATION: Incyte ID No: 182532

<400> SEQUENCE: 36

Met Gly Pro Leu Ser Ala Pro Pro Cys Thr His Leu Ile Thr Trp
 1               5                  10                  15

Lys Gly Val Leu Leu Thr Ala Ser Leu Leu Asn Phe Trp Asn Pro
            20                  25                  30

Pro Thr Thr Ala Gln Val Thr Ile Glu Ala Gln Pro Pro Lys Val
            35                  40                  45

Ser Glu Gly Lys Asp Val Leu Leu Val His Asn Leu Pro Gln
            50                  55                  60

Asn Leu Ala Gly Tyr Ile Trp Tyr Lys Gly Gln Met Thr Tyr Val
            65                  70                  75

Tyr His Tyr Ile Ile Ser Tyr Ile Val Asp Gly Lys Ile Ile Ile
            80                  85                  90

Tyr Gly Pro Ala Tyr Ser Gly Arg Glu Arg Val Tyr Ser Asn Ala
            95                  100                 105

Ser Leu Leu Ile Gln Asn Val Thr Gln Glu Asp Ala Gly Ser Tyr
            110                 115                 120

Thr Leu His Ile Ile Lys Arg Gly Asp Gly Thr Arg Gly Glu Thr
            125                 130                 135

Gly His Phe Thr Phe Thr Leu Tyr Leu Glu Thr Pro Lys Pro Ser
            140                 145                 150

Ile Ser Ser Ser Asn Leu Tyr Pro Arg Glu Asp Met Glu Ala Val
            155                 160                 165

Ser Leu Thr Cys Asp Pro Glu Thr Pro Asp Ala Ser Tyr Leu Trp
            170                 175                 180

Trp Met Asn Gly Gln Ser Leu Pro Met Thr His Ser Leu Gln Leu
            185                 190                 195

Ser Lys Asn Lys Arg Thr Leu Phe Leu Phe Gly Val Thr Lys Tyr
            200                 205                 210

```
Thr Ala Gly Pro Tyr Glu Cys Glu Ile Arg Asn Pro Val Ser Gly
                215                 220                 225

Ile Arg Ser Asp Pro Val Thr Leu Asn Val Leu Tyr Gly Pro Asp
                230                 235                 240

Leu Pro Ser Ile Tyr Pro Ser Phe Thr Tyr Tyr Arg Ser Gly Glu
                245                 250                 255

Asn Leu Tyr Leu Ser Cys Phe Ala Glu Ser Asn Pro Arg Ala Gln
                260                 265                 270

Tyr Ser Trp Thr Ile Asn Gly Lys Phe Gln Leu Ser Gly Gln Lys
                275                 280                 285

Leu Phe Ile Pro Gln Ile Thr Thr Lys His Ser Gly Leu Tyr Ala
                290                 295                 300

Cys Ser Val Arg Asn Ser Ala Thr Gly Met Glu Ser Ser Lys Ser
                305                 310                 315

Met Thr Val Lys Val Ser Ala Pro Ser Gly Thr Gly His Leu Pro
                320                 325                 330

Gly Leu Asn Pro Leu
                335

<210> SEQ ID NO 37
<211> LENGTH: 280
<212> TYPE: PRT
<213> ORGANISM: Homo sapiens
<220> FEATURE:
<221> NAME/KEY: misc_feature
<223> OTHER INFORMATION: Incyte ID No: 239589

<400> SEQUENCE: 37

Met Asp Leu Gln Gly Arg Gly Val Pro Ser Ile Asp Arg Leu Arg
  1               5                  10                  15

Val Leu Leu Met Leu Phe His Thr Met Ala Gln Ile Met Ala Glu
                 20                  25                  30

Gln Glu Val Glu Asn Leu Ser Gly Leu Ser Thr Asn Pro Glu Lys
                 35                  40                  45

Asp Ile Phe Val Val Arg Glu Asn Gly Thr Thr Cys Leu Met Ala
                 50                  55                  60

Glu Phe Ala Ala Lys Phe Ile Val Pro Tyr Asp Val Trp Ala Ser
                 65                  70                  75

Asn Tyr Val Asp Leu Ile Thr Glu Gln Ala Asp Ile Ala Leu Thr
                 80                  85                  90

Arg Gly Ala Glu Val Lys Gly Arg Cys Gly His Ser Gln Ser Glu
                 95                 100                 105

Leu Gln Val Phe Trp Val Asp Arg Ala Tyr Ala Leu Lys Met Leu
                110                 115                 120

Phe Val Lys Glu Ser His Asn Met Ser Lys Gly Pro Glu Ala Thr
                125                 130                 135

Trp Arg Leu Ser Lys Val Gln Phe Val Tyr Asp Ser Ser Glu Lys
                140                 145                 150

Thr His Phe Lys Asp Ala Val Ser Ala Gly Lys His Thr Ala Asn
                155                 160                 165

Ser His His Leu Ser Ala Leu Val Thr Pro Ala Gly Lys Ser Tyr
                170                 175                 180

Glu Cys Gln Ala Gln Gln Thr Ile Ser Leu Ala Ser Ser Asp Pro
                185                 190                 195

Gln Lys Thr Val Thr Met Ile Leu Ser Ala Val His Ile Gln Pro
                200                 205                 210
```

```
Phe Asp Ile Ile Ser Asp Phe Val Phe Ser Glu Glu His Lys Cys
                215                 220                 225

Pro Val Asp Glu Arg Glu Gln Leu Glu Glu Thr Leu Pro Leu Ile
                230                 235                 240

Leu Gly Leu Ile Leu Gly Leu Val Ile Met Val Thr Leu Ala Ile
                245                 250                 255

Tyr His Val His His Lys Met Thr Ala Asn Gln Val Gln Ile Pro
                260                 265                 270

Arg Asp Arg Ser Gln Tyr Lys His Met Gly
                275                 280

<210> SEQ ID NO 38
<211> LENGTH: 210
<212> TYPE: PRT
<213> ORGANISM: Homo sapiens
<220> FEATURE:
<221> NAME/KEY: misc_feature
<223> OTHER INFORMATION: Incyte ID No: 1671302

<400> SEQUENCE: 38

Met Ser Arg Met Phe Cys Gln Ala Ala Arg Val Asp Leu Thr Leu
  1               5                  10                  15

Asp Pro Asp Thr Ala His Pro Ala Leu Met Leu Ser Pro Asp Arg
                 20                  25                  30

Arg Gly Val Arg Leu Ala Glu Arg Arg Gln Glu Val Ala Asp His
                 35                  40                  45

Pro Lys Arg Phe Ser Ala Asp Cys Cys Val Leu Gly Ala Gln Gly
                 50                  55                  60

Phe Arg Ser Gly Arg His Tyr Trp Glu Val Glu Val Gly Gly Arg
                 65                  70                  75

Arg Gly Trp Ala Val Gly Ala Ala Arg Glu Ser Thr His His Lys
                 80                  85                  90

Glu Lys Val Gly Pro Gly Gly Ser Ser Val Gly Ser Gly Asp Ala
                 95                 100                 105

Ser Ser Ser Arg His His His Arg Arg Arg Leu His Leu Pro
                110                 115                 120

Gln Gln Pro Leu Leu Gln Arg Glu Val Trp Cys Val Gly Thr Asn
                125                 130                 135

Gly Lys Arg Tyr Gln Ala Gln Ser Ser Thr Glu Gln Thr Leu Leu
                140                 145                 150

Ser Pro Ser Glu Lys Pro Arg Arg Phe Gly Val Tyr Leu Asp Tyr
                155                 160                 165

Glu Ala Gly Arg Leu Gly Phe Tyr Asn Ala Glu Thr Leu Ala His
                170                 175                 180

Val His Thr Phe Ser Ala Ala Phe Leu Gly Glu Arg Val Phe Pro
                185                 190                 195

Phe Phe Arg Val Leu Ser Lys Gly Thr Arg Ile Lys Leu Cys Pro
                200                 205                 210

<210> SEQ ID NO 39
<211> LENGTH: 279
<212> TYPE: PRT
<213> ORGANISM: Homo sapiens
<220> FEATURE:
<221> NAME/KEY: misc_feature
<223> OTHER INFORMATION: Incyte ID No: 2041858

<400> SEQUENCE: 39
```

```
Met Glu Ala Val Val Asn Leu Tyr Gln Glu Val Met Lys His Ala
 1               5                  10                  15

Asp Pro Arg Ile Gln Gly Tyr Pro Leu Met Gly Ser Pro Leu Leu
            20                  25                  30

Met Thr Ser Ile Leu Leu Thr Tyr Val Tyr Phe Val Leu Ser Leu
            35                  40                  45

Gly Pro Arg Ile Met Ala Asn Arg Lys Pro Phe Gln Leu Arg Gly
            50                  55                  60

Phe Met Ile Val Tyr Asn Phe Ser Leu Val Ala Leu Ser Leu Tyr
65                      70                  75

Ile Val Tyr Glu Phe Leu Met Ser Gly Trp Leu Ser Tyr Thr Thr
            80                  85                  90

Trp Arg Cys Asp Pro Val Asp Tyr Ser Asn Ser Pro Glu Ala Leu
            95                  100                 105

Arg Met Val Arg Val Ala Trp Leu Phe Leu Phe Ser Lys Phe Ile
            110                 115                 120

Glu Leu Met Asp Thr Val Ile Phe Ile Leu Arg Lys Lys Asp Gly
            125                 130                 135

Gln Val Thr Phe Leu His Val Phe His His Ser Val Leu Pro Trp
            140                 145                 150

Ser Trp Trp Trp Gly Val Lys Ile Ala Pro Gly Gly Met Gly Ser
            155                 160                 165

Phe His Ala Met Ile Asn Ser Ser Val His Val Ile Met Tyr Leu
            170                 175                 180

Tyr Tyr Gly Leu Ser Ala Phe Gly Pro Val Ala Gln Pro Tyr Leu
            185                 190                 195

Trp Trp Lys Lys His Met Thr Ala Ile Gln Leu Ile Gln Phe Val
            200                 205                 210

Leu Val Ser Leu His Ile Ser Gln Tyr Tyr Phe Met Ser Ser Cys
            215                 220                 225

Asn Tyr Gln Tyr Pro Val Ile Ile His Leu Ile Trp Met Tyr Gly
            230                 235                 240

Thr Ile Phe Phe Met Leu Phe Ser Asn Phe Trp Tyr His Ser Tyr
            245                 250                 255

Thr Lys Gly Lys Arg Leu Pro Arg Ala Leu Gln Gln Asn Gly Ala
            260                 265                 270

Pro Gly Ile Ala Lys Val Lys Ala Asn
            275

<210> SEQ ID NO 40
<211> LENGTH: 154
<212> TYPE: PRT
<213> ORGANISM: Homo sapiens
<220> FEATURE:
<221> NAME/KEY: misc_feature
<223> OTHER INFORMATION: Incyte ID No: 2198863

<400> SEQUENCE: 40

Met Gly Lys Ser Ala Ser Lys Gln Phe His Asn Glu Val Leu Lys
 1               5                  10                  15

Ala His Asn Glu Tyr Arg Gln Lys His Gly Val Pro Pro Leu Lys
            20                  25                  30

Leu Cys Lys Asn Leu Asn Arg Glu Ala Gln Gln Tyr Ser Glu Ala
            35                  40                  45

Leu Ala Ser Thr Arg Ile Leu Lys His Ser Pro Glu Ser Ser Arg
            50                  55                  60
```

-continued

```
Gly Gln Cys Gly Glu Asn Leu Ala Trp Ala Ser Tyr Asp Gln Thr
                 65                  70                  75

Gly Lys Glu Val Ala Asp Arg Trp Tyr Ser Glu Ile Lys Asn Tyr
             80                  85                  90

Asn Phe Gln Gln Pro Gly Phe Thr Ser Gly Thr Gly His Phe Thr
             95                 100                 105

Ala Met Val Trp Lys Asn Thr Lys Lys Met Gly Val Gly Lys Ala
            110                 115                 120

Ser Ala Ser Asp Gly Ser Ser Phe Val Val Ala Arg Tyr Phe Pro
            125                 130                 135

Ala Gly Asn Val Val Asn Glu Gly Phe Phe Glu Glu Asn Val Leu
            140                 145                 150

Pro Pro Lys Lys

<210> SEQ ID NO 41
<211> LENGTH: 582
<212> TYPE: PRT
<213> ORGANISM: Homo sapiens
<220> FEATURE:
<221> NAME/KEY: misc_feature
<223> OTHER INFORMATION: Incyte ID No: 3250703

<400> SEQUENCE: 41

Met Lys Pro Asn Ile Ile Phe Val Leu Ser Leu Leu Ile Leu
  1               5                  10                  15

Glu Lys Gln Ala Ala Val Met Gly Gln Lys Gly Gly Ser Lys Gly
             20                  25                  30

Arg Leu Pro Ser Glu Phe Ser Gln Phe Pro His Gly Gln Lys Gly
             35                  40                  45

Gln His Tyr Ser Gly Gln Lys Gly Lys Gln Thr Glu Ser Lys
             50                  55                  60

Gly Ser Phe Ser Ile Gln Tyr Thr Tyr His Val Asp Ala Asn Asp
                 65                  70                  75

His Asp Gln Ser Arg Lys Ser Gln Gln Tyr Asp Leu Asn Ala Leu
             80                  85                  90

His Lys Thr Thr Lys Ser Gln Arg His Leu Gly Gly Ser Gln Gln
             95                 100                 105

Leu Leu His Asn Lys Gln Glu Gly Arg Asp His Asp Lys Ser Lys
            110                 115                 120

Gly His Phe His Arg Val Val Ile His Lys Gly Gly Lys Ala
            125                 130                 135

His Arg Gly Thr Gln Asn Pro Ser Gln Asp Gln Gly Asn Ser Pro
            140                 145                 150

Ser Gly Lys Gly Ile Ser Ser Gln Tyr Ser Asn Thr Glu Glu Arg
            155                 160                 165

Leu Trp Val His Gly Leu Ser Lys Glu Gln Thr Ser Val Ser Gly
            170                 175                 180

Ala Gln Lys Gly Arg Lys Gln Gly Gly Ser Gln Ser Ser Tyr Val
            185                 190                 195

Leu Gln Thr Glu Glu Leu Val Ala Asn Lys Gln Gln Arg Glu Thr
            200                 205                 210

Lys Asn Ser His Gln Asn Lys Gly His Tyr Gln Asn Val Val Glu
            215                 220                 225

Val Arg Glu Glu His Ser Ser Lys Val Gln Thr Ser Leu Cys Pro
            230                 235                 240

Ala His Gln Asp Lys Leu Gln His Gly Ser Lys Asp Ile Phe Ser
```

```
                    245                 250                 255
Thr Gln Asp Glu Leu Leu Val Tyr Asn Lys Asn Gln His Gln Thr
                260                 265                 270
Lys Asn Leu Asn Gln Asp Gln Gln His Gly Arg Lys Ala Asn Lys
                275                 280                 285
Ile Ser Tyr Gln Ser Ser Ser Thr Glu Glu Arg Arg Leu His Tyr
                290                 295                 300
Gly Glu Asn Gly Val Gln Lys Asp Val Ser Gln Ser Ser Ile Tyr
                305                 310                 315
Ser Gln Thr Glu Glu Lys Ile His Gly Lys Ser Gln Asn Gln Val
                320                 325                 330
Thr Ile His Ser Gln Asp Gln Glu His Gly His Lys Glu Asn Lys
                335                 340                 345
Ile Ser Tyr Gln Ser Ser Ser Thr Glu Glu Arg His Leu Asn Cys
                350                 355                 360
Gly Glu Lys Gly Ile Gln Lys Gly Val Ser Lys Gly Ser Ile Ser
                365                 370                 375
Ile Gln Thr Glu Glu Gln Ile His Gly Lys Ser Gln Asn Gln Val
                380                 385                 390
Arg Ile Pro Ser Gln Ala Gln Glu Tyr Gly His Lys Glu Asn Lys
                395                 400                 405
Ile Ser Tyr Gln Ser Ser Ser Thr Glu Glu Arg Arg Leu Asn Ser
                410                 415                 420
Gly Glu Lys Asp Val Gln Lys Gly Val Ser Lys Gly Ser Ile Ser
                425                 430                 435
Ile Gln Thr Glu Glu Lys Ile His Gly Lys Ser Gln Asn Gln Val
                440                 445                 450
Thr Ile Pro Ser Gln Asp Gln Glu His Gly His Lys Glu Asn Lys
                455                 460                 465
Met Ser Tyr Gln Ser Ser Ser Thr Glu Glu Arg Arg Leu Asn Tyr
                470                 475                 480
Gly Gly Lys Ser Thr Gln Lys Asp Val Ser Gln Ser Ser Ile Ser
                485                 490                 495
Phe Gln Ile Glu Lys Leu Val Glu Gly Lys Ser Gln Ile Gln Thr
                500                 505                 510
Pro Asn Pro Asn Gln Asp Gln Trp Ser Gly Gln Asn Ala Lys Gly
                515                 520                 525
Lys Ser Gly Gln Ser Ala Asp Ser Lys Gln Asp Leu Leu Ser His
                530                 535                 540
Glu Gln Lys Gly Arg Tyr Lys Gln Glu Ser Ser Glu Ser His Asn
                545                 550                 555
Ile Val Ile Thr Glu His Glu Val Ala Gln Asp Asp His Leu Thr
                560                 565                 570
Gln Gln Tyr Asn Glu Asp Arg Asn Pro Ile Ser Thr
                575                 580

<210> SEQ ID NO 42
<211> LENGTH: 71
<212> TYPE: PRT
<213> ORGANISM: Homo sapiens
<220> FEATURE:
<221> NAME/KEY: misc_feature
<223> OTHER INFORMATION: Incyte ID No: 350287

<400> SEQUENCE: 42

Met Phe Thr Ala Pro Leu Phe Phe Phe Phe Phe Phe Glu Ile Ile
```

```
              1               5              10              15
Asn Ser Met Arg Asn Leu Gly Leu Asn Ile Cys Leu Leu Cys Leu
                        20                  25                  30

Leu Ile Glu His His Ser Arg Pro Ser Val Cys Leu Pro Phe Thr
                        35                  40                  45

Pro Lys Ile Phe Thr Lys Lys Ile Leu Arg Gln Gln Val Thr Ile
                        50                  55                  60

Tyr Arg Cys Leu Asn Asp Phe Leu Ile Phe Ile
                        65                  70

<210> SEQ ID NO 43
<211> LENGTH: 102
<212> TYPE: PRT
<213> ORGANISM: Homo sapiens
<220> FEATURE:
<221> NAME/KEY: misc_feature
<223> OTHER INFORMATION: Incyte ID No: 1618171

<400> SEQUENCE: 43

Met Ala Val Leu Pro Ser Val Leu Leu Val Tyr Ser Leu Phe Phe
  1               5                  10                  15

Cys Leu Arg Phe Cys Met Leu Leu Leu Pro Ser Tyr Ser His
                        20                  25                  30

Ser Arg Ser Gly Arg Gly Pro Gly Arg Tyr Gly His Ile Thr Leu
                        35                  40                  45

Ile Asp Val Ile His Val Ser Val Tyr Trp Phe Phe Glu Ala Leu
                        50                  55                  60

Ser Thr Phe Gln Ile Phe Tyr Tyr Cys Ile Thr Arg Thr Ile Thr
                        65                  70                  75

Val Arg Lys Gly Ile Val Val Ser Arg His Val Asn Glu Ala Gly
                        80                  85                  90

Val Ser Phe Val Ser Tyr Leu Cys Ile Asn Phe Lys
                        95                 100

<210> SEQ ID NO 44
<211> LENGTH: 226
<212> TYPE: PRT
<213> ORGANISM: Homo sapiens
<220> FEATURE:
<221> NAME/KEY: misc_feature
<223> OTHER INFORMATION: Incyte ID No: 1625863

<400> SEQUENCE: 44

Met Pro Thr Thr Lys Lys Thr Leu Met Phe Leu Ser Ser Phe Phe
  1               5                  10                  15

Thr Ser Leu Gly Ser Phe Ile Val Ile Cys Ser Ile Leu Gly Thr
                        20                  25                  30

Gln Ala Trp Ile Thr Ser Thr Ile Ala Val Arg Asp Ser Ala Ser
                        35                  40                  45

Asn Gly Ser Ile Phe Ile Thr Tyr Gly Leu Phe Arg Gly Glu Ser
                        50                  55                  60

Ser Glu Glu Leu Ser His Gly Leu Ala Glu Pro Lys Lys Lys Phe
                        65                  70                  75

Ala Val Leu Glu Ile Leu Asn Asn Ser Ser Gln Lys Thr Leu His
                        80                  85                  90

Ser Val Thr Ile Leu Phe Leu Val Leu Ser Leu Ile Thr Ser Leu
                        95                 100                 105

Leu Ser Ser Gly Phe Thr Phe Tyr Asn Ser Ile Ser Asn Pro Tyr
                       110                 115                 120
```

```
Gln Thr Phe Leu Gly Pro Thr Gly Val Tyr Thr Trp Asn Gly Leu
            125                 130                 135

Gly Ala Ser Phe Val Phe Val Thr Met Ile Leu Phe Val Ala Asn
            140                 145                 150

Thr Gln Ser Asn Gln Leu Ser Glu Glu Leu Phe Gln Met Leu Tyr
            155                 160                 165

Pro Ala Thr Thr Ser Lys Gly Thr Thr His Ser Tyr Gly Tyr Ser
            170                 175                 180

Phe Trp Leu Ile Leu Leu Val Ile Leu Leu Asn Ile Val Thr Val
            185                 190                 195

Thr Ile Ile Ile Phe Tyr Gln Lys Ala Arg Tyr Gln Arg Lys Gln
            200                 205                 210

Glu Gln Arg Lys Pro Met Glu Tyr Ala Pro Arg Asp Gly Ile Leu
            215                 220                 225

Phe

<210> SEQ ID NO 45
<211> LENGTH: 154
<212> TYPE: PRT
<213> ORGANISM: Homo sapiens
<220> FEATURE:
<221> NAME/KEY: misc_feature
<223> OTHER INFORMATION: Incyte ID No: 1638353

<400> SEQUENCE: 45

Met Ala Leu Leu Leu Ser Val Leu Arg Val Leu Leu Gly Gly Phe
  1               5                  10                  15

Phe Ala Leu Val Gly Leu Ala Lys Leu Ser Glu Glu Ile Ser Ala
                 20                  25                  30

Pro Val Ser Glu Arg Met Asn Ala Leu Phe Val Gln Phe Ala Glu
                 35                  40                  45

Val Phe Pro Leu Lys Val Phe Gly Tyr Gln Pro Asp Pro Leu Asn
                 50                  55                  60

Tyr Gln Ile Ala Val Gly Phe Leu Glu Leu Leu Ala Gly Leu Leu
                 65                  70                  75

Leu Val Met Gly Pro Pro Met Leu Gln Glu Ile Ser Asn Leu Phe
                 80                  85                  90

Leu Ile Leu Leu Met Met Gly Ala Ile Phe Thr Leu Ala Ala Leu
                 95                 100                 105

Lys Glu Ser Leu Ser Thr Cys Ile Pro Ala Ile Val Cys Leu Gly
                110                 115                 120

Phe Leu Leu Leu Leu Asn Val Gly Gln Leu Leu Ala Gln Thr Lys
                125                 130                 135

Lys Val Val Arg Pro Thr Arg Lys Lys Thr Leu Ser Thr Phe Lys
                140                 145                 150

Glu Ser Trp Lys

<210> SEQ ID NO 46
<211> LENGTH: 167
<212> TYPE: PRT
<213> ORGANISM: Homo sapiens
<220> FEATURE:
<221> NAME/KEY: misc_feature
<223> OTHER INFORMATION: Incyte ID No: 1726843

<400> SEQUENCE: 46

Met Ala Ser Pro Arg Thr Val Thr Ile Val Ala Leu Ser Val Ala
  1               5                  10                  15
```

```
Leu Gly Leu Phe Phe Val Phe Met Gly Thr Ile Lys Leu Thr Pro
             20                  25                  30

Arg Leu Ser Lys Asp Ala Tyr Ser Glu Met Lys Arg Ala Tyr Lys
             35                  40                  45

Ser Tyr Val Arg Ala Leu Pro Leu Leu Lys Lys Met Gly Ile Asn
             50                  55                  60

Ser Ile Leu Leu Arg Lys Ser Ile Gly Ala Leu Glu Val Ala Cys
             65                  70                  75

Gly Ile Val Met Thr Leu Val Pro Gly Arg Pro Lys Asp Val Ala
             80                  85                  90

Asn Phe Phe Leu Leu Leu Val Leu Ala Val Leu Phe Phe His
             95                 100                 105

Gln Leu Val Gly Asp Pro Leu Lys Arg Tyr Ala His Ala Leu Val
            110                 115                 120

Phe Gly Ile Leu Leu Thr Cys Arg Leu Leu Ile Ala Arg Lys Pro
            125                 130                 135

Glu Asp Arg Ser Ser Glu Lys Lys Pro Leu Pro Gly Asn Ala Glu
            140                 145                 150

Glu Gln Pro Ser Leu Tyr Glu Lys Ala Pro Gln Gly Lys Val Lys
            155                 160                 165

Val Ser
```

<210> SEQ ID NO 47
<211> LENGTH: 545
<212> TYPE: PRT
<213> ORGANISM: Homo sapiens
<220> FEATURE:
<221> NAME/KEY: misc_feature
<223> OTHER INFORMATION: Incyte ID No: 1754506

<400> SEQUENCE: 47

```
Met Ala Gly Ala Ile Ile Glu Asn Met Ser Thr Lys Lys Leu Cys
  1               5                  10                  15

Ile Val Gly Gly Ile Leu Leu Val Phe Gln Ile Ile Ala Phe Leu
             20                  25                  30

Val Gly Gly Leu Ile Ala Pro Gly Pro Thr Thr Ala Val Ser Tyr
             35                  40                  45

Met Ser Val Lys Cys Val Asp Ala Arg Lys Asn His His Lys Thr
             50                  55                  60

Lys Trp Phe Val Pro Trp Gly Pro Asn His Cys Asp Lys Ile Arg
             65                  70                  75

Asp Ile Glu Glu Ala Ile Pro Arg Glu Ile Glu Ala Asn Asp Ile
             80                  85                  90

Val Phe Ser Val His Ile Pro Leu Pro His Met Glu Met Ser Pro
             95                 100                 105

Trp Phe Gln Phe Met Leu Phe Ile Leu Gln Leu Asp Ile Ala Phe
            110                 115                 120

Lys Leu Asn Asn Gln Ile Arg Glu Asn Ala Glu Val Ser Met Asp
            125                 130                 135

Val Ser Leu Ala Tyr Arg Asp Asp Ala Phe Ala Glu Trp Thr Glu
            140                 145                 150

Met Ala His Glu Arg Val Pro Arg Lys Leu Lys Cys Thr Phe Thr
            155                 160                 165

Ser Pro Lys Thr Pro Glu His Glu Gly Arg Tyr Tyr Glu Cys Asp
            170                 175                 180
```

```
Val Leu Pro Phe Met Glu Ile Gly Ser Val Ala His Lys Phe Tyr
            185                 190                 195

Leu Leu Asn Ile Arg Leu Pro Val Asn Glu Lys Lys Lys Ile Asn
            200                 205                 210

Val Gly Ile Gly Glu Ile Lys Asp Ile Arg Leu Val Gly Ile His
            215                 220                 225

Gln Asn Gly Gly Phe Thr Lys Val Trp Phe Ala Met Lys Thr Phe
            230                 235                 240

Leu Thr Pro Ser Ile Phe Ile Ile Met Val Trp Tyr Trp Arg Arg
            245                 250                 255

Ile Thr Met Met Ser Arg Pro Pro Val Leu Leu Glu Lys Val Ile
            260                 265                 270

Phe Ala Leu Gly Ile Ser Met Thr Phe Ile Asn Ile Pro Val Glu
            275                 280                 285

Trp Phe Ser Ile Gly Phe Asp Trp Thr Trp Met Leu Leu Phe Gly
            290                 295                 300

Asp Ile Arg Gln Gly Ile Phe Tyr Ala Met Leu Leu Ser Phe Trp
            305                 310                 315

Ile Ile Phe Cys Gly Glu His Met Met Asp Gln His Glu Arg Asn
            320                 325                 330

His Ile Ala Gly Tyr Trp Lys Gln Val Gly Pro Ile Ala Val Gly
            335                 340                 345

Ser Phe Cys Leu Phe Ile Phe Asp Met Cys Glu Arg Gly Val Gln
            350                 355                 360

Leu Thr Asn Pro Phe Tyr Ser Ile Trp Thr Thr Asp Ile Gly Thr
            365                 370                 375

Glu Leu Ala Met Ala Phe Ile Ile Val Ala Gly Ile Cys Leu Cys
            380                 385                 390

Leu Tyr Phe Leu Phe Leu Cys Phe Met Val Phe Gln Val Phe Arg
            395                 400                 405

Asn Ile Ser Gly Lys Gln Ser Ser Leu Pro Ala Met Ser Lys Val
            410                 415                 420

Arg Arg Leu His Tyr Glu Gly Leu Ile Phe Arg Phe Lys Phe Leu
            425                 430                 435

Met Leu Ile Thr Leu Ala Cys Ala Ala Met Thr Val Ile Phe Phe
            440                 445                 450

Ile Val Ser Gln Val Thr Glu Gly His Trp Lys Trp Gly Gly Val
            455                 460                 465

Thr Val Gln Val Asn Ser Ala Phe Phe Thr Gly Ile Tyr Gly Met
            470                 475                 480

Trp Asn Leu Tyr Val Phe Ala Leu Met Phe Leu Tyr Ala Pro Ser
            485                 490                 495

His Lys Asn Tyr Gly Glu Asp Gln Ser Asn Gly Met Gln Leu Pro
            500                 505                 510

Cys Lys Ser Arg Glu Asp Cys Ala Leu Phe Val Ser Glu Leu Tyr
            515                 520                 525

Gln Glu Leu Phe Ser Ala Ser Lys Tyr Ser Phe Ile Asn Asp Asn
            530                 535                 540

Ala Ala Ser Gly Ile
            545

<210> SEQ ID NO 48
<211> LENGTH: 570
<212> TYPE: PRT
<213> ORGANISM: Homo sapiens
```

```
<220> FEATURE:
<221> NAME/KEY: misc_feature
<223> OTHER INFORMATION: Incyte ID No: 1831378

<400> SEQUENCE: 48

Met Gly Phe Leu Gln Leu Leu Val Val Ala Val Leu Ala Ser Glu
 1               5                  10                  15

His Arg Val Ala Gly Ala Ala Glu Val Phe Gly Asn Ser Ser Glu
            20                  25                  30

Gly Leu Ile Glu Phe Ser Val Gly Lys Phe Arg Tyr Phe Glu Leu
        35                  40                  45

Asn Arg Pro Phe Pro Glu Glu Ala Ile Leu His Asp Ile Ser Ser
    50                  55                  60

Asn Val Thr Phe Leu Ile Phe Gln Ile His Ser Gln Tyr Gln Asn
65                  70                  75

Thr Thr Val Ser Phe Ser Pro Thr Leu Leu Ser Asn Ser Ser Glu
            80                  85                  90

Thr Gly Thr Ala Ser Gly Leu Val Phe Ile Leu Arg Pro Glu Gln
        95                 100                 105

Ser Thr Cys Thr Trp Tyr Leu Gly Thr Ser Gly Ile Gln Pro Val
   110                 115                 120

Gln Asn Met Ala Ile Leu Leu Ser Tyr Ser Glu Arg Asp Pro Val
            125                 130                 135

Pro Gly Gly Cys Asn Leu Glu Phe Asp Leu Asp Ile Asp Pro Asn
        140                 145                 150

Ile Tyr Leu Glu Tyr Asn Phe Phe Glu Thr Thr Ile Lys Phe Ala
    155                 160                 165

Pro Ala Asn Leu Gly Tyr Ala Arg Gly Val Asp Pro Pro Pro Cys
170                 175                 180

Asp Ala Gly Thr Asp Gln Asp Ser Arg Trp Arg Leu Gln Tyr Asp
            185                 190                 195

Val Tyr Gln Tyr Phe Leu Pro Glu Asn Asp Leu Thr Glu Glu Met
        200                 205                 210

Leu Leu Lys His Leu Gln Arg Met Val Ser Val Pro Gln Val Lys
    215                 220                 225

Ala Ser Ala Leu Lys Val Val Thr Leu Thr Ala Asn Asp Lys Thr
230                 235                 240

Ser Val Ser Phe Ser Ser Leu Pro Gly Gln Gly Val Ile Tyr Asn
            245                 250                 255

Val Ile Val Trp Asp Pro Phe Leu Asn Thr Ser Ala Ala Tyr Ile
        260                 265                 270

Pro Ala His Thr Tyr Ala Cys Ser Phe Glu Ala Gly Glu Gly Ser
    275                 280                 285

Cys Ala Ser Leu Gly Arg Val Ser Ser Lys Val Phe Phe Thr Leu
290                 295                 300

Phe Ala Leu Leu Gly Phe Phe Ile Cys Phe Phe Gly His Arg Phe
            305                 310                 315

Trp Lys Thr Glu Leu Phe Phe Ile Gly Phe Ile Met Gly Phe
        320                 325                 330

Phe Phe Tyr Ile Leu Ile Thr Arg Leu Thr Pro Ile Lys Tyr Asp
    335                 340                 345

Val Asn Leu Ile Leu Thr Ala Val Thr Gly Ser Val Gly Gly Met
350                 355                 360

Phe Leu Val Ala Val Trp Trp Arg Phe Gly Ile Leu Ser Ile Cys
            365                 370                 375
```

Met Leu Cys Val Gly Leu Val Leu Gly Phe Leu Ile Ser Ser Val
            380                 385                 390

Thr Phe Phe Thr Pro Leu Gly Asn Leu Lys Ile Phe His Asp Asp
            395                 400                 405

Gly Val Phe Trp Val Thr Phe Ser Cys Ile Ala Ile Leu Ile Pro
            410                 415                 420

Val Val Phe Met Gly Cys Leu Arg Ile Leu Asn Ile Leu Thr Cys
            425                 430                 435

Gly Val Ile Gly Ser Tyr Ser Val Val Leu Ala Ile Asp Ser Tyr
            440                 445                 450

Trp Ser Thr Ser Leu Ser Tyr Ile Thr Leu Asn Val Leu Lys Arg
            455                 460                 465

Ala Leu Asn Lys Asp Phe His Arg Ala Phe Thr Asn Val Pro Phe
            470                 475                 480

Gln Thr Asn Asp Phe Ile Ile Leu Ala Val Trp Gly Met Leu Ala
            485                 490                 495

Val Ser Gly Ile Thr Leu Gln Ile Arg Arg Glu Arg Gly Arg Pro
            500                 505                 510

Phe Phe Pro Pro His Pro Tyr Lys Leu Trp Lys Gln Glu Arg Glu
            515                 520                 525

Arg Arg Val Thr Asn Ile Leu Asp Pro Ser Tyr His Ile Pro Pro
            530                 535                 540

Leu Arg Glu Arg Leu Tyr Gly Arg Leu Thr Gln Ile Lys Gly Leu
            545                 550                 555

Phe Gln Lys Glu Gln Pro Ala Gly Glu Arg Thr Pro Leu Leu Leu
            560                 565                 570

<210> SEQ ID NO 49
<211> LENGTH: 127
<212> TYPE: PRT
<213> ORGANISM: Homo sapiens
<220> FEATURE:
<221> NAME/KEY: misc_feature
<223> OTHER INFORMATION: Incyte ID No: 1864943

<400> SEQUENCE: 49

Met Arg Arg Arg Phe Trp Gly Val Phe Asn Cys Leu Cys Ala Gly
  1               5                  10                  15

Ala Phe Gly Ala Leu Ala Ala Ala Ser Ala Lys Leu Ala Phe Gly
                 20                  25                  30

Ser Glu Val Ser Met Gly Leu Cys Val Leu Gly Ile Ile Val Met
                 35                  40                  45

Ala Ser Thr Asn Ser Leu Met Trp Thr Phe Phe Ser Arg Gly Leu
                 50                  55                  60

Ser Phe Ser Met Ser Ser Ala Ile Ala Ser Val Thr Val Thr Phe
                 65                  70                  75

Ser Asn Ile Leu Ser Ser Ala Phe Leu Gly Tyr Val Leu Tyr Gly
                 80                  85                  90

Glu Cys Gln Glu Val Leu Trp Trp Gly Gly Val Phe Leu Ile Leu
                 95                 100                 105

Cys Gly Leu Thr Leu Ile His Arg Lys Leu Pro Pro Thr Trp Lys
                110                 115                 120

Pro Leu Pro His Lys Gln Gln
                125

<210> SEQ ID NO 50

```
<211> LENGTH: 152
<212> TYPE: PRT
<213> ORGANISM: Homo sapiens
<220> FEATURE:
<221> NAME/KEY: misc_feature
<223> OTHER INFORMATION: Incyte ID No: 1911316

<400> SEQUENCE: 50

Met Asp Asn Val Gln Pro Lys Ile Lys His Arg Pro Phe Cys Phe
 1               5                  10                  15

Ser Val Lys Gly His Val Lys Met Leu Arg Leu Ala Leu Thr Val
                20                  25                  30

Thr Ser Met Thr Phe Phe Ile Ile Ala Gln Ala Pro Glu Pro Tyr
                35                  40                  45

Ile Val Ile Thr Gly Phe Glu Val Thr Val Ile Leu Phe Phe Ile
                50                  55                  60

Leu Leu Tyr Val Leu Arg Leu Asp Arg Leu Met Lys Trp Leu Phe
                65                  70                  75

Trp Pro Leu Leu Asp Ile Ile Asn Ser Leu Val Thr Val Phe
                80                  85                  90

Met Leu Ile Val Ser Val Leu Ala Leu Ile Pro Glu Thr Thr Thr
                95                 100                 105

Leu Thr Val Gly Gly Gly Val Phe Ala Leu Val Thr Ala Val Cys
               110                 115                 120

Cys Leu Ala Asp Gly Ala Leu Ile Tyr Arg Lys Leu Leu Phe Asn
               125                 130                 135

Pro Ser Gly Pro Tyr Gln Lys Lys Pro Val His Glu Lys Lys Glu
               140                 145                 150

Val Leu

<210> SEQ ID NO 51
<211> LENGTH: 777
<212> TYPE: PRT
<213> ORGANISM: Homo sapiens
<220> FEATURE:
<221> NAME/KEY: misc_feature
<223> OTHER INFORMATION: Incyte ID No: 1943120

<400> SEQUENCE: 51

Met Thr Phe Tyr Pro Phe Val Ala Ser Ser Thr Arg Arg Val
 1               5                  10                  15

Asp Asn Ser Asn Thr Arg Leu Ala Val Gln Ile Glu Arg Asp Pro
                20                  25                  30

Gly Asn Asp Asp Asn Asn Leu Asn Ser Ile Phe Tyr Glu His Leu
                35                  40                  45

Thr Arg Thr Leu Leu Glu Ser Leu Cys Gly Asp Leu Val Leu Gly
                50                  55                  60

Arg Trp Gly Asn Tyr Ser Ser Gly Asp Cys Phe Ile Leu Ala Ser
                65                  70                  75

Asp Asp Leu Asn Ala Phe Val His Leu Ile Glu Ile Gly Asn Gly
                80                  85                  90

Leu Val Thr Phe Gln Leu Arg Gly Leu Glu Phe Arg Gly Thr Tyr
                95                 100                 105

Cys Gln Gln Arg Glu Val Glu Ala Ile Met Glu Gly Asp Glu Glu
               110                 115                 120

Asp Arg Gly Cys Cys Cys Cys Lys Pro Gly His Leu Pro His Leu
               125                 130                 135

Leu Ser Arg Asn Ala Ala Phe His Leu Arg Trp Leu Thr Trp Glu
```

```
                140                 145                 150
Ile Thr Gln Thr Gln Tyr Ile Leu Glu Gly Tyr Ser Ile Leu Asp
                155                 160                 165
Asn Asn Ala Ala Thr Met Leu Gln Val Phe Asp Leu Arg Arg Ile
                170                 175                 180
Leu Ile Arg Tyr Tyr Ile Lys Ser Ile Ile Tyr Tyr Met Val Thr
                185                 190                 195
Ser Pro Lys Leu Leu Ser Trp Ile Lys Asn Glu Ser Leu Leu Lys
                200                 205                 210
Ser Leu Gln Pro Phe Ala Lys Trp His Tyr Ile Glu Arg Asp Leu
                215                 220                 225
Ala Met Phe Asn Ile Asn Ile Asp Asp Tyr Val Pro Cys Leu
                230                 235                 240
Gln Gly Ile Thr Arg Ala Ser Phe Cys Asn Val Tyr Leu Glu Trp
                245                 250                 255
Ile Gln His Cys Ala Arg Lys Arg Gln Glu Pro Ser Thr Thr Leu
                260                 265                 270
Asp Ser Asp Glu Asp Ser Pro Leu Val Thr Leu Ser Phe Ala Leu
                275                 280                 285
Cys Thr Leu Gly Arg Arg Ala Leu Gly Thr Ala Ala His Asn Met
                290                 295                 300
Ala Ile Ser Leu Asp Ser Phe Leu Tyr Gly Leu His Val Leu Phe
                305                 310                 315
Lys Gly Asp Phe Arg Ile Thr Ala Arg Asp Glu Trp Val Phe Ala
                320                 325                 330
Asp Met Asp Leu Leu His Lys Val Val Ala Pro Ala Ile Arg Met
                335                 340                 345
Ser Leu Lys Leu His Gln Asp Gln Phe Thr Cys Pro Asp Glu Tyr
                350                 355                 360
Glu Asp Pro Ala Val Leu Tyr Glu Ala Ile Gln Ser Phe Glu Lys
                365                 370                 375
Lys Val Val Ile Cys His Glu Gly Asp Pro Ala Trp Arg Gly Ala
                380                 385                 390
Val Leu Ser Asn Lys Glu Glu Leu Leu Thr Leu Arg His Val Val
                395                 400                 405
Asp Glu Gly Ala Asp Glu Tyr Lys Val Ile Met Leu His Arg Ser
                410                 415                 420
Phe Leu Ser Phe Lys Val Ile Lys Val Asn Lys Glu Cys Val Arg
                425                 430                 435
Gly Leu Trp Ala Gly Gln Gln Gln Glu Leu Ile Phe Leu Arg Asn
                440                 445                 450
Arg Asn Pro Glu Arg Gly Ser Ile Gln Asn Asn Lys Gln Val Leu
                455                 460                 465
Arg Asn Leu Ile Asn Ser Ser Cys Asp Gln Pro Leu Gly Tyr Pro
                470                 475                 480
Met Tyr Val Ser Pro Leu Thr Thr Ser Tyr Leu Gly Thr His Arg
                485                 490                 495
Gln Leu Lys Asn Ile Trp Gly Gly Pro Ile Thr Leu Asp Arg Ile
                500                 505                 510
Arg Thr Trp Phe Trp Thr Lys Trp Val Arg Met Arg Lys Asp Cys
                515                 520                 525
Asn Ala Arg Gln His Ser Gly Gly Asn Ile Glu Asp Val Asp Gly
                530                 535                 540
```

-continued

```
Gly Gly Ala Pro Thr Thr Gly Gly Asn Asn Ala Pro Asn Gly Gly
            545                 550                 555

Ser Gln Glu Ser Ser Ala Glu Gln Pro Arg Lys Gly Gly Ala Gln
            560                 565                 570

His Gly Val Ser Ser Cys Glu Gly Thr Gln Arg Thr Gly Arg Arg
            575                 580                 585

Lys Gly Arg Ser Gln Ser Val Gln Ala His Ser Ala Leu Ser Gln
            590                 595                 600

Arg Pro Pro Met Leu Ser Ser Gly Pro Ile Leu Glu Ser Arg
            605                 610                 615

Gln Thr Phe Leu Gln Thr Ser Thr Ser Val His Glu Leu Ala Gln
            620                 625                 630

Arg Leu Ser Gly Ser Arg Leu Ser Leu His Ala Ser Ala Thr Ser
            635                 640                 645

Leu His Ser Gln Pro Pro Val Thr Thr Thr Gly His Leu Ser
            650                 655                 660

Val Arg Glu Arg Ala Glu Ala Leu Ile Arg Ser Ser Leu Gly Ser
            665                 670                 675

Ser Thr Ser Ser Thr Leu Ser Phe Leu Phe Gly Lys Arg Ser Phe
            680                 685                 690

Ser Ser Ala Leu Val Ile Ser Gly Leu Ser Ala Ala Glu Gly Gly
            695                 700                 705

Asn Thr Ser Asp Thr Gln Ser Ser Ser Val Asn Ile Val Met
            710                 715                 720

Gly Pro Ser Ala Arg Ala Ala Ser Gln Ala Thr Arg Val Arg Gly
            725                 730                 735

Trp Ala Gly Leu Thr Arg Thr Gly Trp Asp Gly Gly Thr Gly Ser
            740                 745                 750

Trp Pro Glu Arg Gly Thr Cys Leu Ala Phe Pro Pro Phe Cys Leu
            755                 760                 765

Gln Asn Pro Ile Pro Phe Ser Met Gly Leu Pro Glu
            770                 775

<210> SEQ ID NO 52
<211> LENGTH: 108
<212> TYPE: PRT
<213> ORGANISM: Homo sapiens
<220> FEATURE:
<221> NAME/KEY: misc_feature
<223> OTHER INFORMATION: Incyte ID No: 2314236

<400> SEQUENCE: 52

Met Phe Lys His Glu Leu Glu Glu Leu Arg Thr Thr Ile Met Tyr
  1               5                  10                  15

Arg Asp Ser His Ser Val Leu Ala Leu Asn Trp Lys Val Val Ala
             20                  25                  30

Thr Leu Lys Tyr Phe Leu Leu Tyr Val Ile Ile Leu Tyr Asn Leu
             35                  40                  45

Glu Arg Asp Asn Gly His Ser Asn Tyr Glu Asn Tyr Glu Leu Gly
             50                  55                  60

Asp Lys Ser Leu Asn Leu Leu Phe Tyr Asn Ser Met Tyr Lys
             65                  70                  75

Leu Val Phe Pro Tyr Ile Phe Thr Phe Ser Ser Phe Leu Ile Ser
             80                  85                  90

Ser Tyr Thr Ser Ile Leu Tyr Lys Met Phe Tyr Ile Gln Arg Thr
             95                 100                 105
```

Val Lys Ser

<210> SEQ ID NO 53
<211> LENGTH: 66
<212> TYPE: PRT
<213> ORGANISM: Homo sapiens
<220> FEATURE:
<221> NAME/KEY: misc_feature
<223> OTHER INFORMATION: Incyte ID No: 2479409

<400> SEQUENCE: 53

```
Met Asn Leu Ser Lys Lys Ser Ile Leu Leu Thr Gln Val Ile Lys
  1               5                  10                  15

Phe Val Asp Ile Arg Leu Phe Ile Met Val Pro Ser Tyr Pro Phe
                 20                  25                  30

Asn Val Phe Arg Ser Cys Val Asp Asn Phe Leu Phe Ile Met Ile
                 35                  40                  45

Leu Val Ile Ser Val Leu Thr Phe Leu Ile Arg Leu Gly Arg Gly
                 50                  55                  60

Leu Ser Val Leu Leu Ile
                 65
```

<210> SEQ ID NO 54
<211> LENGTH: 540
<212> TYPE: PRT
<213> ORGANISM: Homo sapiens
<220> FEATURE:
<221> NAME/KEY: misc_feature
<223> OTHER INFORMATION: Incyte ID No: 2683149

<400> SEQUENCE: 54

```
Met Met Gly Ser Pro Val Ser His Leu Ala Gly Phe Cys Val
  1               5                  10                  15

Trp Val Val Leu Gly Trp Val Gly Gly Ser Val Pro Asn Leu Gly
                 20                  25                  30

Pro Ala Glu Gln Glu Gln Asn His Tyr Leu Ala Gln Leu Phe Gly
                 35                  40                  45

Leu Tyr Gly Glu Asn Gly Thr Leu Thr Ala Gly Gly Leu Ala Arg
                 50                  55                  60

Leu Leu His Ser Leu Gly Leu Gly Arg Val Gln Gly Leu Arg Leu
                 65                  70                  75

Gly Gln His Gly Pro Leu Thr Gly Arg Ala Ala Ser Pro Ala Ala
                 80                  85                  90

Asp Asn Ser Thr His Arg Pro Gln Asn Pro Glu Leu Ser Val Asp
                 95                 100                 105

Val Trp Ala Gly Met Pro Leu Gly Pro Ser Gly Trp Gly Asp Leu
                110                 115                 120

Glu Glu Ser Lys Ala Pro His Leu Pro Arg Gly Pro Ala Pro Ser
                125                 130                 135

Gly Leu Asp Leu Leu His Arg Leu Leu Leu Asp His Ser Leu
                140                 145                 150

Ala Asp His Leu Asn Glu Asp Cys Leu Asn Gly Ser Gln Leu Leu
                155                 160                 165

Val Asn Phe Gly Leu Ser Pro Ala Ala Pro Leu Thr Pro Arg Gln
                170                 175                 180

Phe Ala Leu Leu Cys Pro Ala Leu Leu Tyr Gln Ile Asp Ser Arg
                185                 190                 195

Val Cys Ile Gly Ala Pro Ala Pro Ala Pro Pro Gly Asp Leu Leu
                200                 205                 210
```

```
Ser Ala Leu Leu Gln Ser Ala Leu Ala Val Leu Leu Leu Ser Leu
            215                 220                 225

Pro Ser Pro Leu Ser Leu Leu Leu Arg Leu Leu Gly Pro Arg
            230                 235                 240

Leu Leu Arg Pro Leu Leu Gly Phe Leu Gly Ala Leu Ala Val Gly
            245                 250                 255

Thr Leu Cys Gly Asp Ala Leu Leu His Leu Leu Pro His Ala Gln
            260                 265                 270

Glu Gly Arg His Ala Gly Pro Gly Gly Leu Pro Glu Lys Asp Leu
            275                 280                 285

Gly Pro Gly Leu Ser Val Leu Gly Gly Leu Phe Leu Leu Phe Val
            290                 295                 300

Leu Glu Asn Met Leu Gly Leu Leu Arg His Arg Gly Leu Arg Pro
            305                 310                 315

Arg Cys Cys Arg Arg Lys Arg Arg Asn Leu Glu Thr Arg Asn Leu
            320                 325                 330

Asp Pro Glu Asn Gly Ser Gly Met Ala Leu Gln Pro Leu Gln Ala
            335                 340                 345

Ala Pro Glu Pro Gly Ala Gln Gly Gln Arg Glu Lys Asn Ser Gln
            350                 355                 360

His Pro Pro Ala Leu Ala Pro Pro Gly His Gln Gly His Ser His
            365                 370                 375

Gly His Gln Gly Gly Thr Asp Ile Thr Trp Met Val Leu Leu Gly
            380                 385                 390

Asp Gly Leu His Asn Leu Thr Asp Gly Leu Ala Ile Gly Ala Ala
            395                 400                 405

Phe Ser Asp Gly Phe Ser Ser Gly Leu Ser Thr Thr Leu Ala Val
            410                 415                 420

Phe Cys His Glu Leu Pro His Glu Leu Gly Asp Phe Ala Met Leu
            425                 430                 435

Leu Gln Ser Gly Leu Ser Phe Arg Arg Leu Leu Leu Leu Ser Leu
            440                 445                 450

Val Ser Gly Ala Leu Gly Leu Gly Gly Ala Val Leu Gly Val Gly
            455                 460                 465

Leu Ser Leu Gly Pro Val Pro Leu Thr Pro Trp Val Phe Gly Val
            470                 475                 480

Thr Ala Gly Val Phe Leu Tyr Val Ala Leu Val Asp Met Leu Pro
            485                 490                 495

Ala Leu Leu Arg Pro Pro Glu Pro Leu Pro Thr Pro His Val Leu
            500                 505                 510

Leu Gln Gly Leu Gly Leu Leu Leu Gly Gly Leu Met Leu Ala
            515                 520                 525

Ile Thr Leu Leu Glu Glu Arg Leu Leu Pro Val Thr Thr Glu Gly
            530                 535                 540

<210> SEQ ID NO 55
<211> LENGTH: 87
<212> TYPE: PRT
<213> ORGANISM: Homo sapiens
<220> FEATURE:
<221> NAME/KEY: misc_feature
<223> OTHER INFORMATION: Incyte ID No: 2774051

<400> SEQUENCE: 55

Met Pro Phe Thr Leu Asp Asp Tyr Gly Ala Tyr Ser Ser Gln Lys
  1               5                  10                  15
```

```
Gln Tyr Thr Cys Gln Phe Pro Ser Thr Ile Ala Ile His Ala Glu
                20                  25                  30

Asp Lys Arg Pro Pro Gln Ser Arg Arg Gly Ile Val Leu Gly Pro
                35                  40                  45

Ile Phe Leu Ile Val Leu Lys Ile Ile Arg Trp Thr Val Phe
            50                  55                  60

Cys Glu Asp Phe Leu Phe Pro Ser Ser Lys Lys Pro Cys Gly Lys
                65                  70                  75

Asn Ser Leu Ile Thr Val Leu Ile Phe Phe Phe
                80                  85

<210> SEQ ID NO 56
<211> LENGTH: 100
<212> TYPE: PRT
<213> ORGANISM: Homo sapiens
<220> FEATURE:
<221> NAME/KEY: misc_feature
<223> OTHER INFORMATION: Incyte ID No: 2869038

<400> SEQUENCE: 56

Met Ile Met Ala Gln Lys Ile Gly Gly Leu Thr Trp Trp Ala Ile
  1               5                  10                  15

Met Phe Ile Ile Leu Phe Glu Ile Thr Gly Thr Ser Ser Ser Phe
                20                  25                  30

Leu Arg Ile Asn Ala Leu Pro His Phe Ser Met Asn Arg Cys Gly
                35                  40                  45

Glu Ala Tyr Phe Pro Phe Ser Tyr Leu Tyr Thr Ser Leu Gln Lys
                50                  55                  60

Gln Phe Leu Met Lys Val Ser Gly Ile Val Lys Asn Leu Arg Gly
                65                  70                  75

Met Met Thr Gly Gly Val Trp Gly Phe Phe Leu Tyr Ser Phe Phe
                80                  85                  90

Asn Glu Lys Ser Phe Lys Cys Ser Thr Gly
                95                 100

<210> SEQ ID NO 57
<211> LENGTH: 58
<212> TYPE: PRT
<213> ORGANISM: Homo sapiens
<220> FEATURE:
<221> NAME/KEY: misc_feature
<223> OTHER INFORMATION: Incyte ID No: 2918334

<400> SEQUENCE: 57

Met Asp Leu Leu Tyr Glu Ile Leu Leu Ala Leu Tyr Tyr Asn Ile
  1               5                  10                  15

Cys Tyr Asp Ile Pro Phe Ile Phe Asn Leu Asn Met Met Phe
                20                  25                  30

Tyr Ile Val Leu Asp Leu Arg Ile Val Phe Phe Arg Thr Ile Arg
                35                  40                  45

Glu Tyr Leu Ser Pro Pro Ser Leu Ser Phe Tyr Ile Tyr
                50                  55

<210> SEQ ID NO 58
<211> LENGTH: 61
<212> TYPE: PRT
<213> ORGANISM: Homo sapiens
<220> FEATURE:
<221> NAME/KEY: misc_feature
<223> OTHER INFORMATION: Incyte ID No: 2949916
```

```
<400> SEQUENCE: 58

Met Arg Arg Ile Ile Arg Leu Arg Leu Arg Phe Ser Asp Thr Phe
 1               5                  10                  15

Met Ala Ala Phe Leu Leu Cys Leu Gly Phe Val Leu Met Leu Phe
             20                  25                  30

Pro Ser Leu Leu Arg Asp Gly Gly Ser Ile Ser Ser Cys Arg Asn
         35                  40                  45

Ser Cys Ser Ser Pro Ser Ser Glu Glu Arg His Phe Ser Asn Leu
     50                  55                  60

Glu

<210> SEQ ID NO 59
<211> LENGTH: 50
<212> TYPE: PRT
<213> ORGANISM: Homo sapiens
<220> FEATURE:
<221> NAME/KEY: misc_feature
<223> OTHER INFORMATION: Incyte ID No: 2989375

<400> SEQUENCE: 59

Met Cys Leu Thr Pro His Arg Asp Ser Met Cys Glu Asp Ser Pro
 1               5                  10                  15

Phe Thr His Gln Ile Ile Ser Met Ala Thr Ala Cys Ser Leu Leu
             20                  25                  30

Leu Glu Cys Phe Val Leu Ala Ala Ser Leu Leu Val Cys Val Trp
         35                  40                  45

Ser Glu Trp Arg Arg
     50

<210> SEQ ID NO 60
<211> LENGTH: 310
<212> TYPE: PRT
<213> ORGANISM: Homo sapiens
<220> FEATURE:
<221> NAME/KEY: misc_feature
<223> OTHER INFORMATION: Incyte ID No: 3316764

<400> SEQUENCE: 60

Met Arg Arg Thr Ala Phe Ile Leu Gly Ser Gly Leu Leu Ser Phe
 1               5                  10                  15

Val Ala Phe Trp Asn Ser Val Thr Trp His Leu Gln Arg Phe Trp
             20                  25                  30

Gly Ala Ser Gly Tyr Phe Trp Gln Ala Gln Trp Glu Arg Leu Leu
         35                  40                  45

Thr Thr Phe Glu Gly Lys Glu Trp Ile Leu Phe Phe Ile Gly Ala
     50                  55                  60

Ile Gln Val Pro Cys Leu Phe Phe Trp Ser Phe Asn Gly Leu Leu
 65                  70                  75

Leu Val Val Asp Thr Thr Gly Lys Pro Asn Phe Ile Ser Arg Tyr
             80                  85                  90

Arg Ile Gln Val Gly Lys Asn Glu Pro Val Asp Pro Val Lys Leu
         95                 100                 105

Arg Gln Ser Ile Arg Thr Val Leu Phe Asn Gln Cys Met Ile Ser
        110                 115                 120

Phe Pro Met Val Val Phe Leu Tyr Pro Phe Leu Lys Trp Trp Arg
        125                 130                 135

Asp Pro Cys Arg Arg Glu Leu Pro Thr Phe His Trp Phe Leu Leu
        140                 145                 150
```

-continued

```
Glu Leu Ala Ile Phe Thr Leu Ile Glu Glu Val Leu Phe Tyr Tyr
            155                 160                 165

Ser His Arg Leu Leu His His Pro Thr Phe Tyr Lys Lys Ile His
            170                 175                 180

Lys Lys His His Glu Trp Thr Ala Pro Ile Gly Val Ile Ser Leu
            185                 190                 195

Tyr Ala His Pro Ile Glu His Ala Val Ser Asn Met Leu Pro Val
            200                 205                 210

Ile Val Gly Pro Leu Val Met Gly Ser His Leu Ser Ser Ile Thr
            215                 220                 225

Met Trp Phe Ser Leu Ala Leu Ile Ile Thr Thr Ile Ser His Cys
            230                 235                 240

Gly Tyr His Leu Pro Phe Leu Pro Ser Pro Glu Phe His Asp Tyr
            245                 250                 255

His His Leu Lys Phe Asn Gln Cys Tyr Gly Val Leu Gly Val Leu
            260                 265                 270

Asp His Leu His Gly Thr Asp Thr Met Phe Lys Gln Thr Lys Ala
            275                 280                 285

Tyr Glu Arg His Val Leu Leu Leu Gly Phe Thr Pro Leu Ser Glu
            290                 295                 300

Ser Ile Pro Asp Ser Pro Lys Arg Met Glu
            305                 310

<210> SEQ ID NO 61
<211> LENGTH: 160
<212> TYPE: PRT
<213> ORGANISM: Homo sapiens
<220> FEATURE:
<221> NAME/KEY: misc_feature
<223> OTHER INFORMATION: Incyte ID No: 3359559

<400> SEQUENCE: 61

Met Ala Pro Ala Leu Trp Arg Ala Cys Asn Gly Leu Met Ala Ala
  1               5                  10                  15

Phe Phe Ala Leu Ala Ala Leu Val Gln Val Asn Asp Pro Asp Ala
             20                  25                  30

Glu Val Trp Val Val Tyr Thr Ile Pro Ala Val Leu Thr Leu
             35                  40                  45

Leu Val Gly Leu Asn Pro Glu Val Thr Gly Asn Val Ile Trp Lys
             50                  55                  60

Ser Ile Ser Ala Ile His Ile Leu Phe Cys Thr Val Trp Ala Val
             65                  70                  75

Gly Leu Ala Ser Tyr Leu Leu His Arg Thr Gln Gln Asn Ile Leu
             80                  85                  90

His Glu Glu Glu Gly Arg Glu Leu Ser Gly Leu Val Ile Ile Thr
             95                 100                 105

Ala Trp Ile Ile Leu Cys His Ser Ser Ser Lys Asn Pro Val Gly
            110                 115                 120

Gly Arg Ile Gln Leu Ala Ile Ala Ile Val Ile Thr Leu Phe Pro
            125                 130                 135

Phe Ile Ser Trp Val Tyr Ile Tyr Ile Asn Lys Glu Met Arg Ser
            140                 145                 150

Ser Trp Pro Thr His Cys Lys Thr Val Ile
            155                 160

<210> SEQ ID NO 62
<211> LENGTH: 35
```

```
<212> TYPE: PRT
<213> ORGANISM: Homo sapiens
<220> FEATURE:
<221> NAME/KEY: misc_feature
<223> OTHER INFORMATION: Incyte ID No: 4289208

<400> SEQUENCE: 62

Met Ala Val Val Asp Ala Gly Asn Asn Gly Lys Val Leu Asp Arg
 1               5                  10                  15

Val Cys Val Arg Ser Val Pro Ala Leu Phe Leu Ser Lys Cys Ile
                20                  25                  30

Ser Leu Asp Met Glu
                35

<210> SEQ ID NO 63
<211> LENGTH: 323
<212> TYPE: PRT
<213> ORGANISM: Homo sapiens
<220> FEATURE:
<221> NAME/KEY: misc_feature
<223> OTHER INFORMATION: Incyte ID No: 2454013

<400> SEQUENCE: 63

Met Ala Ala Pro Lys Gly Ser Leu Trp Val Arg Thr Gln Leu Gly
 1               5                  10                  15

Leu Pro Pro Leu Leu Leu Thr Met Ala Leu Ala Gly Gly Ser
                20                  25                  30

Gly Thr Ala Ser Ala Glu Ala Phe Asp Ser Val Leu Gly Asp Thr
                35                  40                  45

Ala Ser Cys His Arg Ala Cys Gln Leu Thr Tyr Pro Leu His Thr
                50                  55                  60

Tyr Pro Lys Glu Glu Leu Tyr Ala Cys Gln Arg Gly Cys Arg
                65                  70                  75

Leu Phe Ser Ile Cys Gln Phe Val Asp Asp Gly Ile Asp Leu Asn
                80                  85                  90

Arg Thr Lys Leu Glu Cys Glu Ser Ala Cys Thr Glu Ala Tyr Ser
                95                  100                 105

Gln Ser Asp Glu Gln Tyr Ala Cys His Leu Gly Cys Gln Asn Gln
                110                 115                 120

Leu Pro Phe Ala Glu Leu Arg Gln Glu Gln Leu Met Ser Leu Met
                125                 130                 135

Pro Lys Met His Leu Leu Phe Pro Leu Thr Leu Val Arg Ser Phe
                140                 145                 150

Trp Ser Asp Met Met Asp Ser Ala Gln Ser Phe Ile Thr Ser Ser
                155                 160                 165

Trp Thr Phe Tyr Leu Gln Ala Asp Asp Gly Lys Ile Val Ile Phe
                170                 175                 180

Gln Ser Lys Pro Glu Ile Gln Tyr Ala Pro His Leu Glu Gln Glu
                185                 190                 195

Pro Thr Asn Leu Arg Glu Ser Ser Leu Ser Lys Met Ser Tyr Leu
                200                 205                 210

Gln Met Arg Asn Ser Gln Ala His Arg Asn Phe Leu Glu Asp Gly
                215                 220                 225

Glu Ser Asp Gly Phe Leu Arg Cys Leu Ser Leu Asn Ser Gly Trp
                230                 235                 240

Ile Leu Thr Thr Thr Leu Val Leu Ser Val Met Val Leu Leu Trp
                245                 250                 255

Ile Cys Cys Ala Thr Val Ala Thr Ala Val Glu Gln Tyr Val Pro
```

```
                            260                 265                 270
Ser Glu Lys Leu Ser Ile Tyr Gly Asp Leu Glu Phe Met Asn Glu
                275                 280                 285

Gln Lys Leu Asn Arg Tyr Pro Ala Ser Ser Leu Val Val Arg
            290                 295                 300

Ser Lys Thr Glu Asp His Glu Glu Ala Gly Pro Leu Pro Thr Lys
                305                 310                 315

Val Asn Leu Ala His Ser Glu Ile
                320

<210> SEQ ID NO 64
<211> LENGTH: 129
<212> TYPE: PRT
<213> ORGANISM: Homo sapiens
<220> FEATURE:
<221> NAME/KEY: misc_feature
<223> OTHER INFORMATION: Incyte ID No: 2454048

<400> SEQUENCE: 64

Met Ala Arg Gly Ser Leu Arg Arg Leu Leu Arg Leu Leu Val Leu
  1               5                  10                  15

Gly Leu Trp Leu Ala Leu Leu Arg Ser Val Ala Gly Glu Gln Ala
                 20                  25                  30

Pro Gly Thr Ala Pro Cys Ser Arg Gly Ser Ser Trp Ser Ala Asp
                 35                  40                  45

Leu Asp Lys Cys Met Asp Cys Ala Ser Cys Arg Ala Arg Pro His
                 50                  55                  60

Ser Asp Phe Cys Leu Gly Cys Ala Ala Pro Pro Ala Pro Phe
             65                  70                  75

Arg Leu Leu Trp Pro Ile Leu Gly Gly Ala Leu Ser Leu Thr Phe
                 80                  85                  90

Val Leu Gly Leu Leu Ser Gly Phe Leu Val Trp Arg Arg Cys Arg
                 95                 100                 105

Arg Arg Glu Lys Phe Thr Thr Pro Ile Glu Glu Thr Gly Gly Glu
                110                 115                 120

Gly Cys Pro Ala Val Ala Leu Ile Gln
                125

<210> SEQ ID NO 65
<211> LENGTH: 461
<212> TYPE: PRT
<213> ORGANISM: Homo sapiens
<220> FEATURE:
<221> NAME/KEY: misc_feature
<223> OTHER INFORMATION: Incyte ID No: 2479282

<400> SEQUENCE: 65

Met Ala Pro Gln Ser Leu Pro Ser Ser Arg Met Ala Pro Leu Gly
  1               5                  10                  15

Met Leu Leu Gly Leu Leu Met Ala Ala Cys Phe Thr Phe Cys Leu
                 20                  25                  30

Ser His Gln Asn Leu Lys Glu Phe Ala Leu Thr Asn Pro Glu Lys
                 35                  40                  45

Ser Ser Thr Lys Glu Thr Glu Arg Lys Glu Thr Lys Ala Glu Glu
                 50                  55                  60

Glu Leu Asp Ala Glu Val Leu Glu Val Phe His Pro Thr His Glu
                 65                  70                  75

Trp Gln Ala Leu Gln Pro Gly Gln Ala Val Pro Ala Gly Ser His
                 80                  85                  90
```

```
Val Arg Leu Asn Leu Gln Thr Gly Glu Arg Glu Ala Lys Leu Gln
             95                 100                 105

Tyr Glu Asp Lys Phe Arg Asn Asn Leu Lys Gly Lys Arg Leu Asp
            110                 115                 120

Ile Asn Thr Asn Thr Tyr Thr Ser Gln Asp Leu Lys Ser Ala Leu
            125                 130                 135

Ala Lys Phe Lys Glu Gly Ala Glu Met Glu Ser Ser Lys Glu Asp
            140                 145                 150

Lys Ala Arg Gln Ala Glu Val Lys Arg Leu Phe Arg Pro Ile Glu
            155                 160                 165

Glu Leu Lys Lys Asp Phe Asp Glu Leu Asn Val Val Ile Glu Thr
            170                 175                 180

Asp Met Gln Ile Met Val Arg Leu Ile Asn Lys Phe Asn Ser Ser
            185                 190                 195

Ser Ser Ser Leu Glu Glu Lys Ile Ala Ala Leu Phe Asp Leu Glu
            200                 205                 210

Tyr Tyr Val His Gln Met Asp Asn Ala Gln Asp Leu Leu Ser Phe
            215                 220                 225

Gly Gly Leu Gln Val Val Ile Asn Gly Leu Asn Ser Thr Glu Pro
            230                 235                 240

Leu Val Lys Glu Tyr Ala Ala Phe Val Leu Gly Ala Ala Phe Ser
            245                 250                 255

Ser Asn Pro Lys Val Gln Val Glu Ala Ile Glu Gly Gly Ala Leu
            260                 265                 270

Gln Lys Leu Leu Val Ile Leu Ala Thr Glu Gln Pro Leu Thr Ala
            275                 280                 285

Lys Lys Lys Val Leu Phe Ala Leu Cys Ser Leu Leu Arg His Phe
            290                 295                 300

Pro Tyr Ala Gln Arg Gln Phe Leu Lys Leu Gly Gly Leu Gln Val
            305                 310                 315

Leu Arg Thr Leu Val Gln Glu Lys Gly Thr Glu Val Leu Ala Val
            320                 325                 330

Arg Val Val Thr Leu Leu Tyr Asp Leu Val Thr Glu Lys Met Phe
            335                 340                 345

Ala Glu Glu Glu Ala Glu Leu Thr Gln Glu Met Ser Pro Glu Lys
            350                 355                 360

Leu Gln Gln Tyr Arg Gln Val His Leu Leu Pro Gly Leu Trp Glu
            365                 370                 375

Gln Gly Trp Cys Glu Ile Thr Ala His Leu Leu Ala Leu Pro Glu
            380                 385                 390

His Asp Ala Arg Glu Lys Val Leu Gln Thr Leu Gly Val Leu Leu
            395                 400                 405

Thr Thr Cys Arg Asp Arg Tyr Arg Gln Asp Pro Gln Leu Gly Arg
            410                 415                 420

Thr Leu Ala Ser Leu Gln Ala Glu Tyr Gln Val Leu Ala Ser Leu
            425                 430                 435

Glu Leu Gln Asp Gly Glu Asp Glu Gly Tyr Phe Gln Glu Leu Leu
            440                 445                 450

Gly Ser Val Asn Ser Leu Leu Lys Glu Leu Arg
            455                 460

<210> SEQ ID NO 66
<211> LENGTH: 264
<212> TYPE: PRT
```

```
<213> ORGANISM: Homo sapiens
<220> FEATURE:
<221> NAME/KEY: misc_feature
<223> OTHER INFORMATION: Incyte ID No: 2483432

<400> SEQUENCE: 66

Met Arg Pro Leu Leu Gly Leu Leu Leu Val Phe Ala Gly Cys Thr
 1               5                  10                  15

Phe Ala Leu Tyr Leu Leu Ser Thr Arg Leu Pro Arg Gly Arg Arg
                20                  25                  30

Leu Gly Ser Thr Glu Glu Ala Gly Gly Arg Ser Leu Trp Phe Pro
                35                  40                  45

Ser Asp Leu Ala Glu Leu Arg Glu Leu Ser Glu Val Leu Arg Glu
                50                  55                  60

Tyr Arg Lys Glu His Gln Ala Tyr Val Phe Leu Leu Phe Cys Gly
                65                  70                  75

Ala Tyr Leu Tyr Lys Gln Gly Phe Ala Ile Pro Gly Ser Ser Phe
                80                  85                  90

Leu Asn Val Leu Ala Gly Ala Leu Phe Gly Pro Trp Leu Gly Leu
                95                 100                 105

Leu Leu Cys Cys Val Leu Thr Ser Val Gly Ala Thr Cys Cys Tyr
               110                 115                 120

Leu Leu Ser Ser Ile Phe Gly Lys Gln Leu Val Val Ser Tyr Phe
               125                 130                 135

Pro Asp Lys Val Ala Leu Leu Gln Arg Lys Val Glu Glu Asn Arg
               140                 145                 150

Asn Ser Leu Phe Phe Phe Leu Leu Phe Leu Arg Leu Phe Pro Met
               155                 160                 165

Thr Pro Asn Trp Phe Leu Asn Leu Ser Ala Pro Ile Leu Asn Ile
               170                 175                 180

Pro Ile Val Gln Phe Phe Phe Ser Val Leu Ile Gly Leu Ile Pro
               185                 190                 195

Tyr Asn Phe Ile Cys Val Gln Thr Gly Ser Ile Leu Ser Thr Leu
               200                 205                 210

Thr Ser Leu Asp Ala Leu Phe Ser Trp Asp Thr Val Phe Lys Leu
               215                 220                 225

Leu Ala Ile Ala Met Val Ala Leu Ile Pro Gly Thr Leu Ile Lys
               230                 235                 240

Lys Phe Ser Gln Lys His Leu Gln Leu Asn Glu Thr Ser Thr Ala
               245                 250                 255

Asn His Ile His Ser Arg Lys Asp Thr
               260

<210> SEQ ID NO 67
<211> LENGTH: 339
<212> TYPE: PRT
<213> ORGANISM: Homo sapiens
<220> FEATURE:
<221> NAME/KEY: misc_feature
<223> OTHER INFORMATION: Incyte ID No: 2493824

<400> SEQUENCE: 67

Met Ala Ala Ala Cys Gly Pro Gly Ala Ala Gly Tyr Cys Leu Leu
 1               5                  10                  15

Leu Gly Leu His Leu Phe Leu Leu Thr Ala Gly Pro Ala Leu Gly
                20                  25                  30

Trp Asn Asp Pro Asp Arg Met Leu Leu Arg Asp Val Lys Ala Leu
                35                  40                  45
```

Thr Leu His Tyr Asp Arg Tyr Thr Thr Ser Arg Arg Leu Asp Pro
            50                  55                  60

Ile Pro Gln Leu Lys Cys Val Gly Thr Ala Gly Cys Asp Ser
        65                  70                  75

Tyr Thr Pro Lys Val Ile Gln Cys Gln Asn Lys Gly Trp Asp Gly
            80                  85                  90

Tyr Asp Val Gln Trp Glu Cys Lys Thr Asp Leu Asp Ile Ala Tyr
            95                  100                 105

Lys Phe Gly Lys Thr Val Val Ser Cys Glu Gly Tyr Glu Ser Ser
            110                 115                 120

Glu Asp Gln Tyr Val Leu Arg Gly Ser Cys Gly Leu Glu Tyr Asn
            125                 130                 135

Leu Asp Tyr Thr Glu Leu Gly Leu Gln Lys Leu Lys Glu Ser Gly
            140                 145                 150

Lys Gln His Gly Phe Ala Ser Phe Ser Asp Tyr Tyr Tyr Lys Trp
            155                 160                 165

Ser Ser Ala Asp Ser Cys Asn Met Ser Gly Leu Ile Thr Ile Val
            170                 175                 180

Val Leu Leu Gly Ile Ala Phe Val Val Tyr Lys Leu Phe Leu Ser
            185                 190                 195

Asp Gly Gln Tyr Ser Pro Pro Tyr Ser Glu Tyr Pro Pro Phe
            200                 205                 210

Ser His Arg Tyr Gln Arg Phe Thr Asn Ser Ala Gly Pro Pro Pro
            215                 220                 225

Pro Gly Phe Lys Ser Glu Phe Thr Gly Pro Gln Asn Thr Gly His
            230                 235                 240

Gly Ala Thr Ser Gly Phe Gly Ser Ala Phe Thr Gly Gln Gln Gly
            245                 250                 255

Tyr Glu Asn Ser Gly Pro Gly Phe Trp Thr Gly Leu Gly Thr Gly
            260                 265                 270

Gly Ile Leu Gly Tyr Leu Phe Gly Ser Asn Arg Ala Ala Thr Pro
            275                 280                 285

Phe Ser Asp Ser Trp Tyr Tyr Pro Ser Tyr Pro Pro Ser Tyr Pro
            290                 295                 300

Gly Thr Trp Asn Arg Ala Tyr Ser Pro Leu His Gly Gly Ser Gly
            305                 310                 315

Ser Tyr Ser Val Cys Ser Asn Ser Asp Thr Lys Thr Arg Thr Ala
            320                 325                 330

Ser Gly Tyr Gly Gly Thr Arg Arg
            335

<210> SEQ ID NO 68
<211> LENGTH: 397
<212> TYPE: PRT
<213> ORGANISM: Homo sapiens
<220> FEATURE:
<221> NAME/KEY: misc_feature
<223> OTHER INFORMATION: Incyte ID No: 2555823

<400> SEQUENCE: 68

Met Val Arg Pro Gly Ala Arg Leu Cys Leu Gly Ser Val Gly Arg
 1               5                  10                  15

Gly Leu Cys Leu Val Leu Pro Leu Leu Cys Leu Gly Ala Gly Phe
                20                  25                  30

Leu Phe Leu Asn Thr Leu Phe Ile Gln Arg Gly Arg His Glu Thr
                35                  40                  45

```
Thr Trp Thr Ile Leu Arg Arg Phe Gly Tyr Ser Asp Ala Leu Glu
             50                  55                  60

Leu Thr Ala Asp Tyr Leu Ser Pro Leu Ile His Val Pro Pro Gly
             65                  70                  75

Cys Ser Thr Glu Leu Asn His Leu Gly Tyr Gln Phe Val Gln Arg
             80                  85                  90

Val Phe Glu Lys His Asp Gln Asp Arg Asp Gly Ala Leu Ser Pro
             95                 100                 105

Val Glu Leu Gln Ser Leu Phe Ser Val Phe Pro Ala Ala Pro Trp
            110                 115                 120

Gly Pro Glu Leu Pro Arg Thr Val Arg Thr Glu Ala Gly Arg Leu
            125                 130                 135

Pro Leu His Gly Tyr Leu Cys Gln Trp Thr Leu Val Thr Tyr Leu
            140                 145                 150

Asp Val Arg Ser Cys Leu Gly His Leu Gly Tyr Leu Gly Tyr Pro
            155                 160                 165

Thr Leu Cys Glu Gln Asp Gln Ala His Ala Ile Thr Val Thr Arg
            170                 175                 180

Glu Lys Arg Leu Asp Gln Glu Lys Gly Gln Thr Gln Arg Ser Val
            185                 190                 195

Leu Leu Cys Lys Val Val Gly Ala Arg Gly Val Gly Lys Ser Ala
            200                 205                 210

Phe Leu Gln Ala Phe Leu Gly Arg Gly Leu Gly His Gln Asp Thr
            215                 220                 225

Arg Glu Gln Pro Pro Gly Tyr Ala Ile Asp Thr Val Gln Val Asn
            230                 235                 240

Gly Gln Glu Lys Tyr Leu Ile Leu Cys Glu Val Gly Thr Asp Gly
            245                 250                 255

Leu Leu Ala Thr Ser Leu Asp Ala Thr Cys Asp Val Ala Cys Leu
            260                 265                 270

Met Phe Asp Gly Ser Asp Pro Lys Ser Phe Ala His Cys Ala Ser
            275                 280                 285

Val Tyr Lys His His Tyr Met Asp Gly Gln Thr Pro Cys Leu Phe
            290                 295                 300

Val Ser Ser Lys Ala Asp Leu Pro Glu Gly Val Ala Val Ser Gly
            305                 310                 315

Pro Ser Pro Ala Glu Phe Cys Arg Lys His Arg Leu Pro Ala Pro
            320                 325                 330

Val Pro Phe Ser Cys Ala Gly Pro Ala Glu Pro Ser Thr Thr Ile
            335                 340                 345

Phe Thr Gln Leu Ala Thr Met Ala Ala Phe Pro His Leu Val His
            350                 355                 360

Ala Glu Leu His Pro Ser Ser Phe Trp Leu Arg Gly Leu Leu Gly
            365                 370                 375

Val Val Gly Ala Ala Val Ala Ala Val Leu Ser Phe Ser Leu Tyr
            380                 385                 390

Arg Val Leu Val Lys Ser Gln
            395
```

<210> SEQ ID NO 69
<211> LENGTH: 301
<212> TYPE: PRT
<213> ORGANISM: Homo sapiens
<220> FEATURE:
<221> NAME/KEY: misc_feature
<223> OTHER INFORMATION: Incyte ID No: 2598242

<400> SEQUENCE: 69

```
Met Glu Leu Ser Asp Val Thr Leu Ile Glu Gly Val Gly Asn Glu
 1               5                  10                  15
Val Met Val Val Ala Gly Val Val Leu Ile Leu Ala Leu Val
                20                  25                  30
Leu Ala Trp Leu Ser Thr Tyr Val Ala Asp Ser Gly Ser Asn Gln
                35                  40                  45
Leu Leu Gly Ala Ile Val Ser Ala Gly Asp Thr Ser Val Leu His
                50                  55                  60
Leu Gly His Val Asp His Leu Val Ala Gly Gln Gly Asn Pro Glu
                65                  70                  75
Pro Thr Glu Leu Pro His Pro Ser Glu Gly Asn Asp Glu Lys Ala
                80                  85                  90
Glu Glu Ala Gly Glu Gly Arg Gly Asp Ser Thr Gly Glu Ala Gly
                95                  100                 105
Ala Gly Gly Val Glu Pro Ser Leu Glu His Leu Leu Asp Ile
                110                 115                 120
Gln Gly Leu Pro Lys Arg Gln Ala Gly Ala Gly Ser Ser Ser Pro
                125                 130                 135
Glu Ala Pro Leu Arg Ser Glu Asp Ser Thr Cys Leu Pro Pro Ser
                140                 145                 150
Pro Gly Leu Ile Thr Val Arg Leu Lys Phe Leu Asn Asp Thr Glu
                155                 160                 165
Glu Leu Ala Val Ala Arg Pro Glu Asp Thr Val Gly Ala Leu Lys
                170                 175                 180
Ser Lys Tyr Phe Pro Gly Gln Glu Ser Gln Met Lys Leu Ile Tyr
                185                 190                 195
Gln Gly Arg Leu Leu Gln Asp Pro Ala Arg Thr Leu Arg Ser Leu
                200                 205                 210
Asn Ile Thr Asp Asn Cys Val Ile His Cys His Arg Ser Pro Pro
                215                 220                 225
Gly Ser Ala Val Pro Gly Pro Ser Ala Ser Leu Ala Pro Ser Ala
                230                 235                 240
Thr Glu Pro Pro Ser Leu Gly Val Asn Val Gly Ser Leu Met Val
                245                 250                 255
Pro Val Phe Val Val Leu Leu Gly Val Val Trp Tyr Phe Arg Ile
                260                 265                 270
Asn Tyr Arg Gln Phe Phe Thr Ala Pro Ala Thr Val Ser Leu Val
                275                 280                 285
Gly Val Thr Val Phe Phe Ser Phe Leu Val Phe Gly Met Tyr Gly
                290                 295                 300
Arg
```

<210> SEQ ID NO 70
<211> LENGTH: 217
<212> TYPE: PRT
<213> ORGANISM: Homo sapiens
<220> FEATURE:
<221> NAME/KEY: misc_feature
<223> OTHER INFORMATION: Incyte ID No: 2634120

<400> SEQUENCE: 70

```
Met Val Glu Val Gln Leu Glu Ser Asp His Glu Tyr Pro Pro Gly
 1               5                  10                  15
```

```
Leu Leu Val Ala Phe Ser Ala Cys Thr Thr Val Leu Val Ala Val
             20                  25                  30

His Leu Phe Ala Leu Met Val Ser Thr Cys Leu Leu Pro His Ile
             35                  40                  45

Glu Ala Val Ser Asn Ile His Asn Leu Asn Ser Val His Gln Ser
             50                  55                  60

Pro His Gln Arg Leu His Arg Tyr Val Glu Leu Ala Trp Gly Phe
             65                  70                  75

Ser Thr Ala Leu Gly Thr Phe Leu Phe Leu Ala Glu Val Val Leu
             80                  85                  90

Val Gly Trp Val Lys Phe Val Pro Ile Gly Ala Pro Leu Asp Thr
             95                 100                 105

Pro Thr Pro Met Val Pro Thr Ser Arg Val Pro Gly Thr Leu Ala
            110                 115                 120

Pro Val Ala Thr Ser Leu Ser Pro Ala Ser Asn Leu Pro Arg Ser
            125                 130                 135

Ser Ala Ser Ala Ala Pro Ser Gln Ala Glu Pro Ala Cys Pro Pro
            140                 145                 150

Arg Gln Ala Cys Gly Gly Gly Ala His Gly Pro Gly Trp Gln
            155                 160                 165

Ala Ala Met Ala Ser Thr Ala Ile Met Val Pro Val Gly Leu Val
            170                 175                 180

Phe Val Ala Phe Ala Leu His Phe Tyr Arg Ser Leu Val Ala His
            185                 190                 195

Lys Thr Asp Arg Tyr Lys Gln Glu Leu Glu Leu Asn Arg Leu
            200                 205                 210

Gln Gly Glu Leu Gln Ala Val
            215

<210> SEQ ID NO 71
<211> LENGTH: 143
<212> TYPE: PRT
<213> ORGANISM: Homo sapiens
<220> FEATURE:
<221> NAME/KEY: misc_feature
<223> OTHER INFORMATION: Incyte ID No: 2765411

<400> SEQUENCE: 71

Met Phe Pro Val Leu Gly Trp Ile Leu Ile Ala Val Val Ile Ile
  1               5                  10                  15

Ile Leu Leu Ile Phe Thr Ser Val Thr Arg Cys Leu Ser Pro Val
             20                  25                  30

Ser Phe Leu Gln Leu Lys Phe Trp Lys Ile Tyr Leu Glu Gln Glu
             35                  40                  45

Gln Gln Ile Leu Lys Ser Lys Ala Thr Glu His Ala Thr Glu Leu
             50                  55                  60

Ala Lys Glu Asn Ile Lys Cys Phe Phe Glu Gly Ser His Pro Lys
             65                  70                  75

Glu Tyr Asn Thr Pro Ser Met Lys Glu Trp Gln Gln Ile Ser Ser
             80                  85                  90

Leu Tyr Thr Phe Asn Pro Lys Gly Gln Tyr Tyr Ser Met Leu His
             95                 100                 105

Lys Tyr Val Asn Arg Lys Glu Lys Thr His Ser Ile Arg Ser Thr
            110                 115                 120

Glu Gly Asp Thr Val Ile Pro Val Leu Gly Phe Val Asp Ser Ser
            125                 130                 135
```

```
Gly Ile Asn Ser Thr Pro Glu Leu
            140
```

```
<210> SEQ ID NO 72
<211> LENGTH: 186
<212> TYPE: PRT
<213> ORGANISM: Homo sapiens
<220> FEATURE:
<221> NAME/KEY: misc_feature
<223> OTHER INFORMATION: Incyte ID No: 2769412

<400> SEQUENCE: 72

Met Ser Gly Ile Ser Gly Cys Pro Phe Phe Leu Trp Gly Leu Leu
 1               5                  10                  15

Ala Leu Leu Gly Leu Ala Leu Val Ile Ser Leu Ile Phe Asn Ile
                20                  25                  30

Ser His Tyr Val Glu Lys Gln Arg Gln Asp Lys Met Tyr Ser Tyr
                35                  40                  45

Ser Ser Asp His Thr Arg Val Asp Glu Tyr Tyr Ile Glu Asp Thr
                50                  55                  60

Pro Ile Tyr Gly Asn Leu Asp Asp Met Ile Ser Glu Pro Met Asp
                65                  70                  75

Glu Asn Cys Tyr Glu Gln Met Lys Ala Arg Pro Glu Lys Ser Val
                80                  85                  90

Asn Lys Met Gln Glu Ala Thr Pro Ser Ala Gln Ala Thr Asn Glu
                95                 100                 105

Thr Gln Met Cys Tyr Ala Ser Leu Asp His Ser Val Lys Gly Lys
               110                 115                 120

Arg Arg Lys Pro Arg Lys Gln Asn Thr His Phe Ser Asp Lys Asp
               125                 130                 135

Gly Asp Glu Gln Leu His Ala Ile Asp Ala Ser Val Ser Lys Thr
               140                 145                 150

Thr Leu Val Asp Ser Phe Ser Pro Glu Ser Gln Ala Val Glu Glu
               155                 160                 165

Asn Ile His Asp Asp Pro Ile Arg Leu Phe Gly Leu Ile Arg Ala
               170                 175                 180

Lys Arg Glu Pro Ile Asn
               185
```

```
<210> SEQ ID NO 73
<211> LENGTH: 364
<212> TYPE: PRT
<213> ORGANISM: Homo sapiens
<220> FEATURE:
<221> NAME/KEY: misc_feature
<223> OTHER INFORMATION: Incyte ID No: 2842779

<400> SEQUENCE: 73

Met Pro Gly Cys Pro Cys Pro Gly Cys Gly Met Ala Gly Pro Arg
 1               5                  10                  15

Leu Leu Phe Leu Thr Ala Leu Ala Leu Glu Leu Leu Gly Arg Ala
                20                  25                  30

Gly Gly Ser Gln Pro Ala Leu Arg Ser Arg Gly Thr Ala Thr Ala
                35                  40                  45

Cys Arg Leu Asp Asn Lys Glu Ser Glu Ser Trp Gly Ala Leu Leu
                50                  55                  60

Ser Gly Glu Arg Leu Asp Thr Trp Ile Cys Ser Leu Leu Gly Ser
                65                  70                  75

Leu Met Val Gly Leu Ser Gly Val Phe Pro Leu Leu Val Ile Pro
```

```
                      80                  85                  90
Leu Glu Met Gly Thr Met Leu Arg Ser Glu Ala Gly Ala Trp Arg
                 95                 100                 105
Leu Lys Gln Leu Leu Ser Phe Ala Leu Gly Gly Leu Leu Gly Asn
                110                 115                 120
Val Phe Leu His Leu Leu Pro Glu Ala Trp Ala Tyr Thr Cys Ser
                125                 130                 135
Ala Ser Pro Gly Gly Glu Gly Gln Ser Leu Gln Gln Gln Gln Gln
                140                 145                 150
Leu Gly Leu Trp Val Ile Ala Gly Ile Leu Thr Phe Leu Ala Leu
                155                 160                 165
Glu Lys Met Phe Leu Asp Ser Lys Glu Glu Gly Thr Ser Gln Ala
                170                 175                 180
Pro Asn Lys Asp Pro Thr Ala Ala Ala Ala Leu Asn Gly Gly
                185                 190                 195
His Cys Leu Ala Gln Pro Ala Ala Glu Pro Gly Leu Gly Ala Val
                200                 205                 210
Val Arg Ser Ile Lys Val Ser Gly Tyr Leu Asn Leu Leu Ala Asn
                215                 220                 225
Thr Ile Asp Asn Phe Thr His Gly Leu Ala Val Ala Ala Ser Phe
                230                 235                 240
Leu Val Ser Lys Lys Ile Gly Leu Leu Thr Thr Met Ala Ile Leu
                245                 250                 255
Leu His Glu Ile Pro His Glu Val Gly Asp Phe Ala Ile Leu Leu
                260                 265                 270
Arg Ala Gly Phe Asp Arg Trp Ser Ala Ala Lys Leu Gln Leu Ser
                275                 280                 285
Thr Ala Leu Gly Gly Leu Leu Gly Ala Gly Phe Ala Ile Cys Thr
                290                 295                 300
Gln Ser Pro Lys Gly Val Glu Gly Thr Ala Ala Trp Val Leu Pro
                305                 310                 315
Phe Thr Ser Gly Gly Phe Leu Tyr Ile Ala Leu Val Asn Val Leu
                320                 325                 330
Pro Asp Leu Leu Glu Glu Glu Asp Pro Trp Arg Ser Leu Gln Gln
                335                 340                 345
Leu Leu Leu Leu Cys Ala Gly Ile Val Val Met Val Leu Phe Ser
                350                 355                 360
Leu Phe Val Asp

<210> SEQ ID NO 74
<211> LENGTH: 605
<212> TYPE: PRT
<213> ORGANISM: Homo sapiens
<220> FEATURE:
<221> NAME/KEY: misc_feature
<223> OTHER INFORMATION: Incyte ID No: 2966260

<400> SEQUENCE: 74

Met Gly Arg Leu Leu Arg Ala Arg Leu Pro Pro Leu Leu Ser
  1               5                  10                  15
Pro Leu Leu Leu Leu Val Gly Gly Ala Phe Leu Gly Ala Cys
                 20                  25                  30
Val Ala Gly Ser Asp Glu Pro Gly Pro Glu Gly Leu Thr Ser Thr
                 35                  40                  45
Ser Leu Leu Asp Leu Leu Leu Pro Thr Gly Leu Glu Pro Leu Asp
                 50                  55                  60
```

Ser Glu Glu Pro Ser Glu Thr Met Gly Leu Gly Ala Gly Leu Gly
              65                  70                  75

Ala Pro Gly Ser Gly Phe Pro Ser Glu Glu Asn Glu Glu Ser Arg
          80                  85                  90

Ile Leu Gln Pro Pro Gln Tyr Phe Trp Glu Glu Glu Glu Glu Leu
              95                 100                 105

Asn Asp Ser Ser Leu Asp Leu Gly Pro Thr Ala Asp Tyr Val Phe
            110                 115                 120

Pro Asp Leu Thr Glu Lys Ala Gly Ser Ile Glu Asp Thr Ser Gln
            125                 130                 135

Ala Gln Glu Leu Pro Asn Leu Pro Ser Pro Leu Pro Lys Met Asn
            140                 145                 150

Leu Val Glu Pro Pro Trp His Met Pro Pro Arg Glu Glu Glu Glu
            155                 160                 165

Glu Glu Glu Glu Glu Glu Met Glu Lys Glu Glu Val Glu Lys
            170                 175                 180

Gln Asp Val Glu Glu Glu Glu Leu Leu Pro Val Asn Gly Ser
            185                 190                 195

Gln Glu Glu Ala Lys Pro Gln Val Arg Asp Phe Ser Leu Thr Ser
            200                 205                 210

Ser Ser Gln Thr Pro Gly Ala Thr Lys Ser Arg His Glu Asp Ser
            215                 220                 225

Gly Asp Gln Ala Ser Ser Gly Val Glu Val Glu Ser Ser Met Gly
            230                 235                 240

Pro Ser Leu Leu Leu Pro Ser Val Thr Pro Thr Ile Val Thr Pro
            245                 250                 255

Gly Asp Gln Asp Ser Thr Ser Gln Glu Ala Glu Ala Thr Val Leu
            260                 265                 270

Pro Ala Ala Gly Leu Gly Val Glu Phe Glu Ala Pro Gln Glu Ala
            275                 280                 285

Ser Glu Glu Ala Thr Ala Gly Ala Ala Gly Leu Ser Gly Gln His
            290                 295                 300

Glu Glu Val Pro Ala Leu Pro Ser Phe Pro Gln Thr Thr Ala Pro
            305                 310                 315

Ser Gly Ala Glu His Pro Asp Glu Asp Pro Leu Gly Ser Arg Thr
            320                 325                 330

Ser Ala Ser Ser Pro Leu Ala Pro Gly Asp Met Glu Leu Thr Pro
            335                 340                 345

Ser Ser Ala Thr Leu Gly Gln Glu Asp Leu Asn Gln Gln Leu Leu
            350                 355                 360

Glu Gly Gln Ala Ala Glu Ala Gln Ser Arg Ile Pro Trp Asp Ser
            365                 370                 375

Thr Gln Val Ile Cys Lys Asp Trp Ser Asn Leu Ala Gly Lys Asn
            380                 385                 390

Tyr Ile Ile Leu Asn Met Thr Glu Asn Ile Asp Cys Glu Val Phe
            395                 400                 405

Arg Gln His Arg Gly Pro Gln Leu Leu Ala Leu Val Glu Glu Val
            410                 415                 420

Leu Pro Arg His Gly Ser Gly His His Gly Ala Trp His Ile Ser
            425                 430                 435

Leu Ser Lys Pro Ser Glu Lys Glu Gln His Leu Leu Met Thr Leu
            440                 445                 450

Val Gly Glu Gln Gly Val Val Pro Thr Gln Asp Val Leu Ser Met

```
                    455                 460                 465

Leu Gly Asp Ile Arg Arg Ser Leu Glu Glu Ile Gly Ile Gln Asn
                470                 475                 480

Tyr Ser Thr Thr Ser Ser Cys Gln Ala Arg Ala Ser Gln Val Arg
                485                 490                 495

Ser Asp Tyr Gly Thr Leu Phe Val Val Leu Val Val Ile Gly Ala
                500                 505                 510

Ile Cys Ile Ile Ile Ile Ala Leu Gly Leu Leu Tyr Asn Cys Trp
                515                 520                 525

Gln Arg Arg Leu Pro Lys Leu Lys His Val Ser His Gly Glu Glu
                530                 535                 540

Leu Arg Phe Val Glu Asn Gly Cys His Asp Asn Pro Thr Leu Asp
                545                 550                 555

Val Ala Ser Asp Ser Gln Ser Glu Met Gln Glu Lys His Pro Ser
                560                 565                 570

Leu Asn Gly Gly Gly Ala Leu Asn Gly Pro Gly Ser Trp Gly Ala
                575                 580                 585

Leu Met Gly Gly Lys Arg Asp Pro Glu Asp Ser Asp Val Phe Glu
                590                 595                 600

Glu Asp Thr His Leu
                605

<210> SEQ ID NO 75
<211> LENGTH: 97
<212> TYPE: PRT
<213> ORGANISM: Homo sapiens
<220> FEATURE:
<221> NAME/KEY: misc_feature
<223> OTHER INFORMATION: Incyte ID No: 2993326

<400> SEQUENCE: 75

Met Thr Gly Arg Phe Lys Ala Cys Gln Val Ile Leu Gly Leu Leu
  1               5                  10                  15

Val Ala Ile Ser Leu Ala Ala Gly Thr Gly Ala Ala Gly Ala
                 20                  25                  30

Ala Leu Val Ile Val Phe Ile Gly Ala Phe Leu Val Leu Leu Phe
                 35                  40                  45

Leu Gly Arg Leu Thr Thr Gly Gly Ser Met Ala Arg Glu Ser Leu
                 50                  55                  60

Val Ala Ala Asn Arg Val Cys Ile Ser Arg Thr Leu Ser Ser Ser
                 65                  70                  75

Val Val Ser Val Cys Ile Ser Gly Gly Lys Gly Ser Pro Arg Leu
                 80                  85                  90

Pro Gly Gly Gly Arg Gly Pro
                 95

<210> SEQ ID NO 76
<211> LENGTH: 247
<212> TYPE: PRT
<213> ORGANISM: Homo sapiens
<220> FEATURE:
<221> NAME/KEY: misc_feature
<223> OTHER INFORMATION: Incyte ID No: 3001124

<400> SEQUENCE: 76

Met Val Thr Leu Val Ser Asp Thr Ala Met Thr Pro Ile Ala Ser
  1               5                  10                  15

Val Asp Thr Ile Ala Val Cys Leu Phe Ala Gly Ala Trp Gly Gly
                 20                  25                  30
```

```
Ala Met Val Pro Met His Leu Leu Gly Arg Leu Glu Lys Pro Leu
             35                  40                  45

Leu Leu Leu Cys Cys Ala Ser Phe Leu Leu Gly Leu Ala Leu Leu
         50                  55                  60

Gly Ile Lys Thr Asp Ile Thr Pro Val Ala Tyr Phe Phe Leu Thr
 65                  70                  75

Leu Gly Gly Phe Phe Leu Phe Ala Tyr Leu Leu Val Arg Phe Leu
             80                  85                  90

Glu Trp Gly Leu Arg Ser Gln Leu Gln Ser Met Gln Thr Glu Ser
         95                 100                 105

Pro Gly Pro Ser Gly Asn Ala Arg Asp Asn Glu Ala Phe Glu Val
            110                 115                 120

Pro Val Tyr Glu Glu Ala Val Val Gly Leu Glu Ser Gln Cys Arg
            125                 130                 135

Pro Gln Glu Leu Asp Gln Pro Pro Tyr Ser Thr Val Val Ile
            140                 145                 150

Pro Pro Ala Pro Glu Glu Gln Pro Ser His Pro Glu Gly Ser
            155                 160                 165

Arg Arg Ala Lys Leu Glu Gln Arg Arg Met Ala Ser Glu Gly Ser
            170                 175                 180

Met Ala Gln Glu Gly Ser Pro Gly Arg Ala Pro Ile Asn Leu Arg
            185                 190                 195

Leu Arg Gly Pro Arg Ala Val Ser Thr Ala Pro Asp Leu Gln Ser
            200                 205                 210

Leu Ala Ala Val Pro Thr Leu Glu Pro Leu Thr Pro Pro Ala
            215                 220                 225

Tyr Asp Val Cys Phe Gly His Pro Asp Asp Ser Val Phe Tyr
            230                 235                 240

Glu Asp Asn Trp Ala Pro Pro
            245

<210> SEQ ID NO 77
<211> LENGTH: 193
<212> TYPE: PRT
<213> ORGANISM: Homo sapiens
<220> FEATURE:
<221> NAME/KEY: misc_feature
<223> OTHER INFORMATION: Incyte ID No: 3120070

<400> SEQUENCE: 77

Met Ile Arg Cys Gly Leu Ala Cys Glu Arg Cys Arg Trp Ile Leu
  1               5                  10                  15

Pro Leu Leu Leu Leu Ser Ala Ile Ala Phe Asp Ile Ile Ala Leu
             20                  25                  30

Ala Gly Arg Gly Trp Leu Gln Ser Ser Asp His Gly Gln Thr Ser
             35                  40                  45

Ser Leu Trp Trp Lys Cys Ser Gln Glu Gly Gly Ser Gly Ser
         50                  55                  60

Tyr Glu Glu Gly Cys Gln Ser Leu Met Glu Tyr Ala Trp Gly Arg
 65                  70                  75

Ala Ala Ala Ala Met Leu Phe Cys Gly Phe Ile Ile Leu Val Ile
             80                  85                  90

Cys Phe Ile Leu Ser Phe Phe Ala Leu Cys Gly Pro Gln Met Leu
             95                 100                 105

Val Phe Leu Arg Val Ile Gly Gly Leu Leu Ala Leu Ala Ala Val
            110                 115                 120
```

-continued

```
Phe Gln Ile Ile Ser Leu Val Ile Tyr Pro Val Lys Tyr Thr Gln
                125                 130                 135

Thr Phe Thr Leu His Ala Asn Pro Ala Val Thr Tyr Ile Tyr Asn
                140                 145                 150

Trp Ala Tyr Gly Phe Gly Trp Ala Ala Thr Ile Ile Leu Ile Gly
                155                 160                 165

Cys Ala Phe Phe Phe Cys Cys Leu Pro Asn Tyr Glu Asp Asp Leu
                170                 175                 180

Leu Gly Asn Ala Lys Pro Arg Tyr Phe Tyr Thr Ser Ala
                185                 190

<210> SEQ ID NO 78
<211> LENGTH: 128
<212> TYPE: PRT
<213> ORGANISM: Homo sapiens
<220> FEATURE:
<221> NAME/KEY: misc_feature
<223> OTHER INFORMATION: Incyte ID No: 3133035

<400> SEQUENCE: 78

Met Asn Met Lys Gln Lys Ser Val Tyr Gln Gln Thr Lys Ala Leu
  1               5                  10                  15

Leu Cys Lys Asn Phe Leu Lys Lys Trp Arg Met Lys Arg Glu Ser
                 20                  25                  30

Leu Leu Glu Trp Gly Leu Ser Ile Leu Leu Gly Leu Cys Ile Ala
                 35                  40                  45

Leu Phe Ser Ser Ser Met Arg Asn Val Gln Phe Pro Gly Met Ala
                 50                  55                  60

Pro Gln Asn Leu Gly Arg Val Asp Lys Phe Asn Ser Ser Ser Leu
                 65                  70                  75

Met Val Val Tyr Thr Pro Ile Ser Asn Leu Thr Gln Gln Ile Met
                 80                  85                  90

Asn Lys Thr Ala Leu Ala Pro Leu Leu Lys Gly Thr Ser Val Ile
                 95                 100                 105

Gly Ala Gln Ile Ile His Thr Trp Thr Lys Tyr Phe Trp Lys Ile
                110                 115                 120

Tyr Ile Cys Tyr Gly Asn His Leu
                125

<210> SEQ ID NO 79
<211> LENGTH: 115
<212> TYPE: PRT
<213> ORGANISM: Homo sapiens
<220> FEATURE:
<221> NAME/KEY: misc_feature
<223> OTHER INFORMATION: Incyte ID No: 3436879

<400> SEQUENCE: 79

Met Ala Val Ala Val Leu Leu Cys Gly Cys Ile Val Ala Thr Val
  1               5                  10                  15

Ser Phe Phe Trp Glu Glu Ser Leu Thr Gln His Val Ala Gly Leu
                 20                  25                  30

Leu Phe Leu Met Thr Gly Ile Phe Cys Thr Ile Ser Leu Cys Thr
                 35                  40                  45

Tyr Ala Ala Ser Ile Ser Tyr Asp Leu Asn Arg Leu Pro Lys Leu
                 50                  55                  60

Ile Tyr Ser Leu Pro Ala Asp Val Glu His Gly Tyr Ser Trp Ser
                 65                  70                  75
```

```
Ile Phe Cys Ala Trp Cys Ser Leu Gly Phe Ile Val Ala Ala Gly
            80                  85                  90

Gly Leu Cys Ile Ala Tyr Pro Phe Ile Ser Arg Thr Lys Ile Ala
            95                 100                 105

Gln Leu Lys Ser Gly Arg Asp Ser Thr Val
            110                 115

<210> SEQ ID NO 80
<211> LENGTH: 1869
<212> TYPE: DNA
<213> ORGANISM: Homo sapiens
<220> FEATURE:
<221> NAME/KEY: misc_feature
<223> OTHER INFORMATION: Incyte ID No: 153831

<400> SEQUENCE: 80
```

| | | | | | |
|---|---|---|---|---|---|
| gcgagcggct | ggcggatccg | acgcgcgaga | ccgggagggg | acgagggcgt | tgcaatcgtt | 60 |
| cggggcgggg | gctttccggg | gagggggtgc | tcaggtgcac | cagcggcggc | ggaccctcag | 120 |
| actctgccct | cccctcccct | taaccccctt | ccagccggac | gggaggcggg | gcagggctga | 180 |
| gcatttgtga | cacctacatt | tccgtggctc | ccttcttttc | ccccgacccc | tgtttatctc | 240 |
| ttcgccttcc | agaagttctt | ttccatcagg | ccgtcgcacc | ttgcgtggga | aggagcaccc | 300 |
| cacttggaag | caggaggcgg | ggttcagatc | ttggccctac | ccctcctgtg | ttaaagtccg | 360 |
| cgagcctcag | tttccctcac | agtatttttt | gcctcgcctt | acccggtttt | gaggatctgt | 420 |
| acgagaaaga | gaaggaagt | ggacatttgt | tgaattcctg | catggccaaa | taccacgcag | 480 |
| actgcttcat | ccgccacgtt | taatccttat | tacttggtgt | tctcagaact | cccatttcat | 540 |
| ggattcttaa | gctcacagag | tcagtgaata | acagaaaggg | attcagatct | agccgtttag | 600 |
| ctgcacagtg | gagttcttct | ccagagtctt | cccttgtctg | ggctctggct | ggaactattc | 660 |
| ctcagccaaa | tcctcgcccc | agaacagtgc | ttcctgtttc | tccagctgag | aagtctccct | 720 |
| ttcagttttcc | ttcttccagc | acggagtaca | ctgctctgcc | tccacttaga | ttacttcaga | 780 |
| aatgaaatgc | agcaaatatt | tatccagcag | tgcagggagt | tgaacttttg | gagtcgggaa | 840 |
| ccttggattc | ttgttctggc | tctgccactt | actgtgtggc | cttgggaagt | cctttgtctt | 900 |
| ctctgagctt | tcttttctct | ttgcgtaaaa | gcggtgctct | tgtcccattc | tccctccctg | 960 |
| tcttccagca | ggctctcccc | ggaggctcag | ccccctctgc | tccccatggg | caactgccag | 1020 |
| gcagggcaca | acctgcacct | gtgtctggcc | caccacccac | ctctggtctg | tgccactttg | 1080 |
| atcctgctgc | tccttggcct | ctctggcctg | ggccttggca | gcttcctcct | cacccacagg | 1140 |
| actggcctgc | gcagccctga | catccccag | gactgggtct | cttttttgag | atcttttggc | 1200 |
| cagctgaccc | tgtgtcccag | gaatgggaca | gtcacaggga | agtggcgagg | gtctcacgtc | 1260 |
| gtgggcttgc | tgaccacctt | gaacttcgga | gacggtccag | acaggaacaa | gacccggaca | 1320 |
| ttccaggcca | cagtcctggg | aagtcagatg | ggattgaaag | gatcttctgc | aggacaactg | 1380 |
| gtccttatca | cagccagggt | gaccacagaa | aggactgcag | gaacctgcct | atatttagt | 1440 |
| gctgttccag | gaatcctacc | ctccagccag | ccacccatat | cctgctcaga | ggaggggct | 1500 |
| ggaaatgcca | ccctgagccc | tagaatgggt | gaggaatgtg | ttagtgtctg | gagccatgaa | 1560 |
| ggccttgtgc | tgaccaagct | gctcacctcg | gaggagctgg | ctctgtgtgg | ctccaggctg | 1620 |
| ctggtcttgg | gctccttcct | gcttctcttc | tgtggccttc | tctgctgtgt | cactgctatg | 1680 |
| tgcttccacc | cgcgccggga | gtcccactgg | tctagaaccc | ggctctgagg | gcactggcct | 1740 |
| agttcccgac | ttgtttctca | ggtgtgaatc | aacttcttgg | gccttggctc | tgagttggaa | 1800 |

```
aaggttttag aaaaagtgaa gagctggaat gtgggggaaa ataaaaagct tttttgccca     1860
aaaaaaaaa                                                             1869

<210> SEQ ID NO 81
<211> LENGTH: 1044
<212> TYPE: DNA
<213> ORGANISM: Homo sapiens
<220> FEATURE:
<221> NAME/KEY: misc_feature
<223> OTHER INFORMATION: Incyte ID No: 350629

<400> SEQUENCE: 81
tgcagttaac atctgcacac ttcactatat tttaagtttt tgttaatata aagaataag       60 aaaacagaaa agtattactg ttaaacaata atagagaaat gtatacttta tttacaaatt    120
tctccctcta gctgatcata cagttgacca gttcagggtg cccgctgctg gttggatgcc    180
aggcggaatg tcagggtgtt ctctggtgtc tgttgtggct gtgggatcca cggttactgg    240
gcggagcctg tggtggctgt ggtgccatgg aggggctgcg atcttctgtg gagctggacc    300
ctgagctgac tccagggaag ctggatgagg agatggtggg gctgccaccc catgacgcga    360
gtcctcaagt cactttccac agcctcgatg ggaagacagt ggtgtgtcca cacttcatgg    420
gcttactgct gggtctctta ctttttattga ctttgtctgt taggaaccaa ctctgtgtaa    480
gaggtgaaag gcagcttgca gaaacactgc attcacaggt gaaggagaaa tcccagctca    540
ttggcaagaa aacagattgt agagactgag gcatctttaa aagatgtcag ggtacagaaa    600
aagtctttca acaccccgg ctttgtagat gcctacaaga aggtgaatag caccaacgag     660
atgctgatgg agaaatttac caccctcgtt caagaactga agaagagac atcctccaga     720 ctctcctcaa tgggcggtgc ctccaaatct aaagaatatg gaggtcctgg agcacaccaa    780
gaaatgaggg acttttctt tgcagaaagt ttgaattctg tcttaatgag acagaatgcc     840
atacttgagc acctcatctt ttgctcaaat tgaaatgtca tcgaactgta tttctcaagt    900
caatggtctg taaatatgat ttatgtatta atctcctaag tgaacaattt atattttatc    960
ctctacataa ttatcgtatt atgctttaaa tatatattta gtttatcaat aaagacattc   1020
agtactcaat agcaaaaaaa aaaa                                          1044

<210> SEQ ID NO 82
<211> LENGTH: 3079
<212> TYPE: DNA
<213> ORGANISM: Homo sapiens
<220> FEATURE:
<221> NAME/KEY: misc_feature
<223> OTHER INFORMATION: Incyte ID No: 729171

<400> SEQUENCE: 82
cggctcgagg tcggctggag tcggaggcga tatttctagg ggtgtacttg ttggggtcag      60
ggtaagcacc agccacaaaa acctacaaaa gaagggaaat tactgtcttt aaatattaaa    120
aaaaaacaag atccatgagt gggcatcgat caacaaggaa aagatgtgga gattcccacc    180
cggagtcccc agtgggcttc gggcatatga gtactacagg atgtgtatta aataaattgt    240
ttcagttacc aacaccacca ttgtcaagac accaactaaa gcggctagaa gaacacagat    300
atcaaagtgc tggacggtcc ctgcttgagc ccttagtgca agggtattgg aatggctcg     360 ttagaagagt tccctcctgg attgccccaa atctcatcac catcattgga ctgtcaataa    420
acatctgtac aactatttta ttagtcttct actgccctac agctacagag caggcacctc    480
tgtgggcata tattgcttgt gcctgtggcc ttttcattta ccagtctttg gatgctattg    540
```

```
gtgggaaaca ggcaagaaga accaatagta gttctcctct gggagaactt tttgatcatg   600
gctgtgattc actatcaaca gtttttgtgg ttcttggaac ttgtatagca gtgcagctgg   660
ggacaaaccc tgattggatg ttttttttgtt gttttgcggg gacatttatg ttctattgtg   720
cgcactggca aacgtatgtt tctgaacat tgcgatttgg aataattgat gtgactgaag   780
tgcaaatctt cataataatc atgcatttgc tggcagtgat gggaggacca ccttttttggc   840 aatctatgat tccagtgctg aatattcaaa tgaaaatttt tcctgcactt tgtactgtag   900
cagggaccat atttcctgta acaaattact tccgtgtaat cttcacaggt ggtgttggca   960
aaaatggatc aacaatagca ggaacaagtg tcctttctcc ttttctccat attggatcag  1020
tgattacatt agctgcaatg atctacaaga aatctgcagt tcagcttttt gaaaagcatc  1080
cctgtcttta tatactgaca tttggttttta tgtctgctaa aatcactaat aagcttgtgg  1140
ttgcacacat gacgaaaagt gaaatgcatt tgcatgacac agcattcata ggtccggcac  1200 tttttgtttct ggaccagtat tttaacagct ttattgatga atatattgta ctttggattg  1260
ccctggtttt ctctttcttt gatttgatcc gctactgtgt cagtgtttgc aatcagattg  1320
cgtctcacct gcacatacat gtcttcagaa tcaaggtctc tacagctcat tctaatcatc  1380
attaatgatg taattggtat ataggaacat catgttttct gcaggaaaga aagtaacata  1440
ttaaggagaa tgggggtgga taagaacaaa tataatttat aataatcaat gttgtataac  1500
ttttattctt tattattggt aacacgccct aactatcctg tgtgagaatg ggaatttcaa  1560
gtcccatctt gtaaattgta tatgttgtca tgcagggttt gggccaagaa agcatgcaga  1620
aaaaaatgcc atgtgattgt aattatcctg gattcagaat aatactgtga tggggagcca  1680
gatccgcagt ggtggagagt tctaatgttg actgtttgca ggccaaaaga tgattgcttt  1740
ataattttaa caaatcattg tcttttagta acatccttgt ttagtgtctt ctcaagcttt  1800
ctttactgag gaattcagct tgtgacacag atacatccca ctagcttgtg aggtggaact  1860
agtaataaag accttgaatt tggattgaaa agtttcctat ctttacattg ttgaggaagt  1920
cctttttttt ttttttttttt tttttaattg ctcaagaaat gattctctca caggcttggg  1980
aaatcctgtt agcatgcaga ataatgtggt aactttgtca atttcccatt ttattttttt  2040
aaataaatat atgatctaaa agccaacttt ttctcagttt tactcagtgg aaagataaac  2100
taagttttaa tgttatttttt ttaaatttaa gcaaaattta tttctgttct ttaataaata  2160
agaaaatgtg gtccactgca ttgttgtgat gtgtcttgtg acatttctat tttgtagaaa  2220
cttttaaaag gagaactatg ttcattttttc ctgtcaatgg tttttttgtg ttgtagttgt  2280
cacctgtgtg attatcaatc atttagaaat ctcataccct tcccctaaat tttcagcaag  2340
tgcctgggcc tctctaagag gtcacttttgt actctccttt tctggcagtc tcctcttttgg  2400 tatctgtact atcgtttgaa atgggaacca gatatgtttc catttttatac agataattca  2460 gttgcttgaa gaagagggac acaggagaaa agatttaaac tattggctaa aatgaggtgt  2520
cttattattg attttcatct atatcttgtc ccataatcag gaataaacag tagctacact  2580
gccttgtatg gcagccagag cgctgcttgc ttgcactttt aatgattcca tcaataccat  2640
gtagattgaa ttagcaagga gaagtaaacc tttcatttct ttgccagact atattgggaa  2700
atgaaaatcc gtcattactt ttccttgcta gcaattgttc gaatatctgg gataaagaaa  2760
tacatacagg aaaatgttag ggcagaccaa gtattaaaag ctaggacaga gcaggacaaa  2820
ggaggaagga taattctact tgtttggcaa agttacatca gttgtcttac tgacacatca  2880
ggtactatct atagtggaaa ttgaggcccg gagaggttaa atggcatgcc agtgtcactt  2940
```

| | |
|---|---|
| gctattttto agaacaaaaa ttagaatcca gatctgaatc ctggtgcagt gttctctcct | 3000 |
| atgccctact gggctttagt gggctaaagt tctgaagcaa gatgttaagg gctaattgaa | 3060 |
| atgcgtttat tctcctaga | 3079 |

<210> SEQ ID NO 83
<211> LENGTH: 1298
<212> TYPE: DNA
<213> ORGANISM: Homo sapiens
<220> FEATURE:
<221> NAME/KEY: misc_feature
<223> OTHER INFORMATION: Incyte ID No: 1273641

<400> SEQUENCE: 83

| | |
|---|---|
| cccggtgcct gcgggattgc tggagagaac gcggcgatgg agccgggcag gacccagata | 60 |
| aagcttgacc ccaggtacac agcagatctt ctggaggtgc tgaagaccaa ttacggcatc | 120 |
| ccctccgcct gcttctctca gcctcccaca gcagcccact cctgagagcc ctgggccctg | 180 |
| tggaacttgc cctcactagc atcctgacct tgctggcgct gggctccatt gccatcttcc | 240 |
| tggaggatgc cgtctacctg tacaagaaca ccctttgccc catcaagagg cggactctgc | 300 |
| tctggaagag ctcggcaccc acggtggtgt ctgtgctgtg ctgctttggt ctctggatcc | 360 |
| ctcgttccct ggtgctggtg gaaatgacca tcacctcgtt ttatgccgtg tgcttttacc | 420 |
| tgctgatgct ggtcatggtg gaaggctttg ggggaagga ggcagtgctg aggacgctga | 480 |
| gggacacccc gatgatggtc cacacaggcc cctgctgctg ctgctgcccc tgctgtcaac | 540 |
| ggctgctgct caccaggaag aagcttcagc tgctgatgtt gggccctttc caatacgcct | 600 |
| tcttgaagat aacgctgacc tggtgggcct tgttctcgtc cccgacggaa tcttatgacc | 660 |
| cagcagacat ttctgagggg agcacagctc tatggatcaa cactttcctt ggcgtgtcca | 720 |
| cactgctggc tctctggacc ctgggcatca tttcccgtca agccaggcta cacctgggtg | 780 |
| agcagaacat gggagccaaa tttgctctgt tccaggttct cctcatcctg actgccctac | 840 |
| agccctccat cttctcagtc ttggccaacg gtgggcagat tgcttgttcg cctccctatt | 900 |
| cctctaaaac caggtctcaa gtgatgaatt gccacctcct catactggag acttttctaa | 960 |
| tgactgtgct gacacgaatg tactaccgaa ggaaagacca caaggttggg tatgaaactt | 1020 |
| tctcttctcc agacctggac ttgaacctca agcctaagg tggatggctt ggacaatgaa | 1080 |
| aggatgctgt actcattaga atacaagatt cctttactgt ccctcaacct tgaccaaatg | 1140 |
| ggaagcattc cccttgtca acacaagctg gcagatacat ttgactctac agatgaaggt | 1200 |
| gaacaatgtt aggataaaat tgctttggat cttgcctgga aggtgtttta agttttgtaa | 1260 |
| taaacaagat gatgtctgaa aatgtgaaaa aaaaaaaa | 1298 |

<210> SEQ ID NO 84
<211> LENGTH: 2106
<212> TYPE: DNA
<213> ORGANISM: Homo sapiens
<220> FEATURE:
<221> NAME/KEY: misc_feature
<223> OTHER INFORMATION: Incyte ID No: 1427389

<400> SEQUENCE: 84

| | |
|---|---|
| gtggggctgc ggccgggatt tgtcccctct tcggcttccg tagaggaagt ggcgcggacc | 60 |
| ttcatttggg gtttcggttc ccccccttcc ccttccccgg ggtctggggg tgacattgca | 120 |
| ccgcgcccct cgtggggtcg cgttgccacc ccacgcggac tccccagctg gcgcgcccct | 180 |
| cccatttgcc tgtcctggtc aggccccac ccccccttccc acctgaccag ccatgggggc | 240 |

```
tgcggtgttt tcggctgca ctttcgtcgc gttcggcccg gccttcgcgc ttttcttgat        300
cactgtggct ggggacccgc ttcgcgttat catcctggtc gcaggggcat ttttctggct        360
ggtctccctg ctcctggcct ctgtggtctg gttcatcttg gtccatgtga ccgaccggtc        420
agatgcccgg ctccagtacg gcctcctgat ttttggtgct gctgtctctg tccttctaca        480
ggaggtgttc cgctttgcct actacaagct gcttaagaag gcagatgagg ggttagcatc        540
gctgagtgag gacggaagat cacccatctc catccgccag atggcctatg tttctggtct        600
ctccttcggt atcatcagtg gtgtcttctc tgttatcaat attttggctg atgcacttgg        660
gccaggtgtg gttgggatcc atggagactc accctattac ttcctgactt cagccttct        720 gacagcagcc attatcctgc tccatacctt tggggagtt gtgttctttg atgcctgtga        780
gaggagacgg tactgggctt tgggcctggt ggttgggagt cacctactga catcgggact        840
gacattcctg aaccctggt atgaggccag cctgctgccc atctatgcag tcactgtttc        900 catgggctc tgggccttca tcacagctgg agggtccctc cgaagtattc agcgcagcct        960
cttgtgtaag gactgactac ctggactgat cgcctgacag atcccacctg cctgtccact       1020
gcccatgact gagcccagcc ccagcccggg tccattgccc acattctctg tctccttctc       1080
gtcggtctac cccactacct ccagggtttt gctttgtcct tttgtgaccg ttagtctcta       1140
agctttacca ggagcagcct gggttcagcc agtcagtgac tggtgggttt gaatctgcac       1200
ttatccccac cacctgggga ccccttgtt gtgtccagga ctcccctgt gtcagtgctc        1260 tgctctcacc ctgcccaaga ctcacctccc ttccctctg caggccgacg gcaggaggac       1320
agtcgggtga tggtgtattc tgccctgcgc atcccacccg aggactgagg gaacctaggg       1380
gggacccctg ggcctgggt gccctcctga tgtcctcgcc ctgtatttct ccatctccag       1440
ttctggacag tgcaggttgc caagaaaagg gacctagttt agccattgcc ctggagatga       1500
aattaatgga ggctcaagga tagatgagct ctgagttct cagtactccc tcaagactgg       1560
acatcttggt cttttctca ggcctgaggg ggaaccattt ttggtgtgat aaataccct         1620 aactgccttt ttttctttt tgaggtgggg ggagggagga ggtatattgg aactcttcta       1680
acctccttgg gctatatttt ctctcctcga gttgctcctc atggctgggc tcatttcggt       1740 cccttctcc ttggtcccag accttggggg aaaggaagga agtgcatgtt tgggaactgg        1800
cattactgga actaatggtt ttaacctcct taaccaccag catccctcct ctccccaagg       1860
tgaagtggag ggtgctgtgg tgagctggcc actccagagc tgcagtgcca ctggaggagt       1920
cagactacca tgacatcgta gggaaggagg ggagattttt ttgtagtttt taattggggt       1980
gtgggagggg cggggaggtt ttctataaac tgtatcattt tctgctgagg gtggagtgtc       2040
ccatcctttt aatcaaggtg attgtgattt tgactaataa aaaagaattt gtaaaaaaaa       2100
aaaaaa                                                                  2106
```

<210> SEQ ID NO 85
<211> LENGTH: 899
<212> TYPE: DNA
<213> ORGANISM: Homo sapiens
<220> FEATURE:
<221> NAME/KEY: misc_feature
<223> OTHER INFORMATION: Incyte ID No: 1458357

<400> SEQUENCE: 85

```
gctgtattca ggtccccgat gggcatatac atcttagccg gtgatacact acctcttacg         60
tgttgcctct ttgtgttgct tggtgctctt tcgaaaacaa ggtgcttatg gcttcatag        120 actatttcct ttttcatctt tgtcattctt taaaagtgta tgtactggtt acatcaagat        180
```

```
atgttttggt tgttagtact tatttttaatt tgtttggtca cacacttaat aacacgtgaa      240
actatttatg tgaagtcctt gttttatttt aaaattctct ttgtgtattt ggaatcaaag      300
ccagcacatt gtaacctgtg cttgtacgca aaagaattag atttctttgt ttttgtttta      360
ttttttaaat tgttgtaaaa attattatag gccagctaca tctagtagta ggtttggggt      420
acagattggg ggtgtgcca tactgttttt aaagttcatg atcatctgga atgatactta      480
gtgtatatat attttgtaaa gttttaattc agcaaatttt ttgaaattgc tgctgtttta      540
aattataaaa cctttatatt tctgctttgt agaaattata tgttttgtag tattcattga      600
ttttctttca ctgtacttaa atttagtgtt agtactttaa aattttttaat ttaccagtct      660 ttaaagcaac atccagaaaa aaaaaagtct tttcccattt aaaataggct cagccagttc      720
aatgtcgcct tgttatcaga gaaatattag ttcaatactg aaagaaaaat attataccctc     780 ttggtatcta gaaaaacttg ttcatccatt ataaatatat ctttagccac agcaaaccac      840
acttaaccta tctataataa aaatgtgctt taaataaaac caaaaaaaga aaaaaaaaa       899
```

<210> SEQ ID NO 86
<211> LENGTH: 2000
<212> TYPE: DNA
<213> ORGANISM: Homo sapiens
<220> FEATURE:
<221> NAME/KEY: misc_feature
<223> OTHER INFORMATION: Incyte ID No: 1482837

<400> SEQUENCE: 86

```
tttgtccagt tgttcttttg ttcctttccc gcctcccatt ctgctgctct tcctccctct       60
tttccccaac ctcccccgac cctcctgaat tttggaaagc acatttgcaa tattcgtgtt      120
tgctttggga cggaccctcc gtttcatctc atgctttatg tgtaagagtt ttttattatt      180 atttttttctt tcctttctct ctctgagaaa gttgtggctg cgttttgatc ttaggtttta    240
caaagtggtt tagggaagcg gttttgggga gaaggatcac gaggaatgta gggaagccgg      300
agggatgggt gctgctgcga cgaccccccc gtccctcggc cccagccctc ctgccctccc      360
cgtcaatctc atccaccaaa tctgaaggcc ttaaaattgt gtgttgggag gatgtgaatt      420
gggaggacgg tgtcactaga ctgtggatta gggatggtaa agtagggagg atgctatttt      480
gcaactatag taacgactta gtgttttgga aaggaaaaga agttaaactt gaaatacgtg      540
actagaacag ttgtcatgtt tataatgtga aaagggtgaa atcatttaga ggaggggccg      600
tctgtaagaa atcattatgc actatggctt cctcctctgg tctgggaaga agcggggact      660
ggctggccct caggggatct gtaaatccca gaaaacagta ttttaacag caagatgtca       720 ttcaacattg gtgggaagg aagagaaaaa aatcaaacta ttccatagaa ctagctggcc       780
ccctcactcc catgcccttc ccactcagcc tgggcccctc ccgctccat tcataaaagc       840 tgagagggtt gagctaatct tcacaaattg taatatttt gtagtatctg ttagttcctt      900
cgtcagttct gcagaaacctt gccctttcct tttgtaatgt gaataggaag acaaaagaca    960
aaaaaaaaat ccaccaccac caaaatatcc ctttgtacat gtatgtgcgt gtgcgcgtgt    1020
gctttgtgtg tgtggttgtg tgttaaatca tgcagtattg tcgtaatctg gtgttgcagc   1080
aatggatggt actaaatcag cacctggatg ccccacccaa cccgtgggc cctgcagacc     1140 ccagtaggga ggtatgggga gagctcaggg gagtgtggtt tctgagggct actgtctggg    1200
gacacctctg aacttactgt accttcctct ccccatgaag acacctgaat agagtctaac    1260
atgcctcttc tccaacttcc tacctacaac aacagaacag ttctaatgtt gcacggccta    1320
```

| | |
|---|---|
| gtggccaggg ggcaagctaa gaggctgtct ggaggcttta tatgtgtctg gagttaaggg | 1380 |
| gagaggagga gggtagacag gggtctctcc ccaggtggga tctgaatatc tgtcctcccc | 1440 |
| tcttcttcat gccacctgac tccttcggcc ccctggctgc ctttagctgt ggtactgctg | 1500 |
| acaaccctgc ttgctactgc cttatccagc acagtgaaaa acttctccag cctggcaagg | 1560 |
| ccacgttggt taatagtccc tttcccatgt ccagctccta caaatatgtc ccttaatgca | 1620 |
| tttggtgaca tttacacctc actcatgtgc tctttcccta ttcactcctt cactcattca | 1680 |
| aagcattaaa atcctatgta tatataggat agacaaatat atagatatat agatatatat | 1740 |
| atatatagca agagattgat ataaaatagt aaatatcatt gctgctttgg gctgctttgg | 1800 |
| aggaggaggc catgaatatg gggaaggcag atctggggtg caggggtagg tagggaggct | 1860 |
| gggggaccca gtgattcagt acaatccaag ggatgcaacg cgggcttgtt taatctttgt | 1920 |
| gcctgaacag ttttccatg ttgagaaaac tgttcaggca cagagattaa acagttttct | 1980 |
| caacatggga aaaaaaaaa | 2000 |

<210> SEQ ID NO 87
<211> LENGTH: 1359
<212> TYPE: DNA
<213> ORGANISM: Homo sapiens
<220> FEATURE:
<221> NAME/KEY: misc_feature
<223> OTHER INFORMATION: Incyte ID No: 1517434

<400> SEQUENCE: 87

| | |
|---|---|
| tgcccatcct gctgctcagc ctggtcacca tgtgcgtcac gcagctgcgg ctcatcttct | 60 |
| acatggggc tatgaacaac atcctcaagt tcctggtcag cggcgaccag aagacagttg | 120 |
| gcctctacac ctccatcttc ggcgtgctcc agctgctgtg cctgctgacg gccccgtca | 180 |
| ttggctacat catggactgg aggctgaagg agtgtgaaga cgcctccgag gagcccgagg | 240 |
| agaaagacgc caaccaaggc gagaagaaaa agaagaagcg ggaccggcag atccagaaga | 300 |
| tcactaatgc catgcgggcc ttcgccttca ccaacctgct gctcgtgggc tttggggtga | 360 |
| cctgcctcat tcccaacctg cctctccaga tcctctcctt catcctgcac acaatcgtgc | 420 |
| gaggattcat ccactccgct gtcggggggcc tgtacgctgc cgtgtaccc tccacccagt | 480 |
| tcggcagcct cacgggactg cagtctctga tcagcgcgct cttcgccctt ctgcagcagc | 540 |
| cgctgtttct ggccatgatg ggtcctctcc agggagaccc tctgtgggtg aacgtggggc | 600 |
| tgctccttct cagcctgctg ggcttctgcc tcccgctcta cctgatctgc taccggcgcc | 660 |
| agctggagcg gcagctgcag cagaggcagg aggatgacaa actcttcctc aaaatcaacg | 720 |
| gctcgtccaa ccaggaggcc ttcgtgtagt ggctgccgcc tcggaactgc ggtctcctgc | 780 |
| ctgtgcttca gtgactgacc cctgtcctgc ccctccagag taccccacgc accccagga | 840 |
| ccttcgccgt ctccgtgcca gcgttcacgc tccctcccgg ggccctgcct cggagctctg | 900 |
| tggtggaagg acgggagagg gccccggaca cgcgcgtttt ctcctgccga acgcagggc | 960 |
| tgccctgact ttgctctgcc gcccccgggg gacccggggc tggggtctc tgtggtgcct | 1020 |
| gcagcaggag ccaggaacgc ccggcaggca ggcgctctcc cgccagtgtc tggattctgc | 1080 |
| ctcttgccaa gcagaggggg gctgccatcc cctgcctgcc acctgcccct cggctgcatg | 1140 |
| cccacagccg tacctgcctg aggacaaagg cttgcactgt ctcgcccgcg cctgccccc | 1200 |
| acccctcccc cgaccagcct gatcaacatg gtgaagcccc gtctctacta aagatacaaa | 1260 |
| aattagggggg gcatggtggt ggatgcctgt aatcccggct gctcgggagg ctgaggcgga | 1320 |
| tgaatcgctt gaaccaggag gtggaggttg cagtgaggg | 1359 |

```
<210> SEQ ID NO 88
<211> LENGTH: 1397
<212> TYPE: DNA
<213> ORGANISM: Homo sapiens
<220> FEATURE:
<221> NAME/KEY: misc_feature
<223> OTHER INFORMATION: Incyte ID No: 1536052

<400> SEQUENCE: 88
gctggggaag ggaccatgtg gctgccttgg gctctgttgc ttctctgggt cccagcatca      60
acgtcaatga cacctgcaag tatcactgcg gccaagacct caacaatcac aactgcattt     120
ccacctgtat catccactac cctgtttgca gtgggtgcca cccacagtgc cagcatccag     180
gaggaaactg aggaggtggt gaactcacag ctcccgctgc tcctctcccct gctggcattg    240
ttgctgcttc tgttggtggg ggcctccctg ctagcctgga ggatgtttca gaaatggatc    300
aaagctggtg accattcaga gctgtcccag aaccccaagc aggcctcccc cagggaagaa    360
cttcactatg cctcggtggt gtttgattct aacaccaaca ggatagctgc tcagaggcct    420
cgggaggagg aaccagattc agattacagt gtgataagga agacataggc ttttgtcctg    480
cctcgccatc ggagctctca tgggccccag gaagtccagg acagctcccc ttatacctgg    540
cccacgtcct tctcagcctg ccctcgacaa cagtgaccaa cagacaggca gctgggtttc    600
ccaggccatc cctctgttgc catcagcttg attggcttcc ccgagggcca gcagggctgg    660
gggctccgga gagcagcagg aagcactccc agccaccagt gcctgtcacc tcttttcccct   720
ttgcccctgc ttcatcccag ctctgtgtgt ggaggacaaa gcttcttcct gcgtggctcc    780
aggaaaagat gtggctcacg taggtggcac ctgccaatag ctttgtcaat cacagcccca    840
taggaacgtc tggaattgct tgggagttgg ggagaactgt caagaagagt gaagagagtg    900
ccaaagcgga gatctgttca cctgggggcc atggaggggg gacccactaa agatcaagat    960
caaagattct ccccatctca cagacaagga aactgaggcc agaggaggag gagaattgct   1020
catggctcca gaactggtgg caagtttctc tggactctta ggtttatttt taatatgaaa   1080
tataaaaaca gtttcaaata tcttattgag ggagaagtaa aaacttattt aaacaataaa   1140
aaaataaaaa aaaggggcgg gggtcccgag cccgaatccg aaatcaggta aaagctgttc   1200
cctgtgtaaa attgttaccc gcccaaaatt ccacaaaata taggacccgg agccttaaag   1260
tttaaaccccc tggggcccca aattgggtgg gccatccccc atttaattgg cttggccccc   1320
aatggccggt tttcacattg ggggaaacct ttttggccca acggcttttta atgaaatcgg   1380
cccaaaccgc gggggaa                                                   1397

<210> SEQ ID NO 89
<211> LENGTH: 1570
<212> TYPE: DNA
<213> ORGANISM: Homo sapiens
<220> FEATURE:
<221> NAME/KEY: misc_feature
<223> OTHER INFORMATION: Incyte ID No: 1666118

<400> SEQUENCE: 89
atgtccatca tgtcagcagg tgcaaatcac ttttcccctt tgcatgatct gaggcacctc      60
ctcagttgtt tcactgccaa ctcttatttc agaacctgtt tacaaacaag ccttccagtt    120
ggtgaatggt tagccattgg agctcctacc ctgtacatca gcacatcttc tggtttacaa    180
gttgggtaac aatgaaagct ggagatacta aatggaaatc cagcattgca tacccttaga    240
cctgatcaca taccagtaaa agccttaatt tagatgttag ttgtatgtgt tggacagatc    300
```

```
cttgcaaaag tgtgtctgtc tattagttgt aaatttgaaa attataaatc tctgaatctg      360
ctactatcca agtttcatcc cttttgaaga tgaggcatga gcctattaaa atatttataa      420
tcatttttcg tcccctactg caagactttt agattcttac aaatgattac tacaggaata      480
gtggccactt aatgtcagtt actccggtgg aagaatttat ctagtttttt ttcttttctt      540
ttttggaagg atggtgtgaa aaatagcaag attagagaat gagttgtata gttttttcta      600
tcacatttca tctaaaatga tttgaaggac ttttgaagat ttttaccaac atccttaaat      660
caactccagg ttggatgaac aactgattta aaacaaacta agagaacatt aactagatgt      720
gggcttttta aaatatatag gtattgcatt tcctaccttg ttatttattc cactttgaat      780
actttagagg gcttaacttt caactcttta aggtagtaat ggatagtttt atacttgttc      840
tcacaaaatt gttatggtca gtttatatca ttgctccatg cattgattat aaaaattcag      900
tattaatttt ttctgatctt ataagcttta taggagtttt cttttctctt ataaagtgtt      960
tcaccttatg taaaacaaat gcctgcttgc atattggaag atgttgaaat tagttttaga     1020
caaaagtggt ccatcaattc agacactctg cttggatgcc ttacccttttt cattagtgca     1080 ttctttgctt ctgaaacttg gcagaaactc gttagccagt ccactgcctt tctgacaatg     1140
tgtggagtca cgtatgcttg gtatatgcct ttactacttt taaagttcta cagtttatta     1200
cttgcccaag tgttactaaa tccttttctt atgtgtactg gatggagaaa aaattatagc     1260
cagcactttg agaggaaagt tttcagaaac aatattaact ggcactacta actgaaggcc     1320
acaggagatg ctatcaatgt tatttgtaat ctgaagattg aacaaggctg tgaggctcat     1380
ttcaaactat tttgaggtgt taaaatatat atatgctgtt tctcagctgt tccactcaaa     1440
ccgtgttagg actctcaaag gtaaaatgtc acagggggct ttcagttgtt acagagctca     1500
gcagctgtgg ttgcccctgt tctacaccaa tttcagttca ataaaaatgt taactttgaa     1560
aaaaaaaaaa                                                             1570

<210> SEQ ID NO 90
<211> LENGTH: 718
<212> TYPE: DNA
<213> ORGANISM: Homo sapiens
<220> FEATURE:
<221> NAME/KEY: misc_feature
<223> OTHER INFORMATION: Incyte ID No: 1675560

<400> SEQUENCE: 90
ggtggtgcgt gcctgtaatc ccaactactt gggaggctga ggcaggagaa tcgcttgaac       60
ctgggaggca gcggttgcag taagccaaga ctatgccact gcactcccgc ctgggtgaca      120
aagcaatatt ctgtgtcaaa taataaatt cattcttctg ctctcctgac ttagagaaat      180
ggtttgctta aaatgctagt aacaaacatc acagtcaaca ggagcttgct tcatgcgaag      240
gatcaatgtg atttgtggat ggagatgata gtgatgaaat tcctgtttca tggggctgtt      300 tttctttttca tctcactggg cagcaggttt agtgaggcag tgagatgctg ctgctgtgga      360
ttcttgtagc tatgcctcgg cttcttggca tatcaggtag gaacctgtta caagtgaaat      420
acttgaaacc tctctgacca agagcctctg atggagtggg aggtgagcta attctctgac      480
cagcttaggg cactgtttca gccactggtc acattccttg cttcaaactg aaattcagtt      540
tggctttgag tatagggata catggtggat tcatgtactt cagtgtttgt tttgaccaaa      600
gtttattttt ctagtgcatt ttctaagtca aagtggtgaa aatatgtaat aattttagta      660
tgcatgactc agtctgaaac aataaaaatc tctgaaaaat gaaaaaaaaa aaaaaagg       718
```

<210> SEQ ID NO 91
<211> LENGTH: 904
<212> TYPE: DNA
<213> ORGANISM: Homo sapiens
<220> FEATURE:
<221> NAME/KEY: misc_feature
<223> OTHER INFORMATION: Incyte ID No: 1687323

<400> SEQUENCE: 91

| | | | | | |
|---|---|---|---|---|---|
| gcttgtgggg | ggaaaaagaa | acgcaataga | taaagcgggg | cgcatgcgct | cccggcacag | 60 |
| gcttcgattg | tgaggaaggc | cggctagtct | ccgagctcat | cccgccttgc | gcatgcggag | 120 |
| aaggtaaacc | agcgccccga | gttgaggcgc | gggtttggtg | gcgcgtttca | gcgaagtcgc | 180 |
| acgtgaagga | tagcagtggc | ctgagaaaga | cccagtcatg | gcagcctcca | gcatcagttc | 240 |
| accatgggga | aagcatgtgt | tcaaagccat | tctgatggtc | ctagtggccc | ttatcctcct | 300 |
| ccactcagca | ttggcccagt | cccgtcgaga | cttttgcacca | ccaggccaac | agaagagaga | 360 |
| agccccagtt | gatgtcttga | cccagatagg | tcgatctgtg | cgaggacac | tggatgcctg | 420 |
| gattgggcca | gagaccatgc | acctggtgtc | agagtcttcg | tcccaagtgt | tgtgggccat | 480 |
| ctcatcagcc | atttctgtgg | ccttctttgc | tctgtctggg | atcgccgcac | agctgctgaa | 540 |
| tgccttggga | ctagctggtg | attacctcgc | ccagggcctg | aagctcagcc | ctggccaggt | 600 |
| ccagaccttc | ctgctgtggg | gagcaggggc | cctggtcgtc | tactggctgc | tgtctctgct | 660 |
| cctcggcttg | gtcttggcct | tgctggggcg | gatcctgtgg | ggcctgaagc | ttgtcatctt | 720 |
| cctgccggc | ttcgtggccc | tgatgaggtc | ggtgcccgac | ccttccaccc | gggccctgct | 780 |
| actcctggcc | ttgctgatcc | tctacgccct | gctgagccgg | ctcactggct | cccgagcctc | 840 |
| tggggcccaa | ctcgaggcca | aggtgcgagg | gctggaacgc | taggtggagg | agctgcgctg | 900 |
| gcgc | | | | | | 904 |

<210> SEQ ID NO 92
<211> LENGTH: 1948
<212> TYPE: DNA
<213> ORGANISM: Homo sapiens
<220> FEATURE:
<221> NAME/KEY: misc_feature
<223> OTHER INFORMATION: Incyte ID No: 1692236

<400> SEQUENCE: 92

| | | | | | |
|---|---|---|---|---|---|
| gaagacctct | tagcgggccc | atcgctgagg | tgcagggaca | tgtcgcggcc | gaactcacct | 60 |
| cgtggcctcg | gcgtggtgct | ctcagctcat | gcccggaaac | caggtcccga | cgccgcggtc | 120 |
| agacggacct | ctagacgcgt | ccgcctcaat | gccgccagct | gccaggccgc | ccgtgacgcg | 180 |
| ttacgcctgc | gccgcctcct | ggcttcgtga | cgtcacgacg | tccgcgcagt | gcggtcgccg | 240 |
| ccgtcgcacg | agtctttcct | tagtaacctg | ggcgatactg | tggatgtttc | caaggattgt | 300 |
| cttcagtcat | ggccttggga | ttaaagtgct | tccgcatggt | ccaccctacc | tttcgcaatt | 360 |
| atcttgcagc | ctctatcaga | cccgtttcag | aagttacact | gaagacagtg | catgaaagac | 420 |
| aacatggcca | taggcaatac | atggcctatt | cagctgtacc | agtccgccat | tttgctacca | 480 |
| agaaagccaa | agccaaaggg | aaaggacagt | cccaaaccag | agtgaatatt | aatgctgcct | 540 |
| tggttgagga | tataatcaac | ttggaagagg | tgaatgaaga | aatgaagtct | gtgatagaag | 600 |
| ctctcaagga | taatttcaat | ctgactctca | atataagggc | ctcaccagga | tcccttgaca | 660 |
| agattgctgt | ggtaactgct | gacgggaagc | ttgctttaaa | ccagattagc | cagatctcca | 720 |
| tgaagtcgcc | acagctgatt | ttggtgaata | tggccagctt | cccagagtgt | acagctgcag | 780 |

-continued

| | |
|---|---|
| ctatcaaggc tataagagaa agtggaatga atctgaaccc agaagtggaa gggacgctaa | 840 |
| ttcgggtacc cattccccaa gtaaccagag agcacagaga aatgctggtg aaactggcca | 900 |
| aacagaacac caacaaggcc aaagactctt tacggaaggt tcgcaccaac tcaatgaaca | 960 |
| agctgaagaa atccaaggat acagtctcag aggacaccat taggctaata gagaaacaga | 1020 |
| tcagccaaat ggccgatgac acagtggcag aactggacag gcatctggca gtgaagacca | 1080 |
| aagaactcct tggatgaaag tccactgggg ccagcaatac tccagagccc agtttctgct | 1140 |
| ggatcccatg ggtggcacat tgggacttct ctccctcccc catctacaca gaagactgtc | 1200 |
| accatgctga cagaagcctg tccttgtaag gcccagcctt ccaggggaac actcagacat | 1260 |
| gttcattctc ttcctgcttc tgctctgggc cggtgggtgg ctctcagaaa atacttgctg | 1320 |
| ctggcaaaag gcctgtactc aggcatttgc tttgacttga tgttgccaag ggactgaggc | 1380 |
| cattggcagg cttagtacca cctgctcctc atcttaggag tctccttttc aaataattag | 1440 |
| gctctgttcc cattttaaaa ctctgatatt ggccttcacc tgtgactgga cactttacta | 1500 |
| gaggcccatt ttcactaaac aataaaatct aaataaattg gaaggaataa caaccacaaa | 1560 |
| ggaaagaata gagttggtct ggattgatga tcactgagga tctgtatgtg aggcacccat | 1620 |
| aacagtagtt ttgcctgtga gtcgtcttca cacatgctgt tttctctgcc tggctctctc | 1680 |
| ttcccctcct tacctggcca gtcctgttta tcatcaggcc ttgtcttgga tatcacgtcc | 1740 |
| tctgggaagt cttctttttcc cctctaacct aggaccctca ttaccggctc tcatagcaca | 1800 |
| gtctactgct ttgtacgaat tctaagtatt cttgttgcac ttaattagcc tgtatatcct | 1860 |
| cagaactttg tgtaatgcct ggagcatagt aggcagtcat atgttgtatc gtgaataaat | 1920 |
| tgcacatagt agctacccaa aaaaaaaa | 1948 |

<210> SEQ ID NO 93
<211> LENGTH: 990
<212> TYPE: DNA
<213> ORGANISM: Homo sapiens
<220> FEATURE:
<221> NAME/KEY: misc_feature
<223> OTHER INFORMATION: Incyte ID No: 1720847

<400> SEQUENCE: 93

| | |
|---|---|
| acagagactg gcacaggacc tcttcattgc aggaagatgg tagtgtaggc aggtaacatt | 60 |
| gagctctttt caaaaaagga gagctcttct tcaagataag gaagtggtag ttatggtggt | 120 |
| aaccccccggc tatcagtccg gatggttgcc accccctcctg ctgtaggatg gaagcagcca | 180 |
| tggagtggga gggaggcgca ataagacacc cctccacaga gcttggcatc atgggaagct | 240 |
| ggttctacct cttcctggct ccttttgttta aaggcctggc tgggagcctt ccttttgggt | 300 |
| gtctttctct tctccaacca acagaaaaga ctgctcttca aaggtggagg gtcttcatga | 360 |
| aacacagctg ccaggagccc aggcacaggg ctggggggcct ggaaaaagga gggcacacag | 420 |
| gaggagggag gagctggtag ggagatgctg gctttaccta aggtctcgaa caaggaggg | 480 |
| cagaataggc agaggcctct ccgttccagg cccatttttg acagatggcg ggacggaaat | 540 |
| gcaatagacc agcctgcaag aaagacatgt gttttgatga caggcagtgt ggccgggtgg | 600 |
| aacaagcaca ggccttggaa tccaatggac tgaatcagaa ccctaggcct gccatctgtc | 660 |
| agccgggtga cctgggtcaa ttttagcctc taaaagcctc agtctcctta tctgcaaaat | 720 |
| gaggcttgtg ataccctgttt tgaagggttg ctgagaaaat taaagataag ggtatccaaa | 780 |
| atagtctacg gccataccac cctgaacgtg cctaatctcg taagctaagc agggtcaggc | 840 |
| ctggttagta cctggatggg gagagtatgg aaaacatacc tgcccgcagt tggagttgga | 900 |

```
ctctgtctta acagtagcgt ggcacacaga aggcactcag taaatacttg ttgaataaat      960
gaagtagcga tttggtgtga aaaaaaaaaa                                       990
```

<210> SEQ ID NO 94
<211> LENGTH: 1638
<212> TYPE: DNA
<213> ORGANISM: Homo sapiens
<220> FEATURE:
<221> NAME/KEY: misc_feature
<223> OTHER INFORMATION: Incyte ID No: 1752821

<400> SEQUENCE: 94

```
tagatatggc gtcctctttg cttgcgggcg agcgattggt gcgtgctttg ggccccggcg       60
gggagctgga gccagagcgg ctaccccgaa agctgcgggc cgagcttgag gccgcgctgg      120
ggaagaagca aagggcggt gatagctcca gtggccccca acgcttggtt tctttccgtc       180 tcatcccggga tctgcaccag catctgagag aaagggattc caaactatac ctccatgagc    240
tcctagaagg cagtgaaatc tatctcccag aggttgtgaa gcctccacgg aacccagaac     300
tagttgcccg gctggagaag attaagatac agctggccaa tgaggaatat aaacggatca    360
cccgcaacgt cacttgtcag gatacaagac atggtgggac tctcagcgac ctgggaaagc    420
aagtgagatc attgaaggct ctggtcatca ccatcttcaa tttcattgtc acggtggttg    480
ctgccttcgt ctgcacttac cttggaagcc aatatatctt cacagaaatg gcctcgcggg    540
tgctagctgc attgatcgtc gcctctgtgg tgggtctggc cgagctgtat gtcatggtgc    600
gggcaatgga aggcgagctg ggagaactgt aactggtgct tcatcatcaa gtctagaaga    660
gactttgggg gcttcaggct ccaattggca gtcaccgact cagtcaaccc atcagacttt    720
ttgtattcag ctccagttag tcagaagacc agccaggcc agctgctgtt tctgtgggga    780
gccctaatct tctgtgaatt ccaaaggga gcattggagg agattgagat aacacatctt    840
taaaacagaa agaactggtc ttggtctatc agtacctctt cctgaatctg gtacccatct    900
gccttctcca gttcattcta aacactgctg ggactagggt ttttccatca ggagcaaatg    960
gaatccaggc cttcccagaa gtagaccata ctgccttgaa cttgtccata tgtacaaact   1020
aatcaccagc tttctccata cattttaat gcagacctgt aattgagttc agaagcctcc    1080
aagaaaacag aaaggatccc ctttctccag tttgtgctgg aagaggagct gatcagagac   1140
atcaaataag agaaagatgg gttgctagag gatggtagaa ctggaagcaa ggcagctacc   1200 ttttgcaaa aggaaatggt gttaggcccc ttttccagaa gataagacag actcatagag    1260
attaaatgat cactatggtc cttcttctgt taaatggagc caaagacgcc tatgttgttc   1320
tgaagtcttg taatgtttaa cttctgagaa cttagattag tggtgtgatg atagagtctg   1380
tataacgcat tgaaaagggt atcaggctta gttatttatc caataaatat ttattgtatg   1440
cagggtattc ctattttaac tcctgtgaca acacaaagca tagcgatttc catagttcta   1500
actgttcagg gtctgctcct cctggtacac tcttttggt tcactgtatg tactcctgtt    1560 gtctttttt ttttttccaa agcactttc tgttttcata aattatatac tcattcactc    1620
agtggacaaa aaaaaaaa                                                  1638
```

<210> SEQ ID NO 95
<211> LENGTH: 595
<212> TYPE: DNA
<213> ORGANISM: Homo sapiens
<220> FEATURE:
<221> NAME/KEY: misc_feature
<223> OTHER INFORMATION: Incyte ID No: 1810923

<400> SEQUENCE: 95

```
gtgggcgcgt ccagtgatga ctgggggatc ccggcaagta acatgactaa aaagaagcgg      60
gagaatctgg gcgtcgctct agagatcgat gggctagagg agaagctgtc ccagtgtcgg     120
agagacctgg aggccgtgaa ctccagactc cacagccggg agctgagccc agaggccagg     180
aggtccctgg agaaggagaa aaacagccta atgaacaaag cctccaacta cgagaaggaa     240
ctgaagtttc ttcggcaaga gaaccggaag aacatgctgc tctctgtggc catctttatc     300
ctcctgacgc tcgtctatgc ctactggacc atgtgagcct ggcacttccc cacaaccagc     360
acaggcttcc acttggcccc ttgatcagga tcaagcaggc acttcaagcc tcaataggac     420
caaggtgctg gggtgttccc ctcccaacct agtgttcaag catggcttcc tggcggccca     480
ggccttgcct ccctggcctg ctgggggggtt ccggtctcc agaaggacat ggtgctggtc     540
cctcccttag cccaagggag aggcaataaa gaacacaaag ctgtaaaaaa aaaaa         595
```

<210> SEQ ID NO 96
<211> LENGTH: 1858
<212> TYPE: DNA
<213> ORGANISM: Homo sapiens
<220> FEATURE:
<221> NAME/KEY: misc_feature
<223> OTHER INFORMATION: Incyte ID No: 1822315

<400> SEQUENCE: 96

```
aaaagtctag atcacagtgg ggctctagga gggctagtcg ttggatttat cctaaccatt      60
gcaaatttca gcttttttac ctctttgctg atgttttttct tgtcttcttc gaaactcact    120
aaatggaagg gagaagtgaa gaagcgtcta gattcagaat ataaggaagg tgggcaaagg    180
aattgggttc agtgttctg taatggagct gtacccacag aactggccct gctgtacatg    240
atagaaaatg gccccgggga atcccagtc gattttttcca agcagtactc cgcttcctgg    300
atgtgtttgt ctctcttggc tgcactggcc tgctctgctg gagacacatg ggcttcagaa    360
gttggcccag ttctgagtaa aagttctcca agactgataa caacctggga gaaagttcca    420
gttggtacca atggaggagt tacagtggtg ggccttgtct ccagtctcct tggtggtacc    480
tttgtgggca ttgcatactt cctcacacag ctgattttttg tgaatgattt agacatttct    540
gccccgcagt ggccaattat tgcatttggt ggtttagctg gattactagg atcaattgtg    600
gactcatact taggggctac aatgcagtat actgggttgg atgaaagcac tggcatggtg    660
gtcaacagcc caacaaataa ggcaaggcac atagcaggga aacccattct tgataacaac    720
gcgtggatct gttttcttct gttcttattg ccctcttgct cccaactgct gcttggggtt    780
tttggcccag ggggtgaact ttatttcatt tccacaggtt gaaactggtg agtccagcta    840
aatttgcaat tccaactttc atcctaagaa taataactgt aatggcaaag cggaaatgcc    900
agttcctcct gtattccatt gagatgggat ttcacattttt cctctcatca actcccctgt    960
aatagctagc gtcttttctag tgaaagagaa gaattcctag aacttatgca tttttttcct   1020
gctgaatgga agtcttgagc aatgaagcta tattgtccct acatattact atatattgaa   1080
ctgaaagttc ttacataatc aatgtcaagt tttgtcttat tttgttttgt tgtttaaac    1140
cagtgtagga aataaaagtg atgatattta aaatagttct cagttgaagc agagaaatgc   1200
cactgtgcta gttgcccaaa tgttgtatct attttaaata gtttaagctg atgtgtatgg   1260
gagcctaaac aagtgtagta tcctgaactt ctcccattaa ttgctattca caattgggaa   1320
aagtgtggag attggttcct agtgagtttt gtggcctact ccacatttgt tcttccttcc   1380
```

```
tcagggttag tgatgaaaaa aagtaaatat cttttcata tgtccattag aatgtatgaa    1440
aaaaatcatt ttaactaaaa gcaaagaat tttatcttat atctaaaaaa tatataactt    1500
actatatgtt tcagttgctc tctgaacaaa aattatcttc aatttaatat gtggaatgtg    1560 tttctagct ttctttgaat tatgtatggc aacctggttt agcactggca tcctgaacag    1620
ttaagagtca ctgggaaatt attgtatttc tttataaatt tactgtcata tcaattgctg    1680
gaaaatgcta tgattttct attattaccct tctaagttgt attctctctt acactgtagc    1740
ctcaactaag gcaattctgc tatgtttgtt cttcactatg atttactgtg tgccaaagga    1800
gttttgacag ggtacagagt attttactaa aagtattttt aaatgttaaa aaaaaaa      1858
```

<210> SEQ ID NO 97
<211> LENGTH: 698
<212> TYPE: DNA
<213> ORGANISM: Homo sapiens
<220> FEATURE:
<221> NAME/KEY: misc_feature
<223> OTHER INFORMATION: Incyte ID No: 1877777

<400> SEQUENCE: 97

```
tgggtgtccg catgacaacc gacgttggag tttggaggtg cttgccttag agcaagggaa     60
acagctctca ttcaaaggaa ctagaagcct ctccctcagt ggtagggaga cagccaggag    120
cggttttctg ggaactgtgg gatgtgccct tggggcccg agaaaacaga aggaagatgc    180
tccagaccag taactacagc ctggtgctct ctctgcagtt cctgctgctg tcctatgacc    240
tctttgtcaa ttccttctca gaactgctcc aaaagactcc tgtcatccag cttgtgctct    300
tcatcatcca ggatattgca gtcctcttca acatcatcat catttttcctc atgttcttca    360 acaccttcgt cttccaggct ggcctggtca acctcctatt ccataagttc aaagggacca    420
tcatcctgac agctgtgtac tttgccctca gcatctccct tcatgtctgg gtcatgaact    480
tacgctggaa aaactccaac agcttcatat ggacagatgg acttcaaatg ctgtttgtat    540
tccagagact agcagcagtg ttgtactgct acttctataa acggacagcc gtaagactag    600
gcgatcctca cttctaccag gactctttgt ggctgcgcaa ggagttcatg caagttcgaa    660
ggtgacctct tgtcacactg atggatactt ttccttcc                            698
```

<210> SEQ ID NO 98
<211> LENGTH: 1476
<212> TYPE: DNA
<213> ORGANISM: Homo sapiens
<220> FEATURE:
<221> NAME/KEY: misc_feature
<223> OTHER INFORMATION: Incyte ID No: 1879819

<400> SEQUENCE: 98

```
caaggacgag gctctggcca agctgggtat caacggtgcc cactcgtccc cgccgatgct     60
gtcccccagc ccaggaaagg gccccccgcc agctgtggct cctcgaccca aggcccgct    120 acagcttggg ccctctagct ccatcaagga aaagcagggg cccttctgg acctgtttgg    180 ccagaagctg cctattgccc acacaccccc acctccacca gcgccaccac tgcctctgcc    240
cgaggaccca gggaccctttt cagcagagcg tcgttgcttg acacagcccg tggaggacca    300
gggggtctcc acccagctac tcgcgccctc tggcagcgtg tgcttctcct acaccggcac    360
gccctggaag ttgttcctac gcaaggaggt gttctaccca cgggagaact tcagccatcc    420
ctactacctg aggctcctct gtgagcagat cctacgggac accttctccg agtcctgtat    480
ccggatttcc cagaatgagc ggcggaaaat gaaagacct ctgggaggct tggaggtgga    540
```

```
cctggattct ctcaccacca ccgaagacag cgtcaagaag cgcatcgtgg tggccgctcg    600
ggacaactgg gccaattact tctcccgctt ctttcctgtc tcgggcgaga gtggcagcga    660
cgtgcagctg ttagccgtgt cccaccgtgg gctgcgactg ctcaaggtga cccaaggccc    720
cggcctccgc cccgaccagc tgaagattct ctgctcatac agctttgcgg aggtgctggg    780
tgtggagtgc cggggcggct ccaccctgga gctgtcactg aagagcgagc agctggtgct    840
gcacacagcc cgggcaaggg ccatcgagcg gctggttgag ctattcctga atgagcttaa    900
gaaggactcc ggctatgtca tcgccctgcg cagctacatc actgacaact gcagcctcct    960
cagcttccac cgtggggacc tcatcaagct gctgccggtg tgccaccctg agccaggct   1020
ggcagtttgg ctctgccggg ggccgttccg gactcttcc tgccgacata gtgcagccgg   1080
ctgccgctcc cgactttcc ttctccaagg agcagaggag tggctggcac aagggtcagc   1140
tgtccaacgg ggaaccaggg ctggctcggt gggacagggc ctcagaggtg aggaagatgg   1200
gagagggaca agcagaggca aggcctgcct gagactgagg aaggaaaggg gtttgaccac   1260
tcccgaggct gccatgcggt gggaccaccc tgctgtccgt ctcctgtggc tgcccctctg   1320
cccgctcctg atggctcgcc ttgtctctcc agcaagactg tgcactcctt gcaggcaggg   1380
gctgggctgg atgctgctct tgtgtcccac gtggtactta gttcaaggct gccccagcag   1440
atgcttaata acagctctt cactttaaaa aaaaaa                              1476

<210> SEQ ID NO 99
<211> LENGTH: 646
<212> TYPE: DNA
<213> ORGANISM: Homo sapiens
<220> FEATURE:
<221> NAME/KEY: misc_feature
<223> OTHER INFORMATION: Incyte ID No: 1932945

<400> SEQUENCE: 99
ccggctggag gtgacgctga ggcggcgagg gtgagtcggc gccggccgct accgcacttc     60
gggcgctcgt ccctcatttc tctgtggtga atggcgacgg gatggagcgc gaggggagcg    120
gcggcagcgg cgggtcggcc gggctcctgc agcagatcct gagcctgaag gttgtgccgc    180
gggtgggcaa cgggacccctg tgccccaact ctacttccct ctgctccttc ccagagatgt    240
ggtatggtgt attcctgtgg gcactggtgt cttctctctt cttcatgtc cctgctggat    300
tactggccct cttcacccctc agacatcaca aatatggtag gttcatgtct gtaagcatcc    360
tgttgatggg catcgtggga ccaattactg ctggaatctt gacaagtgca gctattgctg    420
gagtttaccg agcagcaggg aaggaaatga taccatttga agccctcaca ctgggcactg    480
gacagacatt ttgcgtcttg gtggtctcct ttttacggat tttagctact ctatagcata    540
catccttatg ctgagatgtt gaacttaaac tttatggaat cctccaaaag aatacattat    600
ggagtgtagt gttttcttag ttcttccaaa gggagccact tggatg                   646

<210> SEQ ID NO 100
<211> LENGTH: 1735
<212> TYPE: DNA
<213> ORGANISM: Homo sapiens
<220> FEATURE:
<221> NAME/KEY: misc_feature
<223> OTHER INFORMATION: Incyte ID No: 2061026

<400> SEQUENCE: 100
gccggctgcg ccatggcgtt ggcgttggcg gcgctggcgg cggtcgagcc ggcctgcggc     60
agccggtacc agcagttgca gaatgaagaa gagtctggag aacctgaaca ggctgcaggt    120
```

-continued

| | |
|---|---|
| gatgctcctc caccttacag cagcatttct gcagagagcg cagcatattt tgactacaag | 180 |
| gatgagtctg ggtttccaaa gcccccatct tacaatgtag ctacaacact gcccagttat | 240 |
| gatgaagcgg agaggaccaa ggctgaagct actatccctt tggttcctgg gagagatgag | 300 |
| gattttgtgg gtcgggatga ttttgatgat gctgaccagc tgaggatagg aaatgatggg | 360 |
| attttcatgt taacttttt catggcattc ctctttaact ggattgggtt tttcctgtct | 420 |
| ttttgcctga ccacttcagc tgcaggaagg tatgggggcca tttcaggatt tggtctctct | 480 |
| ctaattaaat ggatcctgat tgtcaggttt tccacctatt tccctggata ttttgatggt | 540 |
| cagtactggc tctggtgggt gttccttgtt ttaggctttc tcctgtttct cagaggattt | 600 |
| atcaattatg caaaagttcg aagatgcca gaaactttct caaatctccc caggaccaga | 660 |
| gttctcttta tttattaaag atgttttctg gcaaaggcct tcctgcattt atgaattctc | 720 |
| tctcaagaag caagagaaca cctgcaggaa gtgaatcaag atgcagaaca cagaggaata | 780 |
| atcacctgct ttaaaaaaat aaagtactgt tgaaaagatc attctctct atttgttcct | 840 |
| aggtgtaaaa ttttaatagt taatgcagaa ttctgtaatc attgaatcat tagtggttaa | 900 |
| tgtttgaaaa agctcttgca atcaagtctg tgatgtatta ataatgcctt atatattgtt | 960 |
| tgtagtcatt ttaagtagca tgagccatgt ccctgtagtc ggtaggggc agtcttgctt | 1020 |
| tattcatcct ccatctcaaa atgaacttgg aattaaatat tgtaagatat gtataatgct | 1080 |
| ggccatttta aaggggtttt ctcaaaagtt aaactttgt tatgactgtg tttttgcaca | 1140 |
| taatccatat ttgctgttca agttaatcta gaaatttatt caattctgta tgaacacctg | 1200 |
| gaagcaaaat catagtgcaa aaatacattt aaggtgtggt caaaaataag tctttaattg | 1260 |
| gtaaataata agcattaatt ttttatagcc tgtattcaca attctgcggt accttattgt | 1320 |
| acctaaggga ttctaaaggt gttgtcactg tataaaacag aaagcactag gatacaaatg | 1380 |
| aagcttaatt actaaaatgt aattcttgac actctttcta taattagcgt tcttcacccc | 1440 |
| cacccccacc cccaccccc ttatttcct tttgtctcct ggtgattagg ccaaagtctg | 1500 |
| ggagtaagga gaggattagg tacttaggag caaagaaaga agtagcttgg aacttttgag | 1560 |
| atgatcccta acatactgta ctacttgctt ttacaatgtg ttagcagaaa ccagtgggtt | 1620 |
| ataatgtaga atgatgtgct ttctgcccaa gtggtaattc atcttggttt gctatgttaa | 1680 |
| aactgtaaat acaacagaac attaataaat atctcttgtg tagcaaaaaa aaaaa | 1735 |

<210> SEQ ID NO 101
<211> LENGTH: 2329
<212> TYPE: DNA
<213> ORGANISM: Homo sapiens
<220> FEATURE:
<221> NAME/KEY: misc_feature
<223> OTHER INFORMATION: Incyte ID No: 2096687
<220> FEATURE:
<221> NAME/KEY: unsure
<222> LOCATION: 2084, 2101, 2110, 2128, 2137, 2156, 2177, 2226, 2265,
      2296, 2303, 2310, 2325
<223> OTHER INFORMATION: a, t, c, g, or other

<400> SEQUENCE: 101

| | |
|---|---|
| gcagggatca ctagcatgtc tgcggagagc ggccctggga cgagattgag aaatctgcca | 60 |
| gtaatggggg atggactaga aacttcccaa atgtctacaa cacaggccca ggcccaaccc | 120 |
| cagccagcca acgcagccag caccaacccc ccgcccccag agacctccaa ccctaacaag | 180 |
| cccaagaggc agaccaacca actgcaatac ctgctcagag tggtgctcaa gacactatgg | 240 |
| aaacaccagt ttgcatggcc tttccagcag cctgtggatg ccgtcaagct gaacctccct | 300 |

```
gattactata agatcattaa aacgcctatg gatatgggaa caataaagaa gcgcttggaa    360
aacaactatt actggaatgc tcaggaatgt atccaggact tcaacactat gtttacaaat    420
tgttacatct acaacaagcc tggagatgac atagtcttaa tggcagaagc tctggaaaag    480
ctcttcttgc aaaaaataaa tgagctaccc acagaagaaa ccgagatcat gatagtccag    540
gcaaaaggaa gaggacgtgg gaggaaagaa cagggacag caaaacctgg cgtttccacg     600
gtaccaaaca caactcaagc atcgactcct ccgcagaccc agaccctca gccgaatcct     660
cctcctgtgc aggccacgcc tcacccttc cctgccgtca ccccggacct catcgtccag      720
accctgtca tgacagtggt gcctccccag ccactgcaga cgcccccgcc agtgcccccc      780
cagccacaac ccccacccgc tccagctccc agcccgtac agagccaccc acccatcatc     840
gcggccaccc cacagcctgt gaagacaaag aagggagtga agaggaaagc agacaccacc    900
acccccacca ccattgaccc cattcacgag ccaccctcgc tgcccccgga gcccaagacc    960
accaagctgg gccagcggcg ggagagcagc cggcctgtga acctccaaa gaaggacgtg     1020
cccgactctc agcagcaccc agcaccagag aagagcagca aggtctcgga gcagctcaag    1080
tgctgcagcg gcatcctcaa ggagatgttt gccaagaagc acgccgccta cgcctggccc    1140
ttctacaagc ctgtggacgt ggaggcactg ggcctacacg actactgtga catcatcaag    1200
caccccatgg acatgagcac aatcaagtct aaactggagg cccgtgagta ccgtgatgct    1260
caggagtttg gtgctgacgt ccgattgatg ttctccaact gctataagta caaccctcct    1320
gaccatgagg tggtggccat ggcccgcaag ctccaggatg tgttcgaaat gcgctttgcc    1380
aagatgccgg acgagcctga ggagccagtg gtggccgtgt cctccccggc agtgcccccct   1440
cccaccaagg ttgtggcccc gccctcatcc agcgacagca gcagcgatag ctcctcggac    1500
agtgacagtt cgactgatga ctctgaggag gagcgagccc agcggctggc tgagctccag    1560
gagcagctca agccgtgca cgagcagctt gcagccctct ctcagcccca gcagaacaaa    1620
ccaaagaaaa aggagaaaga caagaaggaa aagaaaaaag aaaagcacaa aaggaaagag    1680
gaagtggaag agaataaaaa aagcaaagcc aaggaacctc ctcctaaaaa gacgaagaaa    1740
aataatagca gcaacagcaa tgtgagcaag aaggagccag cgcccatgaa gagcaagccc    1800
cctcccacgt atgagtcgga ggaagaggac aagtgcaagc ctatgtccta tgaggagaag    1860
cggcagctca gcttggacat caacaagctc cccggcgaga gctgggccg cgtggtgcac    1920
atcatccagt cacgggagcc ctccctgaag aattccaacc ccgacagagat tgaaatcgac    1980
tttgagaccc tgaagccgtc cacactgcgt gagcttggag cgctatgtca cctcctgttt    2040
gcggaagaaa aggaaaacctt caagctgaga aagttgatgt gatntgccgg gttcctccaa    2100
natgaaaggn ttctcggtct tcaagagncg ggagagnctc ccagttgaat tccaanttct    2160
tttgacaagc ggaaganttc cggaaaacaa agggtccttg gccttaaatt caatttggga    2220
aaaccnggga cttccttaaa tttaaaaaaa ggggcttttt caagntttcc caaggaattt    2280
ccttttcccc caaggnaaag gcntaattan gcctttaaaa ggttnccca                 2329
```

<210> SEQ ID NO 102
<211> LENGTH: 1451
<212> TYPE: DNA
<213> ORGANISM: Homo sapiens
<220> FEATURE:
<221> NAME/KEY: misc_feature
<223> OTHER INFORMATION: Incyte ID No: 2100530
<220> FEATURE:
<221> NAME/KEY: unsure
<222> LOCATION: 1346, 1373, 1430
<223> OTHER INFORMATION: a, t, c, g, or other

<400> SEQUENCE: 102

```
ctcgagcggc ggcatttcct ggtgtctgag cctggcgcgg aggctatggg cagccaggag      60
gtgctgggcc acgcggcccg gctggcctcc tccggtctcc tcctgcaggt gttgtttcgg     120
ttgatcacct ttgtcttgaa tgcatttatt cttcgcttcc tgtcaaagga aatcgttggc     180
gtagtaaatg taagactaac gctgctttac tcaaccaccc tcttcctggc cagagaggcc     240
ttccgcagag catgtctcag tgggggcacc cagcgagact ggagccagac cctcaacctg     300
ctgtggctaa cagtccccct gggtgtgttt tggtccttat tcctgggctg gatctggttg     360
cagctgcttg aagtgcctga tcctaatgtt gtccctcact atgcaactgg agtggtgctg     420
tttggtctct cggcagtggt ggagcttcta ggagagccct tttgggtctt ggcacaagca     480
catatgtttg tgaagctcaa ggtgattgca gagagcctgt cggtaattct taagagcgtt     540
ctgacagctt ttctcgtgct gtggttgcct cactggggat tgtacatttt ctctttggcc     600
cagcttttct ataccacagt tctggtgctc tgctatgtta tttatttcac aaagttactg     660
ggttccccag aatcaaccaa gcttcaaact cttcctgtct ccagaataac agatctgtta     720
cccaatatta caagaaatgg agcgtttata aactggaaag aggctaaact gacttggagt     780
tttttcaaac agtctttctt gaaacagatt ttgacagaag gcgagcgata tgtgatgaca     840
tttttgaatg tattgaactt tggtgatcag ggtgtgtatg atatagtgaa taatcttggc     900
tcccttgtgg ccagattaat tttccagcca atagaggaaa gttttttatat atttttttgct     960
aaggtgctgg agaggggaaa ggatgccaca cttcagaagc aggaggacgt tgctgtggct    1020
gctgcagtct tggagtccct gctcaagctg gccctgctgg ccggcctgac catcactgtt    1080
tttggctttg cctattctca gctggctctg gatatctacg gagggaccat gcttagctca    1140
ggatccggtc ctgttttgct gcgttcctac tgtctctatg ttctcctgct tgccatcaat    1200
ggagtgacag agtgtttcac atttgctgcc atgagcaaag aggaggtcga caggtattcc    1260
tctgctgtga gcagggctgg ccagccagac tggcacacat tgctgtgggg gccttctgtc    1320
tgggagcaac tctcgggaca gcattnctca cagagaccaa gctgatccat ttnctcagga    1380
ctcagttagg tgtgcccaga cggactgaca aaatgacgtg acttcagggn aggctgggac    1440
aaacgaggca a                                                        1451
```

<210> SEQ ID NO 103
<211> LENGTH: 1685
<212> TYPE: DNA
<213> ORGANISM: Homo sapiens
<220> FEATURE:
<221> NAME/KEY: misc_feature
<223> OTHER INFORMATION: Incyte ID No: 2357636

<400> SEQUENCE: 103

```
gcgatcgagg ctgcagcgcg gccgccgggc gcacatgact gccgtcggcg tgcaggccca      60
gaggcctttg ggccaaaggc agccccgccg gtccttcttt gaatccttca tccggaccct     120
catcatcacg tgtgtggccc tggctgtggt cctgtcctcg gtctccattt gtgatgggca     180
ctggctcctg gctgaggacc gcctcttcgg gctctggcac ttctgcacca ccaccaacca     240
gagtgtgccg atctgcttca gagacctggg ccaggcccat gtgcccgggc tggccgtggg     300
catgggcctg gtacgcagcg tgggcgcctt ggccgtggtg gccgccattt ttggcctgga     360
gttcctcatg gtgtcccagt gtgcgagga caaacactca cagtgcaagt gggtcatggg     420
ttccatcctc ctcctggtgt ctttcgtcct ctcctccggc gggctcctgg gtttttgtgat     480
```

-continued

| | |
|---|---|
| cctcctcagg aaccaagtca cactcatcgg cttcacccta atgttttggt gcgaattcac | 540 |
| tgcctccttc ctcctcttcc tgaacgccat cagcggcctt cacatcaaca gcatcaccca | 600 |
| tccctgggaa tgaccgtgga aattttaggc cccctccagg gacatcagat tccacaagaa | 660 |
| aatatggtca aaatgggact tttccagcat gtggcctctg gtggggctgg gttggacaag | 720 |
| ggccttgaaa cggctgcctg tttgccgata acttgtgggt ggtcagccag aaatggccgg | 780 |
| ggggcctctg cacctggtct gcagggccag aggccaggag ggtgcctcag tgccaccaac | 840 |
| tgcacaggct tagccagatg ttgattttag aggaagaaaa aaacatttta aaactccttc | 900 |
| ttgaattttc ttccctggac tggaatacag ttggaagcac aggggtaact ggtacctgag | 960 |
| ctagctgcac agccaaggat agttcatgcc tgtttcattg acacgtgctg ggataggggc | 1020 |
| tgcagaatcc ctggggctcc cagggttgtt aagaatggat cattcttcca gctaagggtc | 1080 |
| caatcagtgc ctattcttcc accagctcaa agggccttcg tatgtatgtc cctggcttca | 1140 |
| gctttggtca tgccaaagag gcagagttca ggattccctc agaatgccct gcacacagta | 1200 |
| ggtttccaaa ccatttgact cggtttgcct ccctgcccgt tgtttaaacc ttacaaaccc | 1260 |
| tggataaccc catcttctag cagctggctg tcccctctgg gagctctgcc tatcagaacc | 1320 |
| ctaccttaag gtgggtttcc ttccgagaag agttcttgag caagctctcc caggagggcc | 1380 |
| cacctgactg ctaatacaca gccctcccca aggcccgtgt gtgcatgtgt ctgtcttttg | 1440 |
| tgagggttag acagcctcag ggcaccattt ttaatcccag aacacatttc aaagagcacg | 1500 |
| tatctagacc tgctggactc tgcagggggt gaggggaac agcgagagct tgggtaatga | 1560 |
| ttaacaccca tgctggggat gcatggaggt gaaggggggcc aggaaccagt ggagatttcc | 1620 |
| atccttgcca gcacgtctgt acttctgttc attaaagtgc tcccttttcta gtcaaaaaaa | 1680 |
| aaaaa | 1685 |

<210> SEQ ID NO 104
<211> LENGTH: 2674
<212> TYPE: DNA
<213> ORGANISM: Homo sapiens
<220> FEATURE:
<221> NAME/KEY: misc_feature
<223> OTHER INFORMATION: Incyte ID No: 2365230

<400> SEQUENCE: 104

| | |
|---|---|
| ctactcctca ccgcgcgagc gcggggaacc agtagccgcg gctgcttcgg ttgccgcggt | 60 |
| cggtggtcgt tatggattct ccatgggacg agttggctct ggccttctcc cgcacgtcca | 120 |
| tgtttccctt ttttgacatc gcgcactatc tagtgtcagt gatggcggtg aaacgtcagc | 180 |
| cgggagcagc tgcattggca tggaagaatc ctatttcaag ctggtttact gctatgctcc | 240 |
| actgttttgg tggaggaatt ttatcctgtc tactgcttgc agagcctcca ttgaagtttc | 300 |
| ttgcaaacca cactaacata ttactggcat cttcaatctg ggtatattac atttttttgc | 360 |
| ccgcatgacc tagtttccca gggctattca tatctacctg ttcaactact ggcttcggga | 420 |
| atgaaggaag tgaccagaac ttggaaaata gtaggtggag tcacacatgc taatagctat | 480 |
| tacaaaaatg gctggatagt catgatagct attggatggg cccgaggtgc aggtggtacc | 540 |
| attataacga attttgagag gttggtaaaa ggagattgga aaccagaagg tgatgaatgg | 600 |
| ctgaagatgt cataccctgc caaggtaacc tgctggggt cagttatctt cacattccag | 660 |
| cacacccagc atctggcaat atcaaagcat aatcttatgt tcctttatac catctttatt | 720 |
| gtggccacaa agataaccat gatgactaca cagacttcta ctatgacatt tgctcccttt | 780 |
| gaggatacat tgagttggat gctatttggc tggcagcagc cgttttcatc atgtgagaag | 840 |

```
aaaagtgaag caaagtcacc ttccaatggc gttgggtcat tggcctcaaa gccggtagat        900
gttgcctcag ataatgttaa aagaaacat actaagaaga atgaataaat ttacgtgatg         960
agctctagca agccaaaaat ttttttctt atctacctgt tatattgtgc taattttcta        1020
tgtatgtgat gtgaaatgaa gactatatat atggaatgga ggtgacagaa agaaagaaat       1080
tctttgtttg agggagactt cccctttctg gattgtattt gtagagtgtt acgagtgtat       1140
catgtgatta tgctttaccg gtaagagaa ttctgttgtg attatttgaa tagttttata        1200
ttaataaaag aagacaaaat tttttaaatg ttagaaaaag cagatctgtc attgcaaagt       1260
aacaaaaatt ttaagctttt aaaaatgtag attttttcata ttttttaaaat ttgaatctat    1320 ttgagcttta gttcagcaga attaaatttt tacttgacat tatcattaaa attgctaggt      1380
atggagaaca attcctattt tattttgaac actgagaaga gtaaacttt cctaaaacac        1440 tttatattat aaatgaaaat aaattgctag tttatatttt agatataaac atcatatttt      1500
ttattaatac ctacatcaaa tggaaatat ctgaaatttt ttttccatag caggtatttt        1560
ctactagaag tagttttact acttttcatt tagaacagag tatgagtctt aatctgaagt      1620 cttttttcatg cccttgtttt aaaaaaacta ctttttttgg cctcaaaaaa atcaagggtg     1680 taattttaa taaattgtta atcctatgtt ttgtaatttt cattttagga gcttgactta       1740 tttttttct ctctcataaa aacacatttg ttttaattgt aggagaaatt ttctcagcat       1800
tttgcatgtt ctttctaatc tttgttggtc tgaatatatt ggtagtaatt actgtaatta     1860
ttcaacaaaa agcatatccg ttcaaaaatt ttttccactat gtcttttttc tagtggctac    1920
tgttttagtt ttctagttga atatctctga caagctttcg tatggttttg ttatattttc    1980
atctacatgt aatgtgttat taattttatt aaatgaaaac taatcacctt catgtggaaa     2040
tgctctgaga attgtcctta ggcatttggt agtaaccagc taaccaagaa gaaacagaga     2100
aaccagaact tcatatggca gtccatttag atgaagaatg atgatataaa atctggttcc    2160
ttcttagcaa ataaaaaac aaacaagaaa agatactaaa tgatgttaat tttcttactt     2220
tatgatttag aagtccagtt ataatattaa aactctgtga catagtttct tttaccaaaa    2280
ccatgaacct actccccgta tcaggtattt tcgatggttt agaagtactc aagtcacatc    2340
acattcaagt tagaagtttt ttttttgttg ttgttatttt aaatttttaa caaatataaa    2400
caccagcaga tactattact tgcttaaaaa attgggaggg ggcacttttc atagtcttgg    2460
aatgctaaga agtttttattt ttaatattgt gacagaaagc tttaagtatt taagagctct   2520
gtattatatt tgatactctt acagttaaaa acttttcaaa attaatacat tgttaattat    2580
tgaccagttt tgaagtttgg gtttaactgt agttgaaatg gaaggactct tgttttacac    2640
ttgtattaaa gataaattta ttaaaataag ttat                                 2674
```

<210> SEQ ID NO 105
<211> LENGTH: 488
<212> TYPE: DNA
<213> ORGANISM: Homo sapiens
<220> FEATURE:
<221> NAME/KEY: misc_feature
<223> OTHER INFORMATION: Incyte ID No: 2455121

<400> SEQUENCE: 105

```
gactacgggg ctgttgacgg cgctgcgatg gctgcctgcg agggcaggag aagcggactc         60
tcggttcctc tcagtcggac ttcctgacgc cgccagttgg cggggcccct tgggccgtcg        120
ccaccactgt agtcatgtac ccaccgccgc cgccgccgcc tcatcgggac ttcatctcgg        180
```

```
tgacgctgag ctttggcgag agctatgaca acagcaagag ttggcggcgg cgctcgtgct    240
ggaggaaatg gaagcaactg tcgagattgc agcggaatat gattctcttc ctccttgcct    300
ttctgctttt ctgtggactc ctcttctaca tcaacttggc tgaccattgg aaagctctgg    360 cttttcaggct aggggaagag cagaagatga ggccagaaat tgctgggtaa aaccagcaaa    420
tccacccgtc ttaccagctc ctcagaaggc ggacaccggc cctgagaact acctgagat    480 ttcgtcac                                                              488
```

<210> SEQ ID NO 106
<211> LENGTH: 1028
<212> TYPE: DNA
<213> ORGANISM: Homo sapiens
<220> FEATURE:
<221> NAME/KEY: misc_feature
<223> OTHER INFORMATION: Incyte ID No: 2472514

<400> SEQUENCE: 106

```
ccagcagctc ggtcctaggg cgatgttgac agacagacag aggggcggat gcagcctacc     60
tcctgggcag tgagctgcgg tctgaggccc ctgcccagct ggaaaccaca gggaggggaa    120
gggaggggag gagaggagag gagaggaacc gtcatgggcc cttggagtcg agtcagggtt    180
gccaaatgcc agatgctggt cacctgcttc tttatcttgc tgctgggcct ctctgtggcc    240
accatggtga ctcttaccta cttcggggcc cactttgctg tcatccgccg agcgtccctg    300
gagaagaacc cgtaccaggc tgtgcaccaa tgggccttct ctgcggggtt gagcctggtg    360
ggcctcctga ctctgggagc cgtgctgagc gctgcagcca ccgtgaggga ggcccagggc    420
ctcatggcag ggggcttcct gtgcttctcc ctggcgttct gcgcacaggt gcaggtggtg    480
ttctggagac tccacagccc cacccaggtg gaggacgcca tgctggacac ctacgacctg    540
gtatatgagc aggcgatgaa aggtacgtcc cacgtccggc ggcaggagct ggcggccatc    600
caggacgtgg tgagcgtggg gacggctggg tggcagggcg tcagcttct gcttggactg    660 cagttcagag aacaggcgca gggtggccag tgagaggtct ggccaggcac cgagggggtt    720
ccaggacaca ggccagagtt gcccctcagg gctgggggca aaagctccc accctctgtc    780 tgcccaggac aaggccgcct accagattct cgaggcccag tgcaaaacga gagggcaggg    840
ccctgtattc agaaacactg aaggatttca agagcattaa agcaaatacg gggccgaaca    900
tagtggctca cacctgtaat cccagcactt tgggaggagg ttgaggcagg tgaattgctt    960
gagcccagga gttcgagacc agcctgagca acatagggag accttgtctc tactttaaaa   1020
aaaaaaaa                                                             1028
```

<210> SEQ ID NO 107
<211> LENGTH: 1551
<212> TYPE: DNA
<213> ORGANISM: Homo sapiens
<220> FEATURE:
<221> NAME/KEY: misc_feature
<223> OTHER INFORMATION: Incyte ID No: 2543486

<400> SEQUENCE: 107

```
ctgcgcctgg gctgccggtg acctgggccg agccctcccg gtcggctaag attgctgagg     60
aggcggcggg tagctggcag gcgccgactt ccgaaggccg ccgtccggc gaggtgtcct    120 catgacttct cttgtggacc atgtccgtga tctttttgc ctgcgtggta cgggtaaggg    180
atggactgcc cctctcagcc tctactgatt tttaccacac ccaagatttt ttggaatgga    240
ggagacggct caagagttta gccttgcgac tggcccagta tccaggtcga ggttctgcag    300
```

-continued

```
aaggttgtga ctttagtata catttttctt ctttcgggga cgtggcctgc atggctatct      360
gctcctgcca gtgtccagca gccatggcct tctgcttcct ggagaccctg tggtgggaat      420
tcacagcttc ctatgacact acctgcattg gcctagcctc caggccatac gcttttcttg      480
agtttgacag catcattcag aaagtgaagt ggcattttaa ctatgtaagt tcctctcaga      540
tggagtgcag cttggaaaaa attcaggagg agctcaagtt gcagcctcca gcggttctca      600
ctctggagga cacagatgtg gcaaatgggg tgatgaatgg tcacacaccg atgcacttgg      660
agcctgctcc taatttccga atggaaccag tgacagccct gggtatcctc tccctcattc      720
tcaacatcat gtgtgctgcc ctgaatctca ttcgaggagt tcaccttgca gaacattctt      780
tacaggttgc ccatgaggaa attggaaaca ttctggcttt tcttgttcct ttcgtagcct      840
gcattttcca ggatccaagg agctggttct gctggttgga ccaaacctcg tgagccagcc      900 accctgacc caaatgagga gagctctgat tctcccatcc gggagcagtg atgtcaaact      960
tctgctgctg gggaaatctc atcagcaggg agcctgtgga aaagggcatg tcagtgaaat     1020
ctgggaatgg ctggattcgg aaacatctgc ccatgtgtat tgatggcaga gctgttgccc     1080
acaagcgcct tttatttagg gtaaaattaa caaatccatt ctattcctct gacccatgct     1140
tagtacatat gacctttaac ccttacattt atatgattct ggggttgctt cagaagtgtt     1200
atttcatgaa tcattcatat gatttgatcc cccaggattc tattttgttt aatgggcttt     1260
tctactaaaa gcataaaata ctgaggctga tttagtcagg gcaaaaccat ttactttaca     1320 tattcgttttt caatacttgc tgttcatgtt acacaagctt cttacggttt tcttgtaaca     1380
ataaatattt tgagtaaata atgggtacat tttaacaaac tcagtagtac aacctaaact     1440
tgtataaaag tgtgtaaaaa tgtatagcca tttatatcct atgtataaat taaatgaggt     1500
ggcttcagaa atggcagaat aaatctaaag tgtttattaa caaaaaaaaa a              1551
```

<210> SEQ ID NO 108
<211> LENGTH: 922
<212> TYPE: DNA
<213> ORGANISM: Homo sapiens
<220> FEATURE:
<221> NAME/KEY: misc_feature
<223> OTHER INFORMATION: Incyte ID No: 2778171

<400> SEQUENCE: 108

```
gcttgcggct cgggtggctg agcgcgcggg gaaatggcca cggggacaga ccaggtggtg       60
ggactcggcc tcgtcgccgt tagcctgatc atcttcacct actacaccgc ctgggtgatt      120
ctcttgccat tcatcgacag tcagcatgtc atccacaagt atttcctgcc ccgagcctat      180
gctgtcgcca tcccactggc tgcaggcctc ctgctgctcc tgtttgtggg actgttcatc      240
tcctacgtga tgctgaagag caagagagtg accaagaagg ctcagtgaag gtcccgcagg      300
atgaggctgc cagcccccttc tctgcttccc ctccagcaca gggaccaagt ggggagcct      360 gcagaacctg tccaggcaca gtggctcctc aagcctgcct gtcctgcaga gtccccatgg      420
catggagctt acacctgact gactggagcc cctccccga ctcccacttc cagaagctag      480
gagggaggga tacctggaag actccggtca cctccttctt gctcagggcc taaaagatgc      540
tggtcctccc aacctcactc tcagactccc tgccaccttt tccctgggt tctgccgtct      600 tgcctcactt cccctcctgt cacatgctga cgttggactt agcaggttct aaggccacat      660
gtgtgacctc tctgacttct cttcctccac caaggcagct ttccttaccc tgacacagcc      720
ccagacccca caaagccttc tggacctgga aagcctgggg aaggactgac agaccccagg      780
accagccctg gggctcaggg cagccacccc gggccgctga ccgactgacc tctcctcacg      840
```

```
gaggcccagc cccaaagccc cagggctggc ccgtttggga cagctgacca ataaacactg    900
atggtgtgtt aaaaaaaaaa aa                                             922

<210> SEQ ID NO 109
<211> LENGTH: 985
<212> TYPE: DNA
<213> ORGANISM: Homo sapiens
<220> FEATURE:
<221> NAME/KEY: misc_feature
<223> OTHER INFORMATION: Incyte ID No: 2799575

<400> SEQUENCE: 109
gcccaggagg cgcccgggtg aggcacgggt gcgcaagcga ggagttccgg ctggagaccc     60
gtgctctggg ccggcgcctt caccatggcc tcggcagagc tggactacac catcgagatc    120
ccggatcagc cctgctggag ccagaagaac agccccagcc caggtgggaa ggaggcagaa    180
actcggcagc tgtggtgat tctcttgggc tggggtggct gcaaggacaa gaaccttgcc    240
aagtacagtg ccatctacca caaaagggc tgcatcgtaa tccgatacac agccccgtgg    300
cacatggtct tcttctccga gtcactgggt atcccttcac ttcgtgtttt ggcccagaag    360
ctgctcgagc tgctctttga ttatgagatt gagaaggagc ccctgctctt ccatgtcttc    420
agcaacggtg gcgtcatgct gtaccgctac gtgctggagc cctgcagac ccgtcgcttc    480 tgccgcctgc gtgtggtggg caccatcttt gacagcgctc ctggtgacag caacctggta    540
ggggctctgc gggccctggc agccatcctg gagcgccggg ccgccatgct gcgcctgttg    600
ctgctggtgg cctttgccct ggtggtcgtc ctgttccacg tcctgcttgc tcccatcaca    660
gccctcttcc acacccactt ctatgacagg ctacaggacg cgggctctcg ctggcccgag    720
ctctacctct actcgagggc tgacgaagta gtcctggcca gagacataga acgcatggtg    780
gaggcacgcc tggcacgccg ggtcctggcg cgttctgtgg atttcgtgtc atctgcacac    840
gtcagccacc tccgtgacta ccctacttac tacacaagcc tctgtgtcga cttcatgcgc    900
aactgcgtcc gctgctgagg ccattgctcc atctcacctc tgctccagaa ataaatgcct    960
gacacctccc cacaaaaaaa aaaaa                                          985

<210> SEQ ID NO 110
<211> LENGTH: 1562
<212> TYPE: DNA
<213> ORGANISM: Homo sapiens
<220> FEATURE:
<221> NAME/KEY: misc_feature
<223> OTHER INFORMATION: Incyte ID No: 2804955

<400> SEQUENCE: 110
tgcgtccaga ggctggcatg gcgcgggccg agtactgagc gcacggtcgg ggcacagcag     60
ggccggtggg tgcagctggc tcgcgcctcc tctccggccg ccgtctcctc cggtccccgg    120
cgaaagcatt gagacaccag ctggacgtca cgcgccggag catgtctggg agtcagagcg    180
aggtggctcc atccccgcag agtccgcgga gccccgagat gggacgggac ttgcggcccg    240
ggtcccgcgt gctcctgctc ctgcttctgc tcctgctggt gtacctgact cagccaggca    300
atggcaacga gggcagcgtc actgaagtt gttattgtgg taaagaatt tcttccgact    360 ccccgccatc ggttcagttc atgaatcgtc tccggaaaca cctgagagct taccatcggt    420
gtctatacta cacgaggttc cagctccttt cctggagcgt gtgtggaggc aacaaggacc    480
catgggttca ggaattgatg agctgtcttg atctcaaaga atgtggacat gcttactcgg    540
ggattgtggc ccaccagaag catttacttc ctaccagccc cccaatttct caggcctcag    600
```

```
aggggggcatc ttcagatatc cacacccctg cccagatgct cctgtccacc ttgcagtcca      660
ctcagcgccc caccctccca gtaggatcac tgtcctcgga caaagagctc actcgtccca      720
atgaaaccac cattcacact gcgggccaca gtctggcagc tgggcctgag gctggggaga      780
accagaagca gccggaaaaa aatgctggtc ccacagccag gacatcagcc acagtgccag      840
tcctgtgcct cctggccatc atcttcatcc tcaccgcagc cctttcctat gtgctgtgca      900
agaggaggag ggggcagtca ccgcagtcct ctccagatct gccggttcat tatatacctg      960
tggcacctga ctctaatacc tgagccaaga atggaagttt gtgaggagac ggactctatg     1020
ttgcccaggc tgttatggaa ctcctgagtc aagtgatcct cccaccttgg cctctgaagg     1080
tgcgaggatt ataggcgtca cctaccacat ccagcctaca cgtatttgtt aatatctaac     1140
ataggactaa ccagccactg ccctctctta ggcccctcat ttaaaaacgg ttatactata     1200
aaatctgctt ttcacactgg gtgataataa cttggacaaa ttctatgtgt attttgtttt     1260
gttttgcttt gctttgtttt gagacggagt ctcgctctgt catccaggct ggagtgcagt     1320
ggcatgatct cggctcactg caaccccat ctcccaggtt caagcgattc tcctgcctcc      1380
tcctaagtag ctgggactac aggtgctcac caccacaccc ggctaatttt ttgtattttt     1440
agtagagacg gggtttcacc atgttgacca ggctggtctc gaactcctga cctggtgatc     1500
tgcccaccag gcctcccaaa gtgctgggat taaaggtgtg agccacatgg ctggcctatg     1560
tt                                                                    1562

<210> SEQ ID NO 111
<211> LENGTH: 1851
<212> TYPE: DNA
<213> ORGANISM: Homo sapiens
<220> FEATURE:
<221> NAME/KEY: misc_feature
<223> OTHER INFORMATION: Incyte ID No: 2806395

<400> SEQUENCE: 111
gctctgcaga gtggtggccg ggccagggc cggggtgccc tccctcccac cttctcccgc        60
catgagccag ggaagtccgg gggactgggc cccctagat cccaccccg gaccccagc         120 atccccaac cccttcgtgc atgagttaca tctctctcgc ctccagaggg ttaagttctg       180
cctcctgggg gcattgctgg ccccatccg agtgcttctg gcctttatcg tcctctttct       240
cctctggccc tttgcctggc ttcaagtggc cggtcttagt gaggagcagc ttcaggagcc      300
aattacagga tggaggaaga ctgtgtgcca caacggggtg ctaggcctga gccgcctgct     360 gttttttcctg ctgggcttcc tccggattcg cgttcgtggc cagcgagcct ctcgccttca    420
agcccctgtc cttgttgctg ccccacactc cactttcttt gacccccattg ttctgctgcc    480 ctgtgacctg cccaaagttg tgtcccgagc tgagaacctt tccgttcctg tcattggagc     540
ccttcttcga ttcaaccaag ccatcctggt atcccggcat gacccggctt ctcgacgcag     600
agtggtggag gaggtccgaa ggcgggccac ctcaggaggc aagtggccgc aggtgctatt     660 cttcctgag gcaccctgtt ccaacaagaa ggctttgctt aagttcaaac caggagcctt      720
catcgcaggg gtgcctgtgc agcctgtcct catccgctac cccaacagtc tggacaccac    780
cagctgggca tggaggggtc ctggagtact caaagtcctc tggctcacag cctctcagcc    840
ctgcagcatt gtggatgtgg agttccttcc tgtgtatcac cccagccctg aggagagcag    900
ggaccccacc ctctatgcca acaatgttca gagggtcatg gcacaggctc tgggcattcc    960
agccaccgaa tgtgagtttg tagggagctt acctgtgatt gtggtgggcc ggctgaaggt    1020
```

| | |
|---|---|
| ggcgttggaa ccacagctct gggaactggg aaaagtgctt cggaaggctg ggctgtccgc | 1080 |
| tggctatgtg gacgctgggg cagagccagg ccggagtcga atgatcagcc aggaagagtt | 1140 |
| tgccaggcag ctacagctct ctgatcctca gacggtggct ggtgcctttg gctacttcca | 1200 |
| gcaggatacc aagggtttgg tggacttccg agatgtggcc cttgcactag cagctctgga | 1260 |
| tgggggcagg agcctggaag agctaactcg tctggccttt gagctctttg ctgaagagca | 1320 |
| agcagagggt cccaaccgcc tgctgtacaa agacggcttc agcaccatcc tgcacctgct | 1380 |
| gctgggttca ccccacccctg ctgccacagc tttgcatgct gagctgtgcc aggcaggatc | 1440 |
| cagccaaggc ctctccctct gtcagttcca gaacttctcc ctccatgacc cactctatgg | 1500 |
| gaaactcttc agcacctacc tgcgccccc acacacctct cgaggcacct cccagacacc | 1560 |
| aaatgcctca tccccaggca accccactgc tctggccaat gggactgtgc aagcaccccaa | 1620 |
| gcagaaggga gactgagtgc ctcagcctct caccccctcc tcctcagggc agcgctaggg | 1680 |
| gcctccccta tgcctcagcc ccatctctgc tcctgtttga atttttgttat tgttgtttgg | 1740 |
| ttgttgttttt tttaagttga ttttaatttt ttgtttggtt gatttttttg taaaaaacta | 1800 |
| ttttatatat aaatataaat ctatatctat atctattaaa aaaaatgaat t | 1851 |

<210> SEQ ID NO 112
<211> LENGTH: 992
<212> TYPE: DNA
<213> ORGANISM: Homo sapiens
<220> FEATURE:
<221> NAME/KEY: misc_feature
<223> OTHER INFORMATION: Incyte ID No: 2836858

<400> SEQUENCE: 112

| | |
|---|---|
| ggcgcgaggc agtatggttt gaagtggtga acatggattt ttctcggctt cacatgtaca | 60 |
| gtcctcccca gtgtgtgccg gagaacacgg gctacacgta tgcgctcagt tccagctatt | 120 |
| cttcagatgc tctggatttt gagacggagc acaaattgga ccctgtattt gattctccac | 180 |
| ggatgtcccg ccgtagtttg cgcctggcca cgacagcatg caccctgggg gatggtgagg | 240 |
| ctgtgggtgc cgacagcggc accagcagcg ctgtctccct gaagaaccga gcggccagaa | 300 |
| caacaaaaca gcgcagaagc acaaacaaat cagctttag tatcaaccac gtgtcaaggc | 360 |
| aggtcacgtc ctctggcgtc agccacgcg gcactgtcag cctgcaggat gctgtgactc | 420 |
| gacggcctcc tgtattggac gagtcttgga ttcgtgaaca gaccacagtg gaccacttct | 480 |
| ggggtcttga tgatgatggt gatcttaaag gtggaaataa agctgccatt cagggaaacg | 540 |
| gggatgtggg agccgccgcc gccaccgcgc acaacggctt ctcctgcagc aactgcagca | 600 |
| tgctgtccga gcgcaaggac gtgctcacgg cgcaccccgc ggccccgggg ccgtgtcga | 660 |
| gagtttattc tagggacagg aatcaaaaat gtaagtctca gtcctttaaa actcagaaaa | 720 |
| aggtgtgttt tccaaattta atatttcctt tctgtaagtc tcagtgtctg cactatttgt | 780 |
| cttggagact taaaattatc ccttgaaagc ataagaagta caccccaaac cagctttgtc | 840 |
| cttcctgtcc tcttctagtt tacatttttat gtggttagta attttgtacc taaaagtatt | 900 |
| tgaaattcta taaatttgga cttgacgtga gcaaagaaaa atttctacgt aagcgaaact | 960 |
| aataaaacta cagtcacttt caaaaaaaaa aa | 992 |

<210> SEQ ID NO 113
<211> LENGTH: 1251
<212> TYPE: DNA
<213> ORGANISM: Homo sapiens
<220> FEATURE:
<221> NAME/KEY: misc_feature
<223> OTHER INFORMATION: Incyte ID No: 2844513

<400> SEQUENCE: 113

| | | | | | |
|---|---|---|---|---|---|
| ctctgctggc | cggtctaaag | cggcagccgc | cggggcgcaa | tgcgagcggc | tggcgtaggc | 60 |
| ttggtggact | gtcactgcca | cctctccgcc | ccggactttg | accgcgattt | ggatgatgtg | 120 |
| ttggagaaag | ccaagaaggc | caatgttgtg | gcccttgtgg | cagttgccga | acattcagga | 180 |
| gaatttgaaa | agattatgca | actttcagaa | aggtataatg | ggtttgtcct | gccatgcttg | 240 |
| ggtgttcatc | cagttcaagg | acttccacca | gaagaccaaa | gaagtgtcac | actaaaggat | 300 |
| ttggatgtag | ctttgcccat | tattgagaat | tataaggatc | ggttgttggc | aattggagag | 360 |
| gttggactag | atttctcccc | cagatttgct | ggcactggtg | aacagaagga | agagcaaaga | 420 |
| caagtcctaa | tcagacagat | ccagttagcc | aaaagactaa | atttgcctgt | aaatgtgcac | 480 |
| tcacgctctg | ctggaagacc | taccatcaac | cttttacaag | agcaaggtgc | tgagaaggta | 540 |
| ctgctgcatg | catttgatgg | tcggccatct | gtagccatgg | aaggagtaag | agctgggtac | 600 |
| ttcttctcaa | ttccccttc | tatcataaga | agtggacaga | agcagaaact | tgtgaaacaa | 660 |
| ttgcctttaa | cttctatatg | cttagaaaca | gattcacctg | cactaggacc | agaaaaacag | 720 |
| gtacggaatg | agccctggaa | catttctatt | tcagcagaat | atattgccca | ggtgaaaggg | 780 |
| atctcagtgg | aagaagttat | agaagtgacg | acacagaatg | cattaaaact | gtttcctaag | 840 |
| ctccgacact | tgctccagaa | atagcttcaa | aaccatccat | tacaaaatcg | aatcaactgc | 900 |
| aggggggcagc | atttgaaaaa | tagaaatgtt | ctgatgaaga | atctgaactg | aagaagctgt | 960 |
| tttataggt | tatagaagat | tgtaattgta | gagaaatatt | tctcttagaa | ataaaactgg | 1020 |
| gcttggatcc | tgaaaccctg | ggttctgatt | ctagccttgt | gctgcttttc | aattagccga | 1080 |
| gttctggcag | gatattggga | aaatactgct | acttcttaca | ttgccctttt | atatagaacc | 1140 |
| accacctgaa | ctgaaaccat | tgctactggg | aagggtggct | cccacaggaa | gagtataagc | 1200 |
| actactgtga | tgaggatgga | gtaagctaaa | gtatactttt | tttttttttt | g | 1251 |

<210> SEQ ID NO 114
<211> LENGTH: 1397
<212> TYPE: DNA
<213> ORGANISM: Homo sapiens
<220> FEATURE:
<221> NAME/KEY: misc_feature
<223> OTHER INFORMATION: Incyte ID No: 3000380

<400> SEQUENCE: 114

| | | | | | |
|---|---|---|---|---|---|
| ctaggacgcc | cctggagccg | gaaccccagc | agaagccgga | accagaacca | aatcaccggt | 60 |
| accggctgca | gccccctaaa | cccaggaggc | gccctggccc | cgcgctcgccc | cccagggcct | 120 |
| catgtcggaa | ccacagcctg | acctggaacc | gccccaacat | gggctatata | tgctcttcct | 180 |
| gcttgtgctg | gtcttcttcc | tcatgggcct | ggtaggcttc | atgatctgcc | acgtgctcaa | 240 |
| gaagaagggc | taccgctgcc | gcacgtcgag | gggctctgag | cctgacgatg | cccagcttca | 300 |
| gcccccctgag | gacgatgaca | tgaatgagga | cacagtagag | aggattgttc | gctgcatcat | 360 |
| ccagaatgaa | gtgtggatgc | cacctccagc | ctgcaggacg | agccccctc | ccatcatcac | 420 |
| acagtgcacc | tgggctctgc | agccccttgc | cgtccattgc | agccgcagca | agaggcctcc | 480 |
| acttgtccgt | cagggacgct | ccaaggaagg | aaaaagccgc | cccggacag | gggagaccac | 540 |
| tgtgttctct | gtgggcaggt | tccgggtgac | acacattgag | aagcgctatg | gactgcacga | 600 |
| acaccgtgat | ggctcccccca | cagacaggag | ctggggctct | cgtggggac | aggacccagg | 660 |
| gggtggtcag | gggtctgggg | gagggcaccc | caaggcaggg | atgctgccat | ggagaggctg | 720 |

| | |
|---|---|
| cccccctgag aggccacagc cccaggtcct agccagcccc ccagtacaga atggaggact | 780 |
| cagggacagc agcctaaccc ctcgtgcact tgaagggaac cccagagctt ctgcagagcc | 840 |
| aacactgagg gccggaggga ggggcccaag cccagggctg cccactcaag aggcaaatgg | 900 |
| gcagccaagc aaaccagaca cttctgatca ccaggtgtct ctaccacagg gagcagggag | 960 |
| tatgtgagtc tccttcattg tgctgatgga ctaccagctg gcagggccag ggggtgggtg | 1020 |
| ggcgtgaaag ccctccctc cactggacag cactgccccc cagctgaggg accagctcta | 1080 |
| cttccacctg gagttgcaca gtctcaggct gggggcctca ggagaggtca cagcccctca | 1140 |
| gtctcttctc cttcccctgc ctgcaacagg ctgcctgccc cgccttcccc aacacctcgc | 1200 |
| tccatatgat agagcgtggc agctgggagc aggcccctgc ccgtggtggg ccctaaagc | 1260 |
| aatagcaccg taggccccct gccctcttag cacaagaggc ccaggccctg gcctggcctt | 1320 |
| cgtgcccttt attcattgtc aataaatccg ctcagaccat taaaaaatac aactcaaggg | 1380 |
| gtagccaaaa aaaaaaa | 1397 |

<210> SEQ ID NO 115
<211> LENGTH: 1581
<212> TYPE: DNA
<213> ORGANISM: Homo sapiens
<220> FEATURE:
<221> NAME/KEY: misc_feature
<223> OTHER INFORMATION: Incyte ID No: 182532

<400> SEQUENCE: 115

| | |
|---|---|
| acagcacagc tgacagccgt actcaggaag cttctggtat cctaggctta tctccacaga | 60 |
| ggagaacaca caagcagcag agaccatggg gcccctctca gcccctccct gcacacacct | 120 |
| catcacttgg aaggggtcc tgctcacagc atcactttta aacttctgga atccgcccac | 180 |
| aactgcccaa gtcacgattg aagcccagcc acccaaagtt tctgagggga aggatgttct | 240 |
| tctacttgtc cacaatttgc cccagaatct tgctggctac atttggtaca aagggcaaat | 300 |
| gacatacgtc taccattaca ttatatcgta tatagttgat ggtaaaataa ttatatatgg | 360 |
| gcctgcatac agtggaagag aaagagtata ttccaatgca tccctgctga tccagaatgt | 420 |
| cacgcaggag gatgcaggat cctacacctt acacatcata aagcgaggtg atgggactag | 480 |
| aggagaaact ggacatttca ccttcacctt atacctggag actcccaagc cctccatctc | 540 |
| cagcagcaac ttataccccca gggaggacat ggaggctgtg agcttaacct gtgatcctga | 600 |
| gactccggac gcaagctacc tgtggtggat gaatggtcag agcctcccta tgactcacag | 660 |
| cttgcagttg tccaaaaaca aaaggaccct cttctatttt ggtgtcacaa agtacactgc | 720 |
| aggaccctat gaatgtgaaa tacggaaccc agtgagtggc atccgcagtg acccagtcac | 780 |
| cctgaatgtc ctctatggtc cagacctccc cagcatttac ccttcattca cctattaccg | 840 |
| ttcaggagaa aacctctact tgtcctgctt cgccgagtct aacccacggg cacaatattc | 900 |
| ttggacaatt aatgggaagt tcagctatc aggacaaaag ctctttatcc cccaaattac | 960 |
| tacaaagcat agtgggctct atgcttgctc tgttcgtaac tcagccactg gcatggaaag | 1020 |
| ctccaaatcc atgacagtca aagtctctgc tccttcagga acaggacatc ttcctggcct | 1080 |
| taatccatta tagcagccgt gatgtcattt ctgtatttca ggaagactgg cagacagttg | 1140 |
| ctttcattct tcctcaaagt atttaccatc agctacagtc caaaattgct ttttgttcaa | 1200 |
| ggagatttat gaaagactc tgacaaggac tcttgaatac aagttcctga taacttcaag | 1260 |
| atcataccac tggactaaga actttcaaaa ttttaatgaa caggctgata cttcatgaaa | 1320 |

```
ttcaagacaa agaaaaaaac ccaattttat tggactaaat agtcaaaaca atgttttcat    1380
aattttctat ttgaaaatgt gctgattctt tgaatgtttt attctccaga tttatgcact    1440 tttttcttc agcaattggt aaagtatact tttgtaaaca aaaattgaaa catttgcttt      1500
tgctccctaa gtccccaga attgggaaac tattcatgag tattcatatg tttatggtaa     1560
taaagttatc tgcacaagtt c                                              1581

<210> SEQ ID NO 116
<211> LENGTH: 1566
<212> TYPE: DNA
<213> ORGANISM: Homo sapiens
<220> FEATURE:
<221> NAME/KEY: misc_feature
<223> OTHER INFORMATION: Incyte ID No: 239589

<400> SEQUENCE: 116
cggctcgagt atggatctcc aaggaagagg ggtccccagc atcgacagac ttcgagttct      60
cctgatgttg ttccatacaa tggctcaaat catggcagaa caagaagtgg aaaatctctc     120
aggcctttcc actaaccctg aaaagatat atttgtggtg cgggaaaatg ggacgacgtg      180
tctcatggca gagtttgcag ccaaatttat tgtaccttat gatgtgtggg ccagcaacta     240
cgtagatctg atcacagaac aggccgatat cgcattgacc cggggagctg aggtgaaggg     300
ccgctgtggc cacagccagt cggagctgca agtgttctgg gtggatcgcg catatgcact     360
caaaatgctc tttgtaaagg aaagccacaa catgtccaag ggacctgagg cgacttggag     420
gctgagcaaa gtgcagtttg tctacgactc ctcggagaaa acccacttca agacgcagt     480 cagtgctggg aagcacacag ccaactcgca ccacctctct gccttggtca ccccgctgg     540 gaagtcctat gagtgtcaag ctcaacaaac catttcactg gcctctagtg atccgcagaa    600
gacggtcacc atgatcctgt ctgcggtcca catccaacct tttgacatta tctcagattt    660
tgtcttcagt gaagagcata atgcccagt ggatgagcgg gagcaactgg aagaaacctt    720 gccccctgatt tgggcctca tcttgggcct cgtcatcatg gtaacactcg cgatttacca    780
cgtccaccac aaaatgactg ccaaccaggt gcagatccct cgggacagat cccagtataa    840
gcacatgggc tagaggccgt taggcaggca ccccctattc ctgctccccc aactggatca    900
ggtagaacaa caaagcact tttccatctt gtacacgaga tacaccaaca tagctacaat    960
caaacaggcc tgggtatctg aggcttgctt ggcttgtgtc catgcttaaa cccacggaag   1020
ggggagactc tttcggattt gtagggtgaa atggcaatta ttctctccat gctggggagg   1080 agggggaggag ggtctcagac agctttcgtg ctcatggtgg cttggctttg actctccaaa  1140
gagcaataaa tgccacttgg agctgtatct ggccccaaag tttagggatt gaaaacatgc   1200
ttctttgagg aggaaacccc tttaggttca gaagaatatg gggtgctttg ctcccttgga  1260
cacagctggc ttatcctata cagttgtcaa tgcacacaga atacaacctc atgctccctg   1320
cagcaagacc cctgaaagtg attcatgctt ctggctggca ttctgcatgt ttagtgattg   1380
tcttgggaat gtttcactgc tacccgcatc cagcgactgc agcaccagaa aacgactaat   1440
gtaactatgc agagttgttt ggacttcttc ctgtgccagg tccaagtcgg gggacctgaa   1500
gaatcaatct gtgtgagtct gttttcaaa atgaaataaa acacactatt ctctggcaaa   1560
aaaaaa                                                               1566

<210> SEQ ID NO 117
<211> LENGTH: 1815
<212> TYPE: DNA
<213> ORGANISM: Homo sapiens
```

<220> FEATURE:
<221> NAME/KEY: misc_feature
<223> OTHER INFORMATION: Incyte ID No: 1671302

<400> SEQUENCE: 117

| | |
|---|---|
| tttgtttctc ttattcccag gacatcaagg agactttcaa taggtgtgaa gaggtacagc | 60 |
| tgcagccccc agaggtctgg tcccctgacc cgtgccaacc ccatagccat gacttcctga | 120 |
| cagatgccat cgtgaggaaa atgagccgga tgttctgtca ggctgcgaga gtggacctga | 180 |
| cgctggaccc tgacacggct cacccggccc tgatgctgtc ccctgaccgc ggggggtcc | 240 |
| gcctggcaga gcggcggcag gaggttgctg accatcccaa gcgcttctcg gccgactgct | 300 |
| gcgtactggg ggcccagggc ttccgctccg gccggcacta ctgggaggta gaggtgggcg | 360 |
| ggcggcgggg ctgggcggtg ggtgctgccc gtgaatcaac ccatcataag gaaaaggtgg | 420 |
| gccctggggg ttcctccgtg ggcagcgggg atgccagctc ctcgcgccat caccatcgcc | 480 |
| gccgccggct ccacctgccc cagcagcccc tgctccagcg ggaagtgtgg tgcgtgggca | 540 |
| ccaacggcaa acgctatcag gcccagagct ccacagaaca gacgctgctg agccccagtg | 600 |
| agaaaccaag gcgctttggt gtgtacctgg actatgaagc tgggcgcctg gcttctaca | 660 |
| acgcagagac tctagcccac gtgcacacct tctcggctgc cttcctgggc gagcgtgtct | 720 |
| ttcctttctt ccgggtgctc tccaagggca cccgcatcaa gctctgccct tgattatcct | 780 |
| gccacccgca gggcccctct gtcagcactt gggggtggg tggtgaggg tggcccgtaa | 840 |
| gtttgagggc tcaaaggctc ttcccactgc ttgttactgt gttgcttccc actcccctt | 900 |
| gaccccaggc ccctgcttct ccctctagga gcctaaagaa ccctcctggc ctccagctca | 960 |
| gccttctctc acctactatg tctgtccaac aggtctgcat gggtccctga taatgagaac | 1020 |
| agctgcctgg tcttctctcc cagtctgcct agcccagccc tgggactgga atttgagtag | 1080 |
| gggatgaggg gaaattgtaa tttcattcct taacttcctt ttccccaccc ctgctcttca | 1140 |
| acctctttat cagttctgag gctggagggt ttgggcaagg caacatcccc attccaattc | 1200 |
| cattttctga tgcagatttt agctgaggga tttggaagcc atttggggag gcaggctggg | 1260 |
| ccaaagggta gagctgggta ataaatgtct attctcctgg ggaggaggga ttctaaactt | 1320 |
| tccttccgtc ctcaatttct acctccatag accggccaga atttagcttc acttgagaga | 1380 |
| gatctggaat ggtcgccatg attgaaacca cgcaccatta catcatcatt acattaatta | 1440 |
| catcaacata aattatttct tcccccttcc cttttccagc actcaaccaa ggagcaaagc | 1500 |
| tcatcccacc ccacacccct cccaggtctg ctcactgcca ggctcctctc cccttttgttc | 1560 |
| agtggagctg gcttttctcc cagccccttt ccatgccttt cactccattt ggcaagctct | 1620 |
| gaggggagc ctggggacgg gtttgggtcc ccaggaggag agccttgggt ataatctatt | 1680 |
| tttctaggag cctcttgcct tgtcacttgc agctttcgcc ctctgctttg atggctgagg | 1740 |
| tgaactcatg ttctttggga aaagggaagg cgtgctgtgg aaataaaatg tttatttgct | 1800 |
| tctctaaaaa aaaaa | 1815 |

<210> SEQ ID NO 118
<211> LENGTH: 1566
<212> TYPE: DNA
<213> ORGANISM: Homo sapiens
<220> FEATURE:
<221> NAME/KEY: misc_feature
<223> OTHER INFORMATION: Incyte ID No: 2041858

<400> SEQUENCE: 118

| | |
|---|---|
| caaagagcca ggctccagga gaggaagggc tctgcgagag gagagaggag agcgctggag | 60 |

-continued

```
aggagaggct ggaggtgaga gtcccaggaa aggcagagga gaatcgtagg gacataagtg      120
tcccagcaca ggcaaggagg aatccgagga taaggttctg gagggacaga agggcccaga      180
gagagtcctt agccaggatg gaggctgttg tgaacttgta ccaagaggtg atgaagcacg      240
cagatccccg gatccagggc taccctctga tggggtcccc cttgctaatg acctccattc      300
tcctgaccta cgtgtacttc gttctctcac ttgggcctcg catcatggct aatcggaagc      360
ccttccagct ccgtggcttc atgattgtct acaacttctc actggtggca ctctccctct      420
acattgtcta tgagttcctg atgtcgggct ggctgagcac ctatacctgg cgctgtgacc      480
ctgtggacta ttccaacagc cctgaggcac ttaggatggt tcgggtggcc tggctcttcc      540
tcttctccaa gttcattgag ctgatggaca cagtgatctt tattctccga aagaaagacg      600
ggcaggtgac cttcctacat gtcttccatc actctgtgct tccctggagc tggtggtggg      660
gggtaaagat tgccccggga ggaatgggct ctttccatgc catgataaac tcttccgtgc      720
atgtcataat gtacctgtac tacgattat ctgcctttgg ccctgtggca caaccctacc      780
tttggtggaa aaagcacatg acagccattc agctgatcca gtttgtcctg gtctcactgc      840
acatctccca gtactacttt atgtccagct gtaactacca gtacccagtc attattcacc      900
tcatctggat gtatggcacc atcttcttca tgctgttctc caacttctgg tatcactctt      960
ataccaaggg caagcggctg ccccgtgcac ttcagcaaaa tggagctcca ggtattgcca     1020
aggtcaaggc caactgagaa gcatggccta gataggcgcc cacctaagtg cctcaggact     1080 gcacttagg gcagtgtccg tcagtgccct ctccacctac acctgtgacc aaggcttatg     1140
tggtcaggac tgagcagggg actggccctc ccctccccac agctgctcta cagggaccac     1200
ggctttggtt cctcacccac ttcccccggg cagctccagg gatgtggcct cattgctgtc     1260
tgccactcca gagctggggg ctaaaagggc tgtacagtta tttccccctc cctgccttaa     1320
aacttgggag aggagcactc agggctggcc ccacaaaggg tctcgtggcc tttttcctca     1380
cacagaagag gtcagcaata atgtcactgt ggacccagtc tcactcctcc accccacaca     1440
ctgaagcagt agcttctggg ccaaaggtca gggtgggcgg gggcctggga atacagcctg     1500
tggaggctgc ttactcaact tgtgtcttaa ttaaaagtga cagaggaaac cacggaaaaa     1560
aaaaaa                                                                1566
```

<210> SEQ ID NO 119
<211> LENGTH: 1055
<212> TYPE: DNA
<213> ORGANISM: Homo sapiens
<220> FEATURE:
<221> NAME/KEY: misc_feature
<223> OTHER INFORMATION: Incyte ID No: 2198863
<220> FEATURE:
<221> NAME/KEY: unsure
<222> LOCATION: 1032, 1037, 1042
<223> OTHER INFORMATION: a, t, c, g, or other

<400> SEQUENCE: 119

```
tcagcagcca gcaaggtctt tgagaaacac atggagctca ctgccctgct ccctttcagt       60
ggcttcccat tgccttggat aaagacccaa atgcctaaca gggcccataa ggccccacat      120
gatccacggg ctttagatgt gcagagatgt ggagcgcgat gccaggtagg gtgagcagtg      180
gcgtggagca gggccacttg gctggggtgc caggtgttgg aggggagcag cagcctgtcc      240
acatggccta aggtttgagc tgggtgttgc tgctgggccg ggcagcgca gtgcagcgca      300 ccgcggggag cgaggagcgc gcggaccggc catgggcaag tcagcttcca aacagtttca      360
```

-continued

```
taatgaggtc ctgaaggccc acaatgagta ccggcagaag cacggcgtcc ccccactgaa    420
gctctgcaag aacctcaacc gggaggctca acagtattct gaggccctgg ccagcacgag    480
gatcctcaag cacagcccgg agtccagccg tggccagtgt ggggagaacc ttgcatgggc    540
atcctatgat cagacaggaa aggaggtggc tgatagatgg tacagtgaaa tcaagaacta    600
taacttccag cagcctggct tcacctcggg gactggacac ttcacggcca tggtatggaa    660
gaacaccaag aagatgggcg tggggaaggc gtccgcaagt gacgggtcct cctttgtggt    720
ggccagatac ttcccagcgg ggaatgttgt caatgagggc ttcttcgaag aaaacgtcct    780
gccgccgaag aagtaacttg ttaaatgtaa tgggaaggtg gcagacttaa gaacgtggat    840
atgaagtgcc tagaaccacc acaacctggc tgtgcgtctg tccctgtggg tgaatgtgct    900
tgtgtgtgtg atgcatgtga gcgtctctgg cacacacatt ggcatacagt tccgtgttcg    960
cccatcttat tacaggagtg agcaaaggaa gcatttaccc cgatggttac ctagaccacg   1020
attaattgga tncccngaa anggggatcg gtttt                                1055
```

```
<210> SEQ ID NO 120
<211> LENGTH: 1956
<212> TYPE: DNA
<213> ORGANISM: Homo sapiens
<220> FEATURE:
<221> NAME/KEY: misc_feature
<223> OTHER INFORMATION: Incyte ID No: 3250703
<220> FEATURE:
<221> NAME/KEY: unsure
<222> LOCATION: 1893, 1896, 1899, 1906, 1911, 1921, 1926-1929, 1932,
      1935, 1940, 1948, 1950-1951, 1953
<223> OTHER INFORMATION: a, t, c, g, or other

<400> SEQUENCE: 120
```

```
cactcaagga agatataaat gacaaggtcg gctcagctct cagacaaggt tttccaagca     60
agatgaagcc caacatcatc tttgtacttt ccctgctcct catcttggag aagcaagcag    120
ctgtgatggg acaaaaaggt ggatcaaaag gccgattacc aagtgaattt tcccaatttc    180
cacacggaca aaagggccag cactattctg gacaaaaagg caagcaacaa actgaatcca    240
aaggcagttt ttctattcaa tacacatatc atgtagatgc caatgatcat gaccagtccc    300
gaaaaagtca gcaatatgat ttgaatgccc tacataagac gacaaaatca caacgacatc    360
taggtggaag tcaacaactg ctccataata aacaagaagg cagagaccat gataaatcaa    420
aaggtcattt tcacagggta gttatacacc ataaggagg caaagctcat cgtgggacac    480
aaaatccttc tcaagatcag gggaatagcc catctggaaa gggaatatcc agtcaatatt    540
caaacacaga gaaaggctg tgggttcatg gactaagtaa agaacaaact tccgtctctg    600
gtgcacaaaa aggtagaaaa caaggcggat cccaaagcag ttatgttctc caaactgaag    660
agctagtagc taacaaacaa caacgtgaga ctaaaaattc tcatcaaaat aaagggcatt    720
accaaaatgt ggttgaagtg agagaggaac attcaagtaa agtacaaacc tcactctgtc    780
ctgcgcacca agacaaactc caacatggat ccaaagacat tttttctacc caagatgagc    840
tcctagtata taacaagaat caacaccaga caaaaaatct caatcaagat caacagcatg    900
gccgaaaggc aaataaaata tcataccaat cttcaagtac agaagaaaga cgactccact    960
atggagaaaa tggtgtgcag aaagatgtat cccaaagcag tatttatagc caaactgaag   1020
agaaaataca tggcaagtct caaaaccagg taacaattca tagtcaagat caagagcatg   1080
gccataagga aaataaaata tcataccaat cttcaagtac agaagaaaga catctcaact   1140
gtggagaaaa gggcatccag aaaggtgtat ccaaaggcag tatttcgatc caaactgaag   1200
```

| | |
|---|---|
| agcaaataca tggcaagtct caaaaccagg taagaattcc tagtcaagct caagagtatg | 1260 |
| gccataagga aaataaaata tcataccaat cttcgagtac agaagaaaga cgtctcaaca | 1320 |
| gtggagaaaa ggatgtacag aaaggtgtat ccaaaggcag tatttctatc caaactgaag | 1380 |
| agaaaataca tggcaagtct caaaaccagg taacaattcc tagtcaagat caagagcatg | 1440 |
| gccataagga aaataaaatg tcataccaat cttcaagtac agaagaaaga cgactcaact | 1500 |
| atggaggaaa gagcacgcag aaagatgtat cccaaagcag tatttctttc caaattgaaa | 1560 |
| agctagtaga aggcaagtct caaatccaga caccaaatcc taatcaagat caatggtctg | 1620 |
| gccaaaatgc aaaaggaaag tctggtcaat ctgcagatag caaacaagac ctactcagtc | 1680 |
| atgaacaaaa aggcagatac aaacaggaat ccagtgagtc acataatatt gtaattactg | 1740 |
| agcatgaggt tgcccaagat gatcatttga cacaacaata taatgaagac agaaatccaa | 1800 |
| tatctacata gccctgttgc ttagcaaccc attgaaaagc tggaccaata gcaaggtgtc | 1860 |
| accccgacct cagtgagtta gggttcgttt ganccngant aggaangggt nccggaaggc | 1920 |
| naaaannnnt anttnagccn ctgttgtntn nanacc | 1956 |

<210> SEQ ID NO 121
<211> LENGTH: 1737
<212> TYPE: DNA
<213> ORGANISM: Homo sapiens
<220> FEATURE:
<221> NAME/KEY: misc_feature
<223> OTHER INFORMATION: Incyte ID No: 350287

<400> SEQUENCE: 121

| | |
|---|---|
| gaaatacagt ggctctttat taaaaataat agttggataa tataaactga actatttatg | 60 |
| cattttata tacttataaa tccttccaaa tagttttaat tctatccttt tacatataaa | 120 |
| taacttaata agtgtgctgg aaaaacacag atgttcacag caccactgtt tttttttttt | 180 |
| tttttgaga taataaattc catgagaaat ctgggtttga atatttgttt actttgtctc | 240 |
| ctaattgaac accactccag gccttctgtc tgtctcccct ttaccccaa aatattcaca | 300 |
| aaaaaattt taagacaaca agtaaccata taggtgtt tgaatgattt tctcattttt | 360 |
| atctaatttc atttcataag tcccgagtaa tttacctacc ataggctact atactgataa | 420 |
| tataaatgaa accgaacatt ttttgctact aactctcccc aatttaatgt gttttcgaaa | 480 |
| taaaaattta aattttttc cttttaatta aaaagtcatc tttgaagtcc ttattggctg | 540 |
| tacattttac atgtttgctg gtactattat tttgtcagtg agttaaagct ggcatgtaca | 600 |
| gctcttggct ttaatgaaaa gcacattgac ataatgttag taaattccaa accccggcac | 660 |
| agaatgtgag ttaaaattaa gtcttgctgg gttagtgtac aataaactat acctacagac | 720 |
| ttttttttaa tagaaagaag acaaagctgc tggtatagga tttgttcctt tgaagaaaaa | 780 |
| atgagggaaa caaacacaaa aacctcaatg cagtgtataa ataacatttt gttcaactac | 840 |
| ctcttaatgt ggaattatct actttaatag tttcctgaca gtaatgttaa atagtaactg | 900 |
| ccaaatttgt tattttccca tctctcttaa aaaagtctttt atgattattt tatatagttt | 960 |
| tgagaacttt aaagccactt ttttttaacc ttacatttgc ataaaaatgt ttagcttta | 1020 |
| agtagagagc aaattatgat catatatttt gatattcatg acctgtttga ctataggatt | 1080 |
| tttttaaaa aaatgcactt tggctataaa accatggatg atttgatcca taagatttaa | 1140 |
| atgtgccacc attatagtat tcctagacat gagcttgatg aatggtattc tgtaattata | 1200 |
| acgtgccaca cattattgtg tcttaattgc ccttagcctg aattttaatg atcaatttgt | 1260 |
| tattgttgca gatgtgaata ttgtgcataa acttactaaa tttatgtaaa attgtataaa | 1320 |

| | |
|---|---:|
| atagaattag aagtcactaa gttctttctg tgtagaagta ataaatttat tgtaacacaa | 1380 |
| tgcagttgtg tatatgacat tctgtaattc cttgaactgg atcatatatt cataagttct | 1440 |
| gtagatactt atgcatgaac attttctcat ttagttcttg ggttcattat ttgtattgtg | 1500 |
| tttactactt gtgatcatgt agttgtgcct tactttgtga gaaaggttag ctcagtaaat | 1560 |
| actgcaattt ctaaactcag tgattggaag gttattaatt ataaatgtaa ctgataaagt | 1620 |
| acgtgacagc atttaaatct gtataaagaa caatggaagg atccttattg aattgttgct | 1680 |
| ttttttttaat atgtttaaat attatattaa aaacatttct ttctaaaaaa aaaaaaa | 1737 |

<210> SEQ ID NO 122
<211> LENGTH: 789
<212> TYPE: DNA
<213> ORGANISM: Homo sapiens
<220> FEATURE:
<221> NAME/KEY: misc_feature
<223> OTHER INFORMATION: Incyte ID No: 1618171

<400> SEQUENCE: 122

| | |
|---|---:|
| caagatataa agtagcagtt ggctacctaa aatgaaaaga gcaatgttcc atggcacctg | 60 |
| aaatgttaaa aatattagaa actctcccca ccccatattc ctcccacccc aattgagtct | 120 |
| ctcgcaataa tcttctcgct tctctaacta gttgactttc attatggatg gggataggct | 180 |
| aaaaaacggg cccctgggat ggctgtgctg ccatcagtgc tgttggttta ctcactcttt | 240 |
| ttctgtcttc gttttttgcat gctactgctc ctgccctctt acagccacag tagaagcggt | 300 |
| agaggcccgg gaaggtatgg ccatattact ctgatagatg tgatccatgt gtctgtgtac | 360 |
| tggttttttcg aagctttatc aacatttcaa atattttatt attgcatcac cagaactata | 420 |
| acagtgagaa aaggtatagt tgtttctagg catgttaacg aagcaggtgt ttcctttgtg | 480 |
| tcctatcttt gcattaattt taaataacct tcaccacagc tacagttttt tttctgggct | 540 |
| ctatcagctt taatgcaacg gcagaagctt aagcaactgg tcatgagagg tcaagtggtt | 600 |
| tacttctgta tcccttccat gtacaagaga catccatttg attctcaaga gagccaaata | 660 |
| ggtcagcctc ttcagcgatt ctaaaagatt tcaagagcag aggcaggaag taggactggg | 720 |
| aatttagttc aattcattat ctgaggttgc cctaaggtag ggcaagttta aatttaacctt | 780 |
| tgtttctat | 789 |

<210> SEQ ID NO 123
<211> LENGTH: 1116
<212> TYPE: DNA
<213> ORGANISM: Homo sapiens
<220> FEATURE:
<221> NAME/KEY: misc_feature
<223> OTHER INFORMATION: Incyte ID No: 1625863

<400> SEQUENCE: 123

| | |
|---|---:|
| tttatatttg acaataaagt gttagactcc atttctaaat accagacttc aaaagataag | 60 |
| gttcaaaagt gttataagaa gatattcctt ttttttgtcct agagaactta ttttcctgtg | 120 |
| aaaatgccta ccacaaagaa gacattgatg ttcttatcaa gcttttttcac cagccttggg | 180 |
| tccttcattg taatttgctc tattcttggg acacaagcat ggatcaccag tacaattgct | 240 |
| gttagagact ctgcttcaaa tgggagcatt ttcatcactt acggactttt tcgtggggag | 300 |
| agtagtgaag aattgagtca cggacttgca gaaccaaaga aaagtttgc agttttagag | 360 |
| atactgaata attcttccca aaaaactctg cattcggtga ctatcctgtt cctggtcctg | 420 |
| agtttgatca cgtcgctgct gagctctggg tttaccttct acaacagcat cagcaaccct | 480 |

```
taccagacat tcctggggcc gacggggtg tacacctgga acgggctcgg tgcatccttc      540
gtttttgtga ccatgatact gtttgtggcg aacacgcagt ccaaccaact ctccgaagag      600
ttgttccaaa tgctttaccc ggcaaccacc agtaaaggaa cgacccacag ttacggatac      660
tcgttctggc tcatactgct cgtcattctt ctaaatatag tcactgtaac catcatcatt      720
ttctaccaga aggccagata ccagcggaag caggagcaga aaagccaat ggaatatgct      780 ccaagggacg gaattttatt ctgaattctc tttcatctca ttttggcgtt gcatctattg      840
tacatcagcc ctgagtagta actggttagc ttctctggac aattcagcat ggtaacgtga      900
ctgtcatctg tgacagcatt tgtgtttcat gacactgtgt tcttcattga tgctgtactc      960
ctgaaaattt ttcccacaag gttggggaaa tgaatgggaa atgtcgctgg tctgtgtggt     1020
attcaaagca gtagtatcat gatgagcgta acgacccttc tgacctggtc tcacgatctg     1080
aaataataaa aggctgtgtc atgtttcttt tcaaaa                               1116
```

<210> SEQ ID NO 124
<211> LENGTH: 914
<212> TYPE: DNA
<213> ORGANISM: Homo sapiens
<220> FEATURE:
<221> NAME/KEY: misc_feature
<223> OTHER INFORMATION: Incyte ID No: 1638353

<400> SEQUENCE: 124

```
ggccaaccca cggtgggggg agcgcggcca tggcgctcct gctttcggtg ctgcgtgtac       60
tgctgggcgg cttcttcgcg ctcgtggggt tggccaagct ctcggaggag atctcggctc      120
cagtttcgga gcggatgaat gccctgttcg tgcagtttgc tgaggtgttc ccgctgaagg      180
tatttggcta ccagccagat cccctgaact accaaatagc tgtgggcttt ctggaactgc      240
tggctgggtt gctgctggtc atgggcccac cgatgctgca agagatcagt aacttgttct      300
tgattctgct catgatgggg gctatcttca ccttggcagc tctgaaagag tcactaagca      360
cctgtatccc agccattgtc tgcctggggt tcctgctgct gctgaatgtc ggccagctct      420
tagcccagac taagaaggtg gtcagaccca ctaggaagaa gactctaagt acattcaagg      480
aatcctggaa gtagagcatc tctgtctctt tatgccatgc agctgtcaca gcaggaacat      540
ggtagaacac agagtctatc atcttgttac cagtataata tccagggtca gccagtgttg      600
aaagagacat tttgtctacc tggcactgct ttctcttttt agctttacta ctcttttgtg      660
aggagtacat gttatgcata ttaacattcc tcatgtcata tgaaaataca aaataagcag      720
aaaagaaatt taaatcaacc aaaattctga tgccccaaat aaccacttt aatgccttgg      780 tgtaagtata cctctgaact ttttctgtg cctttaaaca gatatatatt tttttaaat      840 gaaaataaaa ccatatatcc tattttattt cctcctttta aaaccttata aactataaca      900
ctgtaaaaaa aaaa                                                        914
```

<210> SEQ ID NO 125
<211> LENGTH: 2016
<212> TYPE: DNA
<213> ORGANISM: Homo sapiens
<220> FEATURE:
<221> NAME/KEY: misc_feature
<223> OTHER INFORMATION: Incyte ID No: 1726843

<400> SEQUENCE: 125

```
gctgcctgct gcctccgcag cgtccccca gctctccctg tgctaactgc ctgcaccttg       60
gacagagcgg gtgcgcaaat cagaaggatt agttgggacc tgccttggcg accccatggc      120
```

-continued

```
atcccccaga accgtaacta ttgtggccct ctcagtggcc ctgggactct tctttgtttt    180
catggggact atcaagctga ccccaggct cagcaaggat gcctacagtg agatgaaacg    240
tgcttacaag agctatgttc gagccctccc tctgctgaag aaaatgggga tcaattccat    300
tctcctccga aaaagcattg gtgcccttga agtggcctgt ggcatcgtca tgacccttgt    360
gcctgggcgt cccaaagatg tggccaactt cttcctactg ttgctggtgt tggctgtgct    420
cttcttccac cagctggtcg gtgatcctct caaacgctac gcccatgctc tggtgtttgg    480
aatcctgctc acttgccgcc tgctgattgc tcgcaagccc gaagaccggt cttctgagaa    540
gaagcctttg ccagggaatg ctgaggagca accctcctta tatgagaagg cccctcaggg    600
caaagtgaag gtgtcataga aaagtggaag tgcaaagagt ggaccttcca ggcagttgcg    660
tccatgacac caggaagatg tcagtgtgtg tttttcattt gatttattta tcttggggaa    720
agtgaaaaat gtaatctgca agttaatgac cctattggct tgtgtacatc tatatgctaa    780
aatgacttcc ccacattgac atttgtgcgc cacctttaat cactctgggg caactctcac    840
atcttgctgc atgtacatgt atacggctac tattgaagtg taattgtgag atggactcca    900
acaagcatgt gactgtgaga ttgtgtgtgg gaaaatgtat ttaactactc tgtgtgtgtg    960
tgtgtgtgtg tgtgtgcgcg cgcgcgcacg cgcacacact cacgcacaca caagcagaga   1020
aggcgctgat cttgaactaa tcctgcacag gcatccttcc ctttatagat tgattccagc   1080
aaaggcggaa taaacaaat ttcctatgaa gagaatcctg atatgaaaca agtcatgtag    1140
tctcatggcc gggaatctct ccacagatac taacaactta aacttactac tttaggagaa   1200 aaaaaaaac attcaatttc ggacactgag ttatatatga aattaattag gctctagtcc    1260
aacagttgtt tacattttaa atagtccata ttgaatttaa ttaaaacaag ggatgcatgc    1320
agtcaaattg atagtttaat tcttcaagtg ataatatgga agtttcacct tgcctttgtc    1380
caagccccac ctattaaaac cctttactca cagtttgaaa ctgaagcagt aaacttgttt    1440
ccagacatct tttcagatt gtcttaagcc caaagttgcc tcacttccac tattctcagc    1500
agccaaccag gatttggcag ctgctccact gttacggttg agggaacagg gatcagtcct    1560
gttagaagtc tgtgagcctc aaactctacc tgttctctgc aatcatccaa aatttgaaaa    1620
agaagctata tccagtgttt cactgccaaa cagattcact actcttactg attcttcact    1680
gagctttgct agtataagca gagttccaag tctcccctag ggttgtctct acatttcttt    1740
atcattccag tgggtagggt ttagctgggg gaaggacatt tcataagggt tagttggact    1800
gagcagtatg gacatttgct ttttcatta cgtactgttg ttttccttg ttaggtgtgc     1860 tttggtggtt ttaatattat tgtgccaggg atggggaaat ggggggggtt gtgtgggaag   1920
agtacttatt attgtgtttt cttcagtgta attgttcttg gtaattgata cctctctgtt   1980
ttatttctct cattctttca aaataaaact ttttgt                              2016
```

<210> SEQ ID NO 126
<211> LENGTH: 2067
<212> TYPE: DNA
<213> ORGANISM: Homo sapiens
<220> FEATURE:
<221> NAME/KEY: misc_feature
<223> OTHER INFORMATION: Incyte ID No: 1754506

<400> SEQUENCE: 126

```
tgctccttta agcgtccaca ggcggcggac ggccacaatc acagctccgg gcattggggg     60
aacccgagcc ggctgcgccg ggggaatccg tgcgggcgcc ttccgtcccg gtcccatcct    120
```

```
cgccgcgctc cagcacctct gaagttttgc agcgcccaga aaggaggcga ggaaggaggg      180
agtgtgtgag aggagggagc aaaaagctca ccctaaaaca tttatttcaa ggagaaaaga      240
aaaagggggg gcgcaaaaat ggctgggcat attatagaaa acatgagcac caagaagctg      300
tgcattgttg gtgggattct gctcgtgttc caaatcatcg cctttctggt gggaggcttg      360
attgctccag ggcccacaac ggcagtgtcc tacatgtcgg tgaaatgtgt ggatgcccgt      420
aagaaccatc acaagacaaa atggttcgtg ccttggggac ccaatcattg tgacaagatc      480
cgagacattg aagaggcaat tccaagggaa attgaagcca atgacatcgt gttttctgtt      540
cacattcccc tcccccacat ggagatgagt ccttggttcc aattcatgct gtttatcctg      600
cagctggaca ttgccttcaa gctaaacaac caaatcagag aaaatgcaga agtctccatg      660
gacgtttccc tggcttaccg tgatgacgcg tttgctgagt ggactgaaat ggcccatgaa      720
agagtaccac ggaaactcaa atgcaccttc acatctccca agactccaga gcatgagggc      780
cgttactatg aatgtgatgt ccttcctttc atggaaattg gtctgtggcc cataagtttt      840
taccttttaa acatccggct gcctgtgaat gagaagaaga aaatcaatgt gggaattggg      900
gagataaagg atatccggtt ggtggggatc caccaaaatg gaggcttcac caaggtgtgg      960
tttgccatga agaccttcct tacgcccagc atcttcatca ttatggtgtg gtattggagg     1020
aggatcacca tgatgtcccg acccccagtg cttctggaaa aagtcatctt tgcccttggg     1080
atttccatga cctttatcaa tatcccagtg gaatggtttt ccatcgggtt tgactggacc     1140
tggatgctgc tgtttggtga catccgacag ggcatcttct atgcgatgct tctgtccttc     1200
tggatcatct tctgtggcga gcacatgatg gatcagcacg agcggaacca catcgcaggg     1260
tattggaagc aagtcggacc cattgccgtt ggctccttct gcctcttcat atttgacatg     1320
tgtgagagag gggtacaact cacgaatccc ttctacagta tctggactac agacattgga     1380
acagagctgg ccatggcctt catcatcgtg gctggaatct gcctctgcct ctacttcctg     1440
tttctatgct tcatggtatt tcaggtgttt cggaacatca gtgggaagca gtccagcctg     1500
ccagctatga gcaaagtccg gcggctacac tatgagggc taattttttag gttcaagttc     1560 ctcatgctta tcaccttggc ctgcgctgcc atgactgtca tcttcttcat cgttagtcag     1620
gtaacggaag gccattggaa atggggcggc gtcacagtcc aagtgaacag tgccttttc     1680 acaggcatct atgggatgtg aatctgtat gtctttgctc tgatgttctt gtatgcacca     1740
tcccataaaa actatggaga agaccagtcc aatggaatgc aactcccatg taaatcgagg     1800
gaagattgtg ctttgtttgt ttcggaactt tatcaagaat tgttcagcgc ttcgaaatat     1860
tccttcatca atgacaacgc agcttctggt atttgagtca acaaggcaac acatgtttat     1920
cagctttgca tttgcagttg tcacagtcac attgattgta cttgtatacg cacacaaata     1980
cactcattta gcctttatct caaaatgtta aatataagga aaaagcgtc aacaataaat      2040 attctttgag tattgaaaaa aaaaaaa                                          2067
```

<210> SEQ ID NO 127
<211> LENGTH: 2180
<212> TYPE: DNA
<213> ORGANISM: Homo sapiens
<220> FEATURE:
<221> NAME/KEY: misc_feature
<223> OTHER INFORMATION: Incyte ID No: 1831378

<400> SEQUENCE: 127

```
gcgaacgtct gcacctggcg ggcgatgacg cccgatgcgg gcgccccggg atagcgtggg       60
cgaggctgcg gggccccggc gcgcacgccc gcacctctcc ccagccctgg cgtgggccca      120
```

```
gcccggccca ggcagcaatg gggttcctgc agctgctggt cgtagcggtg ctggcatccg      180
aacaccgggt ggctggtgca gccgaggtct tcgggaattc cagcgagggt cttattgaat      240
tttctgtggg gaaatttaga tacttcgagc tcaataggcc ctttccagag gaagctattt      300
tgcatgatat ttcaagcaat gtgacttttc ttattttcca aatacactca cagtatcaga      360
atacaactgt ttccttttct ccgactctcc tttccaattc ctcggaaaca ggcactgcca      420
gtggactggt tttcatcctt agaccagagc agagtacatg cacttggtac ttggggactt      480
caggcataca gcctgtccag aatatggcta tcctactctc ctactcagaa agagatcctg      540
tccctggagg ctgtaatttg gagttcgatt tagatattga tcccaacatt tacttggagt      600
ataatttctt tgaaacgact atcaagtttg ccccagcaaa cctaggctat gcgagaggcg      660
tagatccccc accatgtgac gctgggacag accaggactc caggtggagg ttgcagtatg      720
atgtctatca gtattttctg cctgagaatg acctcactga ggagatgttg ctgaagcatc      780
tgcagaggat ggtcagtgtg ccccaggtga aggccagtgc tctcaaggtg gttaccctaa      840
cagctaatga taagacaagt gtttccttct cctccctccc gggacaaggt gtcatataca      900
atgtcattgt ttgggacccg tttctaaata catctgctgc ctacattcct gctcacacat      960
acgcttgcag ctttgaggca ggagagggta gttgtgcttc cctaggaaga gtgtcttcca     1020
aagtgttctt cactcttttt gccctgcttg gtttcttcat ttgtttcttt ggacacagat     1080
tctggaaaac agaattattc ttcataggct ttatcatcat gggattcttc ttttatatac     1140
tgattacaag actgacacct atcaagtatg atgtgaatct gattctgaca gctgtcactg     1200
gaagcgtcgg tggaatgttc ttggtagctg tgtggtggcg atttggaatc ctctcgatct     1260
gcatgctctg tgttggacta gtgctggggt tcctcatctc gtcagtgact ttctttactc     1320
cactgggaaa cctaaagatt tttcatgatg atggtgtatt ctgggtcact ttctcttgca     1380
tagctatcct cattccagta gttttcatgg gctgcctaag aatactgaac atactgactt     1440
gtggagtcat tggctcctat tcggtggttt tagccattga cagttactgg tccacaagcc     1500
tttcctacat cactttgaac gtactcaaga gagcgctcaa caaggatttc cacagagctt     1560
tcacaaatgt gccttttcaa actaatgact tcattatcct ggcagtatgg ggcatgctgg     1620
ctgtaagtgg aattacgtta cagattcgaa gagagagagg acgaccgttc ttccctcccc     1680
acccatacaa gttatggaag caagagagag agcgccgagt gacaaacatt ctggacccta     1740
gctaccacat tcctccattg agagagaggc tctatggccg attaacccag attaaagggc     1800
tcttccagaa ggagcagcca gctggagaga gaacgccttt gcttctgtag atgcccaggg     1860
gcttggtcag tgtgcctcag ctttggagtt catgcctgga gtggttcaac agtctctggt     1920
gcaagtctaa taagagatca ggcatatata tctgttcttt gcataatatt atggtgccct     1980
tattgatata tggtaagggt gtactagggg attaggatga ttgtaagaga atgagaaaga     2040
tgaccaaaag gttggtggta gggaggcttt ttcttatttc caaatacttg agaaattacc     2100
ttttggttta caaatctatg atcaacttat tccattaaat agatacatta aaaaaattaa     2160
aaactgaaaa aaaaaaaaa                                                 2180
```

<210> SEQ ID NO 128
<211> LENGTH: 991
<212> TYPE: DNA
<213> ORGANISM: Homo sapiens
<220> FEATURE:
<221> NAME/KEY: misc_feature
<223> OTHER INFORMATION: Incyte ID No: 1864943

<400> SEQUENCE: 128

```
cacggtgtca gcaggcaaca tggccgagag gcggggcctc cgggcggcgc cgtgtccgcg      60
accgcgtacc ctgacacccc cgcggaattc cctccgcacc tccaggcggg tgcgatgcgg     120
cgccgctttt ggggcgtatt caactgtctg tgcgccggcg cgttcgggc cctggccgcc      180
gcctccgcca agctggcctt cggcagcgag gtgagcatgg gtttatgcgt cttaggcatt     240
attgtgatgg cgagcaccaa ttctctgatg tggaccttct ttagccgggg cctcagtttc     300
tccatgtctt cagccattgc atctgtcaca gtgactttt caaatatcct cagctcggcc      360
ttcctgggct atgtgctgta tggagagtgc caggaggtct tgtggtgggg aggagtgttc     420
cttattctct gcggactcac cctaatccac aggaagctcc acccacctg gaagcccctt      480
ccacacaagc agcagtagca ccacttggct agacggacca gctggaaaga tcatgatggt     540
ggcccagcct tgggatgtca tgtgggactg tgtcctaggg cgatccagtt gtgcagcctt     600
ctgaccatca gccaagggaa gcaggcctct gatggagcag gctctggctc tgtaaggaga     660
ggtgcagctg cagcagtgtt ctaccggaag tgttttgatc atctgtacag tgctttggat     720
tcttcctccc aggcctaccc cagtgagcct tcgcagatgc tggagatcct ggggttggtc     780
tgctttgtgt atggtacttg aaaccacgct gtaattattg tcctgttgcc aaacaaaagc     840
cagtcatgta actctagaag cagtgactgg tggggcttc tgacagttcc atgctgatgt      900
atcaggccat ctgtgtcatg cttatgtatt atggcaagaa gaggaaaact ggattaataa     960
atacgttttt ttgtaagtta aaaaaaaaa a                                     991
```

<210> SEQ ID NO 129
<211> LENGTH: 637
<212> TYPE: DNA
<213> ORGANISM: Homo sapiens
<220> FEATURE:
<221> NAME/KEY: misc_feature
<223> OTHER INFORMATION: Incyte ID No: 1911316

<400> SEQUENCE: 129

```
ggagggcggt gctccgccgc ggtggcggtt gctatcgctt cgcagaacct actcaggcag      60
ccagctgaga agagttgagg gaaagtgctg ctgctgggtc tgcagacgcg atggataacg     120
tgcagccgaa aataaaacat cgccccttct gcttcagtgt gaaaggccac gtgaagatgc     180
tgcggctggc actaactgtg acatctatga ccttttttat catcgcacaa gcccctgaac     240
catatattgt tatcactgga tttgaagtca ccgttatctt attttcata cttttatatg      300
tactcagact tgatcgatta atgaagtggt tattttggcc tttgcttgat attatcaact     360
cactggtaac aacagtattc atgctcatcg tatctgtgtt ggcactgata ccagaaacca     420
caacattgac agttggtgga ggggtgtttg cacttgtgac agcagtatgc tgtcttgccg     480
acggggccct tatttaccgg aagcttctgt tcaatcccag cggtccttac cagaaaaagc     540
ctgtgcatga aaaaaaagaa gttttgtaat tttatattac tttttagttt gatactaagt     600
attaaacata tttctgtatt cttccaaaaa aaaaaa                              637
```

<210> SEQ ID NO 130
<211> LENGTH: 2631
<212> TYPE: DNA
<213> ORGANISM: Homo sapiens
<220> FEATURE:
<221> NAME/KEY: misc_feature
<223> OTHER INFORMATION: Incyte ID No: 1943120

<400> SEQUENCE: 130

```
ctctcttcct gcagtgtggt aaaactacag caatcgtctt aacctgtgag atctgtcacc    60
tttgcatttt ccactcatgc agctggttct ataaaccaac tcttctgctt gggggatct    120
aatcatgacc ttttacccct tgtggcctc ttctagtaca aggcgagtgg ataattccaa    180
cacaagactg gcagtccaaa ttgaaagaga tccaggaat gatgacaaca atctcaattc    240
cattttttat gaacacttga caaggaccct cctggagtcc ctctgtggag acttagttct    300
tggacgttgg ggcaactaca gctctggcga ttgctttatt ttggcttcag atgacctcaa    360
tgcctttgtt cacctgattg aaattggaaa tggtcttgtc accttcaac ttcgaggact    420
ggaattccga ggaacctact gccagcagag ggaggtagaa gccatcatgg agggcgacga    480
ggaggacaga ggctgctgct gctgcaaacc aggccacttg cctcacctgc tgtcccgcaa    540
cgctgccttt cacctccgct ggctcacctg gaaaatcacg cagacccagt acatcctgga    600
gggctacagc atcctggaca caacgcggc caccatgctg caggtgtttg acctccgaag    660
gatcctcatc cgctactaca tcaagagtat aatatactat atggtaacgt ctcccaaact    720
cctctcctgg atcaaaaatg aatcacttct gaagtccctg cagccctttg ccaagtggca    780
ttacattgag cgtgaccttg caatgttcaa cattaacatt gatgatgact acgtcccgtg    840
tctccagggg atcacacgag ctagcttctg caatgtttat ctagaatgga ttcaacactg    900
tgcacggaaa agacaagagc cttcaacgac cctggacagt gacgaggact ctcccttggt    960
gactctgtcc ttcgccctgt gcaccctggg gaggagagct ctgggaacag ccgctcacaa   1020
tatggccatc agcctggatt ctttcctgta tggcctccat gtcctcttca aaggtgactt   1080
cagaataaca gcacgtgacg agtgggtatt tgctgacatg gacctactgc ataaagttgt   1140
agctccagct atcaggatgt ccctgaaaact tcaccaggac cagttcactt gccctgacga   1200
gtatgaagac ccagcagtcc tctacgaggc catccagtcc ttcgagaaga aggtggtcat   1260
ctgccacgag ggcgacccgg cctggcgggg cgcagtgctg tccaacaagg aagagctgct   1320
caccctgcgg cacgtggtgg acgagggtgc cgacgagtac aaggtcatca tgctccacag   1380
aagcttcctg agcttcaagg tgatcaaggt taacaaagaa tgcgtccgag actttgggc   1440
cgggcagcag caggagctta tatttcttcg caaccgcaat ccggagcgcg gcagtatcca   1500
gaacaataag caggtcctgc ggaacttgat taactcctcc tgcgatcagc ccctggggta   1560
ccccatgtat gtctccccac taaccacatc ctacctaggg acacacaggc agctgaagaa   1620
catctggggt ggacccatca ctttggacag aattaggacc tggttctgga ccaagtgggt   1680
aaggatgcgc aaggattgca atgcccgcca gcacagtggc ggcaacattg aagacgtgga   1740
cggaggaggg gccccgacga caggtggcaa caatgccccg aatggtggca gccaggagag   1800
cagcgcagaa cagcccagaa aaggcggtgc tcagcacggg gtgtcatcct gtgaagggac   1860
acagagaaca ggcaggagga aaggcaggag ccagtccgtg caggcacact cagcgctaag   1920
ccaaaggccg cccatgctga gctcatctgg ccccatctta gagagccgcc aaacattcct   1980
ccagacgtcc acctcagtgc acgagctggc ccagaggctc tcgggcagcc ggctctcctt   2040
gcacgcctcg gccacgtccc tgcactctca gccccgccc gtcaccacca ccggccacct   2100
gagtgtccgt gagcgggccg aggcgctcat caggtccagc ctgggctcct ccaccagctc   2160
caccctgagc ttcctcttcg gcaagaggag cttttccagc gcgctcgtca tttccggact   2220
ctctgctgcg gagggggca ataccagtga cacccagtca tccagcagcg tcaacatcgt   2280
gatgggcccc tcagccaggg ctgccagcca ggccactcgg gtaaggggct gggcagggct   2340
caccaggaca ggctgggatg gtggcacggg ctcctggcct gagcgtggca cctgccttgc   2400
```

| | |
|---|---|
| gttcccaccc ttctgcctgc agaacccat cccttctct atgggctcc cagagtgaca | 2460 |
| aaggacagtg attagacacg aagtggctta gctgctcttg aaagcagaca agatacagag | 2520 |
| cagatatcct gtaaacgata atgcccaggc aggcactgaa aggagtcacc ggatacagag | 2580 |
| gttctgcaga actgtggcca tctgccctac accggggcat gacggagaat g | 2631 |

<210> SEQ ID NO 131
<211> LENGTH: 646
<212> TYPE: DNA
<213> ORGANISM: Homo sapiens
<220> FEATURE:
<221> NAME/KEY: misc_feature
<223> OTHER INFORMATION: Incyte ID No: 2314236

<400> SEQUENCE: 131

| | |
|---|---|
| tacatttact aaaatgatgt aataaataac atgttaatag actcaagctt taccttatga | 60 |
| aattgatgta tttttaccag ttatttctaa tgtaacattg aatatataag atctgacaaa | 120 |
| tgtatgttta aacatgaatt agaagagttg agaactacca ttatgtatag ggattctcat | 180 |
| agtgtcttgg cccttaattg gaaagttgtg gcaactttaa agtactttt actgtatgtt | 240 |
| ataattcttt ataacttaga gagacaat ggtcactcaa actatgagaa ctatgaatta | 300 |
| ggagataaaa gtttaaattt gttgttgttt tataacagta tgtacaagtt agttttccct | 360 |
| tatatattta cgttttcaag tttttaatc tcatcatata catccatact ctataaaatg | 420 |
| ttttatattc aaagaactgt aaaatcctaa acattagttt tcactattga aattgttttt | 480 |
| taaagatagg cataaatagt tgtccttaga cttattcata caaatatagt catttacttc | 540 |
| tatgtagttt gagattctga gagttattcc aactttatga agattgattt caatgtgcct | 600 |
| gctaagtcct aaaagattca gaaagaaaat ttatatatta ttgatt | 646 |

<210> SEQ ID NO 132
<211> LENGTH: 541
<212> TYPE: DNA
<213> ORGANISM: Homo sapiens
<220> FEATURE:
<221> NAME/KEY: misc_feature
<223> OTHER INFORMATION: Incyte ID No: 2479409

<400> SEQUENCE: 132

| | |
|---|---|
| ttcacatttt ttggtttgat cttggtgtca tttaggtaat gaatctatcc aagaaatcta | 60 |
| tccttttgac ccaggttatc aaatttgtag acataaggtt atttataatg gtcccttctt | 120 |
| acccttttaa tgtctttagg agctgtgttg ataatttcct tttcattatg atactggtaa | 180 |
| tttctgttct cactttccta atcaggttgg gtaggggttt atcagtttta ctgatctgac | 240 |
| tttttatttt atttattt ttttgagaca gtcttacact gtctcccagg ctggagtgca | 300 |
| gtggcgcgat ctcggcttac tgcaagctct gccttcgggg ttcatgccat tctcctgcct | 360 |
| cagcctcccc agtagctggg actacaggct cccacaacac gcccggctaa ttttttaaat | 420 |
| tcttagtgga gactggggtt caccggggta accaagaatg gctcggatct cttaaccc | 480 |
| ggggtccacc cgcctcagcc tcccaaaagt gctggggatt acaggggtga gcaccgggcc | 540 |
| c | 541 |

<210> SEQ ID NO 133
<211> LENGTH: 1922
<212> TYPE: DNA
<213> ORGANISM: Homo sapiens
<220> FEATURE:
<221> NAME/KEY: misc_feature
<223> OTHER INFORMATION: Incyte ID No: 2683149

<400> SEQUENCE: 133

```
tggcctccga tccacctgga cacctggagg ctaagcctgg attccccctt ccctgactca      60
ggaactgctt aacgtctaca gcaaggccta atagggggacc tgagggcaca gtcctcagga     120
tgtttcgggg agaataggag ccagaacctg agcccctaag ccattcccct caccaatgat     180
ggggtcccca gtgagtcatc tgctggccgg cttctgtgtg tgggtcgtct tgggctgggt     240
aggggggctca gtccccaacc tgggccctgc tgagcaggag cagaaccatt acctggccca     300
gctgtttggc ctgtacgcg agaatggac gctgactgca gggggcttgg cgcggcttct       360
ccacagcctg gggctaggcc gagttcaggg gcttcgcctg ggacagcatg ggcctctgac     420
tggacgggct gcatccccag ctgcagacaa ttccacacac aggccacaga accctgagct     480
gagtgtggat gtctgggcag gatgcctct gggtccctca gggtgggtg acctggaaga      540
gtcaaaggcc cctcacctac cccgtgggcc agcccctcg ggcctggacc tgcttcacag      600
gcttctgttg ctggaccact cattggctga ccacctgaat gaggattgtc tgaacggctc     660
ccagctgctg gtcaattttg gcttgagccc cgctgctcct ctgacccctc gtcagtttgc     720
tctgctgtgc ccagccctgc tttatcagat cgacagccgc gtctgcatcg cgctccggc     780
ccctgcaccc caggggatc tactatctgc cctgcttcag agtgccctgg cagtcctgtt     840
gctcagcctc ccttctcccc tatccctgct gctgctgcgg ctcctgggac ctcgtctact     900
acggcccttg ctgggcttcc tgggggccct ggcggtgggc actctttgtg gggatgcact     960
gctacatctg ctaccgcatg cacaagaagg gcggcacgca ggacctggcg gactaccaga    1020
gaaggacctg ggcccggggc tgtcagtgct cggaggcctc ttcctgctct ttgtgctgga    1080
gaacatgctg gggcttttgc ggcaccgagg gctcaggcca agatgctgca ggcgaaaacg    1140
aaggaatctc gaaacacgca acttggatcc ggagaatggc agtgggatgg cccttcagcc    1200
cctacaggca gctccagagc caggggctca gggccagagg gagaagaaca gccagcaccc    1260
accagctctg gcccctcctg ggcaccaagg ccacagtcat gggcaccagg gtggcactga    1320
tatcacgtgg atggtcctcc tgggagatgg tctacacaac ctcactgatg ggctggccat    1380
aggtgctgcc ttctctgatg gcttctccag cggcctcagt accaccttag cggtcttctg    1440
ccatgagctg ccccacgaac tgggtgactt tgccatgctg ctccagtcag ggctgtcctt    1500
tcggcggctg ctgctgctga gcctcgtgtc tggagccctg ggattggggg gtgcagtcct    1560
gggggtgggg ctcagcctgg gcctgtccc cctcactccc tgggtgtttg gggtcactgc    1620
tggggtcttc ctctatgtgg cccttgtgga catgctacca gccctgcttc gtcctccgga    1680
gccctgcct acgcccatg tgctcctgca ggggctgggg ctgctgctgg ggggcggcct     1740
catgcttgcc ataaccctgc tggaggagcg gctactgccc gtgaccactg agggctgatg    1800
gggccagtgg aaagggtcg ggttgcccctt ccttccccc aaccacagga atggaggcgg     1860
gacacagggc cagtaggagc aataggattt taataaacag aacccatccc aaaaaaaaaa    1920
aa                                                                   1922
```

<210> SEQ ID NO 134
<211> LENGTH: 840
<212> TYPE: DNA
<213> ORGANISM: Homo sapiens
<220> FEATURE:
<221> NAME/KEY: misc_feature
<223> OTHER INFORMATION: Incyte ID No: 2774051
<220> FEATURE:
<221> NAME/KEY: unsure
<222> LOCATION: 814

<223> OTHER INFORMATION: a, t, c, g, or other

<400> SEQUENCE: 134

| | | | | | |
|---|---|---|---|---|---|
| ggtaattcgt | actggtcatc | ttctctgggt | gtgagtcaaa | tataagttta acaattagct | 60 |
| ctgaaaacat | tccattgagc | tggggaatgc | aacagtctta | ttacctcatc atggaattct | 120 |
| ctagcttagt | taatttaaat | attgtttctt | agtttctggg | tcaattaaat ttaaatgatg | 180 |
| tagtttatgc | ttcgtgacca | attaaattac | taggttatta | caaaaaaaat tatcatcttt | 240 |
| tttgattaaa | gagctgtggg | tacagtatat | tttataagca | attttcatta gttcaaaaat | 300 |
| gttcctttag | gctagattaa | gcagccattc | attgttagag | cctggagacc ttattcgaag | 360 |
| gtgttcatcg | tattcacagt | gcactattac | ttagaactaa | agccaattga acctacttag | 420 |
| caatagcgtt | atgcctttca | cccttgatga | ttatggagct | tatagctctc agaaacaata | 480 |
| cacctgtcag | tttccatcaa | ctatagcaat | ccatgcagaa | gacaagaggc cccctcaaag | 540 |
| caggaggggt | attgttttag | gtccaatttt | tcttattgtt | ctcaaaatca ttataaggtg | 600 |
| gacagtgttt | tgtgaagatt | ttcttttccc | cagctctaag | aaaccatgtg gaaagaattc | 660 |
| attgataact | gttttgattt | ttttcttttt | taagtacag | gttttgctaa gtaatcaccc | 720 |
| ttagtgagcc | tgtgtagttc | agctgcctgt | gagatgtttg | gtgaccagct cagtggtatc | 780 |
| ttgtattcct | gatagagaat | atttcagggg | acanagtgct | ctttcagaca gactcaaata | 840 |

<210> SEQ ID NO 135
<211> LENGTH: 1344
<212> TYPE: DNA
<213> ORGANISM: Homo sapiens
<220> FEATURE:
<221> NAME/KEY: misc_feature
<223> OTHER INFORMATION: Incyte ID No: 2869038

<400> SEQUENCE: 135

| | | | | | |
|---|---|---|---|---|---|
| gcaaattgat | ctaaaagcca | ctaataaatt | ctagggtttg | agtctagaag ccaagcaaac | 60 |
| tgtcaccaat | gtcagttgta | aattagaatg | caacatgagg | cttcagactc atgacaatga | 120 |
| tatacatgaa | acaaaaata | taattgtgtc | taccttccta | ctttcccttt tgacatatgt | 180 |
| agttggaatt | ttacatagtc | ttaaaatcca | tatttagaat | cttacctgtt tctataataa | 240 |
| ttagtaaaat | gccaaagtag | tgatagaata | ttgtggcatt | gaagtagccg aaaaattgtt | 300 |
| agttttagca | tcaaaaaagt | aaatagatgt | tgaaatgaat | ttttgtatgt gccaggttga | 360 |
| agagagtgtg | ccagtgacag | gaagtagtct | aaaaaattaa | cagttatggt tttaatagga | 420 |
| tctgaaagac | aatctttaaa | gaaatgggag | aaattggggg | tatcagtgaa cctataccaa | 480 |
| cctctctttg | tacataaata | tggtgatgta | gctagatata | aaaatcagtg tcttactggc | 540 |
| accatttaca | gtttagaaaa | caatcttttt | cttaaaaatg | cccatctgat ttctattttt | 600 |
| aggagctact | tggatttgta | tgtattttt | ctacgtgaaa | atatatgtac tcttcacttt | 660 |
| tgttccagta | ctataattgc | tcatgcactc | tttctcccct | ttgagaacat tcagtgaaat | 720 |
| acaacttcat | caaagatttg | ctcaaaggag | aagaatcgca | tgagtgtgaa aagtagatgc | 780 |
| tcgtagccag | aacagaaaag | gttacacatg | atcatggcac | agaagatagg aggtttgact | 840 |
| tggtgggcca | taatgtttat | tatccttttt | gaaataacag | ggaccagcag cagttttctc | 900 |
| aggataaatg | ctctacccca | cttctctatg | aacaggtgtg | gggaggctta ctttccattt | 960 |
| tcatatttat | acacctctct | acaaaagcaa | ttttaatga | aggttagtgg aattgttaaa | 1020 |
| aatctgagag | gaatgatgac | tggaggtgtt | tggggttttt | ttctgtattc atttttaat | 1080 |
| gagaaaagtt | ttaaatgtag | tacaggttag | acccaactac | taccttacta ttataggacg | 1140 |

```
attctatgtt tctgttaaag tattcaagta gctttctctg ggggaaaaag taccacttgg   1200
acacttaaag gaattgggat ttttgtctac tttggataag gcagttgact tcttaagtaa   1260
aagcaatagt gtaaaatgtc attttgtttg gaatgttaag tgagcaaata aaaaacatgt   1320
tgaaattgtt gtaaaaaaaa aaaa                                          1344

<210> SEQ ID NO 136
<211> LENGTH: 443
<212> TYPE: DNA
<213> ORGANISM: Homo sapiens
<220> FEATURE:
<221> NAME/KEY: misc_feature
<223> OTHER INFORMATION: Incyte ID No: 2918334

<400> SEQUENCE: 136
ctcgagattt tttatattta tgcatgccat ttagtttgct cctaaaaata gtgatactgg    60
ttttagtttt ttacttacta aatcagtata gccaaatgtc catcttccta gtggtaatat   120
gcgatcagaa tttctgagat tatttatgtg actattttg gaaaagtttc ttttgataaa    180
acatggattt attatatgaa attcttcttg cactgtatta caatatatgc tatgatatcc   240
ctttattttt tttcaactta aatatgatgt tttatattgt tttagactta cgaatcgtgt   300
ttttcagaac cataagggaa tatctatctc ctccctcact ttccttttac atatattgaa   360
aagtctatga aattcaagtc tagcatttga attctctatg ctatcattgc atttacctaa   420
ttatttactt ttaaatttta ggg                                           443

<210> SEQ ID NO 137
<211> LENGTH: 467
<212> TYPE: DNA
<213> ORGANISM: Homo sapiens
<220> FEATURE:
<221> NAME/KEY: misc_feature
<223> OTHER INFORMATION: Incyte ID No: 2949916

<400> SEQUENCE: 137
gccatttaag gagatctgtt ttgcttgaat attctgactg tcagtccgca gacatagggg    60
gtgtgtgagt gtgagtgtgt accaagatga ggaggataat caggctccgg ctccgttttt   120
ctgacacttt tatggctgcc tttcttctgt gcctgggctt cgttctcatg ctctttccct   180
cgttgttgcg ggatggtggc agcatcagca gctgcagaaa ctcttgttca tctcctagct   240
ccgaggagcg tcatttctcc aacttggaat aaaagcccat cctctacctg attgggccac   300
tcagatcaag ggcttaacac tagcaacagt tgctaaggca ctgctagata ccgattagct   360
gaagcctggg tgtctgaacc aatcattgcc aaggggcgg gacttgcccc atccctggaa    420
ctatgaatgt ctcagccct tgagatcacc tgggcgtgga agaaagt                  467

<210> SEQ ID NO 138
<211> LENGTH: 902
<212> TYPE: DNA
<213> ORGANISM: Homo sapiens
<220> FEATURE:
<221> NAME/KEY: misc_feature
<223> OTHER INFORMATION: Incyte ID No: 2989375

<400> SEQUENCE: 138
cactgcactc cagtctaggt gacagagaag gactcgtctc aaaaaataaa aataaataaa    60
aaggaagcaa ggctaatcat cagtatgtgc ttgttacaag agctatgatg aaggcactcc   120
ttcgagttta accaaatgag atcatctctg tcatgtgcct cacgcctcac agggactcca   180
```

```
tgtgtgaaga ttccccttc  actcaccaga tcatctccat ggcaacagct tgcagcctgc      240
tcttggagtg ctttgttttg gcagcttctc tgctagtttg tgtatggagt gaatggagga      300
ggtaaatcca cagattaaga atatgctgtc aggagtcagg cagccaaggt cagaagccag      360
ctctgcttct cagtgctttc tctttacaac acaggacttt gcaaggaaca tataattctg      420
tgactagcgc catttggaaa atgttgaaac tgaagtagag atgagagatc ttacgtctgc      480
ctacccagtg agatacgagg aaggtcaagg gaaaaaaaat tccaagctct tctttatctg      540
ctataggaaa tgaacattca atttttttgca tgcaacgaca agaggtcaag gaccccagaa     600
gccagcccgc tacttccaag ttgagagccc ctggtcatac cctccagttg agctcagatt      660
tgtcacaaat ttacccctct cctttccttc cattccccat gacctgcaga gagagatgtc      720
agataccttc ctcttggcct cccatgggca tccataagaa acttacttga agcaagaagc      780
ccagtatagg tgtctgggca gttggacatt tcctctagcc agatctgtcc gaatagagcc      840
atctgggtac atgacgcaga gggcatttga taaataactg gaaaagtcaa taaatctttg      900
tc                                                                    902

<210> SEQ ID NO 139
<211> LENGTH: 1332
<212> TYPE: DNA
<213> ORGANISM: Homo sapiens
<220> FEATURE:
<221> NAME/KEY: misc_feature
<223> OTHER INFORMATION: Incyte ID No: 3316764

<400> SEQUENCE: 139
cgcagatgtg ccttcctggt tggttgagat gctgatccta cagcactccc gctgtgcctc       60
agcagtgagc tgggtgtaaa ggcaggaggc ttgctggggt ctgacacttc cctgccctcc      120
tccaggaggg acacatctgg ggctctatga ggaggacagc tttcatcctg ggctctggac      180
ttctctcatt tgtggccttc tggaactcag tgacatggca tcttcagaga ttttggggtg      240
cttctggcta cttttggcaa gcccagtggg agaggctgct gactacattt gaagggaagg      300
agtggatcct cttctttata ggtgccatcc aagtgccttg tctcttcttc tggagcttca      360
atgggcttct attggtggtt gacacaacag gaaaacctaa cttcatctct cgctaccgaa      420
ttcaggtcgg caagaatgaa cctgtggatc ctgtgaaact gcgccagtct atccgcacag      480
ttcttttcaa ccagtgcatg atatctttcc ccatggtggt cttcctctat cccttcctca      540
aatggtggag agaccctgc  cgccgtgagc tacccacctt ccactggttc ctcctggagc      600
tggccatctt cacgctgatc gaggaagtct tgttctacta ttcacaccgg ctccttcacc      660
acccaacatt ctacaagaaa atccacaaga aacaccatga gtggacagct cccattggcg      720
tgatctctct ctatgcccac cctatagagc atgcagtctc caacatgcta ccggtgatag      780
tgggcccatt agtaatgggc tcccacttgt cctccatcac catgtggttt tccttggccc      840
tcatcatcac caccatctcc cactgtggct accaccttcc cttcctgcct tcgcctgaat      900
tccacgacta ccaccatctc aagttcaacc agtgctatgg ggtgctgggt gtgctggacc      960
acctccatgg gactgacacc atgttcaagc agaccaaggc ctacgagaga catgtcctcc     1020
tgctgggctt caccccgctc tctgagagca tcccagactc cccaaagagg atggagtgag     1080
agacagccta agtgtcatcc tggctgtccc tcagccatgg gatgcagaca cggcttcctg     1140
attgcaccta caatttgcc  tccttcggcc acacgcccta atgatggcac caccagggta     1200
gagggaaggt cggcttcccg gaaaagcagg gccaaggat  aggctttctt caaactactg     1260
cccttgatgt ccctcaatgg gatcaggagt tagcttaaaa aaaaaaaaaa acaactgcgg     1320
```

```
ccgcaagctt at                                                   1332

<210> SEQ ID NO 140
<211> LENGTH: 1252
<212> TYPE: DNA
<213> ORGANISM: Homo sapiens
<220> FEATURE:
<221> NAME/KEY: misc_feature
<223> OTHER INFORMATION: Incyte ID No: 3359559

<400> SEQUENCE: 140
gtgaggaagg tagctttagt gaaaacaggg tttggagttg aacctatacg ggttcaaatt    60
cgacttccgt ccaccaccga gacctgcgct ccctgaggga ctcgctttcc catccgcgaa   120
accaggacgg cgccgcctac accccgcggc gttcggggcg ggctgaatgg gtcgctgagt   180
aggggctaca cccacgccct tcgctcccg  ccccggcac  ggagcgacgg ccacggcagt   240
gtccccaagg caccgaaacc gaggcggggg tctcggtccc tccgcgcaag gagggaggcg   300
gaccgtacgt ggcaggactc accgccccgc acgtggcagg actcaccgcc ccgcgccgtg   360
ttctccgagc catggcgcca gcgctgtggc gggcctgcaa cggactcatg gccgccttct   420
tcgcgctggc ggccttggtg caggtaaatg acccagatgc agaggtgtgg gtggtggtgt   480
acacaatccc tgcagtactg accctgcttg ttggacttaa ccctgaagtc acaggtaatg   540
ttatttggaa aagtatctct gcaatacaca tactcttttg tacggtgtgg gctgttggct   600
tggcgtccta cctcttgcat cgtacacaac agaacatctt acatgaggaa gaaggcaggg   660
agctgtctgg tctggtgatt attacagcat ggattatcct gtgccacagt tcctcaaaga   720
atccagttgg tggaagaatt caattggcta ttgccattgt aatcacactt ttcccattta   780
tctcatgggt ctacatatat attaacaagg aaatgcggtc ctcttggcca actcactgca   840
agacagtaat ttaaataaat tcaagaactt cgttttaaaa atgaatattt tcaatcaatt   900
ttttataaac attaggggaa caagccagga gtttatttca ggtaatttgg gctaatagtt   960
ttaaaactcc aaataacttt ttaagggtgc atataattcg atgtaagatt ggatgggaca  1020
agtaagagat ggtctgatat tttccagacg actttctgca gggtcttgtg tcataatgta  1080
gtggaaaagg ctagagaata gaagtttaaa aatacgagtt ctaacttaac tttgtaacta  1140
tgtaatttgg gcaaatatat aaacctcctg gtggatattt atctataaaa taggattaat  1200
gccagagtgt acttacttac acagtaacaa ggatcaatct agataatgta tg           1252

<210> SEQ ID NO 141
<211> LENGTH: 721
<212> TYPE: DNA
<213> ORGANISM: Homo sapiens
<220> FEATURE:
<221> NAME/KEY: misc_feature
<223> OTHER INFORMATION: Incyte ID No: 4289208

<400> SEQUENCE: 141
ggagactgca ttccctgccc tgaaggaatg tatttctaag gcaaataggc aacttggtac    60
tatcttattc tgagtagaga gtggagaaag tattttcaga ctgaagaaaa ctttgaaaag   120
tcaggagcta agctgctcgg agctcagtgc cgcagcatgg ctgtggtgga cgcgggaaac   180
aacgggaaag ttcttgacag agtctgtgtc cgctcagtcc ctgcactttt cctttccaaa   240
tgcatctcgt tggatatgga atagatcgta gatgttgtag actgagattt gggactatgt   300
tgggaccgta caggtgaatg tgccacctcc acaaatggct tctccgagtg agtcacgtca   360
cctggtgcgt ggaggtggag ctgcggctgg agtaaggctt gctgtgggac gccctcgtac   420
```

```
tttgctcccc ttgcgggtgg ttgccgaccc gagagcattg ggatcctccc ccgactggtg      480
gctaagtttg tcctgtcccg ggttggctgg ggaaggggg gttgtgggtt cgggaaaaaa       540
aagttccggg gaaattcctc ctggcaaaat tccggttggt tcacattggg aacctggtta      600
acctaaattt gggtaaaagg ggtccctaat aattcgccct gggaaattcg tgggggggtt     660
ccccaaggaa cccctcgga gtcccagggg ggagaaattt gaagagcccc tttcgaaatg       720
g                                                                     721
```

<210> SEQ ID NO 142
<211> LENGTH: 1704
<212> TYPE: DNA
<213> ORGANISM: Homo sapiens
<220> FEATURE:
<221> NAME/KEY: misc_feature
<223> OTHER INFORMATION: Incyte ID No: 2454013

<400> SEQUENCE: 142

```
cgcttcgcgc taacgcttgc gatggttgaa ttcccctcct cacgccagcc taggagaaga      60
agttcgtagt cccagaggtg aggcaggagg cggcagtttc tggcgggtga gggcggagct      120
gaagtgacag cggaggcgga agcaacggtc ggtggggcgg agaaggggc tggccccagg      180 aggaggagga aacccttccg agaaaacagc aacaagctga gctgctgtga cagaggggaa      240
caagatggcg gcgccgaagg ggagcctctg ggtgaggacc caactggggc tcccgccgct      300
gctgctgctg accatggcct tggcggagg ttcggggacc gcttcggctg aagcatttga       360
ctcggtcttg ggtgatacgg cgtcttgcca ccgggcctgt cagttgacct accccttgca      420 cacctacccct aaggaagagg agttgtacgc atgtcagaga ggttgcaggc tgttttcaat    480
ttgtcagttt gtggatgatg aattgactt aaatcgaact aaattggaat gtgaatctgc       540
atgtacagaa gcatattccc aatctgatga gcaatatgct tgccatcttg gttgccagaa      600
tcagctgcca ttcgctgaac tgagacaaga acaacttatg tccctgatgc aaaaatgca      660 cctactcttt cctctaactc tggtgaggtc attctggagt gacatgatgg actccgcaca      720
gagcttcata acctcttcat ggacttttta tcttcaagcc gatgacggaa aaatagttat      780
attccagtct aagccagaaa tccagtacgc accacatttg gagcaggagc ctacaaattt     840
gagagaatca tctctaagca aaatgtccta tctgcaaatg agaaattcac aagcgcacag      900
gaattttctt gaagatggag aaagtgatgg cttttttaaga tgcctctctc ttaactctgg    960
gtggatttta actacaactc ttgtcctctc ggtgatggta ttgctttgga tttgttgtgc    1020
aactgttgct acagctgtgg agcagtatgt tccctctgag aagctgagta tctatggtga     1080
cttggagttt atgaatgaac aaaagctaaa cagatatcca gcttcttctc ttgtggttgt    1140
tagatctaaa actgaagatc atgaagaagc agggcctcta cctacaaaag tgaatcttgc    1200
tcattctgaa atttaagcat ttttcttta aagacaagt gtaatagaca tctaaaattc      1260
cactcctcat agagctttta aaatggtttc attggatata ggccttaaga aatcactata     1320
aaatgcaaat aaagttactc aaatctgtga agactgtatt tgctataact ttattggtat    1380 tgttttgta gtaatttaag aggtggatgt ttgggattgt attattattt tactaatatc     1440
tgtagctatt ttgttttttg ctttggttat tgttttttc cctttcctta gctatgagct     1500
gatcattgct ccttctcacc tcctgccatg atactgtcag ttaccttagt taacaagctg    1560
aatatttagt agaaatgatg cttctgctca ggaatggccc acaaatcgt aatttgaaat     1620 ttagcaggaa atgacctta atgacactac attttcagga actgaaatca ttaaaatttt    1680
```

```
atttgaataa ttaaaaaaaa aaaa                                           1704

<210> SEQ ID NO 143
<211> LENGTH: 964
<212> TYPE: DNA
<213> ORGANISM: Homo sapiens
<220> FEATURE:
<221> NAME/KEY: misc_feature
<223> OTHER INFORMATION: Incyte ID No: 2454048

<400> SEQUENCE: 143
cagacagcgg cgggcgcagg acgtgcacta tggctcgggg ctcgctgcgc cggttgctgc     60
ggctcctcgt gctgggctc tggctggcgt tgctgcgctc cgtggccggg gagcaagcgc    120
caggcaccgc ccctgctcc cgcggcagct cctggagcgc ggacctggac aagtgcatgg    180
actgcgcgtc ttgcagggcg cgaccgcaca gcgacttctg cctgggctgc gctgcagcac    240
ctcctgcccc cttccggctg ctttggccca tccttggggg cgctctgagc ctgaccttcg    300
tgctggggct gctttctggc tttttggtct ggagacgatg ccgcaggaga gagaagttca    360
ccacccccat agaggagacc ggcggagagg gctgcccagc tgtggcgctg atccagtgac    420
aatgtgcccc ctgccagccg gggctcgccc actcatcatt cattcatcca ttctagagcc    480
agtctctgcc tcccagacgc ggcgggagcc aagctcctcc aaccacaagg ggggtggggg    540
gcggtgaatc acctctgagg cctgggccca gggttcaggg gaaccttcca aggtgtctgg    600
ttgccctgcc tctggctcca gaacagaaag ggagcctcac gctggctcac acaaaacagc    660
tgacactgac taaggaactg cagcatttgc acagggggagg ggggtgccct ccttcctaga   720
ggccctgggg gccaggctga cttgggggggc agacttgaca ctaggcccca ctcactcaga   780
tgtcctgaaa ttccaccacg ggggtcaccc tgggggggtta gggacctatt tttaacacta   840
gggggctggc ccactaggag ggctggccct aagatacaga ccccccccaac tccccaaagc    900
ggggaggaga tatttatttt ggggagagtt tggaggggag ggagaattta ttaataaaag    960
aatc                                                                  964

<210> SEQ ID NO 144
<211> LENGTH: 1564
<212> TYPE: DNA
<213> ORGANISM: Homo sapiens
<220> FEATURE:
<221> NAME/KEY: misc_feature
<223> OTHER INFORMATION: Incyte ID No: 2479282

<400> SEQUENCE: 144
ggaattgtgg gagttgtgtc tgccactcgg ctgccggagg ccgaaggtcc ctgactatgg     60
ctccccagag cctgccttca tctaggatgg ctcctctggg catgctgctt gggctgctga    120
tggccgcctg cttcaccttc tgcctcagtc atcagaacct gaaggagttt gccctgacca    180
acccagagaa gagcagcacc aaagaaacag agagaaaaga aaccaaagcc gaggaggagc    240
tggatgccga agtcctggag gtgttccacc cgacgcatga gtggcaggcc cttcagccag    300
ggcaggctgt ccctgcagga tcccacgtac ggctgaatct tcagactggg gaaagagagg    360
caaaactcca atatgaggac aagttccgaa ataatttgaa aggcaaaagg ctggatatca    420
acaccaacac ctacacatct caggatctca agagtgcact ggcaaaattc aaggaggggg    480
cagagatgga gagttcaaag gaagacaagg caaggcaggc tgaggtaaag cggctcttcc    540
gccccattga ggaactgaag aaaagactttg atgagctgaa tgttgtcatt gagactgaca    600
tgcagatcat ggtacggctg atcaacaagt tcaatagttc cagctccagt ttggaagaga    660
```

-continued

| | |
|---|---|
| agattgctgc gctctttgat cttgaatatt atgtccatca gatggacaat gcgcaggacc | 720 |
| tgctttcctt tggtggtctt caagtggtga tcaatgggct gaacagcaca gagcccctcg | 780 |
| tgaaggagta tgctgcgttt gtgctgggcg ctgccttttc cagcaacccc aaggtccagg | 840 |
| tggaggccat cgaaggggga gccctgcaga agctgctggt catcctggcc acggagcagc | 900 |
| cgctcactgc aaagaagaag gtcctgtttg cactgtgctc cctgctgcgc acttcccct | 960 |
| atgcccagcg gcagttcctg aagctcgggg ggctgcaggt cctgaggacc ctggtgcagg | 1020 |
| agaagggcac ggaggtgctc gccgtgcgcg tggtcacact gctctacgac ctggtcacgg | 1080 |
| agaagatgtt cgccgaggag gaggctgagc tgacccagga tgtccccca gagaagctgc | 1140 |
| agcagtatcg ccaggtacac ctcctgccag gcctgtggga cagggctggg tgcgagatca | 1200 |
| cggcccacct cctggcgctg cccgagcatg atgcccgtga aaggtgctg cagacactgg | 1260 |
| gcgtcctcct gaccacctgc cgggaccgct accgtcagga cccccagctc ggcaggacac | 1320 |
| tggccagcct gcaggctgag taccaggtgc tggccagcct ggagctgcag gatggtgagg | 1380 |
| acgagggcta cttccaggag ctgctgggct ctgtcaacag cttgctgaag gagctgagat | 1440 |
| gaggccccac accaggactg gactgggatg ccgctagtga ggctgagggg tgccagcgtg | 1500 |
| ggtgggcttc tcaggcagga ggacatcttg gcagtgctgg cttggccatt aaatggaaac | 1560 |
| ctgg | 1564 |

<210> SEQ ID NO 145
<211> LENGTH: 1385
<212> TYPE: DNA
<213> ORGANISM: Homo sapiens
<220> FEATURE:
<221> NAME/KEY: misc_feature
<223> OTHER INFORMATION: Incyte ID No: 2483432

<400> SEQUENCE: 145

| | |
|---|---|
| gtccgcccgc cgctgcgtcc cggagtgcaa gtgagcttct cggctgcccc gcgggccggg | 60 |
| gtgcggagcc gacatgcgcc cgcttctcgg cctccttctg gtcttcgccg gctgcacctt | 120 |
| cgccttgtac ttgctgtcga cgcgactgcc ccgcgggcgg agactgggct ccaccgagga | 180 |
| ggctggaggc aggtcgctgt ggttcccctc cgacctggca gagctgcggg agctctctga | 240 |
| ggtccttcga gagtaccgga aggagcacca ggcctacgtg ttcctgctct ctgcggcgc | 300 |
| ctacctctac aaacagggct tgccatccc cggctccagc ttcctgaatg ttttagctgg | 360 |
| tgccttgttt gggccatggc tggggcttct gctgtgctgt gtgttgacct cggtgggtgc | 420 |
| cacatgctgc tacctgctct ccagtatttt tggcaaacag ttggtggtgt cctactttcc | 480 |
| tgataaagtg gccctgctgc agagaaaggt ggaggagaac agaaacagct tgttttttttt | 540 |
| cttattgttt ttgagacttt tccccatgac accaaactgg ttcttgaacc tctcggcccc | 600 |
| aattctgaac attcccatcg tgcagttctt cttctcagtt cttatcggtt tgatcccata | 660 |
| taatttcatc tgtgtgcaga cagggtccat cctgtcaacc ctaacctctc tggatgctct | 720 |
| tttctcctgg gacactgtct ttaagctgtt ggccattgcc atggtggcat taattcctgg | 780 |
| aaccctcatt aaaaaattta gtcagaaaca tctgcaattg aatgaaacaa gtactgctaa | 840 |
| tcatatacac agtagaaaag acacatgatc tggattttct gtttgccaca tccctggact | 900 |
| cagttgctta tttgtgtaat ggatgtggtc ctctaaagcc cctcattgtt tttgattgcc | 960 |
| ttctataggt gatgtggaca ctgtgcatca atgtgcagtg tcttttcaga aaggacactc | 1020 |
| tgctcttgaa ggtgtattac atcaggtttt caaaccagcc ctggtgtagc agacactgca | 1080 |
| acagatgcct cctagaaaat gctgtttgtg gccgggcgcg gtggctcacg cctgtaatcc | 1140 |

```
cagcactttg ggaggccgag gccggtgatt cacaaggtca ggagttcaag accagcctgg    1200
ccaagatggt gaaatcctgt ctctaataaa aatacaaaaa ttagccaggc gtggtggcag    1260
gcacctgtaa tcccagctac tcgggaggct gaggcaggag aattgcttga accaaggtgg    1320
cagaggttgc agtaagccaa gatcacacca ctgcactcca gcctgggtga tagagtgaga    1380
ccaca                                                                1385
```

<210> SEQ ID NO 146
<211> LENGTH: 2031
<212> TYPE: DNA
<213> ORGANISM: Homo sapiens
<220> FEATURE:
<221> NAME/KEY: misc_feature
<223> OTHER INFORMATION: Incyte ID No: 2493824

<400> SEQUENCE: 146

```
tgggcggggg cccacggcgg ccactcactg agcccacgg gccgcagcgg cagtgacgta      60 ggggttggcgc acggatccgt tgcggctgca gctctgcagt cgggccgttc cttcgccgcc   120
gccaggggta gcggtgtagc tgcgcagcgt cgcgcgcgct accgcaccca ggttcggccc    180
ataggcgtct ggcagcccgg cgccatcttc atcgagcgcc atggccgcag cctgcgggcc    240
gggagcggcc gggtactgct tgctcctcgg cttgcatttg tttctgctga ccgcgggccc    300
tgccctgggc tggaacgacc ctgacagaat gttgctgcgg gatgtaaaag ctcttaccct    360
ccactatgac cgctatacca cctcccgcag gctggatccc atcccacagt tgaaatgtgt    420
tggaggcaca gctggttgtg attcttatac cccaaaagtc atacagtgtc agaacaaagg    480
ctgggatggg tatgatgtac agtgggaatg taagacggac ttagatattg catacaaatt    540
tggaaaaact gtggtgagct gtgaaggcta tgagtcctct gaagaccagt atgtactaag    600
aggttcttgt ggcttggagt ataattttaga ttatacagaa cttggcctgc agaaactgaa    660
ggagtctgga aagcagcacg gctttgcctc tttctctgat tattattata agtggtcctc    720
ggcggattcc tgtaacatga gtggattgat taccatcgtg gtactccttg ggatcgcctt    780
tgtagtctat aagctgttcc tgagtgacgg gcagtattct cctccaccgt actctgagta    840
tcctccattt tcccaccgtt accagagatt caccaactca gcaggacctc ctcccccagg    900
ctttaagtct gagttcacag gaccacagaa tactggccat ggtgcaactt ctggttttgg    960
cagtgctttt acaggacaac aaggatatga aaattcagga ccagggttct ggacaggctt   1020
gggaactggt ggaatactag atatttgtt tggcagcaat agagcggcaa caccccttctc   1080 agactcgtgg tactacccgt cctatcctcc ctcctaccct ggcacgtgga atagggctta   1140 ctcaccccctt catggaggct cgggcagcta ttccggtatgt tcaaactcag acacgaaaac   1200
cagaactgca tcaggatatg gtggtaccag gagacgataa agtagaaagt tggagtcaaa   1260
cactggatgc agaaattttg gattttcat cactttctct ttagaaaaaa agtactacct    1320
gttaacaatt gggaaaaggg gatattcaaa agttctgtgg tgttatgtcc agtgtagctt    1380
tttgtattct attatttgag gctaaaagtt gatgtgtgac aaaatactta tgtgttgtat   1440
gtcagtgtaa catgcagatg tatattgcag tttttgaaag tgatcattac tgtggaatgc   1500
taaaaataca ttaatttcta aaacctgtga tgccctaaga agcattaaga atgaaggtgt   1560
tgtactaata gaaactaagt acagaaaatt tcagttttag gtggttgtag ctgatgagtt   1620
attacctcat agagactata atattctatt tggtattata ttatttgatg tttgctgttc   1680
ttcaaacatt taaatcaagc tttggactaa ttatgctaat ttgtgagttc tgatcacttt   1740
```

| | | |
|---|---|---|
| tgagctctga agctttgaat cattcagtgg tggagatggc cttctggtaa ctgaatatta | 1800 | |
| ccttctgtag gaaaaggtgg aaaataagca tctagaaggt tgttgtgaat gactctgtgc | 1860 | |
| tggcaaaaat gcttgaaacc tctatatttc tttcgttcat aagaggtaaa ggtcaaattt | 1920 | |
| ttcaacaaaa gtcttttaat aacaaaagca tgcagttctc tgtgaaatct caaatattgt | 1980 | |
| tgtaatagtc tgtttcaatc ttaaaaagaa tcaataaaaa caaaaaaaaa a | 2031 | |

<210> SEQ ID NO 147
<211> LENGTH: 1790
<212> TYPE: DNA
<213> ORGANISM: Homo sapiens
<220> FEATURE:
<221> NAME/KEY: misc_feature
<223> OTHER INFORMATION: Incyte ID No: 2555823

<400> SEQUENCE: 147

| | |
|---|---|
| gcgggaggac cggctgaccc tggatggtga ggccgggtgc ccgcctgtgc ctggggagtg | 60 |
| tggggagggg gctgtgcctg gtgctccccc tgctttgtct cggtgcaggt ttcctcttcc | 120 |
| tgaacacgct cttcatccag cgcggccggc acgagaccac ctggaccatc ctgcggcgct | 180 |
| tcggctacag cgatgccctg gagctgactg cggactatct ctcccctctg atccacgtgc | 240 |
| cccccggctg cagcacggag ctcaaccacc ttggctacca gtttgtgcag agagtgtttg | 300 |
| agaagcacga ccaggaccgc gacggcgccc tctcgcccgt ggagctgcaa agccttttca | 360 |
| gtgtgttccc agcagcgccc tggggccccg agctcccacg cacagtccgc acagaggccg | 420 |
| gccggttgcc cctgcacgga tacctctgcc agtggaccct ggtgacctac ctggacgtcc | 480 |
| ggagctgcct tggacaccta ggctacctgg ctacccccac cctctgtgag caggaccagg | 540 |
| cccatgccat cacagtcact cgtgagaaga ggctggacca ggagaaggga cagacgcagc | 600 |
| ggagcgtcct cctgtgcaag gtggtagggg cccgtggagt gggcaagtct gccttcctgc | 660 |
| aggcctttct cggccgcggc ctggggcacc aggacacgag ggagcagcct cccggctacg | 720 |
| ccatcgacac ggtgcaggtc aatggacagg agaagtactt gatcctctgt gaggtgggca | 780 |
| cagatggtct gctggccaca tcgctggacg ccacctgtga cgttgcctgc ttgatgtttg | 840 |
| atggcagtga cccaaagtcc tttgcacatt gtgccagcgt ctacaagcac cattacatgg | 900 |
| acggcagac cccctgcctc tttgtctcct ccaaggccga cctgcccgaa ggtgtcgcgg | 960 |
| tgtctggccc atcaccggcc gagttttgcc gcaagcaccg gctacccgct cccgtgccgt | 1020 |
| tctcctgtgc tggcccagcc gagcccagca ccaccatctt cacccagctc gccaccatgg | 1080 |
| ccgccttccc acatttggtc cacgcagagc tgcatccctc ttccttctgg ctccggggggc | 1140 |
| tgctgggggt gtcggggcc gccgtggccg cagtcctcag cttctcactc tacagggtcc | 1200 |
| tggtgaagag ccagtgaggc ccctggtacc caagccccct cccctgacct gggtgtgcct | 1260 |
| cgctgctggg gctctgcagg ggcagcacag ctggggtgca ggccaggctg ccactccggg | 1320 |
| aacgcctttg cgccgggact ttttgtttct gaaggcagtc gatctgcagc ggggccttat | 1380 |
| gctgccatgc actgccctgg ctcctgccgg accccaggg tgggccgtgg caggtggctg | 1440 |
| agcaggagct cccaagtgcc ggccaccgct gtcaggggatt gcccaccccct gggcatcatg | 1500 |
| tgtgtgggc cggggagcac aggtgtggga gctggtgacc ccagaccag aattctcagg | 1560 |
| gctctacccc ccttttcctgg tcctaggtgg ccagtgggta tgaggaggc tggaaggcag | 1620 |
| agctttgggc caaaagcagg cgttgggggg tccccctca gtttggagc cgtttccgtg | 1680 |
| gttgtagcag aggaccggag gttgggttcc tgattaaact tcactgtgtg ttttctatct | 1740 |
| cggatcccag tctctgaaga caacttgctt tgattcaacc taaaaaaaaa | 1790 |

<210> SEQ ID NO 148
<211> LENGTH: 1979
<212> TYPE: DNA
<213> ORGANISM: Homo sapiens
<220> FEATURE:
<221> NAME/KEY: misc_feature
<223> OTHER INFORMATION: Incyte ID No: 2598242

<400> SEQUENCE: 148

| | | | | | |
|---|---|---|---|---|---|
| ctactcctca | ctggccggga | caactggtct | tatcacggag | gctggggcca | ggcagccctt | 60 |
| cggttcgggt | gggcccatgg | accccagtcc | aacgccgagg | gaataggacc | atccaaaagc | 120 |
| ggaaccttcg | cctcagaaaa | agggtgcggg | acccctcctc | accgtgcggt | cacgcgtgga | 180 |
| ccctgccagc | agccaggcca | tggagctctc | tgatgtcacc | ctcattgagg | gtgtgggtaa | 240 |
| tgaggtgatg | gtggtggcag | gtgtggtggt | gctgattcta | gccttggtcc | tagcttggct | 300 |
| ctctacctac | gtagcagaca | gcggtagcaa | ccagctcctg | ggcgctattg | tgtcagcagg | 360 |
| cgacacatcc | gtcctccacc | tggggcatgt | ggaccacctg | gtggcaggcc | aaggcaaccc | 420 |
| cgagccaact | gaactccccc | atccatcaga | gggtaatgat | gagaaggctg | aagaggcggg | 480 |
| tgaaggtcgg | ggagactcca | ctggggaggc | tggagctggg | ggtggtgttg | agcccagcct | 540 |
| tgagcatctc | cttgacatcc | aaggcctgcc | caaaagacaa | gcaggtgcag | gcagcagcag | 600 |
| tccagaggcc | cccctgagat | ctgaggatag | cacctgcctc | cctcccagcc | ctggcctcat | 660 |
| cactgtgcgg | ctcaaattcc | tcaatgatac | cgaggagctg | gctgtggcta | ggccagagga | 720 |
| taccgtgggt | gccctgaaga | gcaaatactt | ccctggacaa | gaaagccaga | tgaaactgat | 780 |
| ctaccagggc | cgcctgctac | aagacccagc | ccgcacactg | cgttctctga | acattaccga | 840 |
| caactgtgtg | attcactgcc | accgctcacc | cccagggtca | gctgttccag | gcccctcagc | 900 |
| ctccttggcc | ccctcggcca | ctgagccacc | cagccttggt | gtcaatgtgg | gcagcctcat | 960 |
| ggtgcctgtc | tttgtggtgc | tgttgggtgt | ggtctggtac | ttccgaatca | attaccgcca | 1020 |
| attcttcaca | gcacctgcca | ctgtctcct | ggtgggagtc | accgtcttct | tcagcttcct | 1080 |
| agtatttggg | atgtatggac | gataaggaca | taggaagaaa | atgaaaggca | tggtcttct | 1140 |
| cctttatggc | ctccccactt | ttcctggcca | gagctgggcc | caagggccgg | ggagggaggg | 1200 |
| gtggaaagga | tgtgatggaa | atcctcctcca | taggacacag | gaggcaagta | tgcggcctcc | 1260 |
| ccttctcatc | cacaggagta | cagatgtccc | tcccgtgcga | gcacaactca | ggtagaaatg | 1320 |
| aggatgtcat | cttccttcac | ttttagggtc | tctgaagga | gttcaaagct | gctggccaag | 1380 |
| ctcagtgggg | agcctgggct | ctgagattcc | ctcccacctg | tggttctgac | tcttcccagt | 1440 |
| gtcctgcatg | tctgccccca | gcacccaggg | ctgcctgcaa | gggcagctca | gcatggcccc | 1500 |
| agcacaactc | cgtagggagc | ctggagtatc | cttccatttc | tcagccaaat | actcatcttt | 1560 |
| tgagactgaa | atcacactgg | cgggaatgaa | gattgtgcca | gccttctctt | atgggcacct | 1620 |
| agccgccttc | accttcttcc | tctacccctt | agcaggaata | gggtgtcctc | ccttctttca | 1680 |
| aagcactttg | cttgcattt | atttatttt | tttaagagtc | cttcatagag | ctcagtcagg | 1740 |
| aaggggatgg | ggcaccaagc | caagccccca | gcattgggag | cggccaggcc | acagctgctg | 1800 |
| ctcccgtagt | cctcaggctg | taagcaagag | acagcactgg | cccttggcca | gcgtcctacc | 1860 |
| ctgcccaact | ccaaggactg | ggtatggatt | gctgggccct | aggctcttgc | ttctggggct | 1920 |
| attggagggt | cagtgtctgt | gactgaataa | agttccattt | tgtggtcaaa | aaaaaaaaa | 1979 |

<210> SEQ ID NO 149

<211> LENGTH: 1810
<212> TYPE: DNA
<213> ORGANISM: Homo sapiens
<220> FEATURE:
<221> NAME/KEY: misc_feature
<223> OTHER INFORMATION: Incyte ID No: 2634120

<400> SEQUENCE: 149

```
cccccctgccc gcctctccgc acaatacttg aacattcatc tgtactgaag tgttacttga       60
accgggggaa tctcggacct gggggagccg gggtgtgagg ggactggacc agcttggact      120
gagacctgag accgggccgg tgggcgccca tttgggactg cgccaccccc aggcttgttc      180
ttgttttact gtattgagcg gcggcacccg ccggacccgc attatggctg ggggcgccag      240
ccaagaatgg ggaccatggg actcctccag cctggctctt cccactcttt catcgtcatg      300
gaaacttgta tcccatttgc ccagggaact gccactcctg gttgccatgg aaatagcagc      360
caacggacac ctcccgatgc cagtgctaag gctggaaatg gccccctctt agttgccatg      420
ggaacctagt aacagactct gctggccctc cttccctgcc ccttcctcga gcgcggggtg      480
gggcttcggg accccgggga tgagccgggc caggtcccgc ccctccgcgc aggcctccgg      540
ggggccgggg cttaccatgt aggggagggg agatctatcc acatacctca ggtggccatg      600
gtggaggtgc agctggagag tgaccacgag tacccaccag gcctgctggt ggccttcagt      660
gcctgcacca ccgtgctggt ggctgtgcac ctctttgcac tcatggtctc cacgtgtctg      720
ctgccccaca ttgaagctgt gagcaacatc cacaacctca actctgtcca ccagtcgcca      780
caccagagac tgcaccgcta cgtggagctg gcctggggct tctccactgc cctgggcacc      840
tttctcttcc ttgctgaagt tgtcctggtt ggttgggtca agtttgtgcc cattggggct      900
cccttggaca caccgacccc catggtgccc acatcccggg tgcccgggac tctggcacca      960
gtggctacct cccttagtcc agcttccaat ctcccacggt cctctgcgtc tgcagcaccg     1020
tcccaggctg agccagcctg cccacccccgg caagcctgtg gtggtggtgg ggcccatggg     1080
ccaggctggc aagcagccat ggcctccaca gccatcatgg tacccgtggg gctcgtgttt     1140
gtggcctttg ccctgcatt ctaccgctcc ttggtggcac acaagacaga ccgctacaag     1200
caggaactag aggaactgaa tcgcctgcag ggggagctgc aggctgtgtg agactggtgt     1260
tagccaccgc tcactgcaag cactgcctcc ctccggggtc tgtaagaggc cgcaggggcc     1320
tacagacctc atcccccat cccctggctg gagccacttc cagtggccac tctcaggcag     1380
agttcagatt cctgcccgca ggtcctctgg gctgggcctt ggggcagctc ccacattccc     1440
agggatttc cccatcagtc tgtcccttgg gttttgcaag ctactctgca cctgggctgg     1500
cctcagttga aggatcatgc agtagataga ggggaggcag ggagagcttg tgggaccttc     1560
agtgctgact ttagccacca tttccattcc tatacaggat gtgaaggtca gaaggcagcc     1620
aattgttggt ttaattttt ttttttttga cacagtctgt ttcccaggct ggagtgtagt     1680
gatacagtca cagctcactg tagcctcgac cttccaggct caaaagatgc tcccaccaca     1740
gcctcccagg tagtgagtag ctggtactac aggtgtgtgc tgccacaccc gactaatttt     1800
tttgtagaga                                                           1810
```

<210> SEQ ID NO 150
<211> LENGTH: 535
<212> TYPE: DNA
<213> ORGANISM: Homo sapiens
<220> FEATURE:
<221> NAME/KEY: misc_feature
<223> OTHER INFORMATION: Incyte ID No: 2765411

-continued

<400> SEQUENCE: 150

| gaggaaccag | aaatttgtcc | ttgaataatg | tttcccgtgt | tgggctggat | cttgatagca | 60 |
| gttgttatca | tcattcttct | gattttaca | tctgtcaccc | gatgcctatc | tccagttagt | 120 |
| tttctgcagc | tgaaattctg | gaaaatctat | tggaacagg | agcagcagat | ccttaaaagt | 180 |
| aaagccacag | agcatgcaac | tgaattggca | aaagagaata | ttaaatgttt | ctttgagggc | 240 |
| tcgcatccaa | aagaatataa | cactccaagc | atgaaagagt | ggcagcaaat | tcatcactg | 300 |
| tatactttca | atccgaaggg | ccagtactac | agcatgttgc | acaaatatgt | caacagaaaa | 360 |
| gagaagactc | acagtatcag | gtctactgaa | ggagatacgg | tgattcctgt | tcttggcttt | 420 |
| gtagattcat | ctggtataaa | cagcactcct | gagttatgac | cttttgaatg | agtagaaaaa | 480 |
| aaaattgttt | tgaattattg | ctttattaaa | aataaacat | tggtaaaaaa | aaaaa | 535 |

<210> SEQ ID NO 151
<211> LENGTH: 891
<212> TYPE: DNA
<213> ORGANISM: Homo sapiens
<220> FEATURE:
<221> NAME/KEY: misc_feature
<223> OTHER INFORMATION: Incyte ID No: 2769412

<400> SEQUENCE: 151

| gaaaagaatc | cgaggcacag | ataaagataa | gttttactgt | catgctgctt | ttaacataac | 60 |
| agagcaacat | cacctaggaa | aaagtttgt | aggaggattt | ttaatccata | tatttgtctt | 120 |
| atggctagat | aaagatttct | ctgaaaaaaa | gaagcatgtc | aggaatctct | gggtgcccct | 180 |
| ttttcctctg | gggacttcta | gcattgttgg | gcttggcttt | ggttatatca | ctgatcttca | 240 |
| atatttccca | ctatgtggaa | aagcaacgac | aagataaaat | gtacagctac | tccagtgacc | 300 |
| acaccagggt | tgatgagtat | tatattgaag | acacaccaat | ttatggtaac | ttagatgata | 360 |
| tgatttcaga | accaatggat | gaaaattgct | atgaacaaat | gaaagcccga | ccagagaaat | 420 |
| ctgtaaataa | gatgcaggaa | gccaccccat | ctgcacaggc | aaccaatgaa | acacagatgt | 480 |
| gctacgcctc | acttgatcac | agcgttaagg | ggaagcgtag | aaagcccagg | aaacagaata | 540 |
| ctcatttctc | agacaaggat | ggagatgagc | aactacatgc | aatagatgcc | agcgtttcta | 600 |
| agaccacctt | agtagacagt | ttctccccag | aaagccaggc | agtagaggaa | acattcatg | 660 |
| atgatcccat | cagactgttt | ggattgatcc | gtgctaagag | agaacctata | aactagctgg | 720 |
| accatgatct | agttcaatga | tttggctcct | attgaagatg | gcttctaaga | aaacaagatg | 780 |
| cacagaggac | acagaaggac | ttggcagcag | ggtgatgacc | tgatcatttg | ttgatgggat | 840 |
| ggtggcttac | ctcttattca | cagcttacac | ttatgcatgc | caaatgtaag | g | 891 |

<210> SEQ ID NO 152
<211> LENGTH: 2311
<212> TYPE: DNA
<213> ORGANISM: Homo sapiens
<220> FEATURE:
<221> NAME/KEY: misc_feature
<223> OTHER INFORMATION: Incyte ID No: 2842779

<400> SEQUENCE: 152

| gggcgcggca | ccgcagctgg | atggctgggg | ccgcccggat | cgccgccgcc | gccgccgccg | 60 |
| cacgtacgtg | gcatgcctgg | atgtccctgc | cctggctgtg | catggcggg | cccaaggctc | 120 |
| ctcttcctca | ctgcccttgc | cctggagctc | ttgggaaggg | ctgggggttc | ccagccggcc | 180 |
| ctccggagcc | gggggactgc | gacggcctgt | cgcctggaca | caaggaaag | cgagtcctgg | 240 |

| | |
|---|---|
| ggggctctgc tgagcggaga gcggctggac acctggatct gctccctcct gggttccctc | 300 |
| atggtggggc tcagtggggt cttcccgttg cttgtcattc ccctagagat ggggaccatg | 360 |
| ctgcgctcag aagctggggc ctggcgcctg aagcagctgc tcagcttcgc cctgggggga | 420 |
| ctcttgggca atgtgtttct gcatctgctg cccgaagcct gggcctacac gtgcagcgcc | 480 |
| agccctggtg gtgaggggca gagcctgcag cagcagcaac agctggggct gtgggtcatt | 540 |
| gctggcatcc tgaccttcct ggcgttggag aagatgttcc tggacagcaa ggaggagggg | 600 |
| accagccagg cccccaacaa agaccccact gctgctgccg ccgcactcaa tggaggccac | 660 |
| tgtctggccc agccggctgc agagcccggc tcggtgccg tggtccggag catcaaagtc | 720 |
| agcggctacc tcaacctgct ggccaacacc atcgataact cacccacgg gctggctgtg | 780 |
| gctgccagct tccttgtgag caagaagatc gggctcctga caaccatggc catcctcctg | 840 |
| catgagatcc cccatgaggt gggcgacttt gccatcctgc tccgggccgg ctttgaccga | 900 |
| tggagcgcag ccaagctgca actctcaaca gcgctggggg gcctactggg cgctggcttc | 960 |
| gccatctgta cccagtcccc caagggagta gaggagacgg cagcctgggt cctgcccttc | 1020 |
| acctctggcg gctttctcta catcgccttg gtgaacgtgc tccctgacct cttggaagaa | 1080 |
| gaggacccgt ggcgctccct gcagcagctg cttctgctct gtgcgggcat cgtggtaatg | 1140 |
| gtgctgttct cgctcttcgt ggattaactt tccctgatgc cgacgcccct gcccctgca | 1200 |
| gcaataagat gctcggattc actctgtgac cgcatatgtg agaggcagag agggcgagtg | 1260 |
| gctgcgagag agaatgagcc tcccgccaga caggagggag gtgcgtgtgg atgtatgtgg | 1320 |
| tgtgcacatg tggccagagg tgtgtgcgcg agaccgacac tgtgatccct gtgctgggtc | 1380 |
| cggggcccag tgtagcgcct gtccccagcc atgctgtggt tacctctcct gccgccctg | 1440 |
| tcaccttcac ctcctggagt aagcagcgag gaagagcagc actggtccca agcagaggcc | 1500 |
| ttgccctgct gggaccccgg gagtgagagc agcccaagga tcccagggtg cagggaactc | 1560 |
| cagagctgcc cacctcccac tgcccctca gcacacacac agtccccagg cggcctaggg | 1620 |
| gccaaggctg gggcggcttt ggtccctttt cctggcccctt ccttcccac ttctaagcca | 1680 |
| aagaaaggag aggcaggtgc tcctgtaccc cagccccact cagcactgac agtccccagc | 1740 |
| tcctagtagt gagctgggag gcgcttccta agacccttc ctcagggctg ccctgggagc | 1800 |
| tcattcctgg ccaacacgcc ctggcagcac cagcagctct tgccacctcc agctgccaaa | 1860 |
| cagcagcctg ccgggcaggg agcagcccca ggccagagag gcctcccggt ccagctcagg | 1920 |
| gatgctcctg ccagcacagg ggccagggac tcctggagca ggcacatagt gagcccgggc | 1980 |
| agccctgccc agctcaggcc cctttccttc cccattgagg ttggggtagg tggggcggt | 2040 |
| gagggctcca cgttgtcagc gctcaggaat gtgctccggc agagtgctga agccataatc | 2100 |
| cccaaccatt tcccttgtct gacgcccagg tactcagctg gcccactcca cagccaggcc | 2160 |
| tggccctgcc cttcaccgtg gatgttttca gaagtggcca tcgagaggtc tggatggttt | 2220 |
| tatagcaact ttgctgtgat tccgtttgta tctgtaaata tttgttctat agataagata | 2280 |
| caaataaata ttatccacat aaaaaaaaaa a | 2311 |

<210> SEQ ID NO 153
<211> LENGTH: 2169
<212> TYPE: DNA
<213> ORGANISM: Homo sapiens
<220> FEATURE:
<221> NAME/KEY: misc_feature
<223> OTHER INFORMATION: Incyte ID No: 2966260

<400> SEQUENCE: 153

```
gctgcaggcg gcgacggcta caccatgggc cggctgctgc gggccgcccg gctgccgccg      60
ctgctttcgc cgctgctgct tctgctggtt gggggagcgt tcctgggtgc ctgtgtggct     120
gggtctgatg agcctggccc agagggcctc acctccacct ccctgctaga cctcctgctg     180
cccactggct tggagccact ggactcagag gagcctagtg agaccatggg cctgggagct     240
gggctgggag cccctggctc aggcttcccc agcgaagaga atgaagagtc tcggattctg     300
cagccaccac agtacttctg ggaagaggag gaagagctga atgactcaag tctggacctg     360
ggacccactg cagattatgt ttttcctgac ttaactgaga aggcaggttc cattgaagac     420
accagccagg ctcaagagct gccaaacctc ccctctccct tgcccaagat gaatctggtt     480
gagcctccct ggcatatgcc tcccagagag gaggaagaag aggaaggaga agaggaggag     540
atggagaagg aagaggtaga gaaacaagat gtggaggaag aggaggagct gctccctgtg     600
aatggatccc aagaagaagc caagcctcag gtccgtgact tttctctcac cagcagcagc     660
cagaccccag gggccaccaa aagcaggcat gaagactccg ggaccaggc ctcatcaggt      720 gtggaggtgg agagcagcat ggggcccagc ttgctgctgc cttcagtcac cccaactata     780
gtgactccgg gggaccagga ctccaccagc caagaggcag aggccacagt gctgccagct     840
gcagggcttg gggtagagtt cgaggctcct caggaagcaa gcgaggaagc cactgcagga     900
gcagctggtt tgtctggcca gcacgaggag gtgccggcct tgccttcatt ccctcaaacc     960
acagctccca gtggggccga gcacccagat gaagatcccc ttggctctag aacctcagcc    1020
tcttccccac tggcccctgg agacatgaaa ctgacacctt cctctgctac cttgggacaa    1080
gaagatctca accagcagct cctagaaggg caggcagctg aagctcaatc caggatacc     1140 tgggattcta cgcaggtgat ctgcaaggac tggagcaatc tggctgggaa aaactacatc    1200
attctgaaca tgacagagaa catagactgt gaggtgttcc ggcagcaccg ggggccacag    1260
ctcctggccc tggtggaaga ggtgctgccc cgccatggca gtggccacca tggggcctgg    1320
cacatctctc tgagcaagcc cagcgagaag gagcagcacc ttctcatgac actggtgggc    1380
gagcaggggg tggtgcccac tcaagatgtc ctttccatgc tgggtgacat ccgcaggagc    1440
ctggaggaga ttggcatcca gaactattcc acaaccagca gctgccaggc gcgggccagc    1500
caggtgcgca gcgactacgg cacgctcttc gtggtgctgg tggtcattgg gccatctgc     1560 atcatcatca ttgcgcttgg cctgctctac aactgctggc agcgccggct gcccaagctc    1620
aagcacgtgt cgcacggcga ggagctgcgc ttcgtggaga acggctgcca cgacaacccc    1680
acgctggacg tggccagcga cagccagtcg gagatgcagg agaagcaccc cagcctgaac    1740
ggcggcgggg ccctcaacgg cccggggagc tgggggcgc tcatgggggg caagcgggac    1800
cccgaggact cggacgtgtt cgaggaggac acgcacctgt gagcgcagcc gaggcgcagg    1860
ccgagtgggc cgccaggacc aagcgaggtg accccgaaa cggacggccc ggagccagca     1920
caagccccga gcctacccgg gccgcccccg cggcctggcc ctcggcgcgg gctccttccc    1980
gcttcccccg acttcacacg gcggacttcg gaccaactcc ctcactcccg cccgaggggc    2040
aggcctcaaa gcccgccttg gccccgcttt ccgcccctg aacccggcc ccgcgggcgg      2100 cgggcggcgc ttcctgcgcc ccgggactca attaaacccg cccggagacc acgccgggcc    2160
cagcgaaaa                                                            2169

<210> SEQ ID NO 154
<211> LENGTH: 1480
<212> TYPE: DNA
<213> ORGANISM: Homo sapiens
```

```
<220> FEATURE:
<221> NAME/KEY: misc_feature
<223> OTHER INFORMATION: Incyte ID No: 2993326

<400> SEQUENCE: 154
ggatggggat ctttgtctgg tccttaacca acaggtattt caccaactta ttagcccttt      60
cttgtaaaat ggccacatct cgcggtggtg caggcctccg gccccatggg atccgcctgt     120
aattactgcc acttctctca tccccattca gatgcttgga ctttcggttt cttttgcccc     180
gggtcctggt tgtgggctcc aggctcaact gagccagata gtcatctgcc agggcctgga     240
cagcagcagc aacctgagtc tcaagggcac ttacgttggt ctgagcagag gctatcttgg     300
cctgggcccc ttggtcagca tttggagtct ggctttcagt tgcccgagcc ttagtggcag     360
ccttccgagc cctagaccct ctcttgaccc gcagggtggc tgccagggct tggtttgtga     420
ctatctgagt ggcaagtggg gcctcagaga tctcagagac agaatttggg ccctgctgg     480
cagccttctt gccctggat ttttggcc tgatagccac tactgaggcc tcaatctgcc     540
tggtagctgc gtcagtgaca tttagagcct ctatatgctc agtgtcagta tttatgacct     600
tagcaattgt cttcctggct ttggaggctt tcttggttcg gatggaggct gctgtggtgt     660
ggatactggc tgtctcattg gtaatttggc cttgggtggt agctgtatgg gtggcagttg     720
cagccagcga gacctcggtg gcactagcta tggccttatt tgcagccttc ttagccttgg     780
aagctttctt aggcttgata gaggttatca aggcttggga actggctgac tcattggcaa     840
ttggagcgtg aatattctgt gagatgactg gtagctttag gacctgcaag ggtgacttca     900
gctgtatagt gccaccctca tggccagttg gggattggga gccttgggct gccttggcag     960
taactctctt catcttgttg gctttcttag gctgagcagt gactgaagaa gcctgagtat    1020
tggttacctc agtggtaggt aaagcctggc tgatctgggt aatgactggc aggtttaaag    1080
cctgccaagt tattttgggc ttgttggtgg caatctcatt ggcagctggg actggagggg    1140
cagcaggtgc agccttagta atagtcttta taggggcctt cttggtcttg cttttcttag    1200
gccggttgac aactggtggg tccatggcca gggagtcctt ggttgccgcc aacagggtat    1260
gcatcagcag gacactgtcc tcttctgtgg tctcagtctg tatatctgga gggaaggaa    1320
gccccaggct ccccggggga ggcagagggc cctgaaatag aggcacccta tatccgtagt    1380
catttctcct atccatcttt ctgggaggcc gagtaacagg tgagcctcgt cttcttgaat    1440
ccagaaggcg tctgctctct ccaagtctgc tctctccaag                          1480

<210> SEQ ID NO 155
<211> LENGTH: 1222
<212> TYPE: DNA
<213> ORGANISM: Homo sapiens
<220> FEATURE:
<221> NAME/KEY: misc_feature
<223> OTHER INFORMATION: Incyte ID No: 3001124

<400> SEQUENCE: 155
agaaatatca tatggttact ttggtatctg acacagccat gacaccaatt gctagtgtag      60
acacaatagc tgtgtgtctt tttgcaggag cctggggagg ggccatggtg ccaatgcact     120
tactggggag actggagaag ccgcttctcc tcctgtgctg cgcctccttc ctactggggc     180
tggctttgct gggcataaag acggacatca ccccgttgc ttatttctttt ctcacattgg     240
gtggcttctt cttgtttgcc tatctcctgg tccggtttct ggaatggggg cttcggtccc     300
agctccaatc aatgcagact gagagcccag ggccctcagg caatgcacgg acaatgaag     360
cctttgaagt gccagtctat gaagaggccg tggtgggact agaatcccag tgccgcccc     420
```

-continued

```
aagagttgga ccaaccaccc ccctacagca ctgttgtgat accccccagca cctgaggagg    480 aacaacctag ccatccagag gggtccagga gagccaaact ggaacagagg cgaatggcct    540
cagaggggtc catggcccag gaaggaagcc ctggaagagc tccaatcaac cttcggcttc    600
ggggaccacg ggctgtgtcc actgctcctg atctgcagag cttggcggca gtccccacat    660
tagagcctct gactccaccc cctgcctatg atgtctgctt tggtcaccct gatgatgata    720 gtgttttta tgaggacaac tgggcacccc cttaaatgac tctcccaaga tttctcttct    780
ctccacacca gacctcgttc atttgactaa cattttccag cgcctactat gtgtcagaaa    840
caagtgtttc tgcctggaca tcataaatgg ggacttggac cctgaggaga gtcaggccac    900
ggtaagccct tcccagctga gatatgggtg gcataatttg agtcttctgg caacatttgg    960
tgacctaccc catatccaat atttccagcg ttagattgag gatgaggtag ggaggtgatc   1020
cagagaaggc ggagaaggaa gaagtaacct ctgagtggcg gctattgctt ctgttccagg   1080
tgctgttcga gctgttagaa cccttaggct tgacagcttt tgagttatt attgaaaaat   1140 gaggattcca agagtcagag gagtttgata atgtgcacga gggcacactg ctagtaaata   1200
acattaaaat aactcgaatg ac                                             1222
```

<210> SEQ ID NO 156
<211> LENGTH: 1983
<212> TYPE: DNA
<213> ORGANISM: Homo sapiens
<220> FEATURE:
<221> NAME/KEY: misc_feature
<223> OTHER INFORMATION: Incyte ID No: 3120070

<400> SEQUENCE: 156

```
ggaaccgcct ccccgcggcc tcttcgcttt tgtggcggcg cccgcgctcg caggccactc     60
tctgctgtcg cccgtcccgc gcgctcctcc gacccgctcc gctccgctcc gctcggcccc    120
gcgccgcccg tcaacatgat ccgctgcggc ctggcctgcg agcgctgccg ctggatcctg    180
cccctgctcc tactcagcgc catcgccttc gacatcatcg cgctggccgg ccgcggctgg    240
ttgcagtcta gcgaccacgg ccagacgtcc tcgctgtggt ggaaatgctc ccaagagggc    300
ggcggcagcg ggtcctacga ggagggctgt cagagcctca tggagtacgc gtggggtaga    360
gcagcggctg ccatgctctt ctgtggcttc atcatcctgg tgatctgttt catcctctcc    420
ttcttcgccc tctgtggacc ccagatgctt gtcttcctga gagtgattgg aggtctcctt    480
gccttggctg ctgtgttcca gatcatctcc ctggtaattt accccgtgaa gtacacccag    540
accttcaccc ttcatgccaa ccctgctgtc acttacatct ataactgggc ctacggcttt    600
gggtgggcag ccacgattat cctgattggc tgtgccttct tcttctgctg cctccccaac    660
tacgaagatg accttctggg caatgccaag cccaggtact tctacacatc tgcctaactt    720
gggaatgaat gtgggagaaa atcgctgctg ctgagatgga ctccagaaga agaaactgtt    780
tctccaggcg acttgaacc cattttttgg cagtgttcat attattaaac tagtcaaaaa    840
tgctaaaata atttgggaga aaatattttt taagtagtgt tatagtttca tgtttatctt    900
ttattatgtt ttgtgaagtt gtgtctttc actaattacc tatactatgc caatatttcc    960
ttatatctat ccataacatt tatactacat ttgtaagaga atatgcacgt gaaacttaac   1020
actttataag gtaaaaatga ggtttccaag atttaataat ctgatcaagt tcttgttatt   1080
tccaaataga atggactcgg tctgttaagg gctaaggaga agaggaagat aaggttaaaa   1140
gttgttaatg accaaacatt ctaaaagaaa tgcaaaaaaa aagtttattt tcaagccttc   1200
```

```
gaactattta aggaaagcaa aatcatttcc taaatgcata tcatttgtga gaatttctca    1260
ttaatatcct gaatcattca tttcagctaa ggcttcatgt tgactcgata tgtcatctag    1320
gaaagtacta tttcatggtc caaacctgtt gccatagttg gtaaggcttt cctttaagtg    1380
tgaaatattt agatgaaatt ttctcttttta aagttcttta tagggttagg gtgtgggaaa    1440
atgctatatt aataaatctg tagtgttttg tgtttatatg ttcagaacca gagtagactg    1500
gattgaaaga tggactgggt ctaatttatc atgactgata gatctggtta agttgtgtag    1560
taaagcatta gggtcattcc tgtcacaaaa gtgccactaa aacagcctca ggagaataaa    1620
tgacttgctt ttctaaatct caggtttatc tgggctctat catatagaca ggcttctgat    1680
agtttgcaac tgtaagcaga aacctacata tagttaaaat cctggtcttt cttggtaaac    1740
agattttaaa tgtctgatat aaaacatgcc acaggagaat tcggggattt gagtttctct    1800
gaatagcata tatatgatgc atcggatagg tcattatgat ttttttaccat ttcgacttac    1860 ataatgaaaa ccaattcatt ttaaatatca gattattatt ttgtaagttg tggaaaaagc    1920
taattgtagt tttcattatg aagttttccc aataaaccag gtattctaaa cttgaaaaaa    1980
aaa                                                                 1983

<210> SEQ ID NO 157
<211> LENGTH: 1835
<212> TYPE: DNA
<213> ORGANISM: Homo sapiens
<220> FEATURE:
<221> NAME/KEY: misc_feature
<223> OTHER INFORMATION: Incyte ID No: 3133035

<400> SEQUENCE: 157
accaggctgt gtaagagctg ctggagtagg cacccattta agaaaaaat gaagaagcag      60 caataaagaa gttgtaatcg ttacctagac aaacagagaa ctggttttga cagtgtttct    120
agagtgcttt ttattatttt cctgacagtt gtgttccacc atgattactt tctccttcag    180
cgaataggct aaatgaatat gaaacagaaa agcgtgtatc agcaaaccaa agcacttctg    240
tgcaagaatt ttcttaagaa atggaggatg aaaagagaga gcttattgga atggggcctc    300
tcaatacttc taggactgtg tattgctctg ttttccagtt ccatgagaaa tgtccagttt    360
cctggaatgg ctcctcagaa tctgggaagg gtagataaat ttaatagctc ttctttaatg    420
gttgtgtata caccaatatc taatttaacc cagcagataa tgaataaaac agcacttgct    480
cctcttttga aaggaacaag tgtcattggg gcacaaataa tacacacatg gacgaaatac    540
ttctggaaaa tttacatatg ctatgggaat catctttaat gaaactttct cttataagtt    600 aatattttc cagggatata acagtccact ttggaaagaa gatttctcag gtgactttcc    660
atatcaaata tcattatgga atttttcatg ttttcaacat aaagaacaga ggaggttggg    720
caacagagat gctttcaatg cacacatgaga aaacagggaa agcccatttc attgctgaac    780
ttatttcaag gtcaatcgta tgttcctact acaggatgac tgcaaaaatt gtagagtcat    840
ccaacatata tgtgttgagc atgcagatgc atgtgtcaaa ggacacatga gtaacccaag    900
actgacaggc cccagcctca ggtgagattc caggttagca gcaaagacag acattgaaca    960
attaatgaca agtacaagaa aaagtgtttc atgggcactt agaccagggg ttcctaatag   1020
tgggacctag agaagtccta cctggggaaa tgatgtttaa agggagacca gaatgaatag   1080
caggtgtgag gtgctagaag cattgtgttt cagatagaag aaaggtaatt gtgaagaccc   1140
tgaggtgaga aaggacatct gttcctagat ctggaagaag agcagtatag ctgaacaagg   1200
aacatgaaaa ggaatgtaat gggagagtga agctgaagtc actcaagtgc tacctcctgt   1260
```

-continued

```
ggcatcttgt aaacctaggc aaggaatagc cactgagtca ctttaatcac ggcaaaagtg    1320
taattcggtt tccaaaatta ggggaacact ccagatatag cccgggggaat agattgccaa   1380 gaggctatgg agaatgtcaa gaaacaagga gtccattatg gctggagcag agtgtttgct   1440
ttcatctcct tttatttttc taagactttc taagcatgct gtggtctgca agaataaaat   1500
tgctttatta aaaactttca tttatttgct tcctttttct atgtagttaa aagtctactg   1560
gtgggccagc catggtggct cacacctgta atcccagcac tttgagaggc cgaggtgcac   1620
ggatcacctg aggtcaggag ttcgagacca gcctggccaa catggtgaaa gcctgtctct   1680
actaaaaata caaaaattag ctagacaacg tggcctgtgc ctataatccc agctttggga   1740
ggctgaggta ggagaatcac ttgaacccag gaggtggagg ttgcagtgag ctgagatcgc   1800
accactgcac tccagcatgg gcaacagagt gagat                              1835

<210> SEQ ID NO 158
<211> LENGTH: 819
<212> TYPE: DNA
<213> ORGANISM: Homo sapiens
<220> FEATURE:
<221> NAME/KEY: misc_feature
<223> OTHER INFORMATION: Incyte ID No: 3436879

<400> SEQUENCE: 158
cacgactcac tatagggaat ttggccctcg aggcaagaat tcggcacgag gtcgacaccc     60
tcatcctgaa aggtattgcg cacgatgcac ggccatcaag taccactttt ctcagcccat    120
ccgcttgcga aacattcctt ttaatttaac caagaccata cagcaagatg agtggcacct    180
gcttcattta agaagaatca ctgctggctt cctcggcatg gccgtagccg tccttctctg    240
cggctgcatt gtggccacag tcagtttctt ctgggaggag agcttgaccc agcacgtggc    300
tggactcctg ttcctcatga cagggatatt ttgcaccatt tccctctgta cttatgccgc    360
cagtatctcg tatgatttga accggctccc aaagctaatt tatagcctgc ctgctgatgt    420
ggaacatggt tacagctggt ccatcttttg cgcctggtgc agtttaggct ttattgtggc    480
agctggaggt ctctgcatcg cttatccgtt tattagccgg accaagattg cacagctaaa    540
gtctggcaga gactccacgg tatgactgtc ctcactgggc ctgtccacag tgcgagcgac    600
tcctgagggg aacagcgcgg agttcaggag tccaagcaca aagcggtctt ttacattcca    660
acctgttgcc tgccagccct ttctggatta ctgatagaaa atcatgcaaa acctcccaac    720
ctttctaagg acaagactac tgtggattca agtgctttaa tgactattta tgcgttgact    780
gtgagaatag ggagccatgc catgggacat ttctaggtg                           819
```

HUMAN TRANSMEMBRANE PROTEINS

CROSS-REFERENCE TO RELATED APPLICATIONS

This application is a Divisional of U.S. patent application Ser. No. 09/700,590, filed Apr. 16, 2001, which is the National Phase of International Application No. PCT/US99/11904, filed May 28, 1999, and published as WO 99/61471, which claims priority to U.S. Provisional Application Nos. 60/087,260, filed May 29, 1998, 60/091,674, filed Jul. 2, 1998, 60/102,954, filed Oct. 2, 1998, and 60/109,869, filed Nov. 24, 1998, the contents of which are all hereby incorporated by reference.

TECHNICAL FIELD

This invention relates to nucleic acid and amino acid sequences of human transmembrane proteins and to the use of these sequences in the diagnosis, treatment, and prevention of immune, reproductive, smooth muscle, neurological, gastrointestinal, developmental, and cell proliferative disorders.

BACKGROUND OF THE INVENTION

Eukaryotic organisms are distinct from prokaryotes in possessing many intracellular organelle and vesicle structures. Many of the metabolic reactions which distinguish eukaryotic biochemistry from prokaryotic biochemistry take place within these structures. In particular, many cellular functions require very stringent reaction conditions, and the organelles and vesicles enable compartmentalization and isolation of reactions which might otherwise disrupt cytosolic metabolic processes. The organelles include mitochondria, smooth and rough endoplasmic reticula, sarcoplasmic reticulum, and the Golgi body. The vesicles include phagosomes, lysosomes, endosomes, peroxisomes, and secretory vesicles. Organelles and vesicles are bounded by single or double membranes.

Biological membranes are highly, selective permeable barriers made up of lipid bilayer sheets composed of phosphoglycerides, fatty acids, cholesterol, phospholipids, glycolipids, proteoglycans, and proteins. Membranes contain ion pumps, ion channels, and specific receptors for external stimuli which transmit biochemical signals across the membranes. These membranes also contain second messenger proteins which interact with these pumps, channels, and receptors to amplify and regulate transmission of these signals.

Plasma Membrane Proteins

Plasma membrane proteins (MPs) are divided into two groups based upon methods of protein extraction from the membrane. Extrinsic or peripheral membrane proteins can be released using extremes of ionic strength or pH, urea, or other disruptors of protein interactions. Intrinsic or integral membrane proteins are released only when the lipid bilayer of the membrane is dissolved by detergent.

Transmembrane proteins (TM) are characterized by an extracellular, a transmembrane, and an intracellular domain. TM domains are typically comprised of 15 to 25 hydrophobic amino acids which are predicted to adopt an α-helical conformation. TM proteins are classified as bitopic (Types I and II) proteins, which span the membrane once, and polytopic (Types III and IV) (Singer, S. J. (1990) Annu. Rev. Cell Biol. 6:247-96) proteins which contain multiple membrane-spanning segments. TM proteins that act as cell-surface receptor proteins involved in signal transduction include growth and differentiation factor receptors, and receptor-interacting proteins such as Drosophila to pecanex and frizzled proteins, LIV-1 protein, NF2 protein, and GNS1/SUR4 eukaryotic integral membrane proteins. TM proteins also act as transporters of ions or metabolites, such as gap junction channels (connexins), and ion channels, and as cell anchoring proteins, such as lectins, integrins, and fibronectins. TM proteins are found in vesicle organelle-forming molecules, such as calveolins; or cell recognition molecules, such as cluster of differentiation (CD) antigens, glycoproteins, and mucins.

Many membrane proteins (MPs) contain amino acid sequence motifs that serve to localize proteins to specific subcellular sites. Examples of these motifs include PDZ domains, KDEL, RGD, NGR, and GSL sequence motifs, von Willebrand factor A (vWFA) domains, and EGF-like domains. RGD, NGR, and GSL motif-containing peptides have been used as drug delivery agents in targeted cancer treatment of tumor vasculature (Arap, W. et al. (1998) Science, 279:377-380). Membrane proteins may also contain amino acid sequence motifs that serve to interact with extracellular or intracellular molecules, such as carbohydrate recognition domains.

Chemical modification of amino acid residue side chains alters the manner in which MPs interact with other molecules, for example, phospholipid membranes. Examples of such chemical modifications to amino acid residue side chains are covalent bond formation with glycosaminoglycans, oligosaccharides, phospholipids, acetyl and palmitoyl moieties, ADP-ribose, phosphate, and sulphate groups.

RNA-encoding membrane proteins may have alternative splice sites which give rise to proteins encoded by the same gene but with different messenger RNA and amino acid sequences. Splice variant membrane proteins may interact with other ligand and protein isoforms.

G-Protein Coupled Receptors

G-protein coupled receptors (GPCR) are a superfamily of integral membrane proteins which transduce extracellular signals. GPCRs include receptors for biogenic amines, lipid mediators of inflammation, peptide hormones, and sensory signal mediators.

The structure of these highly-conserved receptors consists of seven hydrophobic transmembrane (serpentine) regions, cysteine disulfide bridges between the second and third extracellular loops, an extracellular N-terminus, and a cytoplasmic C-terminus. Three extracellular loops alternate with three intracellular loops to link the seven transmembrane regions. The most conserved parts of these proteins are the transmembrane regions and the first two cytoplasmic loops. A conserved, acidic-Arg-aromatic residue triplet present in the second cytoplasmic loop may interact with G proteins. A GPCR consensus pattern is characteristic of most proteins belonging to this superfamily (ExPASy PROSITE document PS00237; and Watson, S. and S. Arkinstall (1994) The G-protein Linked Receptor Facts Book, Academic Press, San Diego, Calif., pp 2-6). Mutations and changes in transcriptional activation of GPCR-encoding genes have been associated with neurological disorders such as schizophrenia, Parkinson's disease, Alzheimer's disease, drug addiction, and feeding disorders.

Scavenger Receptors

Macrophage scavenger receptors with broad ligand specificity may participate in the binding of low density lipoproteins (LDL) and foreign antigens. Scavenger receptors types I and II are trimeric membrane proteins with each subunit containing a small N-terminal intracellular domain, a transmembrane domain, a large extracellular domain, and a C-terminal cysteine-rich domain. The extracellular domain contains a short spacer domain, an α-helical coiled-coil domain, and a triple helical collagenous domain. These receptors have been shown to bind a spectrum of ligands, including chemically modified lipoproteins and albumin, polyribonucleotides, polysaccharides, phospholipids, and asbestos (Matsumoto, A. et al. (1990) Proc. Natl. Acad. Sci. 87:9133-9137; and Elomaa, O. et al. (1995) Cell 80:603-609). The scavenger receptors are thought to play a key role in atherogenesis by mediating uptake of modified LDL in arterial walls, and in host defense by binding bacterial endotoxins, bacteria, and protozoa.

Tetraspan Family Proteins

The transmembrane 4 superfamily (TM4SF) or tetraspan family is a multigene family encoding type III integral membrane proteins (Wright, M. D. and Tomlinson, M. G. (1994) Immunol. Today 15:588). TM4SF is comprised of membrane proteins which traverse the cell membrane four times. Members of the TM4SF include platelet and endothelial cell membrane proteins, melanoma-associated antigens, leukocyte surface glycoproteins, colonal carcinoma antigens, tumor-associated antigens, and surface proteins of the schistosome parasites (Jankowski, S. A. (1994) Oncogene 9:1205-1211). Members of the TM4SF share about 25-30% amino acid sequence identity with one another.

A number of TM4SF members have been implicated in signal transduction, control of cell adhesion, regulation of cell growth and proliferation, including development and oncogenesis, and cell motility, including tumor cell metastasis. Expression of TM4SF proteins is associated with a variety of tumors and the level of expression may be altered when cells are growing or activated.

Tumor Antigens

Tumor antigens are surface molecules that are differentially expressed in tumor cells relative to normal cells. Tumor antigens distinguish tumor cells immunologically from normal cells and provide diagnostic and therapeutic targets for human cancers (Takagi, S. et al. (1995) Int. J. Cancer 61: 706-715; Liu, E. et al. (1992) Oncogene 7: 1027-1032).

Ion Channels

Ion channels are found in the plasma membranes of virtually every cell in the body. For example, chloride channels mediate, a variety of cellular functions including regulation of membrane potentials and absorption and secretion of ions across epithelial membranes. When present in intracellular membranes of the Golgi apparatus and endocytic vesicles, chloride channels also regulate organelle pH (see, e.g., Greger, R. (1988) Annu. Rev. Physiol. 50:111-122). Electro-physiological and pharmacological properties of chloride channels, including ion conductance, current-voltage relationships, and sensitivity to modulators, suggest that different chloride channels exist in muscles, neurons, fibroblasts, epithelial cells, and lymphocytes.

Many channels have sites for phosphorylation by one or more protein kinases including protein kinase A, protein kinase C, tyrosine kinase, and casein kinase II, all of which regulate ion channel activity in cells. Inappropriate phosphorylation of proteins in cells has been linked to changes in cell cycle progression and cell differentiation. Changes in the cell cycle have been linked to induction of apoptosis or cancer. Changes in cell differentiation have been linked to diseases and disorders of the reproductive system, immune system, and skeletal muscle.

Proton Pumps

Proton ATPases are a large class of membrane proteins that use the energy of ATP hydrolysis to generate an electrochemical proton gradient across a membrane. The resultant gradient may be used to transport other ions across the membrane ($Na^+$, $K^+$, or $Cl^-$) or to maintain organelle pH. Proton ATPases are further subdivided into the mitochondrial F-ATPases, the plasma membrane ATPases, and the vacuolar ATPases. The vacuolar ATPases establish and maintain an acidic pH within various vesicles involved in the processes of endocytosis and exocytosis (Mellman, I. et al. (1986) Ann. Rev. Biochem. 55:663-700).

Proton-coupled, 12 membrane-spanning domain transporters such as PEPT 1 and PEPT 2 are responsible for gastrointestinal absorption and for renal reabsorbtion of peptides using an electrochemical $H^+$ gradient as the driving force. Another type of peptide transporter, the TAP transporter, is a heterodimer consisting of TAP 1 and TAP 2 and is associated with antigen processing. Peptide antigens are transported across the membrane of the endoplasmic reticulum by TAP so they can be expressed on the cell surface in association with MHC molecules. Each TAP protein consists of multiple hydrophobic membrane spanning segments and a highly conserved ATP-binding cassette (Boll, M. et al. (1996) Proc. Natl. Acad. Sci. 93:284-289). Pathogenic microorganisms, such as herpes simplex virus, may encode inhibitors of TAP-mediated peptide transport in order to evade immune surveillance (Marusina, K. and Manaco, J. J. (1996) Curr. Opin. Hematol. 3:19-26).

ABC Transporters

The ATP-binding cassette (ABC) transporters, also called the "traffic ATPases", comprise a superfamily of membrane proteins that mediate transport and channel functions in prokaryotes and eukaryotes (Higgins, C. F. (1992) Annu. Rev. Cell Biol. 8:67-113). ABC proteins share a similar overall structure and significant sequence homology. All ABC proteins contain a conserved domain of approximately two hundred amino acid residues which includes one or more nucleotide binding domains. Mutations in ABC transporter genes are associated with various disorders, such as hyperbilirubinemia II/Dubin-Johnson syndrome, recessive Stargardt's disease, X-linked adrenoluekodystrophy, multidrug resistance, celiac disease, and cystic fibrosis.

Membrane Proteins Associated with Intercellular Communication

Intercellular communication is essential for the development and survival of multicellular organisms. Cells communicate with one another through the secretion and uptake of protein signaling molecules. The uptake of proteins into the cell is achieved by endocytosis, in which the interaction of signaling molecules with the plasma membrane surface, often via binding to specific receptors, results in the formation of plasma membrane-derived vesicles that enclose and transport the molecules into the cytosol. The secretion of proteins from the cell is achieved by exocytosis, in which molecules inside of the cell are packaged into membrane-bound transport vesicles derived from the trans-Golgi network. These vesicles fuse with the plasma membrane and release their contents into the surrounding extracellular space. Endocytosis and exocytosis result in the removal and addition of plasma membrane components and the recycling of these components is essential to maintain the integrity, identity, and functionality of both the plasma membrane and internal membrane-bound compartments.

Lysosomes are the site of degradation of intracellular material during autophagy and of extracellular molecules following endocytosis. Lysosomal enzymes are packaged into vesicles which bud from the trans-Golgi network. These vesicles fuse with endosomes to form the mature lysosome in which hydrolytic digestion of endocytosed material occurs. Lysosomes can fuse with autophagosomes to form a unique compartment in which the degradation of organelles and other intracellular components occurs. Protein sorting by transport vesicles, such as the endosome, has important consequences for a variety of physiological processes including cell surface growth, the biogenesis of distinct intracellular organelles, endocytosis, and the controlled secretion of hormones and neurotransmitters (Rothman, J. E. and Wieland, F. T. (1996) Science 272:227-234). In particular, neurodegenerative disorders and other neuronal pathologies are associated with biochemical flaws during endosomal protein sorting or endosomal biogenesis (Mayer R. J. et al. (1996) Adv. Exp. Med. Biol. 389:261-269).

Peroxisomes are organelles independent from the secretory pathway. They are the site of many peroxide-generating oxidative reactions in the cell. Peroxisomes are unique among eukaryotic organelles in that their size, number, and enzyme content vary depending upon organism, cell type, and metabolic needs. The majority of peroxisome-associated proteins are membrane-bound or are found proximal to the cytosolic or the lumenal side of the peroxisome membrane (Waterham, H. R. and Cregg, J. M. (1997) BioEssays 19:57-66).

Genetic defects in peroxisome proteins which result in peroxisomal deficiencies have been linked to a number of human pathologies, including Zellweger syndrome, rhizomelic chonrodysplasia punctata, X-linked adrenoleukodystrophy, acyl-CoA oxidase deficiency, bifunctional enzyme deficiency, classical Refsum's disease, DHAP alkyl transferase deficiency, and acatalasemia (Moser, H. W. and Moser, A. B. (1996) Ann. NY Acad. Sci. 804:427-441). In addition, Gartner, J. et al. (1991; Pediatr. Res. 29:141-146) found a 22 kDa integral membrane protein associated with lower density peroxisome-like subcellular fractions in patients with Zellweger syndrome.

Normal embryonic development and control of germ cell maturation is modulated by a number of secretory proteins which interact with their respective membrane-bound receptors. Cell fate during embryonic development is determined by members of the activin/TGF-β superfamily, cadherins, IGF-2, and other morphogens. In addition, proliferation, maturation, and redifferentiation of germ cell and reproductive tissues are regulated, for example, by IGF-2, inhibins, activins, and follistatins (Petraglia, F. (1997) Placenta 18:3-8; Mather, J. P. et al. 1997) Proc. Soc. Exp. Biol. Med. 215:209-222).

Endoplasmic Reticulum Membrane Proteins

The normal functioning of the eukaryotic cell requires that all newly synthesized proteins be correctly folded, modified, and delivered to specific intra- and extracellular sites. Newly synthesized membrane and secretory proteins enter a cellular sorting and distribution network during or immediately after synthesis and are routed to specific locations inside and outside of the cell. The initial compartment in this process is the endoplasmic reticulum (ER) where proteins undergo modifications such as glycosylation, disulfide bond formation, and assembly into oligomers. The modified proteins are then transported through a series of membrane-bound compartments which include the various cisternae of the Golgi complex, where further carbohydrate modifications occur. Transport between compartments occurs by means of vesicles that bud and fuse in a manner specific to the type of protein being transported. Once within the secretory pathway, proteins do not have to cross a membrane to reach the cell surface.

Although the majority of proteins processed through the ER are transported out of the organelle, some are retained. The signal for retention in the ER in mammalian cells consists of the tetrapeptide sequence, KDEL, located at the carboxyl terminus of proteins (Munro, S. (1986) Cell 46:291-300). Proteins containing this sequence leave the ER but are quickly retrieved from the early Golgi cisternae and returned to the ER, while proteins lacking this signal continue through the secretory pathway.

Disruptions in the cellular secretory pathway have been implicated in several human diseases. In familial hypercholesterolemia the low density lipoprotein receptors remain in the ER, rather than moving to the cell surface (Pathak, R. K. (1988) J. Cell Biol. 106:1831-1841). Altered transport and processing of the β-amyloid precursor protein (βAPP) involves the putative vesicle transport protein presenilin, and may play a role in early-onset Alzheimer's disease (Levy-Lahad. E. et al. (1995) Science 269:973-977). Changes in ER-derived calcium homeostasis have been associated with diseases such as cardiomyopathy, cardiac hypertrophy, myotonic dystrophy, Brody disease, Smith-McCort dysplasia, and diabetes mellitus.

Mitochondrial Membrane Proteins

The mitochondrial electron transport (or respiratory) chain is a series of three enzyme complexes in the mitochondrial membrane that is responsible for the transport of electrons from NADH to oxygen and the coupling of this oxidation to the synthesis of ATP (oxidative phosphorylation). ATP then provides the primary source of energy for driving the many energy-requiring reactions, of a cell.

Most of the protein components of the mitochondrial respiratory chain are the products of nuclear encoded genes that are imported into the mitochondria and the remainder are products of mitochondrial genes. Defects and altered expression of enzymes in the respiratory chain are associated with a variety of disease conditions in man, including, for example, neurodegenerative diseases, myopathies, and cancer.

Lymphocyte and Leukocyte Membrane Proteins

The B-cell response to antigens, which is modulated through receptors, is an essential component of the normal immune system. Mature B cells recognize foreign antigens through B cell receptors (BCR) which are membrane-bound, specific antibodies that bind foreign antigens. The antigen/receptor complex is internalized and the antigen is proteolytically processed. To generate an efficient response to complex antigens, the BCR, BCR-associated proteins, and T cell response are all required. Proteolytic fragments of the antigen are complexed with major histocompatability complex-II (MHCII) molecules on the surface of the B cells where the complex can be recognized by T cells. In contrast, macrophages and other lymphoid cells present antigens in association with MHCI molecules to T cells. T cells recognize and are activated by the MHCI-antigen complex through interactions with the T cell receptor/CD3 complex, a T cell-surface multimeric protein located in the plasma membrane. T cells activated by antigen presentation secrete a variety of lymphokines that induce B cell maturation and T cell proliferation and activate macrophages, which kill target cells.

Leukocytes have a fundamental role in the inflammatory and immune response and include monocytes/macrophages, mast cells, polymorphonucleoleukocytes, natural killer cells, neutrophils, eosinophils, basophils, and myeloid precursors. Leukocyte membrane proteins include members of the CD antigens, N-CAM, I-CAM, human leukocyte antigen (HLA) class I and HLA class II gene products, immunoglobulins, immunoglobulin receptors, complement, complement receptors, interferons, interferon receptors, interleukin receptors, and chemokine receptors.

Abnormal lymphocyte and leukocyte activity has been associated with acute disorders, such as AIDS, immune hypersensitivity, leukemias, leukopenia, systemic lupus, granulomatous disease, and eosinophilia.

Apoptosis-Associated Membrane Proteins

A variety of ligands, receptors, enzymes, tumor suppressors, viral gene products, pharmacological agents, and inorganic ions have important positive or negative roles in regulating and implementing the apoptotic destruction of a cell. Although some specific components of the apoptotic pathway have been identified and characterized, many interactions between the proteins involved are undefined, leaving major aspects of the pathway unknown.

A requirement for calcium in apoptosis was previously suggested by studies showing the involvement of calcium levels in DNA cleavage and Fas-mediated cell death (Hewish, D. R and L. A. Burgoyne (1973) Biochem. Biophys. Res. Comm. 52:504-510; Vignaux, F. et al. (1995) J. Exp. Med. 181:781-786; Oshimi, Y. and S. Miyazaki (1995) J. Immunol. 154:599-609). Other studies show that intracellular calcium concentrations increase when apoptosis is triggered in thymocytes by either T cell receptor cross-linking or by glucocorticoids and cell death can be prevented by blocking this increase (McConkey, D. J. et al. (1989) J. Immunol. 143: 1801-1806; McConkey, D. J. et al. (1989) Arch. Biochem. Biophys. 269:365-370). Therefore, membrane proteins such as calcium channels are important for the apopoptic response.

Tumorgenesis

Tumorgenesis is associated with the activation of oncogenes which are derived from normal cellular genes. These oncogenes encode oncoproteins which are capable of converting normal cells into malignant cells. Some oncoproteins are mutant isoforms of the normal protein and other oncoproteins are abnormally expressed with respect to location or level of expression. The latter category of oncoprotein causes cancer by altering transcriptional control of cell proliferation. Five classes of oncoproteins are known to affect the cell cycle controls. These classes include growth factors, growth factor receptors, intracellular signal transducers, nuclear transcription factors, and cell-cycle control proteins. These proteins include those which are modified by glycosylation, phosphorylation, glycosaminoglycan attachment, sulphation, and lipidation.

Modulation of factors which act in the coordination of the human cell division cycle may provide an important means to reduce tumorgenesis. An example of the metastasis-associated proteins is the lysosomal membrane glycoprotein P2B/LAMP-1 which is also expressed in normal tissues. (Heffernan, M. et al. (1989) Cancer Res. 49:6077-6084.) In addition, mammalian proteins homologous to the plant pathogenesis-related proteins have been identified in hyperplastic glioma. (Murphy, E. V. et al. (1995) Gene 159:131-135.)

The discovery of new human transmembrane proteins and the polynucleotides encoding them satisfies a need in the art by providing new compositions which are useful in the diagnosis, prevention, and treatment of immune, reproductive, smooth muscle, neurological, gastrointestinal, developmental, and cell proliferative disorders.

SUMMARY OF THE INVENTION

The invention features substantially purified polypeptides, human transmembrane proteins, referred to collectively as "HTMPN" and individually as "HTMPN-1", "HTMPN-2", "HTMPN-3", "HTMPN-4", "HTMPN-5", "HTMPN-6", "HTMPN-7", "HTMPN-8", "HTMPN-9", "HTMPN-10", "HTMPN-11", "HTMPN-12", "HTMPN-13", "HTMPN-14", "HTMPN-15", "HTMPN-16", "HTMPN-17", "HTMPN-18", "HTMPN-19", "HTMPN-20", "HTMPN-21", "HTMPN-22", "HTMPN-23", "HTMPN-24", "HTMPN-25", "HTMPN-26", "HTMPN-27", "HTMPN-28", "HTMPN-29", "HTMPN-30", "HTMPN-31", "HTMPN-32", "HTMPN-33", "HTMPN-34", "HTMPN-35", "HTMPN-36", "HTMPN-37", "HTMPN-38", "HTMPN-39", "HTMPN-40", "HTMPN-41", "HTMPN-42", "HTMPN-43", "HTMPN-44", "HTMPN-45", "HTMPN-46", "HTMPN-47", "HTMPN-48", "HTMPN-49", "HTMPN-50", "HTMPN-51", "HTMPN-52", "HTMPN-53", "HTMPN-54", "HTMPN-55", "HTMPN-56", "HTMPN-57", "HTMPN-58", "HTMPN-59", "HTMPN-60", "HTMPN-61", "HTMPN-62", "HTMPN-63", "HTMPN-64", "HTMPN-65", "HTMPN-66", "HTMPN-67", "HTMPN-68", "HTMPN-69", "HTMPN-70", "HTMPN-71", "HTMPN-72", "HTMPN-73", "HTMPN-74", "HTMPN-75", "HTMPN-76", "HTMPN-77", "HTMPN-78", and "HTMPN-79". In one aspect, the invention provides a substantially purified polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79 (SEQ ID NO:1-79), and fragments thereof.

The invention further provides a substantially purified variant having at least 90% amino acid identity to at least one of the amino acid sequences selected from the group consisting of SEQ ID NO:1-79, and fragments thereof. The invention also provides an isolated and purified polynucleotide encoding the polypeptide comprising an amino acid sequence selected from the group consisting SEQ ID NO:1-79, and fragments thereof. The invention also includes an isolated and purified polynucleotide variant having at least 90% polynucleotide sequence identity to the polynucleotide encoding the polypeptide comprising an amino acid sequence selected from the group consisting of SEQ ID NO:1-79, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1-79, and fragments thereof. The invention also provides an isolated and purified polynucleotide having a sequence which is complementary to the polynucleotide encoding the polypeptide comprising the amino acid sequence selected from the group consisting of SEQ ID NO:1-79, and fragments thereof.

The invention also provides an isolated and purified polynucleotide comprising a polynucleotide sequence selected from the group consisting of SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, and SEQ ID NO:158 (SEQ ID NO:80-158), and fragments thereof. The invention further provides an isolated and purified polynucleotide variant having at least 90% polynucleotide sequence identity to the polynucleotide sequence selected from the group consisting of SEQ ID NO:80-158, and fragments thereof. The invention also provides an isolated and purified polynucleotide having a sequence which is complementary to the polynucleotide comprising polynucleotide sequence selected from the group consisting of SEQ ID NO:80-158, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO:1-79, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1-79, and fragments thereof, in conjunction with a suitable pharmaceutical carrier.

The invention further includes a purified antibody which binds to a polypeptide selected from the group consisting of SEQ ID NO:1-79, and fragments thereof. The invention also provides a purified agonist and a purified antagonist to the polypeptide.

The invention also provides a method for treating or preventing a disorder associated with decreased expression or activity HTMPN, the method comprising administering to a subject in need of such treatment an effective amount of a pharmaceutical composition comprising a substantially purified polypeptide having the amino acid sequence selected from the group consisting of SEQ ID NO:1-79, and fragments thereof, in conjunction with a suitable pharmaceutical carrier.

The invention also provides a method for treating or preventing a disorder associated with increased expression or activity of HTMPN, the method comprising administering to a subject in need of such treatment an effective amount of an antagonist of a polypeptide having an amino acid sequence selected from the group consisting of SEQ ID NO:1-79, and fragments thereof.

BRIEF DESCRIPTION OF THE TABLES

Table 1 shows nucleotide and polypeptide sequence identification numbers (SEQ ID NOs), clone identification numbers (clone ID), cDNA libraries, and cDNA fragments used to assemble full-length sequences encoding HTMPN.

Table 2 shows features of each polypeptide sequence including predicted transmembrane sequences, potential motifs, homologous sequences, and methods and algorithms used for identification of HTMPN.

Table 3 shows the tissue-specific expression patterns of each nucleic acid sequence as determined by northern analysis, diseases, disorders, or conditions associated with these tissues, and the vector into which each cDNA was cloned.

Table 4 describes the tissues used to construct the cDNA libraries from which Incyte cDNA clones encoding HTMPN were isolated.

Table 5 shows the programs, their descriptions, references, and threshold parameters used to analyze HTMPN.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"HTMPN" refers to the amino acid sequences of substantially purified HTMPN obtained from any species, particularly a mammalian species, including bovine, ovine, porcine, murine, equine, and preferably, the human species, from any source, whether natural, synthetic, semi-synthetic, or recombinant.

The term "agonist" refers to a molecule which, when bound to HTMPN, increases or prolongs the duration of the effect of HTMPN. Agonists may include proteins, nucleic acids, carbohydrates, or any other molecules which bind to and modulate the effect of HTMPN.

An "allelic variant" is an alternative form of the gene encoding HTMPN. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HTMPN include those sequences with deletions, insertions, or substitutions of different nucleotides, resulting in a polynucleotide the same as HTMPN or a polypeptide with at least one functional characteristic of HTMPN. Included within this definition are polymorphisms which may or may not be readily detectable using a particular oligonucleotide probe of the polynucleotide encoding HTMPN, and improper or unexpected hybridization to allelic variants, with a locus other than the normal chromosomal locus for the polynucleotide sequence encoding HTMPN. The encoded protein may also be "altered," and may contain deletions, insertions, or substitutions of amino acid residues which produce a silent change and result in a functionally equivalent HTMPN. Deliberate amino acid substitutions may be made on the basis of similarity in polarity, charge, solubility, hydrophobicity, hydrophilicity, and/or the amphipathic nature of the residues, as long as the biological or immunological activity of HTMPN is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide or protein sequence, or a fragment of any of these, and to naturally occurring or synthetic molecules. In this context, "fragments," "immunogenic fragments," or "antigenic fragments" refer to fragments of HTMPN which are preferably at least 5 to about 15 amino acids in length, most preferably at least 14 amino acids, and which retain some biological activity or immunological activity of HTMPN. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to HTMPN, decreases the amount or the duration of the effect of the biological or immunological activity of HTMPN. Antagonists may include proteins, nucleic acids, carbohydrates, antibodies, or any other molecules which decrease the effect of HTMPN.

The term "antibody" refers to intact molecules as well as to fragments thereof, such as Fab, $F(ab')_2$, and Fv fragments, which are capable of binding the epitopic determinant. Antibodies that bind HTMPN polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic HTMPN, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding HTMPN or fragments of HTMPN may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW Fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding HTMPN, by northern analysis is indicative of the presence of nucleic acids encoding HTMPN in a sample, and thereby correlates with expression of the transcript from the polynucleotide encoding HTMPN.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237-244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626-645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of HTMPN. For example, modulation may cause an increase or a decrease in protein activity, binding characteristics, or any other biological, functional, or immunological properties of HTMPN.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding HTMPN, or fragments thereof, or HTMPN itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HTMPN polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino, acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to HTMPN. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of new human transmembrane proteins (HTMPN), the polynucleotides encoding HTMPN, and the use of these compositions for the diagnosis, treatment, or prevention of immune, reproductive, smooth muscle, neurological, gastrointestinal, developmental, and cell proliferative disorders.

Table 1 lists the Incyte Clones used to derive full length nucleotide sequences encoding HTMPN. Columns 1 and 2 show the sequence identification numbers (SEQ ID NOs) of the amino acid and nucleic acid sequences, respectively. Column 3 shows the Clone ID of the Incyte Clone in which nucleic acids encoding each HTMPN were identified, and column 4, the cDNA libraries from which these clones were isolated. Column 5 shows Incyte clones, their corresponding cDNA libraries, and shotgun sequences. The clones and shotgun sequences are part of the consensus nucleotide sequence of each HTMPN and are useful as fragments in hybridization technologies.

The columns of Table 2 show various properties of the polypeptides of the invention: column 1 references the SEQ ID NO; column 2 shows the number of amino acid residues in each polypeptide; column 3, potential phosphorylation sites; column 4, potential glycosylation sites; column 5, the amino acid residues comprising signature sequences and motifs; column 6, the identity of each protein; and column 7, analytical methods used to identify each protein through sequence homology and protein motifs. Hidden Markov Model analysis indicates the presence of one or more potential transmembrane motifs in each of SEQ ID NO:63, SEQ ID NO:64, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, and SEQ ID NO:79; as well as the presence of one or more potential signal peptide motifs in each of SEQ ID NO:63, SEQ ID NO:64, SEQ ID NO:66, SEQ ID NO:67, SEQ ID NO:71, SEQ ID NO:72, SEQ ID NO:75, SEQ ID NO:77, and SEQ ID NO:79.
Motifs analysis indicates the presence of a potential ATP/GTP binding site in SEQ ID NO:68, a potential calcium-binding site also in SEQ ID NO:68, a potential leucine zipper gene regulatory motif in each of SEQ ID NO:68 and SEQ ID NO:73; and a potential microbody (single-membraned organelle, targeting signal site in SEQ ID NO:78. BLOCKS analysis indicates the presence of two potential PMP-22 integral membrane glycoprotein motifs and a trehalase motif, all in SEQ ID NO:77, as well as a potential protein-splicing motif in SEQ ID NO:66. PRINTS analysis indicates the presence of a potential G-protein coupled receptor motif in SEQ ID NO:79.

The columns of Table 3 show the tissue-specificity and diseases, disorders, or conditions associated with nucleotide sequences encoding HTMPN. The first column of Table 3 lists the nucleotide sequence identifiers. The second column lists tissue categories which express HTMPN as a fraction of total tissue categories expressing HTMPN. The third column lists the diseases, disorders, or conditions associated with those tissues expressing HTMPN. The fourth column lists the vectors used to subclone the cDNA library. Of particular note is the expression of HTMPN in tissue involved in inflammation and the immune response and with cell proliferative conditions including cancer, and in reproductive, gastrointestinal, fetal, smooth muscle, cardiovascular, urologic, endocrine, developmental, and nervous tissue.

The following fragments of the nucleotide sequences encoding HTMPN are useful in hybridization or amplification technologies to identify SEQ ID NO:121-158 and to distinguish between SEQ ID NO:121-158 and related polynucleotide sequences. The useful fragments are the fragment of SEQ ID NO:121 from about nucleotide 151 to about nucleotide 189; the fragment of SEQ ID NO:122, from about nucleotide 280 to about nucleotide 318; the fragment of SEQ ID NO:123, from about nucleotide 505 to about nucleotide 558; the fragments of SEQ ID NO:124 from about nucleotide 1 to about nucleotide 21 and from about nucleotide 694 to about nucleotide 720; the fragment of SEQ ID NO:125 from about nucleotide 331 to about nucleotide 378; the fragment of SEQ ID NO:126 from about nucleotide 1012 to about nucleotide 1047; the fragment of SEQ ID NO:127 from about nucleotide 1070 to about nucleotide 1106; the fragment of SEQ ID NO:128 from about nucleotide 133 to about nucleotide 186; the fragment of SEQ ID NO:129 from about nucleotide 432 to about nucleotide 482; the fragments of SEQ ID NO:130 from about nucleotide 1745 to about nucleotide 1795 and from about nucleotide 1910 to about nucleotide 1979; the fragment of SEQ ID NO:131 from about nucleotide 322 to about nucleotide 375; the fragment of SEQ ID NO:132 from about nucleotide 147 to about nucleotide 203; the fragment of SEQ ID NO:133 from about nucleotide 557 to about nucleotide 613; the fragment of SEQ ID NO:134 from about nucleotide 509 to about nucleotide 595; the fragment of SEQ ID NO:135 from about nucleotide 808 to about nucleotide 848; the fragment of SEQ ID NO:136 from about nucleotide 216 to about nucleotide 260; the fragment of SEQ ID NO:137 from about nucleotide 132 to about nucleotide 188; the fragment of SEQ ID NO:138 from about nucleotide 231 to about nucleotide 278; the fragment of SEQ ID NO:139 from about nucleotide 303 to about nucleotide 350; the fragment of SEQ ID NO:140 from about nucleotide 507 to about nucleotide 550; the fragment of SEQ ID NO:141 from about nucleotide 433 to about nucleotide 477; the fragment of SEQ ID NO:142 from about nucleotide 266 to about nucleotide 314; the fragment of SEQ ID:143 from about nucleotide 3 to about nucleotide 48; the fragment of SEQ ID NO:144 from about nucleotide 76 to about nucleotide 122; the fragment of SEQ ID NO:145 from about nucleotide 93 to about nucleotide 139; the fragment of SEQ ID NO:146 from about nucleotide 241 to about nucleotide 286; the fragment of SEQ ID NO:147 from about nucleotide 43 to about nucleotide 89; the fragment of SEQ ID NO:148 from about nucleotide 219 to about nucleotide 265; the fragment of SEQ ID NO:149 from about nucleotide 619 to about nucleotide 663; the fragment of SEQ ID NO:150 from about nucleotide 25 to about nucleotide 69; the fragment of SEQ ID NO:151 from about nucleotide 175 to about nucleotide 221; the fragment of SEQ ID NO:152 from about nucleotide 94 to about nucleotide 138; the fragment of SEQ ID NO:153 from about nucleotide 46 to about nucleotide 90; the fragment of SEQ ID NO:154 from about nucleotide 1081 to about nucleotide 1127; the fragment of SEQ ID NO:155 from about nucleotide 31 to about nucleotide 77; the fragment of SEQ ID NO:156 from about nucleotide 157 to about nucleotide 201; the fragment of SEQ ID NO:157 from about nucleotide 216 to about nucleotide 259; and the fragment of SEQ ID NO:158 from about nucleotide 517 to about nucleotide 561. The polypeptides encoded by these fragments may be useful, for example, as antigenic polypeptides.

The invention also encompasses HTMPN variants. A preferred HTMPN variant is one which has at least about 80%, more preferably at least about 90%, and most preferably at least about 95% amino acid sequence identity to the HTMPN amino acid sequence, and which contains at least one functional or structural characteristic of HTMPN.

The invention also encompasses polynucleotides which encode HTMPN. In a particular embodiment, the invention encompasses a polynucleotide sequence comprising a sequence selected from the group consisting of SEQ ID NO:80-158, which encodes HTMPN.

The invention also encompasses a variant of a polynucleotide sequence encoding HTMPN. In particular, such a variant polynucleotide sequence will have at least about 80%, more preferably at least about 90%, and most preferably at least about 95% polynucleotide sequence identity to the polynucleotide sequence encoding HTMPN. A particular aspect of the invention encompasses a variant of a polynucleotide sequence comprising a sequence selected from the group consisting of SEQ ID NO:80-158 which has at least about 80%, more preferably at least about 90%, and most preferably at least about 95% polynucleotide sequence identity to a nucleic acid sequence selected from the group consisting of SEQ ID NO:80-158. Any one of the polynucleotide variants described above can encode an amino acid sequence which contains at least one functional or structural characteristic of HTMPN.

It will be appreciated by those skilled in the art that as a result of the degeneracy of the genetic code, a multitude of polynucleotide sequences encoding HTMPN, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HTMPN, and all such variations are to be considered as being specifically disclosed.

Although nucleotide sequences, which encode HTMPN and its variants are preferably capable of hybridizing to the nucleotide sequence of the naturally occurring HTMPN under appropriately selected conditions of stringency, it may be advantageous to produce nucleotide sequences encoding HTMPN or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HTMPN and its derivatives without altering the encoded amino acid sequences include the productions of RNA transcripts having more desirable properties, such as a greater half-life, than transcripts produced from the naturally occurring sequence.

The invention also encompasses production of DNA sequences which encode HTMPN and HTMPN derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HTMPN or any fragment thereof.

Also encompassed by the invention are polynucleotide sequences that are capable of hybridizing to the claimed polynucleotide sequences, and, in particular, to those shown in SEQ ID NO:80-158 and fragments thereof under various conditions of stringency. (See, e.g., Wahl, G. M. and S. L. Berger (1987) Methods Enzymol. 152:399-407; Kimmel, A. R. (1987) Methods Enzymol. 152:507-511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodiun citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), Peltier Thermal Cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer) or the MEGABACE 1000 DNA sequencing system (Molecular Dynamics. Sunnyvale Calif.). The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856-853.)

The nucleic acid sequences encoding HTMPN may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318-322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M., et al. (1919) PCR Methods Applic. 1:111-119.) In this method, multiple restriction enzyme digestions and ligations may be used to insert an engineered double-stranded sequence into a region of unknown sequence before performing PCR. Other methods which may, be used to retrieve unknown sequences are known in the art. (See, e.g., Parker, J. D. et al. (1991) Nucleic Acids Res. 19:3055-306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HTMPN may be cloned in recombinant DNA molecules that direct expression of HTMPN, or fragments or functional equivalents thereof, in appropriate host cells. Due to the inherent degeneracy of the genetic code, other DNA sequences which encode substantially the same or a functionally equivalent amino acid sequence may be produced and used to express HTMPN.

The nucleotide sequences of the present invention can be engineered using methods generally known in the art in order to alter HTMPN-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HTMPN may be synthesized, in whole or in part, using chemical methods well known in the art. (See, e.g., Caruthers, M. H. et al. (1980) Nucl. Acids Res. Symp. Ser. 215-223, and Horn, T. et al. (1980) Nucl. Acids Res. Symp. Ser. 225-232.) Alternatively, HTMPN itself or a fragment thereof may be synthesized using chemical methods. For example, peptide synthesis can be performed using various solid-phase techniques. (See, e.g., Roberge, J. Y. et al. (1995) Science 269:202-204.) Automated synthesis may be achieved using the ABI 431A Peptide Synthesizer (Perkin-Elmer). Additionally, the amino acid sequence of HTMPN, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392-421.) The composition of the synthetic peptides may be confirmed by amino acid analysis or by sequencing. (See, e.g., Creighton, T. (1984) *Proteins, Structures and Molecular Properties*, WH Freeman, New York N.Y.)

In order to express a biologically active HTMPN, the nucleotide sequences encoding HTMPN or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HTMPN. Such elements may vary in their strength and specificity. Specific initiation signals may also be used to achieve more efficient translation of sequences encoding HTMPN. Such signals include the ATG initiation codon and adjacent sequences, e.g. the Kozak sequence. In cases where sequences encoding HTMPN and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125-162.)

Methods which are well known to those skilled in the art may be used to construct expression vectors containing sequences encoding HTMPN and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16-17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding HTMPN. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HTMPN. For example, routine cloning, subcloning, and propagation of polynucleotide sequences encoding HTMPN can be achieved using a multifunctional E. coli vector such as PBLUESCRIPT (Stratagene, La Jolla Calif.) or pSPORT1 plasmid (Life Technologies). Ligation of sequences encoding HTMPN into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503-5509.) When large quantities of HTMPN are needed, e.g. for the production of antibodies, vectors which direct high level expression of HTMPN may be used. For example, vectors containing the strong, inducible T5 or T7 bacteriophage promoter may be used.

Yeast expression systems may be used for production of HTMPN. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516-54; and Scorer, C. A. et al. (1994) Bio/Technology 12:181-184.)

Plant systems may also be used for expression of HTMPN. Transcription of sequences encoding HTMPN may be driven viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used. (See, e.g., Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191-196.)

In mammalian cells, a number of viral-based expression systems may be utilized. In cases where an adenovirus is used as an expression vector, sequences encoding HTMPN may be ligated into an adenovirus transcription/translation complex consisting of the late promoter and tripartite leader sequence. Insertion in a non-essential E1 or E3 region of the viral genome may be used to obtain infective virus which expresses HTMPN in host cells. (See, e.g., Logan, J. and T. Shenk (1984) Proc. Natl. Acad. Sci. 81:3655-3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345-355.)

For long term production of recombinant proteins in mammalian systems, stable expression of HTMPN in cell lines is preferred. For example, sequences encoding HTMPN can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ or apr$^-$ cells, respectively. (See, e.g., Wigler. M. et al. (1977) Cell 11:223-232; Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567-3570; Colbere-Garapin, F. et al. (1981) J. Mol. Biol. 150:1-14.) Additional selectable genes have been described, e.g., trpB and hisD, which alter cellular requirements for metabolites. (See, e.g., Hartman, S. C. and R. C. Mulligan (1988) Proc. Natl. Acad. Sci., 85:8047-80551.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121-131.)

Although the presence/absence of marker gene expression suggests that the gene of interest is also present, the presence and expression of the gene may need to be confirmed. For example, if the sequence encoding HTMPN is inserted within a marker gene sequence, transformed cells containing sequences encoding HTMPN can be identified by the absence of marker gene function. Alternatively, a marker gene can be placed in tandem with a sequence encoding HTMPN under the control of a single promoter. Expression of the marker gene in response to induction or selection usually indicates expression of the tandem gene as well.

In general, host cells that contain the nucleic acid sequence encoding HTMPN and that express HTMPN may be identified by a variety of procedures known to those of skill in the art. These procedures include, but are not limited to, DNA-DNA or DNA-RNA hybridizations. PCR amplification, and protein bioassay or immunoassay techniques which include membrane, solution, or chip based technologies for the detection and/or quantification of nucleic acid or protein sequences.

Immunological methods for detecting and measuring the expression of HTMPN using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HTMPN is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding HTMPN include oligo-labeling, nick translation, end-labeling, or PCR amplification using a labeled nucleotide. Alternatively, the sequences encoding HTMPN, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HTMPN may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HTMPN may be designed to contain signal sequences which direct secretion of HTMPN through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda Md.) and may be chosen to ensure the correct modification and processing of the foreign protein.

In another embodiment of the invention, natural, modified, or recombinant nucleic acid sequences encoding HTMPN may be Ligated to a heterologous sequence resulting in translation of a fusion protein in any of the aforementioned host systems. For example, a chimeric HTMPN protein containing a heterologous moiety that can be recognized by a commercially available antibody may facilitate the screening of peptide libraries for inhibitors of HTMPN activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HTMPN encoding sequence and the heterologous protein sequence, so that HTMPN may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled HTMPN may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HTMPN may be produced not only by recombinant production, but also by direct peptide synthesis using solid phase techniques. (See, e.g., Creighton, supra pp. 55-60.) Protein synthesis may be performed by manual techniques or by automation. Automated synthesis may be achieved, for example, using the ABI 431A Peptide Synthesizer (Perkin-Elmer). Various fragments of HTMPN may be synthesized separately and then combined to produce the full length molecule.

Therapeutics

Chemical and structural similarity, e.g., in the context of sequences and motifs, exists between regions of HTMPN and human transmembrane proteins. In addition, the expression of HTMPN is closely associated with tissue involved in inflammation and the immune response and with cell proliferative conditions including cancer, and in reproductive, gastrointestinal, fetal, smooth muscle, cardiovascular, developmental, and nervous tissue. Therefore, HTMPN appears to play a role in immune, reproductive, smooth muscle, neurological, gastrointestinal, developmental, and cell proliferative disorders. In the treatment of immune, reproductive, smooth muscle, neurological, gastrointestinal, developmental, and cell proliferative disorders associated with increased HTMPN expression or activity, it is desirable to decrease the expression or activity of HTMPN. In the treatment of the above conditions associated with decreased HTMPN expression or activity, it is desirable to increase the expression or activity of HTMPN.

Therefore, in one embodiment, HTMPN or a fragment or derivative thereof may be administered to a subject to treat or prevent a disorder associated with decreased expression or activity of HTMPN. Examples of such disorders include, but are not limited to, an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis and extracorporeal circulation, viral, bacterial, fungal, parasitic, protozoal, and helminthic infections, and trauma, a reproductive disorder such as a disorder of prolactin production; infertility, including tubal disease, ovulatory defects, and endometriosis; a disruption of the estrous cycle, a disruption of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, impotence, carcinoma of the male breast, and gynecomastia; a smooth muscle disorder such as angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia; a neurological disorder such as epilepsy, ischemic cerebrovascular disease, stroke, cerebral neoplasms, Alzheimer's disease, Pick's disease. Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous, system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder; a gastrointestinal disorder such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, and acquired immunodeficiency syndrome (AIDS) enteropathy, cirrhosis, jaundice, cholestasis, hereditary hyperbilirubinemia, hepatic encephalopathy, hepatorenal syndrome, hepatitis, hepatic steatosis, hemochromatosis, Wilson's disease, $\alpha_1$-antitrypsin deficiency, Reye's syndrome, primary sclerosing cholangitis, liver infarction, portal vein obstruction and thrombosis, passive congestion, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas; a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and a developmental disorder including, but not limited to, those listed above.

In another embodiment, a vector capable of expressing HTMPN or a fragment or derivative thereof may be administered to a subject to treat or prevent a disorder associated with decreased expression or activity of HTMPN including, but not limited to, those described above.

In a further embodiment, a pharmaceutical composition comprising a substantially purified HTMPN in conjunction with a suitable pharmaceutical carrier may be administered to a subject to treat or prevent a disorder associated with decreased expression or activity of HTMPN including; but not limited to, those provided above.

In still another embodiment, an agonist which modulates the activity of HTMPN may be administered to a subject to treat or prevent a disorder associated with decreased expression or activity of HTMPN including, but not limited to, those listed above.

In a further embodiment, an antagonist of HTMPN may be administered to a subject to treat or prevent a disorder associated with increased expression or activity of HTMPN. Examples of such disorders include, but are not limited to, those described above. In one aspect, an antibody which specifically binds HTMPN may be used directly as an antagonist or indirectly as a targeting or delivery mechanism for bringing a pharmaceutical agent to cells or tissue which express HTMPN.

In an additional embodiment, a vector expressing the complement of the polynucleotide encoding HTMPN may be administered to a subject to treat or prevent a disorder associated with increased expression or activity of HTMPN including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HTMPN may be produced using methods which are generally known in the art. In particular, purified HTMPN may be used to produce antibodies or to screen libraries of pharmaceutical agents to identify those which specifically bind HTMPN. Antibodies to HTMPN may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HTMPN or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HTMPN have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HTMPN amino acids may be fused with those of another protein, such as KLH, and antibodies to the chimeric molecule may be produced.

Monoclonal antibodies to HTMPN may be prepared using any technique which provides for the production of antibody molecules by continuous cell lines in culture. These include, but are not limited to, the hybridoma technique, the human B-cell hybridoma technique and the EBV-hybridoma technique. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851-6855; Neuberger, M. S. et al. (1984) Nature 312:604-608; and Takeda, S. et al. (1985) Nature 314:452-454.) Alternatively, techniques described for the production of single chain antibodies may be adapted, using methods known in the art, to produce HTMPN-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833-3837; Winter, G. et al. (1991) Nature 349:293-299.)

Antibody fragments which contain specific binding sites for HTMPN may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275-1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HTMPN and its specific antibody. A two-site, monoclonal-based immunoassay utilizing monoclonal antibodies reactive to two non-interfering HTMPN epitopes is preferred, but a competitive binding assay may also be employed (Pound, supra).

Various methods such as Scatchard analysis in conjunction with radioimmunoassay techniques may be used to assess the affinity of antibodies for HTMPN. Affinity is expressed as an association constant, $K_a$, which is defined as the molar concentration of HTMPN-antibody complex divided by the molar concentrations of free antigen and free antibody under equilibrium conditions. The $K_a$ determined for a preparation of polyclonal antibodies, which are heterogeneous in their affinities for multiple HTMPN epitopes, represents the average affinity, or avidity, of the antibodies for HTMPN. The $K_a$ determined for a preparation of monoclonal antibodies, which are monospecific for a particular HTMPN epitope, represents a true measure of affinity. High-affinity antibody preparations with $K_a$ ranging from about $10^9$ to $10^{12}$ L/mole are preferred for use in immunoassays in which the HTMPN-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HTMPN, preferably in active form, from the antibody (Catty, D. (1988) *Antibodies. Volume I: A Practical Approach*, IRL Press, Washington, D.C.; Liddell. J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is preferred for use in procedures requiring precipitation of HTMPN-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding HTMPN, or any fragment or complement thereof, may be used for therapeutic purposes. In one aspect, the complement of the polynucleotide encoding HTMPN may be used in situations in which it would be desirable to block the transcription of the mRNA. In particular, cells may be transformed with sequences complementary to polynucleotides encoding HTMPN. Thus, complementary molecules or fragments may be used to modulate HTMPN activity, or to achieve regulation of gene function. Such technology is now well known in the art, and sense or antisense oligonucleotides or larger fragments can be designed from various locations along the coding or control regions of sequences encoding HTMPN.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HTMPN. (See, e.g., Sambrook, supra; Ausubel, 1995, supra.)

Genes encoding HTMPN can be turned off by transforming a cell or tissue with expression vectors which express high levels of a polynucleotide, or fragment thereof, encoding HTMPN. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HTMPN. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163-177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HTMPN.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HTMPN. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See. e.g., Goldman, C. K. et al. (1997) Nature Biotechnology 15:462-466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HTMPN, antibodies to HTMPN, and mimetics, agonists, antagonists, or inhibitors of HTMPN. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HTMPN, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HTMPN or fragments thereof, antibodies of HTMPN, and agonists, antagonists or inhibitors of HTMPN, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HTMPN may be used for the diagnosis of disorders characterized by expression of HTMPN, or in assays to monitor patients being treated with HTMPN or agonists, antagonists, or inhibitors of HTMPN. Antibodies useful for diagnostic purposes may be prepared in the same manner as described above for therapeutics. Diagnostic assays for HTMPN include methods which utilize the antibody and a label to detect HTMPN in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HTMPN, including ELISAs, RIAs, and FACS, are known in the art and provide a basis for diagnosing altered or abnormal levels of HTMPN expression. Normal or standard values for HTMPN expression are established by combining body fluids or cell extracts taken from normal mammalian subjects, preferably human, with antibody to HTMPN under conditions suitable for complex formation. The amount of standard complex formation may be quantitated by various methods, preferably by photometric means. Quantities of HTMPN expressed in subject, control, and disease samples from biopsied tissues are compared with the standard values. Deviation between standard and subject values establishes the parameters for diagnosing disease.

In another embodiment of the invention, the polynucleotides encoding HTMPN may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HTMPN may be correlated with disease. The diagnostic assay may be used to determine absence, presence, and excess expression of HTMPN, and to monitor regulation of HTMPN levels during therapeutic intervention.

In one aspect, hybridization with PCR probes which are capable of detecting polynucleotide sequences, including genomic sequences, encoding HTMPN or closely related molecules may be used to identify nucleic acid sequences which encode HTMPN. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HTMPN, allelic variants, or related sequences.

Probes may also be used for the detection of related sequences, and should preferably have at least 50% sequence identity to any of the HTMPN encoding sequences. The hybridization probes of the subject invention may be DNA or RNA and may be derived from the sequence of SEQ ID NO:80-158 or from genomic sequences including promoters, enhancers, and introns of the HTMPN gene.

Means for producing specific hybridization probes for DNAs encoding HTMPN include the cloning of polynucleotide sequences encoding HTMPN or HTMPN derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HTMPN may be used for the diagnosis of disorders associated with expression of HTMPN. Examples of such disorders include, but are not limited to, an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a reproductive disorder such as a disorder of prolactin production; infertility, including tubal disease, ovulatory defects, and endometriosis; a disruption of the estrous cycle, a disruption of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, impotence, carcinoma of the male breast, and gynecomastia; a smooth muscle disorder such as angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder; a gastrointestinal disorder such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, and acquired immunodeficiency syndrome (AIDS) enteropathy, cirrhosis, jaundice, cholestasis, hereditary hyperbilirubinemia, hepatic encephalopathy, hepatorenal syndrome, hepatitis, hepatic steatosis, hemochromatosis, Wilson's disease, $\alpha_1$-antitrypsin deficiency, Reye's syndrome, primary sclerosing cholangitis, liver infarction, portal vein obstruction and thrombosis, passive congestion, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas; a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary, thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and a developmental disorder including, but not limited to, those listed above. The polynucleotide sequences encoding HTMPN may be used in Southern or northern analysis, dot blot, or other membrane-based technologies; in PCR technologies; in dipstick, pin, and multiformat ELISA-like assays; and in microarrays utilizing fluids or tissues from patients to detect altered HTMPN expression. Such qualitative or quantitative methods are well known in the art.

In a particular aspect, the nucleotide sequences encoding HTMPN may be useful in assays that detect the presence of associated disorders, particularly those mentioned above. The nucleotide sequences encoding HTMPN may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encodes, HTMPN in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HTMPN, a normal or standard profile for expression is established. This may be accomplished by combining body fluids or cell extracts taken from normal subjects, either animal or human, with a sequence, or a fragment thereof, encoding HTMPN, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HTMPN may involve the use of PCR. These oligomers may be chemically synthesized, generated enzymatically, or produced in vitro. Oligomers will preferably contain a fragment of a polynucleotide encoding HTMPN, or a fragment of a polynucleotide complementary to the polynucleotide encoding HTMPN, and will be employed under optimized conditions for identification of a specific gene or condition. Oligomers may also be employed under less stringent conditions for detection or quantitation of closely related DNA or RNA sequences.

Methods which may also be used to quantitate the expression of HTMPN include radiolabeling or biotinylating nucleotides, coamplification of a control nucleic acid, and interpolating results from standard curves. (See, e.g., Melby, P. C. et al. (1993) J. Immunol. Methods 159:235-244; Duplaa, C. et al. (1993) Anal. Biochem. 212:229-236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan. T. M. et al. (1995) U.S. Pat. No. 5,474,796; Schena, M. et al. (1996) Proc. Natl. Acad. Sci. 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662.)

In another embodiment of the invention, nucleic acid sequences encoding HTMPN may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345-355; Price, C. M. (1993) Blood Rev. 7:127-134; and Trask, B. J. (1991) Trends Genet. 7:149-154.)

Fluorescent in situ hybridization (FISH) may be correlated with other physical chromosome mapping techniques and genetic map data. (See, e.g., Heinz-Ulrich, et al. (1995) in Meyers, supra, pp. 965-968.) Examples of genetic map data can be found in various scientific journals or at the Online Mendelian Inheritance in Man (OMIM) site. Correlation between the location of the gene encoding HTMPN on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal-preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577-580.) The nucleotide sequence of the subject invention may also be used to detect differences in the chromosomal location due to translocation, inversion, etc., among normal, carrier, or affected individuals.

In another embodiment of the invention, HTMPN, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HTMPN and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with HTMPN, or fragments thereof, and washed. Bound HTMPN is then detected by methods well known in the art. Purified HTMPN can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HTMPN specifically compete with a test compound for binding HTMPN. In this manner, antibodies can be used to detect the presence of any peptide which shares one or more antigenic determinants with HTMPN.

In additional embodiments, the nucleotide sequences which encode HTMPN may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosure of all applications, patents, and publications, cited above and below, and of U.S. provisional applications 60/087,260 (filed May 29, 1998), 60/091,674 (filed Jul. 2, 1998), 60/102.954 (filed Oct. 2, 1998), and 60/109.869 (filed Nov. 24, 1998) is hereby incorporated by reference.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Valencia Calif.), or an OLIGOTEX mRNA purification kit (QIAGEN). Alternatively, RNA was isolated directly from tissue lysates using other RNA isolation kits, e.g., the POLY (A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1-6.6). Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), pSPORT1 plasmid (Life Technologies), or pINCY (Incyte Pharmaceuticals, Palo Alto Calif.). Recombinant plasmids were transformed into competent E. coli cells including XL1-Blue, XL1-BlueMRF, or SOLR from Stratagene or DH5α, DH10B, or ElectroMAX DH10B from Life Technologies.

II. Isolation of cDNA Clones

Plasmids were recovered from host cells by in vivo excision, using the UNIZAP vector system (Stratagene) or cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the REAL Prep 96 plasmid kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a Fluoroskan II fluorescence scanner (Labsystems Oy, Helsinki, Finland).

III. Sequencing and Analysis

The cDNAs were prepared for, sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel. 1997, supra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 5 summarizes the software programs, descriptions, references, and threshold parameters used. The first column of Table 5 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, South San Francisco Calif.) and LASERGENE software (DNASTAR).

The polynucleotide sequences were validated by removing vector, linker, and polyA sequences and by masking ambiguous bases, using algorithms and programs based on BLAST dynamic programming, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, Prosite, and Hidden Markov Model (HMM)-based protein family databases such as PFAM. HMM is a probalistic approach which analyzes consensus primary structures of gene families. (See, e.g., Eddy, S. R. (1996) Cur. Opin. Str. Biol. 6:361-365.)

The programs described above for the assembly and analysis of full length polynucleotide and amino acid sequences were also used to identify polynucleotide sequence fragments from SEQ ID NO:80-158. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \% \text{ maximum } BLAST \text{ score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding HTMPN occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in Table 3.

V. Extension of HTMPN Encoding Polynucleotides

Full length nucleic acid sequences of SEQ ID NOs:80-120 were produced by extension of the component fragments described in Table 1, column 5, using oligonucleotide primers based on these fragments. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR™ kit (The Perkin-Elmer Corp., Norwalk, Conn.) and thoroughly mixing the enzyme and reaction mix. PCR was performed using the PTC-200 thermal cycler (MJ Research, Inc., Watertown, Mass.), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |

-continued

| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

The full length nucleic acid sequences of SEQ ID NO:121-158 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C. 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 µl PICOGREEN quantitation reagent (0.25% (v/v) PICOGREEN; Molecular Probes, Eugene Oreg.) dissolved in 1×TE and 0.5 µL of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 1.8 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethylsulphoxide (1:2, v/v), and sequenced using DYENAMIC energy transfer sequencing primers and the DYENAMIC DIRECT kit (Amersham. Pharmacia Biotech) or the ABI PRISM BIGDYE Terminator cycle sequencing ready reaction kit (Perkin-Elmer).

In like manner, the nucleotide sequences of SEQ ID NO:80-158 are used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:80-158 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT-AR film (Eastman Kodak, Rochester N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements.

After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena. M. et al. (1995) Science 270:467-470; Shalon, D. et al. (1996) Genome Res. 6:639-645.) Fluorescent probes are prepared and used for hybridization to the elements on the substrate. The substrate is analyzed by procedures described above.

VIII. Complementary Polynucleotides

Sequences complementary to the HTMPN-encoding sequences, or any parts thereof, are used to detect, decrease, or inhibit expression of naturally occurring HTMPN. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of HTMPN. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HTMPN-encoding transcript.

IX. Expression of HTMPN

Expression and purification of HTMPN is achieved using bacterial or virus-based expression systems. For expression of HTMPN in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express HTMPN upon induction with isopropyl beta-D-thiogalactopyranoside (IPTG). Expression of HTMPN in eukaryotic cells is achieved by infecting insect or mammalian cell lines with recombinant Autographica californica nuclear polyhedrosis virus (AcMNPV), commonly known as baculovirus. The nonessential polyhedrin gene of baculovirus is replaced with cDNA encoding HTMPN by either homologous recombination or bacterial-mediated transposition involving transfer plasmid intermediates. Viral infectivity is maintained and the strong polyhedrin promoter drives high levels of cDNA transcription. Recombinant baculovirus is used to infect Spodoptera frugiperda (Sf9) insect cells in most cases, or human hepatocytes, in some cases. Infection of the latter requires additional genetic modifications to baculovirus. (See Engelhard, E. K. et al. (1994) Proc.

Natl. Acad. Sci. USA 9.1:3224-3227; Sandig, V. et al. (1996) Hum. Gene Ther. 7:1937-1945.)

In most expression systems, HTMPN is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from HTMPN at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified HTMPN obtained by these methods can be used directly in the following activity assay.

X. Demonstration of HTMPN Activity

Given the chemical and structural similarity between the HTMPN and other members of the transmembrane protein families, HTMPN is identified as a new member of the membrane spanning proteins and is presumed to be involved in the regulation of cell growth. To demonstrate that increased levels of HTMPN expression correlates with decreased cell motility and increased cell proliferation, expression vectors encoding HTMPN are electroporated into highly motile cell lines, such as U-937 (ATCC CRL 1593), HEL 92.1.7 (ATCC TIB 180) and MAC10, and the motility of the electroporated and control cells are compared. Methods for the design and construction of an expression vector capable of expressing HTMPN in the desired mammalian cell line(s) chosen are well known to the art. Assays for examining the motility of cells in culture are known to the art (cf Miyake, M. et al. (1991) J. Exp). Med. 174:1347-1354 and Ikeyama, S. et al. (1993) J. Exp. Med. 177:1231-1237). Increasing the level of HTMPN in highly motile cell lines by transfection with an HTMPN expression vector inhibits or reduces the motility of these cell lines, and the amount of this inhibition is proportional to the activity of HTMPN in the assay.

Alternatively, the activity of HTMPN may be measured using an assay based upon the property of MPs to support in vitro proliferation of fibroblasts and tumor cells under serum-free conditions. (Chiquet-Ehrismann, R. et al. (1986) Cell 47:131-139.) Wells in 96 well cluster plates (Falcon, Fisher Scientific, Santa Clara, Calif.) are coated with HTMPN by incubation with solutions at 50-100 µg HTMPN/ml for 15 min at ambient temperature. The coating solution is aspirated, and the wells washed with Dulbecco's medium before cells are plated. Rat fibroblast cultures or rat mammary tumor cells are prepared as described. (Chiquet-Ehrismann, R. et al. supra.) and plated at a density of $10^4$-$10^5$ cells/ml in Dulbecco's medium supplemented with 10% fetal calf serum.

After three days the medium is removed, and the cells washed three times with phosphate-buffered saline (PBS), pH 7.0, before addition of serum-free Dulbecco's medium containing 0.25 mg/ml bovine serum albumin (BSA, Fraction V, Sigma Chemical Company, St. Louis. Mo.). After 2 days the medium is aspirated, and 100 µl of [$^3$H]thymidine (NEN) at 2 µCi/ml in fresh Dulbecco's medium containing 0.25 mg/ml BSA is added. Parallel plates are fixed and stained to determine cell numbers. After 16 hr, the medium is aspirated, the cell layer washed with PBS, and the 10% trichloroacetic acid-precipitable radioactivity in the cell lay determined by liquid scintillation counting (normalized to relative cell numbers; Chiquet-Ehrismann, R. et al. supra). The amount of radioisotope-labeled DNA incorporated into chromatin under serum-free conditions is proportional to the activity of HTMPN.

Alternatively, HTMPN, or biologically active fragments thereof, are labeled with $^{125}$I Bolton-Hunter reagent (See, e.g., Bolton et al. (1973) Biochem. J. 133:529). Candidate molecules previously arrayed in the wells of a multi-well plate are incubated with the labeled HTMPN, washed, and any wells with labeled HTMPN complex are assayed. Data obtained using different concentrations of HTMPN are used to calculate values for the number, affinity, and association of HTMPN with the candidate molecules.

XI. Functional Assays

HTMPN function is assessed by expressing the sequences encoding HTMPN at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5-10 µg of recombinant vector are transiently transfected into a human cell line, preferably of endothelial or hematopoietic origin, using either liposome formulations or electroporation. 1-2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of HTMPN on gene expression can be assessed using highly purified populations of cells transfected with sequences encoding HTMPN and either CD64 or CD64-GFP. CD64 and CD64-GFP are expressed on the surface of transfected cells and bind to conserved regions of human inmmunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HTMPN and other genes of interest can be analyzed by northern analysis or microarray techniques.

XII. Production of HTMPN Specific Antibodies

HTMPN substantially purified using polyacrylamide gel electrophoresis (PAGE; see, e.g., Harrington, M. G. (1990) Methods Enzymol. 182:488-495), or other purification techniques, is used to immunize rabbits and to produce-antibodies using standard protocols.

Alternatively, the HTMPN amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art (See, e.g., Ausubel, 1995, supra, ch. 11.)

Typically, oligopeptides 15 residues in length are synthesized using an ABI 431A Peptide Synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HTMPN Using Specific Antibodies

Naturally occurring or recombinant HTMPN is substantially purified by immunoaffinity chromatography using antibodies specific for HTMPN. An immunoaffinity column is constructed by covalently coupling anti-HTMPN antibody to an activated chromatographic resin, such as CNBr-activated SEPHAROSE (Amersham Pharmacia Biotech). After the coupling, the resin is blocked and washed according to the manufacturer's instructions.

Media containing HTMPN are passed over the immunoaffinity column, and the column is washed under conditions that allow the preferential absorbance of HTMPN (e.g., high ionic strength buffers in the presence of detergent). The column is eluted under conditions that disrupt antibody/HTMPN binding (e.g., a buffer of pH 2 to pH 3, or a high concentration of a chaotrope, such as urea or thiocyanate ion), and HTMPN is collected.

XIV. Identification of Molecules which Interact with HTMPN

HTMPN, or biologically active fragments thereof, are labeled with $^{125}$I Bolton-Hunter reagent (See, e.g., Bolton et al. (1973) Biochem. J. 133:529). Candidate molecules previously arrayed in the wells of a multi-well plate are incubated with the labeled HTMPN, washed, and any wells with labeled HTMPN complex are assayed. Data obtained using different concentrations of HTMPN are used to calculate values for the number, affinity, and association of HTMPN with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Protein SEQ ID NO: | Nucleotide SEQ ID NO: | Clone ID | Library | Fragments |
|---|---|---|---|---|
| 1 | 80 | 153831 | THPIPLB02 | 153831 (THPIPLB02), 2700741111 (OVARTUT10), 88L348R1 (THYRNOT02), 1856588F6 (PROSNOT18) |
| 2 | 81 | 350629 | LVENNOT01 | 350629 and 350629T6 (LVENNOT01), 3499109H1 (PROSTUT13) |
| 3 | 82 | 729171 | LUNGNOT03 | 729171 and 729171R6 (LUNGNOT03), 164534311 (HEARFET01), 680519X2 and 680519X1 (UTRSNOT02), 625051R6 (PGANNOT01), 1459466F1 (COLNFET02), 1225759T1 (COLNNOT01), 2590526H1 (LUNGNOT22), 2807811H1 (BLADTUT08) |
| 4 | 83 | 1273641 | TESTTUT02 | 1273641 and 1273641F6 (TESTTUT02), 1308181F6 and 1308181F1 (COLNFET02), 1427606F1 (SINTBST01), 756171H1 (BRAITUT02), 2416518F6 (HNT3AZT01), 4242346H1 (SYNWDIT01) |
| 5 | 84 | 1427389 | SINTBST01 | 1427389 (SINTBST01), 3097151H1 (CERVNOT03), 723779R1 (SYNOOAT01) |
| 6 | 85 | 1458357 | COLNFET02 | 1458357 (COLNFET02), SAOA01955F1, SAOA03146F1, SAOA03356F1, SAOA00213F1 |
| 7 | 86 | 1482837 | CORPNOT02 | 1482837 and 1482837T6 (CORPNOT02), 869453H1 (LUNGAST01), 3564972F6 (SKINNOT05), 663983H1 (SCORNOT01), 1315073F6 (BLADTUT02), 3809242H1 (CONTTUT01), 311459T6 (LUNGNOT02), 1798893F6 (COLNNOT27) |
| 8 | 87 | 1517434 | PANCTUT01 | 1517434 (PANCTUT01), 2848842H1 (BRSTTUT13), 586843X1 (UTRSNOT01), 1261245R1 (SYNORAT05), 1554505F1 (BLADTUT04) |
| 9 | 88 | 1536052 | SPLNNOT04 | 1536052 and 1531447T6 (SPLNNOT04), 1729124T6 (BRSTTUT08) |
| 10 | 89 | 1666118 | BRSTNOT09 | 1666118 (BRSTNOT09), 907075R2 (COLNNOT08), 1524914T1 (UCMCL5T01), 1283459F6 (COLNNOT16) |
| 11 | 90 | 1675560 | BLADNOT05 | 1675560 and 1675560T6 (BLADNOT05) |
| 12 | 91 | 1687323 | PROSTUT10 | 1687323 and 1687323F6(PROSTUT10), 2292356R3 (BRAINON01) |
| 13 | 92 | 1692236 | PROSTUT10 | 1692236 (PROSTUT10), 2786557F6 (BRSTNOT13), 602869R6 and 602869T6 (BRSTTUT01), 2258230H1 (OVARTUT01), 780083T1 (MYOMNOT01), 2057230T6 (BEPINOT01), 288105R1 (EOSIHET02) |
| 14 | 93 | 1720847 | BLADNOT06 | 1720847, 1722250F6, and 1722250T6 (BLADNOT06) |
| 15 | 94 | 1752821 | LIVRTUT01 | 1752821 (LIVRTUT01), 3180328H1 (TLYJNOT01), 1969457T6 (BRSTNOT04), 2608504H1 (BONTNOT01), 2455688T6 and 2455688F6 (ENDANOT01), 1816354F6 (PROSNOT20) |
| 16 | 95 | 1810923 | PROSTUT12 | 1810923 and 1810923T6 (PROSTUT12), 3221260H1 (COLNNON03) |
| 17 | 96 | 1822315 | GBLATUT01 | 1822315 (GBLATUT01), 1841726H1 (COLNNOT07), 1598582T6 (BLADNOT03), 1264125R1 (SYNORAT05), 645048H1 (BRSTTUT02), 1474782H1 (LUNGTUT03), 352739F1 (LVENNOT01), 876001R1 (LUNGAST01) |

TABLE 1-continued

| Protein SEQ ID NO: | Nucleotide SEQ ID NO: | Clone ID | Library | Fragments |
|---|---|---|---|---|
| 18 | 97 | 1877777 | LEUKNOT03 | 1877777 (LEUKNOT03), 1219656H1 (NEUTGMT01), 1471553T1 (LUNGTUT03) |
| 19 | 98 | 1879819 | LEUKNOT03 | 1879819 (LEUKNOT03), 1734538H1 (COLNNOT22), 1428615F6 (SINTBST01), 3558710H1 (LUNGNOT31), 1996096R6 (BRSTTUT03) |
| 20 | 99 | 1932945 | COLNNOT16 | 1932945 (COLNNOT16), 2383333H1 (ISLTNOT01), 2706050F6 (PONSAZT01), |
| 21 | 100 | 2061026 | OVARNOT03 | 2061026 (OVARNOT03) |
| 22 | 101 | 2096687 | BRAITUT02 | 2096687 (BRAITUT02), 2204640H1 (SPLNFET02) |
| 23 | 102 | 2100530 | BRAITUT02 | 2100530 (BRAITUT02), 2740969F6 (BRSTTUT14) |
| 24 | 103 | 2357636 | LUNGNOT20 | 2357636 (LUNGNOT20), 2693537H1 (LUNGNOT23), 1794235T6 (PROSTUT05), 235425R6 (SINTNOT02), 760091R1 (BRAITUT02), 887877R1 (PANCNOT05) |
| 25 | 104 | 2365230 | ADRENOT07 | 2365230 (ADRENOT07), 2921195H1 (SININOT04) |
| 26 | 105 | 2455121 | ENDANOT01 | 2455121 and 2455121F6 (ENDANOT01) |
| 27 | 106 | 2472514 | THPINOT03 | 2472514 (THPINOT03), 3212904H1 (BLADNOT08) |
| 28 | 107 | 2543486 | UTRSNOT11 | 2543486 (UTRSNOT11), 2374764I11 (ISLTNOT01), 1359576F1 (LUNGNOT12), 1357170H1 (LUNGNOT09) |
| 29 | 108 | 2778171 | OVARTUT03 | 2778171 (OVARTUT03), 1822045H1 (GBLATUT01), 1692535F6 (COLNNOT23), 1905275F6 (OVARNOT07) |
| 30 | 109 | 2799575 | PENCNOT01 | 2799575 (PENCNOT01). 874115111 (LUNGAST01), 967837R1 (BRSTNOT05), 3235248T6 and 3235248F6 (COLNUCT03) |
| 31 | 110 | 2804955 | BLADTUT08 | 2804955 (BLADTUT08), 732534H1 (LUNGNOT03), 402168R1 (TMLR3DT01), 3481814H1 (KIDNNOT31), 1485989F1 (CORPNOT02) |
| 32 | 111 | 2806395 | BLADTUT08 | 2806395 (BLADTUT08), 1579109H1 (DUODNOT01), 1533572F1 (SPLNNOT04), 1889837F6 and 1889837T6 (BLADTUT07), 2414178F6 (HNT3AZT01) |
| 33 | 112 | 2836858 | TLYMNOT03 | 2836858 and 2836858CT1 (TLYMNOT03), 2127516H1 (KIDNNOT05) |
| 34 | 113 | 2844513 | DRGLNOT01 | 2844513 and 2844513T6 (DRGLNOT01), 388885T6 (THYMNOT02), 287344F1 (EOSIHET02), 3867626H1 (BMARNOT03) |
| 35 | 114 | 3000380 | TLYMNOT06 | 3000380 (TLYMNOT06), 1930658H1 (COLNTUT03), 2395295F6 (THPIAZT01), 1242456R6 (LUNGNOT03) |
| 36 | 115 | 182532 | PLACNOB01 | 062374H1, 062962R6, 064457R6, and 182532H1 (PLAGNOB01), 3144248X12F1 (HNT2AZS07) |
| 37 | 116 | 239589 | HIPONOT01 | 239589H1 and 239589X13 (HIPONOT01), 264805R6 (HNT2AGT01), 552683X17 (SCORNOT01), 1595053F1 (BRAINOT14) |
| 38 | 117 | 1671302 | BMARNOT03 | 399804H1 (PITUNOT02), 1458549H1 (COLNFET02), 1671302F6 and 1671302H1 (BMARNOT03), 2093453R6 (PANCNOT04), 2498385F6 and 2498385T6 (ADRETUT05) |
| 39 | 118 | 2041858 | HIPONON02 | 063184R1 (PLACNOB01), 1294823F1 (PGANNOT03), 1303974F1 (PLACNOT02), 1648770F6 (PROSTUT09), 2041858H1 (HIPONON02) |
| 40 | 119 | 2198863 | SPLNFET02 | 1880470F6 (LEUKNOT03), 1888946F6 (BLADTUT07), 2198863F6 and 2198863H1 (SPLNFET02) |
| 41 | 120 | 3250703 | SEMVNOT03 | 1317728H1, 1318433H1, 1319354H1, 1319380F1, 1320494H1, and 1320812F1 (BLADNOT04), 3247874H1, 3249188H1, 3249385H1, and 3250703H1 (SEMVNOT03) |
| 42 | 121 | 350287 | LVENNOT01 | 062018F1 (PLACNOB01), 350287H1 (LVENNOT01), 869320R1 (LUNGAST01), 1416927F6 (BRAINOT12), 3083789H1 (OVARTUN01) |
| 43 | 122 | 1618171 | BRAITUT12 | 1618171F6 and 1618171H1 (BRAITUT12), 3316315F6 (PROSBPT03) |
| 44 | 123 | 1625863 | COLNPOT01 | 1625863H1 and 1625863T6 (COLNPOT01), 2100364R6 (BRAITUT02) |
| 45 | 124 | 1638353 | UTRSNOT06 | 1638353H1 (UTRSNOT06), 3733085H1 (SMCCNOS01, 3882774T6 (SPLNNOT11), 1626195T6 (COLNPOT01), 1495745H1 (PROSNON01) |
| 46 | 125 | 1726843 | PROSNOT14 | 826000T1 (PROSNOT06), 1726843F6 and 1726843H1 (PROSNOT14), 2225762F6 (SEMVNOT01), 2480248H1 (SMCANOT01), 2600692F6 (UTRSNOT10), 2728257F6 (OVARTUT05) |
| 47 | 126 | 1754506 | LIVRTUT01 | 907854R2 (COLNNOT09), 1354345F1 (LUNGNOT09), 1359472F1 (LUNGNOT12), 1397284F1 (BRAITUT08), 1557921F1 (BLADNOT04), 1754506F6 and 1754506H1 (LIVRTUT01) |
| 48 | 127 | 1831378 | THP1AZT01 | 441541R1 (MPHGNOT03), 712292R6 (SYNORAT04), 1311835F1 (COLNFET02), 1555765F6 (BLADNOT04), 1831378H1 (THPIAZT01), 1865502F6 (PROSNOT19), 3077521H1 (BONEUNT01), 3555043H1 (SYNONOT01), 3774618H1 (BRSTNOT19) |
| 49 | 128 | 1864943 | PROSNOT19 | 714070F1 (PROSTUT01), 736327R1 (TONSNOT01), 1864943H1 (PROSNOT19), 2672921F6 (KIDNNOT19) |
| 50 | 129 | 1911316 | CONNTUT01 | 777070F1 (COLNNOT05), 1911316H1 and 1911316T6(CONNTUT01) |
| 51 | 130 | 1943120 | HIPONOT01 | 1516263F1 (PANCTUT01), 1943120H1 (HIPONOT01), 2469009F6 (THYRNOT08), 2522459F6 (BRAITUT21), 3202972F6 (PENCNOT02), 4383679H1 (BRAVUTT02) |
| 52 | 131 | 2314236 | NGANNOTO1 | 2314236H1 (NGANNOT01), 2812085F6 (OVARNOT10), 3949704T6 (DRGCNOT01) |
| 53 | 132 | 2479409 | SMCANOT01 | 2479409F6 and 2479409H1 (SMCANOT01) |
| 54 | 133 | 2683149 | SINIUCT01 | 760389H1 (RRAITUT02), 1634372F6 (COLNNOT19), 1695052F6 (COLNNOT23), 1736429F6 (COLNNOT22), 2048429F6 (LIVRFET02), 2683149H1 (SINIUCT01), 3282234F6 (STOMFET02) |
| 55 | 134 | 2774051 | PANCNOT15 | 1852505F6 (LUNGFET03), 2774051F6 and 277405H1 (PANCNOT15) |
| 56 | 135 | 2869038 | THYRNOTI0 | 536017R6 (ADRENOT03), 2770632F6 (COLANOT02), 2795420F6(NPOLNOT01), 2869038F6 and 2869038H1 (THYRNOT10), 3323992H1 (PTHYNOT03) |
| 57 | 136 | 2918334 | THYMFET03 | 2918334H1 (THYMFET03), SBMA01788F1 |
| 58 | 137 | 2949916 | KIDNFET01 | 2949916H1 (KIDNFET01), SBMA00738F1 |
| 59 | 138 | 2989375 | KIDNFET02 | 437481R6 and 437481T6 (THYRNOT01), 2989375H1 (KIDNFET02) |
| 60 | 139 | 3316764 | PROSBPT03 | 1328462F1 (PANCNOT07), 1691807F6(PROSTUT10), 1851237F6 (LUNGFET03), 3316764H1 (PROSBPT03), 5092348H1 (UTRSTMR01) |
| 61 | 140 | 3359559 | PROSTUT16 | 943684 and 943564 (ADRENOT03), 1697079F6 (COLNNOT23), 2717735H1 (THYRNOT09), 2792705H1 (COLNTUT16), 3359559H1 (PROSTUT16) |
| 62 | 141 | 4289208 | BRABDIR01 | 3990421R6 (LUNGNON03), 4289208H1 (BRABDIR01) |
| 63 | 142 | 2454013 | ENDANOT01 | 014571R1 (THP1PLB01), 1303790T1 (PLACNOT02), 1342791T1 (COLNTUT03), 1351680F1 (LATRTUT02), 1359607T1 (LUNGNOT12), 2454013F6 and 2454013H1 (ENDANOT01) |
| 64 | 143 | 2454048 | ENDANOT01 | 551329R1 and 2056675R6 (BEPINOT01), 819281R1 (KERANOT02), 2454048H1 (ENDANOT01), 3143588H1 (HNT2AZS07) |

TABLE 1-continued

| Protein SEQ ID NO: | Nucleotide SEQ ID NO: | Clone ID | Library | Fragments |
|---|---|---|---|---|
| 65 | 144 | 2479282 | SMCANOT01 | 873307R1 (LUNGAST01), 2479282H1 and 2479282T6 (SMCANOT01), 2610082F6 (COLNTUT15), SANA03636F1 |
| 66 | 145 | 2483432 | SMCANOT01 | 940455T1 (ADRENOT03), 1863558T6 (PROSNOT19), 2483432H1 (SMCANOT01), 2641345H1 (LUNGTUT08), 3245089T6 (BRAINOT19), SBCA02765F1 |
| 67 | 146 | 2493824 | ADRETUT05 | 489685F1 (HNT2AGT01), 530794H1 (BRAINOT03), 735826R1 (TONSNOT01), 2056809R6 (BEPINOT01), 2493824H1 (ADRETUT05), 2763162F6 (BRSTNOT12), 2812426H1 (OVARNOT10) |
| 68 | 147 | 2555823 | THYMNOT03 | 1266972F6 (BRAINOT09), 133546IT1 (COLNNOT13), 1900947F6(BLADTUT06), 1942256T6 (HIPONOT01), 2555823H1 (THYMNOT03), SARB01019F1, SARB01303F1 |
| 69 | 148 | 2598242 | OVARTUT02 | 320268F1 (EOSIHET02), 738915R1 (PANCNOT04), 1250161F1 (LUNGFET03), 2598242F6 and 2598242H1 (OVARTUT02), 5020793H1 (OVARNON03), SASA00178F1 |
| 70 | 149 | 2634120 | COLNTUT15 | 1398694F1 (BRAITUT08), 1506594F1 (BRAITUT07), 2120954F6 (BRSTNOT07), 2634120F6 and 2634120H1 (COLNTUT15), 2761586H1 (BRAINOS12), 2806841F6 (BLADTUT08) |
| 71 | 150 | 2765411 | BRSTNOT12 | 2765236T6 and 27654H1H (BRSTNOT12), 4058218H1 (SPLNNOT13) |
| 72 | 151 | 2769412 | COLANOT02 | 1715480F6 (UCMCNOT02), 2769412H1 (COLANOT02), SBDA04076F1 |
| 73 | 152 | 2842779 | DRGLNOT01 | 12627HR1 (SYNORAT05), 1710449T6 (PROSNOT16), 2842779F6(DRGLNOT01), 2842779H1 (DRGLNOT01), 2850941F6 (BRSTTUT13), 3123378H1 (LNODNOT05), 3457873H1 (293TFIT01). SBGA04623F1, SAOA02667F1 |
| 74 | 153 | 2966260 | SCORNOT04 | 530242H1 (BRAINOT03), 2113607H1 (BRAITUT03), 2125619F6(BRSTNOT07), 2155349H1 and 2156022H1 (BRAINOT09), 2966260F6, 2966260H1, and 2966260T6 (SCORNOT04), 3270731H1 (BRAINOT20), 3272328F6 (PROSBPT06) |
| 75 | 154 | 2993326 | KIDNFET02 | 190217F1 (SYNORAB01), 815990R1 and 815990T1 (OVARTUT01), 2993326H1 (KIDNFET02), 3629860H1 (COLNNOT38) |
| 76 | 155 | 3001124 | TLYMNOT06 | 2123347T6 (BRSTNOT07), 3001124H1 (TLYMNOT06), SBEA07088F3 |
| 77 | 156 | 3120070 | LUNGTUT13 | 021565F1 (ADENINB01), 144798R1 (TLYMNOR01), 1216676H1 (BRSTTUT01), 2024357H1 (KERANOT02), 2616322H1 (GBLANOT01), 2742604H1 (BRSTTUT14), 2746025H1 (LUNGTUT11), 2924884H1 (SININOT04), 3120070H1 (LUNGTUT13) |
| 78 | 157 | 3133035 | SMCCNOT01 | 1478001F1 and 1482667H1 (CORPNOT02), 2812193F6 and 2812193T6(OVARNOT10), 3133035H1 and 3133035T6 (SMCCNOT01), 5025075F6 (OVARNON03) |
| 79 | 158 | 3436879 | PENCNOT05 | 3323031F6 (PTHYNOT03), 3436879F6 and 3436879H1 (PENCNOT05), 4247733H1 (BRABDIT01) |

TABLE 2

| SEQ ID NO: | Amino Acid Residues | Potential Phosphorylation Sites | Potential Glycosylation Sites | Signature Sequence | Identification | Analytical Methods |
|---|---|---|---|---|---|---|
| 1 | 240 | S233 S159 T194 T43 T77 T129 T134 S171 | N73 N101 N167 | S33-G36 L198-L219 | Somatostatin receptor tyrosine kinase | BLAST, BLOCKS, HMM |
| 2 | 100 | S6 S64 | | | Meningioma-expressed antigen II | BLAST, PRINTS, HMM |
| 3 | 416 | S14 S62 T109 T177 T340 S365 S380 S6 T7 T205 S327 T331 Y56 | N144 N277 | | PMP-22/EMP/MP20 family | BLOCKS, PRINTS, HMM |
| 4 | 224 | T31 T57 S86 S173 S214 | | | B cell growth factor | BLAST |
| 5 | 247 | S103 T60 S113 S235 | | | 5-hydroxytryptamine receptor | PRINTS |
| 6 | 72 | | | | Frizzled protein | PRINTS, HMM |
| 7 | 106 | S97 S9 S24 T31 | | | Dopamine 2 receptor | BLAST, PRINTS, HMM |
| 8 | 239 | S233 | N230 | | PB39 protein | BLAST, HMM |
| 9 | 150 | S53 S111 T127 | | | CD44 antigen precursor | PRINTS, HMM |
| 10 | 110 | S12 | N92 | | Anion exchanger | BLOCKS, PRINTS, HMM |
| 11 | 58 | | N5 N9 | | Neurofibromatosis type 2 | BLAST, PRINTS, HMM |
| 12 | 221 | S35 S178 S60 S183 | | | mitsugumin 23 | BLAST, HMM |
| 13 | 262 | T33 S94 S150 T225 T245 T14 S22 T30 T57 S137 T201 S207 T230 | N104 | | C5a-anaphylatoxin receptor | PRINTS, HMM |
| 14 | 90 | S67 T52 | | | Frizzled protein | PRINTS, HMM |
| 15 | 208 | T119 T123 T132 S56 S142 | N121 | | Rieske iron-sulphur protein | BLOCKS, PRINTS, HMM |
| 16 | 97 | S61 T2 | | | Endothelin B receptor | PRINTS, HMM |
| 17 | 243 | S82 T104 S168 T181 S6 S99 T195 Y24 | | | Thromboxane receptor | PRINTS, HMM |
| 18 | 162 | S26 | N6 | | G protein-couple receptor | BLOCKS, PRINTS, HMM |
| 19 | 470 | S285 S29 T136 S145 T167 T168 S199 S236 S249 T401 | N118 N298 N466 | R306-D308 | Molluscan rhodopsin C-terminus | PRINTS, HMM |

TABLE 2-continued

| SEQ ID NO: | Amino Acid Residues | Potential Phosphorylation Sites | Potential Glycosylation Sites | Signature Sequence | Identification | Analytical Methods |
|---|---|---|---|---|---|---|
| | | S172 S209 S254 T264 S335 T385 | | | | |
| 20 | 144 | S42 S21 T72 | N30 N36 | | Lysosome-associated membrane protein | PRINTS, HMM |
| 21 | 221 | S75 T82 | | S151-G154 | Glycoprotein hormone receptor | BLAST, PRINTS, HMM |
| 22 | 688 | T60 T186 T103 T298 S405 S484 S488 S492 S494 S498 S499 S503 S584 S601 S611 S647 T663 T109 T188 T284 T315 S324 S347 T402 T573 S643 T658 T681 Y118 | N198 N576 N577 N582 | S5-G8 A80-N140 | Ring3 | BLAST, PRINTS |
| 23 | 439 | T75 T257 S397 S424 S210 S435 | N227 | S365-G368 | Prostanoid EP3 receptor | BLOCKS, PRINTS |
| 24 | 192 | S20 S44 | N68 | | PMP-22/EMP/MP20 family | BLOCKS, PRINTS, HMM |
| 25 | 175 | T171 T43 S136 T7 | | | Progesterone receptor | PRINTS |
| 26 | 91 | S34 S19 S29 | | | Similar to mouse dishevelled-3(Dvl-3). | BLAST, BLOCKS, PRINTS, HMM |
| 27 | 214 | T34 S83 T118 T152 S17 | | | Somatostatin receptor tyrosine kinasre | BLOCKS, PRINTS, HMM |
| 28 | 250 | S64 S132 T154 | | | Sec22 homolog | BLAST, HMM |
| 29 | 84 | T80 T3 S76 | | | DPM2 protein | BLAST, HMM |
| 30 | 277 | T140 S217 S19 S85 T129 | | | Somatomedin B domain protein | BLOCKS, PRINTS, HMM |
| 31 | 273 | S64 S4 S114 S179 S256 S14 T167 T218 | N187 | | Anion exchanger family | BLOCKS, PRINTS, HMM |
| 32 | 524 | T190 S5 T131 S148 S171 S262 S275 T302 S356 S404 S473 S177 S207 T492 | N152 N471 N501 N513 | L46-L67 | G protein-coupled receptor | BLOCKS, PRINTS, HMM |
| 33 | 257 | S48 S52 S55 T64 S82 T90 S96 T97 S123 T129 T144 S192 S224 T227 S250 | N98 N187 | | Nucleoporin p62 homolog | BLAST |
| 34 | 274 | S16 T84 S249 S56 S113 | N234 | | Molluscan rhodopsin C-terminus | PRINTS |
| 35 | 281 | S52 T150 S165 S263 T48 S116 T167 T226 T241 | | G125-S132 S185-G188 | ABC-2 type transport protein | BLOCKS, PRINTS, HMM |
| 36 | 335 | S96 T113 T131 T308 T14 T146 T292 S302 S312 T317 Y258 | N104 N111 | E296 to A307 R127 to G129 | pregnancy-specific beta 1-glycoprotein 4 precursor | Blast, BLOCKS, PRINTS, Motifs |
| 37 | 280 | T41 S102 T135 S148 | N35 N53 N127 | T56 to Y70 | lysosomal membrane glycoprotein-type A precursor | Blast, BLOCKS, PRINTS, Motifs |
| 38 | 210 | S50 S143 S151 S63 S107 S153 | | | Butyrophilin | Blast |
| 39 | 279 | T90 | N66 N171 | | Plasma membrane glycoprotein CIG30. | Blast |
| 40 | 154 | T75 S121 S48 S58 T112 Y84 Y90 | | G101 to G122 V115 to F130 | Pathogenesis-related protein PR-1 | Blast, BLOCKS, PRINTS |
| 41 | 582 | S160 S255 T256 S291 S292 S316 S351 S352 S411 S412 S471 S472 T485 S533 T559 S79 T93 S96 S151 S231 | | G520 to S527 | semenogelin II | Blast, Motifs |
| 42 | 71 | S17 T45 T50 | | M1 to T50 P5 to C29 | Integral membrane protein | BLOCKS, PRINTS |
| 43 | 102 | T44 S33 T75 | | S6 to L24 S33 to G36 I49 to I74 A2 to S29 | TM4SF | BLOCKS, PRINTS, HMM |
| 44 | 226 | S60 T3 T4 S85 T169 | N46 N82 N83 | I184 to R205 G128 to Q152 Y179 to Y201 | Cation-dependant mannose transporter protein | PRINTS, HMM |
| 45 | 154 | T145 T148 S33 T134 T141 S152 | | M1 to A22 P56 to M78 P58 to M82 L91 to S110 L109 to L125 | Frizzled protein | PRINTS, HMM |
| 46 | 167 | S154 S3 T25 T29 T126 S140 | | E72 to F103 | GPCR | BLOCKS, PRINTS, HMM |
| 47 | 545 | T257 S513 S10 T11 S47 S166 S408 S495 | N8 N406 | E376 to K410 | Human secreted protein K640 variant | Blast, BLOCKS, PRINTS, HMM |
| 48 | 570 | T529 S128 S130 T184 T235 T161 S293 Y199 | N27 N61 N75 N87 N264 | V296 to C309 F321 to F332 | GPCR | Blast, BLOCKS, PRINTS, HMM |
| 49 | 127 | S24 T118 | | N10 to G30 | Anion exchanger | PRINTS, HMM |
| 50 | 152 | T49 S16 | | L78 to L99 L85 to L106 | TM4SF GNS1/SUR4 family | BLOCKS, HMM, Motifs |

TABLE 2-continued

| SEQ ID NO: | Amino Acid Residues | Potential Phosphorylation Sites | Potential Glycosylation Sites | Signature Sequence | Identification | Analytical Methods |
|---|---|---|---|---|---|---|
| 51 | 777 | T48 S66 S162 T268 S272 T322 T355 S393 S471 S559 S574 S624 S660 S700 T742 S750 S11 T12 S196 S346 T400 S423 T493 T579 T582 S599 S723 | N64 N205 N470 N706 | V47 to Y63 Y45 to V94 T20 to D34 R122 to L132 L598 to L619 D331 to L349 R565 to T582 | pecanex protein | Blast, PRINTS, Motifs |
| 52 | 108 | S52 T31 T105 | | L76 to Y92 | GNS1/SUR4 family | BLOCKS, PRINTS, PROFILESCAN |
| 53 | 66 | S4 S35 | N2 | F22 to G58 | NF2 protein | Blast, BLOCKS, PRINTS, HMM |
| 54 | 540 | S135 S149 T527 T82 T94 T177 S441 | N50 N92 N160 N334 N395 | S115 to G118 L295 to L308 L490 to L518 | LIV-1 protein | Blast, PRINTS, HMM, Motifs |
| 55 | 87 | T4 S13 S37 S68 S69 | | 146 to L82 | calvcolin | BLOCKS, HMM |
| 56 | 100 | S94 | | 17 to N34 G8 to F21 K65 to N91 T78 to C97 | ammonium ion transporters | BLOCKS, PRINTS, HMM |
| 57 | 58 | T43 | | | shox protein | BLAST, HMM |
| 58 | 61 | S51 S58 S42 | | R2 to L23 | carboxyl ester lipase | Blast, PRINTS, HMM |
| 59 | 50 | S9 | | C33 to W45 C11 to L40 | Lipoxygenase; growth factor and cytokines receptor family | BLOCKS, PRINTS, HMM, Motifs |
| 60 | 310 | T46 T156 S301 T81 S108 S166 S305 | | A153 to S166 | C4 methyl-sterol oxidase | Blast, PRINTS, HMM |
| 61 | 160 | S114 | | L71 to W84 Y143 to T154 | C5A-anaphylatoxin receptor | Blast, BLOCKS, PRINTS, HMM |
| 62 | 35 | | | K11 to M34 | steroid hormone receptor | PRINTS |
| 63 | 323 | T92 S105 S182 T263 S301 S271 | N90 | M1-G31 Signal Peptide M1-A27 Signal Peptide L234-L254 TM Protein | Signal Peptide Containing Transmembrane Protein | Motifs SPScan HMM |
| 64 | 129 | T112 T117 S5 S54 | | M1-G27 Signal Peptide M1-G27 Signal Peptide I81-V100 TM Prot. | Signal Peptide Containing Transmembrane Protein | Motifs SPScan HMM |
| 65 | 461 | T56 T41 S47 T56 T127 S146 S147 S197 S198 T407 S8 S47 T51 T284 T341 T407 | N193 N236 | | Signal Peptide Containing Transmembrane Protein | Motifs |
| 66 | 264 | S243 T264 S33 T211 S260 S22 S243 S260 | N172 N250 | M1-A17 Signal Peptide M1-S22 Signal Peptide L173-Y195TM Prot. M1-L21 TM Prot. L25-R30 Prot. Splicing | Protein Splicing Protein | Motifs SPScan HMM BLOCKS |
| 67 | 339 | T99 S119 S157 S166 S321 T54 S55 T77 S149 S211 S279 T336 Y105 | N172 | M1-G30 Signal Peptide M1-G26 Signal Peptide L176-L194 TM Prot. | Signal Peptide Containing Transmembrane Protein | Motifs SPScan HMM |
| 68 | 397 | S104 T148 T166 T259 S303 S317 T127 T191 S302 | | G202-S209 ATP/GTP binding L10-L31 Leucine zipper D106-L108 Ca binding S367-L384 Signal Peptide M1-G29 Transmembr. Prot. | Gene Regulatory Protein | Motifs SPScan BLAST HMM |
| 69 | 301 | T7 S52 S100 S133 S239 T155 T206 | N162 N211 | V12-A32 TM. Prot. V282-G300 TMr. Prot. L59-V64 aatRNA ligase | Aminoacyl tRNA ligase | Motifs HMM BLOCKS |
| 70 | 217 | S8 S142 T112 T197 | | W73-I99 TM. Prot. | Cell Proliferation Protein | Motifs HMM |
| 71 | 143 | S81 T120 S139 S116 | | M1-C26 Signal Peptide M1-R25 Signal Peptide M1-V22 TM Prot. | Signal Peptide Containing Transmembrane Protein | Motifs SPScan HMM |
| 72 | 186 | T50 S132 T151 S116 Y43 | N29 N104 | M1-S25 Signal Peptide M1-S31 Signal Peptide F9-F28 TM Prot. A27-G891 T-cell receptor interacting molecule | T-cell Receptor Interacting Molecule | Motifs SPScan HMM BLAST |
| 73 | 364 | S172 S213 S243 S302 | N229 | L234-L255 Leucine zipper M1-G28 Signal Peptide L151-L170 TM Prot. L72-E92 TM Prot. | Gene Regulatory Protein | Motifs SPScan HMM |

TABLE 2-continued

| SEQ ID NO: | Amino Acid Residues | Potential Phosphorylation Sites | Potential Glycosylation Sites | Signature Sequence | Identification | Analytical Methods |
|---|---|---|---|---|---|---|
| 74 | 605 | S46 T54 S108 S129 S195 S220 S231 T254 T261 S316 S440 S472 S536 S560 T124 | N106 N193 N395 N480 | M1-A32 Signal Peptide V494-I515 TM. Prot. L17-E36 TM Prot. | 2-Membrane Spanning Signal Peptide Containing Transmembrane Protein | Motifs SPScan HMM |
| 75 | 97 | T2 S87 | | M1-G26 Signal Peptide M1-G23 Signal Peptide V35-M54 TM. Prot I11-I34 TM Prot. | 2-Membrane Spanning Signal Peptide Containing Transmembrane Protein | Motifs SPScan HMM |
| 76 | 247 | S160 T204 S165 | | F72-L90 Transmembr. Prot. L45-T64 Transmembr. Prot. | 2-Membrane Spanning Signal Peptide Containing Transmembrane Protein | Motifs HMM |
| 77 | 193 | S60 S67 | | M1-D26 Signal Peptide M1-A31 Signal Peptide M80-M104 TM Prot. R109-Y129 TM Prot. S67-L108 PMP-22 Y149-Y176 PMP-22 N150-A159 Trehalase | Peripheral Myclin Protein 22 | Motifs SPScan HMM BLOCKS |
| 78 | 128 | S30 S30 S50 | N71 N84 N91 | N126-L128 microbodies targeting motif | Microbody Protein | Motifs |
| 79 | 115 | S109 | | M1-S16 Signal Peptide M1-T24 Signal Peptide M1-W19 TM Prot. V27-Y46 TM Prot. V5-V15 G Prot. Receptor | G Protein Receptor | Motifs SPScan HMM PRINTS |

TABLE 3

| Nucleotide SEQ ID NO: | Tissue Expression (Fraction of Total) | Disease Class (Fraction of Total) | Vector |
|---|---|---|---|
| 80 | Reproductive (0.321) Cardiovascular (0.143) Gastrointestinal (0.134) | Cancer (0.527) Inflammation (0.232) Fetal (0.170) | pBLUESCRIPT |
| 81 | Cardiovascular (0.500) Gastrointestinal (0.250) Other (0.250) | Cancer (0.500) Fetal (0.250) Other (0.250) | pBLUESCRIPT |
| 82 | Reproductive (0.260) Cardiovascular (0.220) Gastrointestinal (0.120) | Cancer (0.500) Inflammation (0.180) Fetal (0.160) | pSPORT I |
| 83 | Nervous (0.400) Gastrointestinal (0.300) Developmental (0.100) | Cancer (0.500) Inflammation (0.300) Fetal (0.200) | pINCY I |
| 84 | Reproductive (0.266) Gastrointestinal (0.141) Cadiovascular (0.125) | Cancer (6.469) Inflammation (0.250) Fetal (0.195) | pINCY I |
| 85 | Reproductive (0.750) Developmental (0.250) | Cancer (0.750) Fetal (0.250) | pINCY I |
| 86 | Reproductive (0.250) Cardiovascular (0.143) Nervous (0.143) | Inflammation (0.321) Trauma (0.286) Cancer (0.250) | pINCY I |
| 87 | Reproductive (0.368) Developmental (0.158) Cardiovascular (0.105) | Cancer (0.421) Fetal (0.368) Inflammation (0.211) | pINCY I |
| 88 | Hematopoietic/Immune (0.417) Cardiovascular (0.250) Reproductive (0.167) | Inflammation (0.417) Cancer (0.333) Fetal (0.167) | pINCY I |
| 89 | Cardiovascular (0.220) Nervous (0.171) Reproductive (0.122) | Cancer (0.463) Inflammation (0.195) Trauma (0.171) | pINCY I |
| 90 | Gastrointestinal (0.200) Reproductive (0.200) Urologic (0.200) | Cancer (0.500) Inflammation (0.300) Other (0.100) | pINCY I |
| 91 | Reproductive (0.306) Cardiovascular (0.204) Nervous (0.122) | Cancer (0.510) Inflammation (0.204) Fetal (0.143) | pINCY I |
| 92 | Reproductive (0.227) Hematopoietic/Immune (0.182) Cardiovascular (0.136) | Cancer (0.432) Fetal (0.273) Inflammation (0.273) | pINCY I |
| 93 | Gastrointestinal (0.375) Reproductive (0.188) Cardiovascular (0.125) | Cancer (0.500) Inflammation (0.250) Trauma (0.125) | pINCY I |
| 94 | Reproductive (0.333) Cardiovascular (0.214) Gastrointestinal (0.143) | Cancer (0.548) Inflammation (0.167) Fetal (0.143) | pINCY I |
| 95 | Cardiovascular (0.231) Gastrointestinal (0.231) Reproductive (0.192) | Cancer (0.500) Inflammation (0.231) Fetal (0.154) | pINCY I |
| 96 | Gastrointestinal (0.208) Cardiovascular (0.167) Reproductive (0.167) | Cancer (0.542) Inflammation (0.292) Other (0.083) | pINCY I |
| 97 | Hematopoietic/Immune (0.341) Reproductive (0.268) Cardiovascular (0.122) | Cancer (0.415) Inflammation (0.415) Fetal (0.195) | pINCY I |
| 98 | Gastrointestinal (0.346) Reproductive (0.231) Hematopoietic/Immune (0.154) | Inflammation (0.462) Cancer (0.385) Fetal (0.115) | pSPORT I |
| 99 | Gastrointestinal (0.400) Developmental (0.200) Nervous (0.200) | Cancer (0.400) Fetal (0.200) Neurological (0.200) | pSPORT I |

TABLE 3-continued

| Nucleotide SEQ ID NO: | Tissue Expression (Fraction of Total) | Disease Class (Fraction of Total) | Vector |
|---|---|---|---|
| 100 | Reproductive (0.231) Nervous (0.168) Cardiovascular (0.140) | Cancer (0.441) Inflammation (0.231) Fetal (0.133) | pSPORT I |
| 101 | Hematopoietic/Immune (0.225) Reproductive (0.225) Gastrointestinal (0.125) | Cancer (0.475) Inflammation (0.325) Fetal (0.175) | pINCY I |
| 102 | Reproductive (0.333) Gastrointestinal (0.185) Nervous (0.148) | Cancer (0.630) Fetal (0.185) Inflammation (0.111) | pINCY I |
| 103 | Gastrointestinal (0.242) Reproductive (0.182) Developmental (0.121) | Cancer (0.455) Inflammation (0.364) Fetal (0.182) | pINCY I |
| 104 | Gastrointestinal (0.188) Hematopoietic/Immune (0.188) Urologic (0.188) | Inflammation (0.438) Cancer (0.281) Fetal (0.250) | pINCY I |
| 105 | Urologic (0.250) Cardiovascular (0.167) Gastrointestinal (0.167) | Fetal (0.500) Cancer (0.417) Inflammation (0.333) | pINCY I |
| 106 | Hematopoietic/Immune (0.333) Urologic (0.333) | Cancer (0.333) Fetal (0.333) Inflammation (0.333) | pINCY I |
| 107 | Reproductive (0.286) Cardiovascular (0.204) Nervous (0.184) | Cancer (0.592) Fetal (0.143) Inflammation (0.143) | pINCY I |
| 108 | Reproductive (0.231) Gastrointestinal (0.215) Hematopoietic/Immune (0.154) | Cancer (0.462) Inflammation (0.292) Fetal (0.185) | pINCY I |
| 109 | Reproductive (0.304) Cardiovascular (0.261) Gastrointestinal (0.130) | Cancer (0.609) Inflammation (0.174) Trauma (0.087) | pINCY I |
| 110 | Reproductive (0.256) Gastrointestinal (0.186) Hematopoietic/Immune (0.186) | Cancer (0.558) Inflammation (0.349) Trauma (0.070) | pINCY I |
| 111 | Nervous (0.200) Reproductive (0.200) Gastrointestinal (0.175) | Cancer (0.550) Fetal (0.175) Inflammation (0.150) | pINCY I |
| 112 | Developmental (0.222) Endocrine (0.222) Hematopoietic/Immune (0.222) | Cancer (0.222) Inflammation (0.222) Fetal (0.222) | pINCY I |
| 113 | Hematopoietic/Immune (0.267) Nervous (0.200) Gastrointestinal (0.133) | Cancer (0.467) Trauma (0.267) Inflammation (0.200) | pINCY I |
| 114 | Hematopoietic/Immune (0.304) Gastrointestinal (0.130) Nervous (0.130) | Inflammation (0.391) Cancer (0.304) Fetal (0.130) | pINCY I |
| 115 | Developmental (0.333) Cardiovascular (0.167) Dermatologic (0.167) | Fetal (0.667) Inflammation (0.500) | pBLUESCRIPT |
| 116 | Nervous (0.478) Gastrointestinal (0.130) Hematopoietic/Immune (0.130) | Cancer (0.565) Fetal (0.217) Inflammation (0.217) | pBLUESCRIPT |
| 117 | Reproductive (0.222) Hematopoietic/Immune (0.200) Nervous (0.156) | Cancer (0.422) Inflammation (0.311) Fetal (0.178) | pINCY |
| 118 | Reproductive (0.256) Gastrointestinal (0.148) Nervous (0.125) | Cancer (0.430) Inflammation (0.259) Fetal (0.196) | pSPORTI |
| 119 | Reproductive (0.190) Nervous (0.167) Developmental (0.143) | Cancer (0.381) Inflammation (0.333) Fetal (0.262) | pINCY |
| 120 | Reproductive (0.800) Urologic (0.100) | Cancer (0.900) Trauma (0.100) | pINCY |
| 121 | Reproductive (0.295) Nervous (0.182) Cardiovascular (0.159) | Cancer (0.455) Inflammation (0.182) Cell Proliferation (0.159) | pBLUESCRIPT |
| 122 | Developmental (0.250) Musculoskeletal (0.250) Nervous (0.250) | Cancer (0.500) Cell Proliferation (0.250) Inflammation (0.250) | pINCY |
| 123 | Gastrointestinal (0.786) Developmental (0.071) Nervous (0.071) | Cancer (0.500) Inflammation (0.429) Cell Proliferation (0.071) | pINCY |
| 124 | Reproductive (0.348) Cardiovascular (0.159) Hematopoietic/Immune (0.130) | Cancer (0.493) Inflammation (0.246) Cell Proliferation (0.145) | pINCY |
| 125 | Nervous (0.405) Reproductive (0.324) Cardiovascular (0.108) | Cancer (0.459) Proliferation (0.189) Inflammation (0.108) | pINCY |
| 126 | Reproductive (0.275) Nervous (0.231) Gastrointestinal (0.154) | Cancer (0.549) Inflammation (0.220) Cell Proliferation (0.154) | pINCY |
| 127 | Reproductive (0.250) Nervous (0.150) Cardiovascular (0.133) | Cancer (0.517) Cell Proliferation (0.350) Inflamalion (0.233) | pINCY |
| 128 | Nervous (0.333) Reproductive (0.333) Hematopoietic/Immune (0.111) | Cancer (0.593) Inflammation (0.259) Neurological (0.111) | pINCY |
| 129 | Hematopoietic/Immune (0.304) Gastrointestinal (0.214) Reproductive (0.196) | Cancer (0.446) Inflammation (0.446) Cell Proliferation (0.161) | pINCY |
| 130 | Nervous (0.400) Reproductive (0.300) Endocrine (0.100) | Cancer (0.300) Inflammation (0.300) Cell Proliferation (0.200) | pBLUESCRIPT |
| 131 | Reproductive (0.364) Cardiovascular (0.227) Nervous (0.227) | Cancer (0.545) Inflammation (0.318) Cell Proliferation (0.091) | pSPORT I |
| 132 | Cardiovascular (0.667) Nervous (0.333) | Cell Proliferation (1.000) Cancer (0.333) | pINCY |
| 133 | Gastrointestinal (0.750) Developmental (0.125) Reproductive (0.083) | Cancer (0.375) Cell Proliferation (0.292) Inflammation (0.250) | pINCY |
| 134 | Cardiovascular (0.250) Developmental (0.250) Gastrointestinal (0.250) | Cancer (0.500) Cell Proliferation (0.500) Inflammation (0.250) | pINCY |
| 135 | Reproductive (0.250) Nervous (0.208) Endocrine (0.167) | Inflammation (0.417) Cancer (0.208) Trauma (0.167) | pINCY |
| 136 | Developmental (0.500) Reproductive (0.500) | Cancer (0.500) Cell Proliferation (0.500) | pINCY |
| 137 | Developmental (1.000) | Cell Proliferation (1.000) | pINCY |
| 138 | Developmental (0.333) Endocrine (0.333) Gastrointestinal (0.333) | Cancer (0.666) Fetal (0.333) | pINCY |
| 139 | Reproductive (0.538) Developmental (0.154) Gastrointestinal (0.154) | Cancer (0.462) Inflammation (0.231) Cell Proliferation (0.154) | pINCY |
| 140 | Gastrointestinal (0.385) Endocrine (0.231) Reproductive (0.231) | Cancer (0.308) Inflammation (0.308) Cell Proliferation (0.077) | pINCY |

TABLE 3-continued

| Nucleotide SEQ ID NO: | Tissue Expression (Fraction of Total) | Disease Class (Fraction of Total) | Vector |
|---|---|---|---|
| 141 | Nervous (0.500) Cardiovascular (0.167) Gastrointestinal (0.167) | Cancer (0.333) Trauma (0.333) Neurological (0.167) | pINCY |
| 142 | Reproductive (0.220) Gastrointestinal (0.155) Nervous (0.152) | Cell Proliferation (0.637) Inflammation (0.312) | pBLUESCRIPT |
| 143 | Cardiovascular (0.202) Reproductive (0.190) Gastrointestinal (0.179) | Cell Proliferation (0.583) Inflammation (0.322) | pBLUESCRIPT |
| 144 | Reproductive (0.242) Nervous (0.158) Gastrointestinal (0.116) | Cell Proliferation (0.632) Inflammation (0.379) | pINCY |
| 145 | Cardiovascular (0.238) Reproductive (0.238) Nervous (0.143) | Cell Proliferation (0.619) Inflammation (0.476) | pINCY |
| 146 | Reproductive (0.235) Nervous (0.189) Hematopoietic/Immune (0.131) | Cell Proliferation (0.625) Inflammation (0.348) | pINCY |
| 147 | Reproductive (0.191) Hematopoietic/Immune (0.173) Nervous (0.145) | Cell Proliferation (0.582) Inflammation (0.455) | pINCY |
| 148 | Reproductive (0.279) Hematopoietic/Immune (0.140) Nervous (0.128) | Cell Proliferation (0.674) Inflammation (0.232) | pINCY |
| 149 | Reproductive (0.286) Nervous (0.214) Cardiovascular (0.095) | Cell Proliferation (0.834) Inflammation (0.215) | pINCY |
| 150 | Hematopoietic/Immune (0.400) Endocrine (0.200) Gastrointestinal (0.200) | Cell Proliferation (0.200) Inflammation (0.800) | pINCY |
| 151 | Hematopoietic/Immune (0.667) Gastrointestinal (0.167) Musculoskeletal (0.167) | Cell Proliferation (0.167) Inflammation (0.667) | pINCY |
| 152 | Reproductive (0.240) Nervous (0.173) Hematopoietic/Immune (0.133) | Cell Proliferation (0.546) Inflammation (0.360) | pINCY |
| 153 | Reproductive (0.308) Nervous (0.231) Gastrointestinal (0.115) | Cell Proliferation (0.885) Inflammation (0.154) | pINCY |
| 154 | Nervous (0.455) Reproductive (0.182) Developmental (0.136) | Cell Proliferation (0.682) Inflammation (0.181) | pINCY |
| 155 | Reproductive (0.286) Urologic (0.286) Cardiovascular (0.143) | Cell Proliferation (0.857) Inflammation (0.429) | pINCY |
| 156 | Reproductive (0.299) Gastrointestinal (0.216) Cardiovascular (0.120) | Cell Proliferation (0.767) Inflammation (0.246) | pINCY |
| 157 | Nervous (0.222) Reproductive (0.222) | Cell Proliferation (0.333) Inflammation (0.222) | pINCY |
| 158 | Reproductive (0.429) Nervous (0.357) | Cell Proliferation (0.286) Inflammation (0.357) | pINCY |

TABLE 4

| Nucleotide SEQ ID NO: | Clone ID | Library | Library Comment |
|---|---|---|---|
| 80 | 153831 | THPIPLB02 | The THPIPLB02 library was constructed by reamplification of THPIPLB01, which was made using RNA isolated from THP-1 cells cultured for 48 hours with 100 ng/ml phorbol ester (PMA), followed by a 4-hour culture in media containing 1 g/ml LPS. THP-1 (ATCC TIB 202) is a human promonocyte line derived from the peripheral blood of a 1-year-old male with acute monocytic leukemia (ref: Int. J. Cancer (1980) 26: 171). |
| 81 | 350629 | LVENNOT01 | The LVENNOT01 library was constructed using RNA isolated from the left ventricle of a 51-year-old Caucasian female, who died from an intracranial bleed. |
| 82 | 729171 | LUNGNOT03 | The LUNGNOT03 library was constructed using polyA RNA isolated from nontumorous lung tissue of a 79-year-old Caucasian male. Tissue had been removed from the upper and lower left lobes of the lung, superior (left paratracheal) and inferior (subclavian) mediastinal lymph nodes, and the right paratracheal region. Pathology for the associated tumor tissue indicated grade 4 carcinoma. Patient history included a benign prostate neoplasm, atherosclerosis, benign hypertension, and tobacco use. |
| 83 | 1273641 | TESTTUT02 | The TESTTUT02 library was constructed using polyA RNA isolated from a testicular tumor removed from a 31-year-old Caucasian male-during unilateral orchiectomy. Pathology indicated embryonal carcinoma forming a largely necrotic mass involving the entire testicle. Rare foci of residual testicle showed intralobular germ cell neoplasia and tumor was identified at the spermatic cord margin. |
| 84 | 1427389 | SINTBST01 | The SINTBST01 library was constructed using polyA RNA isolated from the ileum tissue of an 18-year-old Caucasian female with irritable bowel syndrome (IBS). Pathology indicated Crohn's disease of the ileum, involving 15 cm of the small bowel. Patient history included osteoporosis of the vertebra and abnormal blood chemistry. Family history included cerebrovascular disease and atherosclerotic coronary artery disease. |
| 85 | 1458357 | COLNFET02 | The COLNFET02 library was constructed using RNA isolated from the colon tissue of a Caucasian female fetus, who died at 20 weeks' gestation from fetal demise. Serology was negative. |
| 86 | 1482837 | CORPNOT02 | The CORPNOT02 library was constructed using polyA RNA isolated from diseased corpus callosum tissue removed from the brain of a 74-year-old Caucasian male, who died from Alzheimer's disease. Serologies were negative. |
| 87 | 1517434 | PANCTUT01 | The PANCTUT01 library was constructed using polyA RNA isolated from pancreatic tumor tissue removed from a 65-year-old Caucasian female during radical subtotal pancreatectomy. Pathology indicated an invasive grade 2 adenocarcinoma. Patient history included osteoarthritis, benign hypertension, atherosclerotic coronary artery disease, an acute myocardial infarction, benign neoplasm in the large bowel, and a cataract disorder. Family history included benign hypertension and atherosclerotic coronary artery disease, Type II diabetes, impaired renal function, and stomach cancer. |

TABLE 4-continued

| Nucleotide SEQ ID NO: | Clone ID | Library | Library Comment |
|---|---|---|---|
| 88 | 1536052 | SPLNNOT04 | The SPLNNOT04 library was constructed using polyA RNA isolated from the spleen tissue of a 2-year-old Hispanic male, who died from cerebral anoxia. Past medical history and serologies were negative. |
| 89 | 1666118 | BRSTNOT09 | The BRSTNOT09 library was constructed using polyA RNA isolated from nontumor breast tissue removed from a 45-year-old Caucasian female during unilateral extended simple mastectomy. Pathology for the associated tumor tissue indicated invasive nuclear grade 2-3 adenocarcinoma in the same breast, with 3 of 23 lymph nodes positive for metastatic disease. There were also positive estrogen/progesterone receptors and uninvolved tissue showing proliferative changes. Patient history included valvuloplasty of mitral valve without replacement, rheumatic mitral insufficiency, rheumatic heart disease, and tobacco use. Family history included acute myocardial infarction, atherosclerotic coronary artery disease, and Type II diabetes. |
| 90 | 1675560 | BLADNOT05 | The BLADNOT05 library was constructed using polyA RNA isolated from nontumorous bladder tissue removed from a 60-year-old Caucasian male during a radical cystectomy, prostatectomy, and vasectomy. Pathology for the associated tumor tissue indicated grade 3 transitional cell carcinoma. The patient presented with dysuria. Family history included Type I diabetes, a malignant neoplasm of the stomach, atherosclerotic coronary artery disease, and an acute myocardial infarction. |
| 91 | 1687323 | PROSTUT10 | The PROSTUT10 library was constructed using polyA RNA isolated from prostatic tumor tissue removed from a 66-year-old Caucasian male during radical prostatectomy and regional lymph node excision. Pathology indicated an adenocarcinoma (Gleason grade 2 + 3). Adenofibromatous hyperplasia was also present. The patient presented with elevated prostate specific antigen (PSA). Family history included prostate cancer, secondary bone cancer, and benign hypertension. |
| 92 | 1692236 | PROSTUT10 | The PROSTUT10 library was constructed using polyA RNA isolated from prostatic tumor tissue removed from a 66-year-old Caucasian male during radical prostatectomy and regional lymph node excision. Pathology indicated an adenocarcinoma (Gleason grade 2 + 3). Adenofibromatous hyperplasia was also present. The patient presented with elevated prostate specific antigen (PSA). Family history included prostate cancer, secondary bone cancer, and benign hypertension. |
| 93 | 1720847 | BLADNOT06 | The BLADNOT06 library was constructed using polyA RNA isolated from the posterior wall bladder tissue removed from a 66-year-old Caucasian male during a radical prostatectomy, radical cystectomy, and urinary diversion.<br>Pathology for the associated tumor tissue indicated grade 3 transitional cell carcinoma. The patient presented with prostatic inflammatory disease. Family history included a malignant breast neoplasm, benign hypertension, cerebrovascular disease, atherosclerotic coronary artery disease, and lung cancer. |
| 94 | 1752821 | LIVRTUT01 | The LIVRTUT01 library was constructed using polyA RNA isolated from liver tumor tissue removed from a 51-year-old Caucasian female during a hepatic lobectomy. Pathology indicated metastatic grade 3 adenocarcinoma consistent with colon cancer. Patient history included thrombophlebitis and pure hypercholesterolemia. Patient medications included Premarin and Provera. The patient had also received 8 cycles of fluorouracil and leucovorin in the two years prior to surgery. Family history included a malignant neoplasm of the liver. |
| 95 | 1810923 | PROSTUT12 | The PROSTUT12 library was constructed using polyA RNA isolated from prostate tumor tissue removed from a 65-year-old Caucasian male during a radical prostatectomy. Pathology indicated an adenocarcinoma (Gleason grade 2 + 2). Adenofibromatous hyperplasia was also present. The patient presented with elevated prostate specific antigen (PSA). |
| 96 | 1822315 | GBLATUT01 | The GBLATUT01 library was constructed using polyA RNA isolated from gallbladder tumor tissue removed from a 78-year-old Caucasian female during a cholecystectomy. Pathology indicated invasive grade 3 transitional cell carcinoma. The patient was taking Indural (propranolol hydrochloride) for hypertension. Family history included a cholecystectomy, atherosclerosis, hyperlipidemia, and benign hypertension. |
| 97 | 1877777 | LEUKNOT03 | The LEUKNOT03 library was constructed using polyA RNA isolated from white blood cells of a 27-year-old female with blood type A+. The donor tested negative for cytomegalovirus (CMV). |
| 98 | 1879819 | LEUKNOT03 | The LEUKNOT03 library was constructed using polyA RNA isolated from white blood cells of a 27-year-old female with blood type A+. The donor tested negative for cytomegalovirus (CMV). |
| 99 | 1932945 | COLNNOT16 | The COLNNOT16 library was constructed using polyA RNA isolated from nontumorous sigmoid colon tissue removed from a 62-year-old Caucasian male during a sigmoidectomy and permanent colostomy. Pathology for the associated tumor tissue indicated invasive grade 2 adenocarcinoma. Family history included benign hypertension, atherosclerotic coronary artery disease, hyperlipidemia. breast cancer, and prostate cancer. |
| 100 | 2061026 | OVARNOT03 | The OVARNOT03 library was constructed using polyA RNA isolated from nontumorous ovarian tissue removed from a 43-year-old Caucasian female during a bilateral salpingo-oopherectomy. Pathology for the associated tumor tissue indicated grade 2 mucinous cystadenocarcinoma. Family history included atherosclerotic coronary artery disease, pancreatic cancer, stress reaction, cerebrovascular disease, breast cancer, and uterine cancer. |
| 101 | 2096687 | BRAITUT02 | The BRAITUT02 library was constructed using polyA RNA isolated from brain tumor tissue removed from the frontal lobe of a 58-year-old Caucasian male during excision of a cerebral meningeal lesion. Pathology indicated a grade 2 metastatic hypernephroma. Patient history included a grade 2 renal cell carcinoma, insomnia, and chronic airway obstruction. Previous surgeries included a nephroureterectomy. Patient medications included Decadron (dexamethasone) and Dilantin (phenytoin). Family history included a malignant neoplasm of the kidney. |
| 102 | 2100530 | BRAITUT02 | The BRAITUT02 library was constructed using polyA RNA isolated from brain tumor tissue removed from the frontal lobe of a 58-year-old Caucasian male during excision of a cerebral meningeal lesion. Pathology indicated a grade 2 metastatic hypernephroma. Patient history included a grade 2 renal cell carcinoma, insomnia, and chronic airway obstruction. Previous surgeries included a nephroureterectomy. Patient medications included Decadron (dexamethasone) and Dilantin (phenytoin). Family history included a malignant neoplasm of the kidney. |
| 103 | 2357636 | LUNGNOT20 | The LUNGNOT20 library was constructed using polyA RNA isolated from lung tissue removed from the right upper lobe a 61-year-old Caucasian male during a segmental lung resection. Pathology indicated panacinal emphysema. Family history included a subdural hemorrhage, cancer at an unidentified site, benign hypertension, atherosclerotic coronary artery disease, pneumonia, and an unspecified muscle disorder. |
| 104 | 2365230 | ADRENOT07 | The ADRENOT07 library was constructed using polyA RNA isolated from adrenal tissue removed from a 61-year-old female during a bilateral adrenalectomy. Patient history included an unspecified disorder of the adrenal glands, depressive disorder, benign hypertension, vocal cord paralysis, hemiplegia, subarachnoid hemorrhage, communicating hydrocephalus, neoplasm of uncertain behavior of pituitary gland, hyperlipidemia, Type II diabetes, |

TABLE 4-continued

| Nucleotide SEQ ID NO: | Clone ID | Library | Library Comment |
|---|---|---|---|
| | | | a benign neoplasm of the colon, osteoarthritis, Meckel's diverticulum, and tobacco use. Previous surgeries included total excision of the pituitary gland and a unilateral thyroid lobectomy. Patient medications included Calderol and Premarin (conjugated estrogen). Family history included prostate cancer, benign hypertension, myocardial infarction, atherosclerotic coronary artery disease, congestive heart failure, hyperlipidemia, depression, anxiety disorder, colon cancer, and gas gangrene. |
| 105 | 2455121 | ENDANOT01 | The ENDANOT01 library was constructed using polyA RNA isolated from aortic endothelial cell tissue from an explanted heart removed from a male during a heart transplant. |
| 106 | 2472514 | THPINOT03 | The THPINOT03 library was constructed using polyA RNA isolated from untreated THP-1 cells. THP-1 (ATCC TIB 202) is a human promonocyte line derived from the peripheral blood of a 1-year-old Caucasian male with acute monocytic leukemia (ref: Int. J. Cancer (1980) 26: 171). |
| 107 | 2543486 | UTRSNOT11 | The UTRSNOT11 library was constructed using polyA RNA isolated from uterine myometrial tissue removed from a 43-year-old female during a vaginal hysterectomy and salpingo-oopherectomy. The endometrium was in proliferative phase. Family history included benign hypertension, hyperlipidemia, colon cancer, Type II diabetes, and atherosclerotic coronary artery disease. |
| 108 | 2778171 | OVARTUT03 | The OVARTUT03 library was constructed using polyA RNA isolated from ovarian tumor tissue removed from the left ovary of a 52-year-old mixed ethnicity female during a total abdominal hysterectomy, bilateral salpingo-oopherectomy, peritoneal and lymphatic structure biopsy, regional lymph node excision, and peritoneal tissue destruction. Pathology indicated an invasive grade 3 (of 4) seroanaplastic carcinoma. Pathology also indicated a metastatic grade 3 seroanaplastic carcinoma. Patient history included breast cancer, chronic peptic ulcer, joint pain, and a normal delivery. Family history included colon cancer, cerebrovascular disease, breast cancer, Type II diabetes, esophagus cancer, and depressive disorder. |
| 109 | 2799575 | PENCNOT01 | The PENCNOT01 library was constructed using polyA RNA isolated from penis corpus cavernosum tissue removed from a 53-year-old male. Patient history included an untreated penile carcinoma. |
| 110 | 2804955 | BLADTUT08 | The BLADTUT08 library was constructed using polyA RNA isolated from bladder tumor tissue removed from a 72-year-old Caucasian male during a radical cystectomy and prostatectomy. Pathology indicated an invasive grade 3 (of 3) transitional cell carcinoma. Family history included myocardial infarction, cerebrovascular disease, and brain cancer. |
| 111 | 2806395 | BLADTUT08 | The BLADTUT08 library was constructed using polyA RNA isolated from bladder tumor tissue removed from a 72-year-old Caucasian male during a radical cystectomy and prostatectomy. Pathology indicated an invasive grade 3 (of 3) transitional cell carcinoma. Family history included myocardial infarction, cerebrovascular disease, and brain cancer. |
| 112 | 2836858 | TLYMNOT03 | The TLYMNOT03 library was constructed using polyA RNA isolated from nonactivated Th1 cells. These cells were differentiated from umbilical cord CD4 T cells with IL-12 and B7-transfected COS cells. |
| 113 | 2844513 | DRGLNOT01 | The DRGLNOT01 library was constructed using polyA RNA isolated from dorsal root ganglion tissue removed from the low thoracic/high lumbar region of a 32-year-old Caucasian male, who died from acute pulmonary edema, acute bronchopneumonia, bilateral pleural effusions, pericardial effusion, and malignant lymphoma (natural killer cell type). Patient medications included Difulcan (fluconazole), Deltasone (prednisone), hydrocodone, Lortab, Alprazolam, Reazodone, Cytabom, Etoposide, Cisplatin, Cytarabine, and dexamethasome. The patient received radiation therapy and multiple blood transfusions. |
| 114 | 3000380 | TLYMNOT06 | The TLYMNOT06 library was constructed using polyA RNA isolated from activated Th2 cells. These cells were differentiated from umbilical cord CD4 T cells with IL-4 in the presence of anti-IL-12 antibodies and B7-transfected COS cells, and then activated for six hours with anti-CD3 and anti-CD28 antibodies. |
| 115 | 182532 | PLACNOB01 | The PLACNOB01 library was constructed using RNA isolated from placenta. |
| 116 | 239589 | HIPONOT01 | The HIPONOT01 library was constructed using RNA isolated from the hippocampus tissue of a 72-year-old Caucasian female who died from an intracranial bleed. Patient history included nose cancer, hypertension, and arthritis. |
| 117 | 1671302 | BMARNOT03 | The BMARNOT03 library was constructed using RNA isolated from the left tibial bone marrow tissue of a 16-year-old Caucasian male during a partial left tibial ostectomy with free skin graft. Patient history included an abnormality of the red blood cells. Family history included osteoarthritis. |
| 118 | 2041858 | HIPONON02 | This normalized hippocampus library was constructed from 1.13M independent clones from HIPONOT01 library. RNA was isolated from the hippocampus tissue of a 72-year-old Caucasian female who died from an intracranial bleed. Patient history included nose cancer, hypertension, and arthritis. The normalization and hybridization conditions were adapted from Soares et al. (PNAS (1994) 91: 9928). |
| 119 | 2198863 | SPLNFET02 | The SPLNFET02 library was constructed using RNA isolated from spleen tissue removed from a Caucasian male fetus, who died at 23 weeks gestation. |
| 120 | 3250703 | SEMVNOT03 | The SEMVNOT03 library was constructed using RNA isolated from seminal vesicle tissue removed from a 56-year-old male during a radical prostatectomy. Pathology for the associated tumor tissue indicated adenocarcinoma (Gleason grade 3 + 3). |
| 121 | 350287 | LVENNOT01 | The LVENNOT01 library was constructed using RNA isolated from the left ventricle of a 51-year-old Caucasian female who died from intracranial bleeding |
| 122 | 1618171 | BRAITUT12 | The BRAITUT12 library was constructed using RNA isolated from brain tumor tissue removed from the left frontal lobe of a 40-year-old Caucasian female during excision of a cerebral meningeal lesion. Pathology indicated grade 4 gemistocytic astrocytoma. Medications included dexamethasone and phenytoin sodium. |
| 123 | 1625863 | COLNPOT01 | The COLNPOT01 library was constructed using RNA isolated from colon polyp tissue removed from a 40-year-old Caucasian female during a total colectomy. Pathology indicated an inflammatory pseudopolyp; this tissue was associated with a focally invasive grade 2 adenocarcinoma and multiple tubuvillous adenomas. Patient history included a benign neoplasm of the bowel. Medications included Zantac, betamethasone, furosamide, and amiodarone. |
| 124 | 1638353 | UTRSNOT06 | The UTRSNOT06 library was constructed using RNA isolated From myometrial tissue removed from a 50-year-old Caucasian female during a vaginal hysterectomy. Pathology indicated residual atypical complex endometrial hyperplasia. Pathology for the associated tissue removed during dilation and curettage indicated fragments of atypical complex hyperplasia and a single microscopic focus suspicious for grade I adenocarcinoma. Patient history included benign breast neoplasm, hypothyroid disease, polypectomy, and arthralgia. |

TABLE 4-continued

| Nucleotide SEQ ID NO: | Clone ID | Library | Library Comment |
|---|---|---|---|
| 125 | 1726843 | PROSNOT14 | The PROSNOT14 library was constructed using RNA isolated from diseased prostate tissue removed from a 60-year-old Caucasian male during radical prostatectomy and regional lymph node excision. Pathology indicated adenofibromatous hyperplasia. Pathology for the associated tumor tissue indicated an adenocarcinoma (Gleason grade 3 + 4). The patient presented with elevated prostate specific antigen (PSA). Patient history included a kidney cyst and hematuria. Family history included benign hypertension, cerebrovascular disease, and arteriosclerotic coronary artery disease. |
| 126 | 1754506 | LIVRTUT01 | The LIVRTUT01 library was constructed using RNA isolated from liver tumor tissue removed from a 51-year-old Caucasian female during a hepatic lobectomy. Pathology indicated metastatic grade 3 adenocarcinoma consistent with colon cancer. Medications included Premarin, Provera, and earlier, fluorouracil, and leucovorin. Family history included a malignant neoplasm of the liver. |
| 127 | 1831378 | THPIAZT01 | The THPIAZT01 library was constructed using RNA isolated from THP-1 promonocyte cells treated for 3 days with 0.8 micromolar 5-aza-2'-deoxycitidine. THP-1 (ATCC TIB 202) is a human promonocyte line derived from peripheral blood of a one-year-old Caucasian male with acute monocytic leukemia (Int. J. Cancer(1980) 26: 171) |
| 128 | 1864943 | PROSNOT19 | The PROSNOT19 library was constructed using RNA isolated from diseased prostate tissue removed from a 59-year-old Caucasian male during a radical prostatectomy with regional lymph node excision. Pathology indicated adenofibromatous hyperplasia. Pathology for the associated tumor tissue indicated an adenocarcinoma (Gleason grade 3 + 3). The patient presented with elevated prostate-specific antigen (PSA). Family history included benign hypertension, multiple myeloma, hyperlipidemia, and rheumatoid arthritis. |
| 129 | 1911316 | CONNTUT01 | The CONNTUT01 library was constructed using RNA isolated from a soft tissue tumor removed from the clival area of the skull of a 30-year-old Caucasian female. Pathology indicated chondroid chordoma with neoplastic cells reactive for keratin. Medications included medroxyprogesterone acetate. |
| 130 | 1943120 | HIPONOT01 | The HIPONOT01 library was constructed using RNA isolated from the hippocampus tissue of a 72-year-old Caucasian female who died from intracranial bleeding. Patient history included nose cancer, hypertension, and arthritis. |
| 131 | 2314236 | NGANNOT01 | The NGANNOT01 library was constructed using RNA isolated from tumorous neuroganglion tissue removed from a 9-year-old Caucasian male during a soft tissue excision of the chest wall. Pathology indicated a ganglioneuroma forming an encapsulated lobulated mass. The tissue from the medial aspect pleura surrounding the tumor showed fibrotic tissue with chronic inflammation. Family history included asthma. |
| 132 | 2479409 | SMCANOT01 | The SMCANOT01 library was constructed using RNA isolated from an aortic smooth muscle cell line derived from the explanted heart of a male during a heart transplant. |
| 133 | 2683149 | SINIUCT01 | The SINIUCT01 library was constructed using RNA isolated from ileum tissue obtained from a 42-year-old Caucasian male during a total intra-abdominal colectomy and endoscopic jejunostomy. Previous surgeries included polypectomy, colonoscopy, and spinal canal exploration. Medications included Prednisone, mesalamine, and Deltasone. Family history included cerebrovascular disease, benign hypertension, atherosclerotic coronary artery disease, and type II diabetes. |
| 134 | 2774051 | PANCNOT15 | The PANCNOT15 library was constructed using RNA isolated from diseased pancreatic tissue removed from a 15-year-old Caucasian male during an exploratory laparotomy with distal pancreatectomy and total splenectomy. Pathology indicated islet cell hyperplasia. A single pancreatic lymph node was negative. Family history included prostate cancer and cardiovacular disease. |
| 135 | 2869038 | THYRNOT10 | The THYRNOT10 library was constructed using RNA isolated from the diseased left thyroid tissue removed from a 30-year-old Caucasian female during a unilateral thyroid lobectomy and parathyroid reimplantation. Pathology indicated lymphocytic thyroiditis. Pathology for the associated tumor indicated grade 1 (of 4) papillary carcinoma of the right thyroid gland, follicular variant. Multiple perithyroidal and other lymph nodes were negative. Patient history included hyperlipidemia and benign ovary neoplasm. Medications included Premarian, Provera, and Anaprox. |
| 136 | 2918334 | THYMFET03 | The THYMFET03 library was constructed using RNA isolated from thymus tissue removed from a Caucasian male fetus who died at premature birth. Serology was negative. |
| 137 | 2949916 | KIDNFET01 | The KIDNFET01 library was constructed using RNA isolated from kidney tissue removed from a Caucasian female fetus, who died at 17 weeks gestation from anencephalus. Serology was negative. |
| 138 | 2989375 | KIDNFET02 | The KIDNFET02 library was constructed using RNA isolated from kidney tissue removed from a Caucasian male fetus who was stillborn with a hypoplastic left heart at 23 weeks gestation. Serology was negative. |
| 139 | 3316764 | PROSBPT03 | The PROSBPT03 library was constructed using RNA isolated from diseased prostate tissue removed from a 59-year-old Caucasian male during a radical prostatectomy and regional lymph node excision. Pathology indicated benign prostatic hyperplasia. Pathology for the associated tumor indicated adenocarcinoma, Gleason grade 3 + 3. The patient presented with elevated prostate specific antigen (PSA), benign hypertension, and hyperlipidemia. Medications included Lotensin and Pravachol. Family history included cerebrovascular disease, benign hypertension, and prostate cancer. |
| 140 | 3359559 | PROSTUT16 | The PROSTUT16 library was constructed using RNA isolated from prostate tumor tissue removed from a 55-year-old Caucasian male. Pathology, indicated adenocarcinoma, Gleason grade 5 + 4. Adenofibromatous hyperplasia was also present. The patient presented with elevated prostate specific antigen (PSA). Patient history included calculus of the kidney. Family history included lung cancer and breast cancer. |
| 141 | 4289208 | BRABDIR01 | The BRABDIR01 library was constructed using RNA isolated from diseased cerebellum tissue remove from the brain of a 57-year-old Caucasian male who died from a cerebrovascular accident. Patient history included Huntington's disease, emphysema, and long-term tobacco use. |
| 142 | 2454013 | ENDANOT01 | The ENDANOT01 library was constructed using RNA isolated from aortic endothelial cell tissue from an explanted heart removed from a male during a heart transplant. |
| 143 | 2454048 | ENDANOT01 | The ENDANOT01 library was constructed using RNA isolated from aortic endothelial cell tissue from an explanted heart removed from a male during a heart transplant. |
| 144 | 2479282 | SMCANOT01 | The SMCANOT01 library was constructed using RNA isolated from an aortic smooth muscle cell line derived from the explanted heart of a male during a heart transplant. |
| 145 | 2483432 | SMCANOT01 | The SMCANOT01 library was constructed using RNA isolated from an aortic smooth muscle cell line derived from the explanted heart of a male during a heart transplant. |

TABLE 4-continued

| Nucleotide SEQ ID NO: | Clone ID | Library | Library Comment |
|---|---|---|---|
| 146 | 2493824 | ADRETUT05 | The ADRETUT05 library was constructed using RNA isolated from adrenal tumor tissue removed from a 52-year-old Caucasian female during a unilateral adrenalectomy. Pathology indicated a pheochromocytoma. |
| 147 | 2555823 | THYMNOT03 | The THYMNOT03 library was constructed using 0.5 micrograms of polyA RNA isolated from thymus tissue removed from a 21-year-old Caucasian male during a thymectomy. Pathology indicated an unremarkable thymus and a benign parathyroid adenoma in the right inferior parathyroid. Patient history included atopic dermatitis, a benign neoplasm of the parathyroid, and tobacco use. Patient medications included multivitamins. Family history included atherosclerotic coronary artery disease and benign hypertension. |
| 148 | 2598242 | OVARTUT02 | The OVARTUT02 library was constructed using RNA isolated from ovarian tumor tissue removed from a 51-year-old Caucasian female during an exploratory laparotomy, total abdominal hysterectomy, salpingo-oophorectomy, and an incidental appendectomy. Pathology indicated mucinous cystadenoma presenting as a multiloculated neoplasm involving the entire left ovary. The right ovary contained a follicular cyst and a hemorrhagic corpus luteum. The uterus showed proliferative endometrium and a single intramural leiomyoma. The peritoneal biopsy indicated benign glandular inclusions consistent with endosalpingiosis. Family history included atherosclerotic coronary artery disease, benign hypertension, breast cancer, and uterine cancer. |
| 149 | 2634120 | COLNTUT15 | The COLNTUT15 library was constructed, using RNA isolated from colon tumor tissue obtained from a 64-year-old Caucasian female during a right hemicolectomy with ileostomy and bilateral salpingo-oophorectomy (removal of the fallopian tubes and ovaries). Pathology indicated an invasive grade 3 adenocarcinoma. Patient history included hypothyroidism, depression, and anemia. Family history included colon cancer and uterine cancer. |
| 150 | 2765411 | BRSTNOT12 | The BRSTNOT12 library was constructed using RNA isolated from diseased breast tissue removed from a 32-year-old Caucasian female during a bilateral reduction mammoplasty. Pathology indicated nonproliferative fibrocystic disease. Family history included benign hypertension and atherosclerotic coronary artery disease. |
| 151 | 2769412 | COLANOT02 | The COLANOT02 library was constructed using RNA isolated from diseased ascending colon tissue removed from a 25-year-old Caucasian female during a multiple segmental resection of the large bowel. Pathology indicated moderately to severely active chronic ulcerative colitis, involving the entire colectomy specimen and sparing 2 cm of the attached ileum. Grossly, the specimen showed continuous involvement from the rectum proximally; marked mucosal atrophy and no skip areas were identified. Microscopically, the specimen showed dense, predominantly mucosal inflammation and crypt abscesses. Patient history included benign large bowel neoplasm. |
| 152 | 2842779 | DRGLNOT01 | The DRGLNOT01 library was constructed using RNA isolated from dorsal root ganglion tissue removed from the low thoracic/high lumbar region of a 32-year-old Caucasian male who died from acute pulmonary edema and bronchopneumonia, bilateral pleural and pericardial effusions, and malignant lymphoma (natural killer cell type). Patient history included probable cytomegalovirus, infection, hepatic congestion and steatosis, splenomegaly, hemorrhagic cystitis, thyroid hemorrhage, and Bell's palsy. |
| 153 | 2966260 | SCORNOT04 | The SCORNOT04 library was constructed using RNA isolated from cervical spinal cord tissue removed from a 32-year-old Caucasian male who died from acute pulmonary edema and bronchopneumonia, bilateral pleural and pericardial effusions, and malignant lymphoma (natural killer cell type). Patient history included probable cytomegalovirus, infection, hepatic congestion and steatosis, splenomegaly, hemorrhagic cystitis, thyroid hemorrhage, and Bell's palsy. |
| 154 | 2993326 | KIDNFET02 | The KIDNFET02 library was constructed using RNA isolated from kidney tissue removed from a Caucasian male fetus, who was stillborn with a hypoplastic left heart and died at 23 weeks' gestation. |
| 155 | 3001124 | TLYMNOT06 | The TLYMNOT06 library was constructed using 0.5 micrograms of polyA RNA isolated from activated Th2 cells. These cells were differentiated from umbilical cord CD4 T cells with IL-4 in the presence of anti-IL-12 antibodies and B7-transfected COS cells, and then activated for six hours with anti-CD3 and anti-CD28 antibodies. |
| 156 | 3120070 | LUNGTUT13 | The LUNGTUT13 library was constructed using RNA isolated from tumorous lung tissue removed from the right upper lobe of a 47-year-old Caucasian male during a segmental lung resection. Pathology indicated invasive grade 3 (of 4) adenocarcinoma. Family history included atherosclerotic coronary artery disease, and type II diabetes. |
| 157 | 3133035 | SMCCNOT01 | The SMCCNOT01 library was constructed using RNA isolated from smooth muscle cells removed from the coronary artery of a 3-year-old Caucasian male. |
| 158 | 3436879 | PENCNOT05 | The PENCNOT05 library was constructed using RNA isolated from penis left corpus cavernosum tissue. |

TABLE 5

| Program | Description | Reference |
|---|---|---|
| ABI FACTURA | A program that removes vector sequences and masks ambiguous bases in nucleic acid sequences. | Perkin-Elmer Applied Biosystems, Foster City, CA. |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. |
| ABI AutoAssembler | A program that assembles nucleic acid sequences. | Perkin-Elmer Applied Biosystems, Foster City, CA. |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol 215: 403-410; Altschul, S. F. et al. (1997) Nucleic Acids Res. 25: 3389-3402. |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85: 2444-2448; Pearson, W. R. (1990) Methods Enzymol. 183: 63-98; and Smith, T. F. and M. S. Waterman (1981) Adv. Appl. Math. 2: 482-489. |
| BLIMPS | A BLocks IMProved Searcher that matches a sequence against those in BLOCKS and PRINTS databases to search | Henikoff, S and J. G. Henikoff, Nucl. Acid Res., 19: 6565-72, 1991. J. G. Henikoff and S. Henikoff |

TABLE 5-continued

| | | |
|---|---|---|
| | for gene families, sequence homology, and structural fingerprint regions. | (1996) Methods Enzymol. 266: 88-105; and Attwood, T. K. et al. (1997) J. Chem. Inf. Comput. Sci. 37: 417-424. |
| PFAM | A Hidden Markov Models-based application useful for protein family search. | Krogh, A. et al. (1994) J. Mol. Biol., 235: 1501-1531; Sonnhammer, E. L. L. et al. (1988) Nucleic Acids Res. 26: 320-322. |
| ProfileScan | An algorithm that searches for structural and sequence motifs in protein sequences that match sequence patterns defined in Prosite. | Gribskov, M. et al. (1988) CABIOS 4: 61-66; Gribskov, et al. (1989) Methods Enzymol. 183: 146-159; Bairoch, A. et al. (1997) Nucleic Acids Res. 25: 217-221. |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482-489; Smith, T. F. and M. S. Waterman (1981) J. Mol. Biol. 147: 195-197; and Green, P., University of Washington. Seattle, WA. |
| Consed | A graphical tool for viewing and editing Phrap assemblies | Gordon, D. et al. (1998) Genome Res. 8: 195-202. |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. |
| Motifs | A program that searches amino acid sequences for patterns that matched those defined in Prosite. | Bairoch et al. supra; Wisconsin Package Program Manual, version 9, page M51-59, Genetics Computer Group, Madison, WI. |

| Program | Parameter Threshold |
|---|---|
| ABI FACTURA | |
| ABI/PARACEL FDF | Mismatch <50% |
| ABI AutoAssembler | |
| BLAST | ESTs: Probability value = 1.0E-8 or less Full Length sequences: Probability value = 1.0E-10 or less |
| FASTA | ESTs: fasta E value = 1.06E-6 Assembled ESTs: fasta Identity = 95% or greater and Match length = 200 bases or greater; fastx E value = 1.0E-8 or less Full Length sequences: fastx score = 100 or greater |
| BLIMPS | Score = 1000 or greater; Ratio of Score/Strength = 0.75 or larger; and Probability value = 1.0E-3 or less |
| PFAM | Score = 10-50 bits, depending on individual protein families |
| ProfileScan | Score = 4.0 or greater |
| Phred | |
| Phrap | Score = 120 or greater; Match length = 56 or greater |
| Consed | |
| SPScan | Score = 5 or greater |
| Motifs | |

What is claimed is:

1. An isolated polynucleotide encoding a polypeptide comprising an amino acid sequence having at least about 95% sequence identity to the full-length of SEQ ID NO: 74.

2. The isolated polynucleotide of claim 1, wherein the polypeptide comprises SEQ ID NO: 74.

3. The isolated polynucleotide of claim 1 comprising SEQ ID NO: 153.

4. A recombinant polynucleotide comprising a promoter sequence operably linked to the polynucleotide of claim 1.

5. An isolated cell transformed with the recombinant polynucleotide of claim 4.

6. A method of producing the polypeptide encoded by the polynucleotide of claim 1, the method comprising:
   a) culturing a cell under conditions suitable for expression of the polypeptide, wherein said cell is transformed with a recombinant polynucleotide, and said recombinant polynucleotide comprise a promoter sequence operably linked to the polynucleotide of claim 1, and
   b) recovering the polypeptide so expressed.

7. The method of claim 6, wherein the polypeptide comprises SEQ ID NO: 74.

8. The method of claim 6, wherein the polynucleotide comprises SEQ ID NO: 153.

* * * * *